(12) United States Patent
Hakonarson et al.

(10) Patent No.: US 10,385,398 B2
(45) Date of Patent: Aug. 20, 2019

(54) METHODS FOR USE IN COMBINATION FOR THE TREATMENT AND DIAGNOSIS OF AUTOIMMUNE DISEASES

(71) Applicant: The Children's Hospital of Philadelphia, Philadelphia, PA (US)

(72) Inventors: Hakon Hakonarson, Malvern, PA (US); Yun Rose Li, Philadelphia, PA (US); Brendan Keating, Philadelphia, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 0 days.

(21) Appl. No.: 15/242,091

(22) Filed: Aug. 19, 2016

(65) Prior Publication Data
US 2017/0051351 A1    Feb. 23, 2017

Related U.S. Application Data

(60) Provisional application No. 62/320,400, filed on Apr. 8, 2016, provisional application No. 62/208,383, filed on Aug. 21, 2015.

(51) Int. Cl.
*C12Q 1/68*    (2018.01)
*C12Q 1/6883*    (2018.01)

(52) U.S. Cl.
CPC ..... *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2010/0144903 A1 | 6/2010 | Taylor et al. |
| 2010/0190162 A1 | 7/2010 | Rotter et al. |
| 2011/0177502 A1 | 7/2011 | Hakonarson et al. |

FOREIGN PATENT DOCUMENTS

| | | |
|---|---|---|
| WO | 2015010744 | 7/2011 |
| WO | 2014186750 A1 | 11/2014 |

OTHER PUBLICATIONS

Hirschhorn et al. Genetics in Medicine. vol. 4, No. 2, pp. 45-61, Mar. 2002.*
Chadha et al. European J Human Genetics. 2005. 13: 66-676.*
Hattersley et al. The Lancet. 2005. 366: 1315-1323.*
Mukhopadhyay et al. J Allergy Clin Immunol. 2010. 126:70-76.*
Halushka et al. Nature. Jul. 1999. 22: 239-247.*
Gagneux et al. Molecular Phylogenetics and Evolution. 2001. 18: 2-13.*
ClinicalTrials.gov NCT02804763, NIH, National Library of Medicine; first posted Jun. 17, 2016, available via URL: < clinicaltrials.gov/ct2/show/NCT02804763>, printed on Aug. 21, 2018.*
Li et al Nature Medicine. Aug. 24, 2015. 21(9): 1018.*
Onouchi et al E J Human Genetics. 2004. 12: 1062-1068.*
Garcia-Bermudez et al PLOS One. Nov. 2012. 7(11): e49214.*
NCBI dbSNP submission ss1083150363 for rs2807264, Jul. 10, 2014.*
Rodriguez-Palacios et al. Gastro J. 2014. AGA abstracts, p. S-876, abstract Tu1934.*
Christodoulou et al Gut. 2013. 62: 977-984.*
Cardinale et al. Targeted resequencing identifies defective variants of decoy receptor 3 in pediatric-onset inflammatory bowel disease. Genes Immunol. (2013) 14(7):447-52.
Ordas et al. Anti-TNF monoclonal antibodies in inflammatory bowel disease: pharmacokinetics-based dosing paradigms. Clin Pharmacol Ther. (2012) 91(4):635-46.
International Search Report issued in PCT/US16/47872, dated Dec. 20, 2016.
International Search Report issued in PCT/US16/47857, dated Dec. 29, 2016.
Hinks, Anne et al., "Association between the PTPN22 gene and rheumatoid arthritis and juvenile idiopathic arthritis in a UK population: Further support taht PTPN 22 is an autoimmunity gene", Arthritis & Rheumatism, 52(6): 1694-1699 (2005).
Duerr, Richard H. et al., "A genome-wide association study identifies IL23R as an inflammatory bowel disease gene", Science, American Association for the Advancement of Science, 314(5804): 1461-1463 (2006).
Csongei, Veronika, "Interaction of the major inflammatory bowel disease susceptibility alleles in Crohn's disease patients", World Journal of Gastroenterology, 16(2): 176 (2010).
Li, Yi et al., "The Association Between Interleukin-23 Receptor GEne Polymorphisms and Systemic Lupus Erythematosus", DNA and Cell Biology, 29(2): 79-82 (2010).
Partial Supplementary European Search Report, dated Oct. 31, 2018 issued in corresponding European Patent Application No. 16839901.2.

* cited by examiner

*Primary Examiner* — Carla J Myers
(74) *Attorney, Agent, or Firm* — Kathleen D. Rigaut; Howson & Howson LLP

(57) ABSTRACT

This disclosure provides new genetic targets, diagnostic methods, and therapeutic treatment regimens for multiple autoimmune disorders, including pediatric autoimmune disorders that are co-inherited and genetically shared. The disclosure, for example, provides methods of diagnosing or determining a susceptibility for one or more autoimmune diseases and methods of determining treatment protocols for patients with one or more autoimmune diseases based on determining if the patients have genetic alterations in particular genes.

13 Claims, 26 Drawing Sheets

| Category | Ab | N Annotated | $P_{enrich}$ |
|---|---|---|---|
| cpg | M | 5 | 0.0001 |
| dgv | V | 18 | 1.0000 |
| dnase | S | 19 | 0.1745 |
| eqtl | E | 8 | 0.9084 |
| gad | L | 24 | 0.0001 |
| gerp_phast | C | 15 | 0.2596 |
| mir | R | 5 | 0.0001 |
| sift_pp | A | 2 | 0.0001 |
| tfbs | T | 7 | 0.0034 |

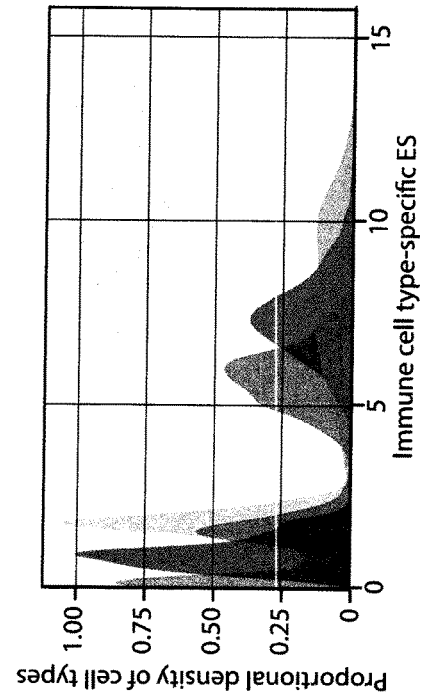
Fig. 3E
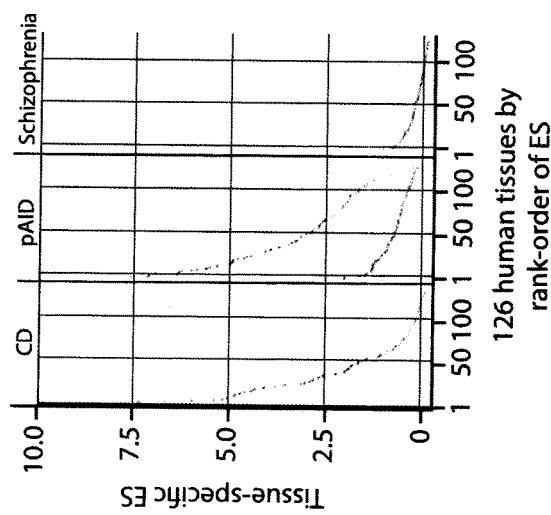
Fig. 4A
Fig. 4B

| SNP | REGION | GENE | pAIDs model | BETA(SE) model | pAID opposite | BETA(SE) opposite | P value |
|---|---|---|---|---|---|---|---|
| rs6679677 | 1p13.2 | PTPN22 | THY\|PS\|T1D\|JIA | 0.59(0.06) | CD | 0.25(0.07) | 1.40E 04 |
| rs2066363 | 1p31.1 | LPHN2 | CVID\|JIA | 0.68(0.05) | CD | 0.08(0.04) | 2.56E 02 |
| rs55705316 | 1q32.1 | IL10 | PS\|SLE\|UC\|CD | 0.21(0.04) | T1D | 0.26(0.07) | 2.88E 04 |
| rs4625 | 3p21.31 | DAG1 | PS\|SLE\|UC\|CD | 0.25(0.03) | AS | 0.35(0.15) | 1.94E 02 |
| rs7672495 | 4p16.2 | CYTL1 | THY\|AS\|CEL\|UC\|T1D\|JIA\|CD | 0.18(0.03) | PS | 0.38(0.18) | 4.17E 02 |
| rs11839053 | 13q33.3 | EFNB2 | CVID\|JIA | 0.76(0.15) | T1D | 0.49(0.17) | 4.61E 03 |
| rs12598357 | 16p11.2 | CBK1 | THY\|AS\|PS\|CEL\|UC\|CD | 0.18(0.03) | T1D | 0.13(0.05) | 1.27E 02 |
| rs12928404 | 16p11.2 | ATXN2L | UC\|CD | 0.17(0.03) | T1D | 0.13(0.05) | 8.94E 03 |
| rs2836882 | 21q22.2 | PSMG1 | UC\|CD | 0.21(0.04) | THY | 0.34(0.17) | 3.79E 02 |

Fig. 7A with the extended MHC without the extended MHC

METHODS FOR USE IN COMBINATION FOR THE TREATMENT AND DIAGNOSIS OF AUTOIMMUNE DISEASES

PRIORITY APPLICATIONS

This application claims priority to U.S. Provisional Application No. 62/208,383, filed Aug. 21, 2015, and 62/320,400, filed Apr. 8, 2016, both of which are incorporated by reference herein in their entirety.

GRANT STATEMENT

This invention was made with funds from the National Institutes of Health, Grant Nos. DP3DK085708, RC1AR058606, U01HG006830, CA127334, and R01-HG006849. Accordingly, the United States Government has rights in this invention.

FIELD OF THE INVENTION

This invention relates to the fields of genetics, autoimmunity and personalized medicine. More specifically the invention provides new genetic targets, diagnostic methods, and therapeutic treatment regimens for multiple autoimmune disorders, including pediatric autoimmune disorders.

BACKGROUND OF THE INVENTION

Several publications and patent documents are cited throughout the specification in order to describe the state of the art to which this invention pertains. Each of these citations is incorporated by reference herein as though set forth in full. Color versions of certain figures and tables included herein have also been published in Y. R. Li et al, *Nature Medicine* Aug. 24, 2015, online publication doi: 10.1038 "backslash" nm.3933, and in the supplemental materials for that publication, and those figures and tables are incorporated by reference herein.

Autoimmune diseases affect up to 7-10% of individuals living in the Western Hemisphere[1], representing a significant cause of chronic morbidity and disability. High rates of autoimmune disease comorbidity and familial clustering suggest that a strong genetic predisposition may underlie autoimmune disease susceptibility. Genome-wide association studies (GWAS) and immune-focused fine-mapping studies of autoimmune thyroiditis (AITD)[2], psoriasis (PSOR)[3], juvenile idiopathic arthritis (JIA)[4], primary biliary cirrhosis (PBC)[5], primary sclerosing cholangitis (PSC)[6], rheumatoid arthritis (RA)[7], celiac disease (CEL)[8], inflammatory bowel disease (IBD, which includes Crohn's Disease (CD) and ulcerative colitis (UC)[9]), and multiple sclerosis (MS), have identified hundreds of autoimmune disease-associated single-nucleotide polymorphisms (SNPs) across the genome[10]. These studies and subsequent meta-analyses demonstrate that over half of all genome-wide significant (GWS) ($P_{GWS} < 5 \times 10^{-8}$) autoimmune disease associations are shared by at least two distinct autoimmune diseases[11,12]. However, when applied to heterogeneous diseases, classical meta-analysis approaches face limitations as they: 1) have limited power when disease-associated variants show variable effect sizes or even directions of effect across the traits, 2) may be affected by phenotypic heterogeneity and subject recruitment bias across studies, 3) often examine a candidate list or previously-discovered loci from single-disease studies, thereby missing the chance to identify novel associations, particularly those due to variants that are rarer or have smaller effect sizes, 4) do not fully adjust for population stratification and cryptic relatedness, and 5) may contain artifacts introduced by the use of multiple genotyping platforms or study sites.

While a few studies have merged case genotypes from multiple diseases in a limited way[13-15], and a few loci have surfaced in independent GWAS studies across multiple autoimmune diseases, such as CLEC16A, first discovered in T1D[16], and subsequently in MS[17], RA[18,19], CD[20], PBC[21], JIA[19], and AA[22], the degree to which genetic variants associated with one disease may be associated with the risk of other autoimmune diseases has not been systematically examined. Clearly, having this information would provide new therapeutic avenues for the treatment of such disorders.

SUMMARY OF THE INVENTION

In accordance with the present invention, new genetic markers are provided for the diagnosis and treatment of autoimmune disease (AID), which includes, for example, pediatric autoimmune disease (pAID). Autoimmune diseases discussed herein include, for example, one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH), as well as several others.

For example, included herein is a method for diagnosing one or more autoimmune disorders (AID) in a patient, comprising: a) obtaining a biological sample from the patient; b) assaying nucleic acid from the sample to determine whether a genetic alteration in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX is present, wherein a genetic alteration in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX is correlated with presence of one or more AID in the patient; and c) diagnosing the patient with one or more AID if a genetic alteration is present in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX.

In some embodiments, the method comprises determining whether a genetic alteration is present in at least 5, such as at least 10, such as at least 15, such as at least 20, such as at least 25, such as at least 30, such as at least 35, such as at least 40, or in each of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, § EFNB2, SMAD3, SBK1, ATXN2L, ADCY7, NOD2, IKZF3, TYK2, FUT2, TNFRSF6B, PSMG1, CD40LG, and RBMX. In some embodiments, the AID is one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH).

In some embodiments, the patient is a pediatric patient, whereas in others the patient is an adult patient. In some embodiments, the genetic alteration is a single nucleotide variant (SNV). The genetic alteration may also be an insertion, deletion, translocation, or copy number variation (CNV), for example.

In some embodiments, the method comprises determining whether a genetic alteration is present in one or more of IL23R, LPHN2, PTPN22, TNM3, ANKRD30A, INS, NOD2, DAG1, SMAD3, ATG16L1, ZNF365, PTGER4, NKX2-3, ANKRD55, IL12B, LRRK2, IL5, SUOX, SBK1, ADCY7, IL2RA, TNFSF15, CD40LG, ZMIZ1, IL21, CARD9, and PSMG1. In some embodiments, the method comprises determining whether a genetic alteration is present in at least 5, such as at least 10, such as at least 15, such as at least 20, or each of IL23R, LPHN2, PTPN22, TNM3, ANKRD30A, INS, NOD2, DAG1, SMAD3, ATG16L1, ZNF365, PTGER4, NKX2-3, ANKRD55, IL12B, LRRK2, IL5, SUOX, SBK1, ADCY7, IL2RA, TNFSF15, CD40LG, ZMIZ1, IL21, CARD9, and PSMG1. In some embodiments, the method comprises determining whether a genetic alteration is present in one or more of LPHN2, TNM3, ANKRD30A, ADCY7, and CD40LG.

In some embodiments, the method comprises determining whether a genetic alteration is present in one or more of IL23R, TNM3, LRRK2, SBK1, IL2RA, ZMIZ1, IL21, and CARD9, wherein a genetic alteration in one or more of IL23R, TNM3, LRRK2, SBK1, IL2RA, ZMIZ1, IL21, and CARD9 indicates that the patient suffers from AS. In some such embodiments, the method further comprises determining whether a genetic alteration in one or more of CRB1, GPR35, CYTL3, IL12B, 8q24.23, JAK2, FNBP1, and SMAD3 is present.

In some embodiments, the method comprises determining whether a genetic alteration in one or more of IL23R, PTPN22, TNM3, DAG1, ATG16L1, SUOX, SBK1, ADCY7, IL2RA, and ZMIZ1 is present, wherein a genetic alteration in one or more of IL23R, PTPN22, TNM3, DAG1, ATG16L1, SUOX, SBK1, ADCY7, IL2RA, and ZMIZ1 indicates that the patient suffers from PS. In some such embodiments, the method further comprises determining whether a genetic alteration in one or more of IL10, TSSC1, IL5, IL2RA, ADCY7, FUT2, and TNFRSF6B is present.

In some embodiments, the method comprises determining whether a genetic alteration in one or more of TNM3, DAG1, SBK1, IL2RA, C40LG, ZMIZ1, and IL21 is present, wherein a genetic alteration in one or more of TNM3, DAG1, SBK1, IL2RA, C40LG, ZMIZ1, and IL21 indicates that the patient suffers from CEL. In some such embodiments, the method further comprises determining whether a genetic alteration in one or more of IL18R1, CYTL1, ERAP2, IL5, IL12B, 8q24.23, IKZF3, CD40LG, and RBMX is present.

In some embodiments, the method comprises determining whether a genetic alteration in one or both of PTPN22 and TNM3 is present, wherein a genetic alteration in one or both of PTPN22 and TNM3 indicates that the patient suffers from SLE. In some such embodiments, the method further comprises determining whether a genetic alteration in one or more of IL10, TSSC1, GPR35, JAK2, ZNF365, TYK2, and TNFRSF6B is present.

In some embodiments, the method comprises determining whether a genetic alteration in one or more of LPHN2, TNM3, and IL21 is present, wherein a genetic alteration in one or more of LPHN2, TNM3, and IL21 indicates that the patient suffers from CVID. In some such embodiments, the method further comprises determining whether a genetic alteration in one or both of EFNB2 and IKZF3 is present.

In some embodiments, the method comprises determining whether a genetic alteration in one or more of IL23R, LPHN2, DAG1, PTGER4, SBK1, TNFSF15, CD40LG, IL21, CARD9, and PSMG1 is present, wherein a genetic alteration in one or more of IL23R, LPHN2, DAG1, PTGER4, SBK1, TNFSF15, CD40LG, IL21, CARD9, and PSMG1 indicates that the patient suffers from UC. In some such embodiments, the method further comprises determining whether a genetic alteration in one or more of IL10, TSSC1, IL18R1, GPR35, CYTL1, IL12B, JAK2, NKX2, SMAD3, ATXN2L, IKZF3, and TNFRSF6B is present.

In some embodiments, the method comprises determining whether a genetic alteration in one or more of PTPN22, INS, SUOX, IL2RA, and IL21 is present, wherein a genetic alteration in one or more of PTPN22, INS, SUOX, IL2RA, and IL21 indicates that the patient suffers from T1D. In some such embodiments, the method further comprises determining whether a genetic alteration in one or more of CYTL1, 8q24.23, TYK2, and FUT2 is present.

In some embodiments, the method comprises determining whether a genetic alteration in one or more of LPHN2, PTPN22, TNM3, ANKRD30A, ANKRD55, IL2RA, CD40LG, and IL21 is present, wherein a genetic alteration in one or more of LPHN2, PTPN22, TNM3, ANKRD30A, ANKRD55, IL2RA, CD40LG, and IL21 indicates that the patient suffers from JIA. In some such embodiments, the method further comprises determining whether a genetic alteration in one or more of CYTL1, ERAP2, 8q24.23, LURAP1L, FNBP1, EFNB2, IKZF3, TYK2, and RBMX is present.

In some embodiments, the method comprises determining whether a genetic alteration in one or more of IL23R, PTPN22, DAG1, ATG16L1, PTGER4, ANKRD55, LRRK2, SBK1, ADCY7, IL2RA, TNFSF15, CD40LG, ZMIZ1, IL21, CARD9, and PSMG1 is present, wherein a genetic alteration in one or more of IL23R, PTPN22, DAG1, ATG16L1, PTGER4, ANKRD55, LRRK2, SBK1, ADCY7, IL2RA, TNFSF15, CD40LG, ZMIZ1, IL21, CARD9, and PSMG1 indicates that the patient suffers from CD. In some such embodiments, the method further comprises determining whether a genetic alteration in one or more of CRB1, IL10, TSSC1, IL18R1, CYTL1, ERAP2, IL5, IL12B, 8q24.23, JAK2, FNBP1, ZNF365, NKX2, SMAD3, ATXN2L, NOD2, IKZF3, TYK2, FUT2, TNFRSF6B, and RBMX is present.

In some embodiments, the method comprises determining whether a genetic alteration in one or both of IL2RA and IL21 is present, wherein a genetic alteration in one or both of IL2RA and IL21 indicates that the patient suffers from AA. In some embodiments, the method comprises determining whether a genetic alteration in one or more of PTGER4, ANKRD55, IL2RA, CD40LG, and ZMIZ1 is present, wherein a genetic alteration in one or more of PTGER4, ANKRD55, IL2RA, CD40LG, and ZMIZ1 indicates that the patient suffers from MS. In some embodiments, the method comprises determining whether a genetic alteration in one or both of IL2A or IL21 is present, wherein a genetic alteration in one or both of IL2A or IL21 indicates that the patient suffers from PSC. In some embodiments, the method comprises determining whether a genetic alteration in one or more of PTPN22, ANKRD55, IL2RA, and IL21 is present, wherein a genetic alteration in one or more of PTPN22, ANKRD55, IL2RA, and IL21 indicates that the patient suffers from RA.

In some embodiments, the method comprises determining whether a genetic alteration in one or more of PTPN22 and IL2RA is present, wherein a genetic alteration in one or both of PTPN22 and IL2RA indicates that the patient suffers from VIT. In some embodiments, the method comprises determining whether a genetic alteration in one or more of PTPN22, TNM3, SBK1, IL2RA, and IL21 is present, wherein a genetic alteration in one or both of PTPN22, TNM3, SBK1, IL2RA, and IL21 indicates that the patient suffers from THY. In some such embodiments, the method further comprises determining whether a genetic alteration in one or more of IL18R1, CYTL1, FNBP1, IKZF3, TYK2, and TNFRSF6B is present.

In any of the above embodiments, the method may further comprise providing a report comprising suggested treatment(s) for the AID based upon the genetic alteration(s) identified in the method. In any of the above embodiments, the method may further comprise administering an effective amount of a treatment to the diagnosed patient after determination of genetic alterations in the patient, such as treatment with a molecule targeting a protein within the interaction network of the gene(s) harboring the genetic alteration(s). In such embodiments, the diagnosed patient may, for example, be prescribed an effective amount of one or more pharmaceutical agents listed in Tables 11 and 12. For instance, these tables list drugs associated with particular genes or gene pathways and the genetic alterations herein may reveal defects in one or more of those pathways that can be treated by a drug targeting that pathway and counteracting the effect of the genetic alteration in the patient.

In any of the above embodiments, genetic alterations may be found in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX at the corresponding chromosomal region and single nucleotide polymorphism (SNP) positions listed herein, for instance, in Tables 2a, 2b, 2c, or 2e.

These same general method steps and above optional embodiments may also be employed to determine whether a subject that does not currently have a particular AID is susceptible to developing one or more autoimmune disorders (AID) in the future. The same general method steps can, as another alternative, be applied to determining genetic alterations in a patient who has already been diagnosed with one or more AID, either to determine if the patient is susceptible to developing yet another AID or to determine possible treatments for the patient based on their particular set of genetic alterations. As above, such methods would comprise a) obtaining a biological sample from the subject; b) assaying nucleic acid from the sample to determine whether a genetic alteration in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX is present in the nucleic acid, wherein a genetic alteration in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX is correlated with presence of one or more AID in a subject; and c) determining that the subject is susceptible to developing one or more AID if a genetic alteration is present in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX. The same optional ways of conducting this method would also apply here as in the method of diagnosing a patient.

Namely, in some embodiments, the method for assessing altered susceptibility comprises determining whether a genetic alteration is present in at least 5, such as at least 10, such as at least 15, such as at least 20, such as at least 25, such as at least 30, such as at least 35, such as at least 40, or in each of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, § EFNB2, SMAD3, SBK1, ATXN2L, ADCY7, NOD2, IKZF3, TYK2, FUT2, TNFRSF6B, PSMG1, CD40LG, and RBMX. In some embodiments, the AID is one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH).

In some embodiments, the patient is a pediatric patient, whereas in others the patient is an adult patient. In some embodiments, the genetic alteration is a single nucleotide variant (SNV). The genetic alteration may also be an insertion, deletion, translocation, or copy number variation (CNV), for example.

In some embodiments, the method for detecting altered susceptibility comprises determining whether a genetic alteration is present in one or more of IL23R, LPHN2, PTPN22, TNM3, ANKRD30A, INS, NOD2, DAG1, SMAD3, ATG16L1, ZNF365, PTGER4, NKX2-3, ANKRD55, IL12B, LRRK2, IL5, SUOX, SBK1, ADCY7, IL2RA, TNFSF15, CD40LG, ZMIZ1, IL21, CARD9, and PSMG1. In some embodiments, the method comprises determining whether a genetic alteration is present in at least 5, such as at least 10, such as at least 15, such as at least 20, or each of IL23R, LPHN2, PTPN22, TNM3, ANKRD30A, INS, NOD2, DAG1, SMAD3, ATG16L1, ZNF365, PTGER4, NKX2-3, ANKRD55, IL12B, LRRK2, IL5, SUOX, SBK1, ADCY7, IL2RA, TNFSF15, CD40LG, ZMIZ1, IL21, CARD9, and PSMG1. In some embodiments, the method comprises determining whether a genetic alteration is present in one or more of LPHN2, TNM3, ANKRD30A, ADCY7, and CD40LG.

In some embodiments, the method for detecting altered susceptibility comprises determining whether a genetic alteration is present in one or more of IL23R, TNM3, LRRK2, SBK1, IL2RA, ZMIZ1, IL21, and CARD9, wherein a genetic alteration in one or more of IL23R, TNM3, LRRK2, SBK1, IL2RA, ZMIZ1, IL21, and CARD9 indicates that the patient suffers from AS. In some such embodiments, the method further comprises determining whether a genetic alteration in one or more of CRB1, GPR35, CYTL3, IL12B, 8q24.23, JAK2, FNBP1, and SMAD3 is present.

In some embodiments, the method for detecting altered susceptibility comprises determining whether a genetic alteration in one or more of IL23R, PTPN22, TNM3, DAG1, ATG16L1, SUOX, SBK1, ADCY7, IL2RA, and ZMIZ1 is present, wherein a genetic alteration in one or more of IL23R, PTPN22, TNM3, DAG1, ATG16L1, SUOX, SBK1, ADCY7, IL2RA, and ZMIZ1 indicates that the patient suffers from PS. In some such embodiments, the method further comprises determining whether a genetic alteration in one or more of IL10, TSSC1, IL5, IL2RA, ADCY7, FUT2, and TNFRSF6B is present.

In some embodiments, the method for detecting altered susceptibility comprises determining whether a genetic alteration in one or more of TNM3, DAG1, SBK1, IL2RA, C40LG, ZMIZ1, and IL21 is present, wherein a genetic alteration in one or more of TNM3, DAG1, SBK1, IL2RA, C40LG, ZMIZ1, and IL21 indicates that the patient suffers from CEL. In some such embodiments, the method further comprises determining whether a genetic alteration in one or more of IL18R1, CYTL1, ERAP2, IL5, IL12B, 8q24.23, IKZF3, CD40LG, and RBMX is present.

In some embodiments, the method comprises determining whether a genetic alteration in one or both of PTPN22 and TNM3 is present, wherein a genetic alteration in one or both of PTPN22 and TNM3 indicates that the patient is at altered risk for SLE. In some such embodiments, the method further comprises determining whether a genetic alteration in one or more of IL10, TSSC1, GPR35, JAK2, ZNF365, TYK2, and TNFRSF6B is present.

In some embodiments, the method comprises determining whether a genetic alteration in one or more of LPHN2, TNM3, and IL21 is present, wherein a genetic alteration in one or more of LPHN2, TNM3, and IL21 indicates that the patient is at altered risk for CVID. In some embodiments, the method further comprises determining whether a genetic alteration in one or both of EFNB2 and IKZF3 is present.

In some embodiments, the method for detecting altered susceptibility comprises determining whether a genetic alteration in one or more of IL23R, LPHN2, DAG1, PTGER4, SBK1, TNFSF15, CD40LG, IL21, CARD9, and PSMG1 is present, wherein a genetic alteration in one or more of IL23R, LPHN2, DAG1, PTGER4, SBK1, TNFSF15, CD40LG, IL21, CARD9, and PSMG1 indicates that the patient is at altered risk for UC. In some such embodiments, the method further comprises determining whether a genetic alteration in one or more of IL10, TSSC1, IL18R1, GPR35, CYTL1, IL12B, JAK2, NKX2, SMAD3, ATXN2L, IKZF3, and TNFRSF6B is present.

In some embodiments, the method for detecting altered susceptibility comprises determining whether a genetic alteration in one or more of PTPN22, INS, SUOX, IL2RA, and IL21 is present, wherein a genetic alteration in one or more of PTPN22, INS, SUOX, IL2RA, and IL21 indicates that the patient suffers from T1D. In some such embodiments, the method further comprises determining whether a genetic alteration in one or more of CYTL1, 8q24.23, TYK2, and FUT2 is present.

In some embodiments, the method for detecting altered susceptibility comprises determining whether a genetic alteration in one or more of LPHN2, PTPN22, TNM3, ANKRD30A, ANKRD55, IL2RA, CD40LG, and IL21 is present, wherein a genetic alteration in one or more of LPHN2, PTPN22, TNM3, ANKRD30A, ANKRD55, IL2RA, CD40LG, and IL21 indicates that the patient is at altered risk for JIA. In some such embodiments, the method further comprises determining whether a genetic alteration in one or more of CYTL1, ERAP2, 8q24.23, LURAP1L, FNBP1, EFNB2, IKZF3, TYK2, and RBMX is present.

In some embodiments, the method for detecting altered susceptibility comprises determining whether a genetic alteration in one or more of IL23R, PTPN22, DAG1, ATG16L1, PTGER4, ANKRD55, LRRK2, SBK1, ADCY7, IL2RA, TNFSF15, CD40LG, ZMIZ1, IL21, CARD9, and PSMG1 is present, wherein a genetic alteration in one or more of IL23R, PTPN22, DAG1, ATG16L1, PTGER4, ANKRD55, LRRK2, SBK1, ADCY7, IL2RA, TNFSF15, CD40LG, ZMIZ1, IL21, CARD9, and PSMG1 indicates that the patient is at altered risk for CD. In some such embodiments, the method further comprises determining whether a genetic alteration in one or more of CRB1, IL10, TSSC1, IL18R1, CYTL1, ERAP2, IL5, IL12B, 8q24.23, JAK2, FNBP1, ZNF365, NKX2, SMAD3, ATXN2L, NOD2, IKZF3, TYK2, FUT2, TNFRSF6B, and RBMX is present.

In some embodiments, the method for detecting altered susceptibility comprises determining whether a genetic alteration in one or both of IL2RA and IL21 is present, wherein a genetic alteration in one or both of IL2RA and IL21 indicates that the patient suffers from AA. In some embodiments, the method comprises determining whether a genetic alteration in one or more of PTGER4, ANKRD55, IL2RA, CD40LG, and ZMIZ1 is present, wherein a genetic alteration in one or more of PTGER4, ANKRD55, IL2RA, CD40LG, and ZMIZ1 indicates that the patient suffers from MS. In some embodiments, the method comprises determining whether a genetic alteration in one or both of IL2A or IL21 is present, wherein a genetic alteration in one or both of IL2A or IL21 indicates that the patient is at altered risk for PSC. In some embodiments, the method comprises determining whether a genetic alteration in one or more of PTPN22, ANKRD55, IL2RA, and IL21 is present, wherein a genetic alteration in one or more of PTPN22, ANKRD55, IL2RA, and IL21 indicates that the patient suffers from RA.

In some embodiments, the method for detecting altered susceptibility comprises determining whether a genetic alteration in one or more of PTPN22 and IL2RA is present, wherein a genetic alteration in one or both of PTPN22 and IL2RA indicates that the patient is at altered risk for VIT. In some embodiments, the method comprises determining whether a genetic alteration in one or more of PTPN22, TNM3, SBK1, IL2RA, and IL21 is present, wherein a genetic alteration in one or both of PTPN22, TNM3, SBK1, IL2RA, and IL21 indicates that the patient suffers from THY. In some such embodiments, the method further comprises determining whether a genetic alteration in one or more of IL18R1, CYTL1, FNBP1, IKZF3, TYK2, and TNFRSF6B is present.

In any of the above embodiments, the method may further comprise providing a report comprising suggested treatment(s) for the AID based upon the genetic alteration(s) identified in the method. In any of the above embodiments, the method may further comprise administering an effective amount of a treatment to the diagnosed patient after determination of genetic alterations in the patient, such as treatment with a molecule targeting a protein within the interaction network of the gene(s) harboring the genetic alteration(s). In such embodiments, the diagnosed patient may, for example, be prescribed an effective amount of one or more pharmaceutical agents listed in Tables 11 and 12. For instance, these tables list drugs associated with particular genes or gene pathways and the genetic alterations herein may reveal defects in one or more of those pathways that can be treated by a drug targeting that pathway and counteracting the effect of the genetic alteration in the patient.

In any of the above embodiments, genetic alterations may be found in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX at the corresponding chromosomal region and single nucleotide polymorphism (SNP) positions listed herein, for instance, in Tables 2a, 2b, 2c, or 2e.

Also included herein are methods of treating a patient with one or more AID, comprising determining whether a genetic alteration is present in the patient according to the methods of any the above methods, and administering an effective amount of one or more pharmaceutical agents listed in Tables 11 and 12 to the patient based upon identification of the genetic alteration(s) determined, i.e. matching a drug targeting a particular gene or network to a patient with a genetic alteration affecting that gene or network.

The present disclosure also includes systems for detecting a genetic alteration in a subject, comprising probes specific for and capable of determining single nucleotide variations (SNVs) in at least 5, such as at least 10, at least 15, at least 20, at least 25, at least 30, at least 35, at least 40, or each of the following genes: IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX. In some embodiments, the system is capable of determining copy number variations (CNVs) in in at least 5, such as at least 10, at least 15, at least 20, at least 25, at least 30, at least 35, at least 40, or each of: IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX. In some embodiments, the system is capable of determining SNVs in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, and RBMX are at the corresponding chromosomal region and SNP positions listed in Tables 2a, 2b, 2c, or 2e. In some embodiments, the probes are comprised on solid support matrix, such as a chip.

The present disclosure also includes methods for treating one or more autoimmune disorders (AID) in a patient, comprising: a) obtaining genotype sequence information from a biological sample obtained from a patient; b) detecting the presence of at least one genetic alteration in a chromosomal region and associated gene selected from:

rs2066363 1p31.1 LPHN2, wherein said pAID is selected from CVID and JIA;

rs7660520 4q35.1 TNM3, wherein said pAID is selected from THY, AS, CEL, SLE, CVID and JIA;

rs7100025 10p11.21 ANKRD30A, wherein said pAID is JIA;

rs77150043 16q12.1 ADCY7, wherein said pAID is PS and CD;

rs2807264 Xq26.3 CD40LG, wherein said pAID is CEL, UC and CD; wherein detection of said one or more of said genetic alterations is correlated with an altered risk for developing one or more AID relative to control patients lacking said genetic alterations; and c) treating the patient with an effective amount of one or more pharmaceutical agents listed in Tables 11 and 12 targeting the indicated pAID associated gene or its interaction network. Such a method may further comprise detection of:

| rs11580078 | 1p31.3  | IL23R;   |
| rs6679677  | 1p13.2  | PTPN22;  |
| rs36001488 | 2q37.1  | ATG16L1; |
| rs4625     | 3p21.31 | DAG1;    |
| rs62324212 | 4q27    | IL21;    |
| rs7725052  | 5p13.1  | PTGER4;  |
| rs7731626  | 5q11.2  | ANKRD55; |
| rs11741255 | 5q31.1  | IL5;     |
| rs755374   | 5q33.3  | IL12B;   |
| rs4246905  | 9q32    | TNFSF15; |
| rs11145763 | 9q34.3  | CARD9;   |
| rs706778   | 10p15.1 | IL2RA;   |
| rs10822050 | 10q21.2 | ZNF365;  |
| rs1250563  | 10q22.3 | ZMIZ1;   |
| rs1332099  | 10q24.2 | NKX2-3;  |
| rs17885785 | 11p15.5 | INS;     |
| rs17466626 | 12q12   | LRRK2;   |
| rs1689510  | 12q13.2 | SUOX;    |
| rs72743477 | 15q22.33| SMAD3;   |

| rs12598357 | 16p11.2 | SBK1; |
| rs117372389 | 16q12.1 | NOD2; and |
| rs2836882 | 21q22.2 | PSMG1. |

In some embodiments, two or more agents are administered to the patient. In some embodiments, the disease is JIA and said drug target is ANKRD30A. In some embodiments, the step of detecting the presence of said genetic alteration further comprises the step of analyzing a polynucleotide sample to determine the presence of said genetic alteration by performing a process selected from the group consisting of detection of specific hybridization, measurement of allele size, restriction fragment length polymorphism analysis, allele-specific hybridization analysis, single base primer extension reaction, and sequencing of an amplified polynucleotide. In some embodiments, the genotype sequence information is obtained from DNA and in some it is obtained from RNA.

Another exemplary method for treating one or more AID, such as one or more pAID, in a patient comprises obtaining genotype sequence information from a biological sample obtained from a patient, detecting the presence of at least one AID associated single nucleotide polymorphism (SNP) in a chromosomal region and associated gene selected from rs2066363 on1p31.1 in LPHN2 wherein said AID is selected from CVID and JIA, rs7660520 on 4q35.1 in TNM3; wherein said AID is selected from THY, AS, CEL, SLE, CVID and JIA; rs7100025 on 10p11.21 in ANKRD30A wherein said AID is JIA, rs77150043 on 16q12.1 in ADCY7 wherein said AID is PS and CD, rs2807264 on Xq26.3 in CD40LG; wherein said AID is CEL, UC and CD wherein detection of said one or more SNP is correlated with an altered risk for developing one or more pAID relative to control patients lacking said SNP. The method may further entail treating patients having an altered propensity for AID with one or more pharmaceutical agents listed in Table 11 or Table 12, which are known to target the indicated AID associated gene(s), thereby reducing symptoms or inhibiting development of said one or more AID. The method can further comprise detection of rs11580078 on 1p31.3 in IL23R, rs6679677 on 1p13.2 in PTPN22, rs36001488 on 2q37.1 in ATG16L1, rs4625 on 3p21.31 in DAG1, rs62324212 on 4q27 in IL21, rs7725052 on 5p13.1 in PTGER4, rs7731626 on 5q11.2 in ANKRD55, rs11741255 on 5q31.1 in IL5, rs755374 on 5q33.3 in IL12B, rs4246905 on 9q32 in TNFSF15, rs11145763 on 9q34.3 in CARD9, rs706778 on 10p15.1 in IL2RA, rs10822050 on 10q21.2 in ZNF365, rs1250563 on 10q22.3 in ZMIZ1, rs1332099 on 10q24.2 in NKX2-3, rs17885785 on 11p15.5 in INS, rs17466626 on 12q12 in LRRK2, rs1689510 on 12q13.2 in SUOX, rs72743477 on 15q22.33 in SMAD3, rs12598357 on 16p11.2 in SBK1, rs117372389 on 16q12.1 in NOD2; and rs2836882 on 21q22.2 in PSMG1, and treating said patient with one or more pharmaceutical agents modulating the activity of the AID associated gene. SNP-containing nucleic acids listed in Table 1, Supplementary Table 1c, or Table 11 may also be detected and patients harboring such SNPs treated with the indicated agents. The SNP containing nucleic acids of the invention may be detected in a variety of different ways including, without limitation, detection via specific hybridization, measurement of allele size, restriction fragment length polymorphism analysis, allele-specific hybridization analysis, single base primer extension reaction, and sequencing of an amplified polynucleotide. In certain embodiments of the invention, the genotype information is provided on a solid support matrix, such as on a chip or otherwise in silico. In any such embodiments, the patient may be a pediatric or an adult patient.

In yet another aspect of the disclosure, a method for identifying agents that alter immune signaling and aberrant autoimmune cellular phenotypes is provided. An exemplary method comprises providing cells expressing at least one SNP containing nucleic acid associated with AID and set forth in Table 1, Supplementary Table 1c, and Table 11, providing cells which express the cognate wild type sequences corresponding to the SNP containing nucleic acid, contacting the cells above with a test agent and analyzing whether said agent alters immune signaling and or aberrant autoimmune phenotypes of cells of step a) relative to those of step b), thereby identifying agents which modulate autoimmune function of proteins encoded by AID associated SNP containing nucleic acids. For example, the present disclosure also comprises methods for identifying an agent that alters immune signaling and aberrant autoimmune phenotypes, comprising: a) providing cells expressing at least one nucleic acid comprising at least one genetic alteration as claimed in any one of the preceding claims; b) providing cells which express the cognate wild type sequences corresponding to the genetic alteration of a); c) contacting the cells of a) and b) with a test agent; and d) analyzing whether said agent alters immune signaling and or aberrant autoimmune phenotypes of cells of step a) relative to those of step b). Host cells, vectors and kits for practicing the methods disclosed herein are also within the scope of the present invention.

BRIEF DESCRIPTION OF THE DRAWINGS

FIG. 1A: The ten pediatric autoimmune diseases studied. Autoimmune Thyroiditis (THY), Ankylosing Spondylitis (AS), Psoriasis (PS), Celiac Disease (CEL), Systemic Lupus Erythematosus (SLE), Type-1-Diabetes (T1D), Juvenile Idiopathic Arthritis (JIA), Common Variable Immunodeficiency (CVID), Ulcerative colitis (UC) and Crohn's Disease (CD). FIG. 1B: Top pAID association signals identified by performing an inverse chi-square meta-analysis. The top 27 loci (where at least one "lead" SNP reached GWS: $P_{META}<5\times10^8$) were annotated with the candidate gene name (HGNC ID). FIG. 1C: Novel and established pAID association loci: (Top Left) rs706778 (chr10p15.1) is a known DNAse I peak, an intronic SNP in IL2RA, and associated with THY, AS, PS, CEL, T1D, and JIA. (Top Right) rs755374 (chr5q33.3) is an intergenic SNP upstream of IL12B and associated with AS, CEL, UC and CD, (Bottom Left) rs2807264 (chrXq26.3) mapping near CD40LG is associated with CEL, UC, and CD, and chr15q22.33 (rs72743477), also mapping to an intronic position in SMAD3, is associated with UC, CD, and AS. (Bottom Right). SNPs are shaded based on their pairwise LD ($r^2$) with respect to the most strongly associated "lead" SNP in the locus. Associated pAIDs are indicated at the upper left. FIG. 1D: "Pleiotropic" candidate genes have pleiotropic effect size and direction across pAIDs. While a few "pleiotropic" SNPs have consistent effect directions across diseases (IL21), for many loci (e.g. PTPN22 and CLEC16A), the candidate SNP may have variable effect directions across the diseases. The radii of the wedges correspond to the absolute value of the Z-scores (beta/se) for each pAID while the shading indicates whether the SNP is protective (grey-shaded) or risk-associated (unshaded) for each disease. FIG. 1E: Genetically-inferred ancestry estimates of included cohorts based on principal components analysis (PCA). PCA results from genome wide SNP genotypes using overlapping SNPs from the genotyped study cohort and from the HapMap 3 reference panel dataset (left, center) or from the former alone (right) along the top two principal components. FIG. 1F: Circle plot of results from the pooled chi-square meta-analysis across the genome. From outside to inside: Chromosome number; CNV hotspots on chromosome; significant trait/disease-associated SNPs (TASs), SNP Density with different shading to distinguish each chromosome; dbSNP SNP density; 1KGP; HapMap; OMIM gene distribution; Variants distribution (DGV); Variants annotated from the genetic associations database (GAD). See the Internet site: "jjwanglab" dot "org" back-slash "gwasrap" for the details of the annotation methods. FIG. 1G: Distribution of pAID associated SNPs by effect size and allele frequency. Distribution of the 27 or 46 GWS or GWM lead SNPs effect sizes based on how many diseases were identified as associated with each SNP based on the results of the model search (left). The top 46 GWM SNPs are grouped by the number of associated pAIDs and distributed by the magnitude of the expected effect size obtained from logistic regression analysis using the disease combination identified by the subtype model search. FIG. 1H: Transcript Consequences for the 27 GWS lead SNPs reported by Ensemble Variant Effect Predictor. For each locus, only the top SNP reaching the most significant P-value was used to avoid redundancy in percentage calculations. FIG. 1I: Distribution and enrichment of experimental and predicted annotations for the top 27 GWS SNPs. Number of SNPs (or LD proxies) out of the 27 SNPs for which annotations were curated, along with the enrichment P-values based on permutation testing of simulated SNP-sets drawn from the 1KGP-RP. The annotation frequencies were used to calculate the relative enrichment of pAID SNPs as compared to 10,000 random 100 SNP-sets drawn from the genome in each annotation category as shown by the histogram.

FIG. 2A: Disease-specific Z-scores (beta/SE) for each SNP identified as having opposite effect directions across the ten pAIDs and as detailed in (FIG. 2A). Graphical markers (with different shapes for each disease) denote diseases where the indicated SNP has an opposite effect as compared to the group of pAID identified based as sharing the lead association based on results of the model search (Black Diamond). FIG. 2B: Clustering of pAIDs across the lead loci based on disease-specific effect sizes. Agglomerative hierarchical clustering across ten pAIDs based on normalized directional z-scores (beta/standard error) resulting from logistic regression analysis in each disease for the 27 lead loci based on those disease combinations identified by the model search analysis as that which produced the strongest association test statistic. FIGS. 2C-1 and 2C-2: QQ plots of summary-level results obtained from the ten disease-specific case-control pAID GWAS using the shared controls either with or without the SNPs across the extended MHC (FIG. 2C-1) or the pooled inverse chi-square meta-analysis. Extended MHC SNPs were included in these FIG. 2C-1 and excluded in FIG. 2C-2.

FIGS. 3A-3E. Integrated annotation of pAID association loci using existing predictive and experimental datasets. FIG. 3A: Biological, functional and literature annotations for the 27 loci reaching GWS on meta-analysis. Loci (identified by the lead SNPs and candidate gene names) are organized by column, where the shaded rug denotes the associated pAIDs, the functional annotations are found at the top of the table and the shaded bar at the bottom illustrates meta-analysis $P_{meta}$-value. For each locus, the lead SNP and proxy SNPs ($r^2>0.8$) are included in the annotation protocol; see Methods for details. Abbreviations: cpg: CpG islands; dgv: copy number variable regions; dnase: DNAse hypersensitivity I sites; eqtl: expression quantitative trail loci; gad: known genetic associations; gerp: conserved positions; mir: miRNAs; sift: functional mutations in SIFT; tfbs: transcription factor binding sites. FIG. 3B: Distribution and enrichment of experimental and predicted annotations for the top 27 GWS SNPs. The annotation frequencies were used to calculate the relative enrichment of pAID SNPs (black bar) as compared to 10,000 random 100 SNP-sets drawn from the genome in each annotation category as shown by the histogram. FIGS. 3C and 3D: Disease-specific GWAS results across the extended MHC for T1D and JIA. Summary-level association results from the disease-specific, case-control GWAS showing that the top signals obtained across markers mapping to the extended MHC analysis as observed for T1D (a) and JIA (b). The shaded scale is based on the p-values (most significant: dark grey at top to least significant: white). FIG. 3E: Association of Top MHC region signal from each pAID with the other pAIDs. P-values from each of the ten pAIDs are tabulated at the 10 SNPs that were identified as being the lead signals for each respective pAID (as annotated in the first column).

FIGS. 4A-4D. Tissue-Specific Gene Set Enrichment Analysis (TGSEA) identifies autoimmune-associated gene expression patterns across immune cells and tissues using pediatric and adult autoimmune datasets. FIG. 4A: Expression enrichment of autoimmune-associated genes across human tissues. Distribution of TGSEA enrichment scores (ES) values across 126 tissues for pAID-associated genes (Center) either with (Circles) or without (Triangles) the extended MHC (for clarity, also labeled in the plot with a (+) or (−), respectively). Results for the pAID gene set is compared to those obtained for known genes associated with Crohn's Disease (Left) and Schizophrenia (Right). Tissues/cell types are classified as immune or non-immune and ranked left to right in each panel based on the magnitude of the ES test statistic. FIG. 4B: Enrichment of pAID-associated gene expression across diverse murine immune cell types. Distribution of pAID-associated gene ES values across murine immune cell types either including (darker shaded peak located between 5 and 10) or excluding the genes within the MHC (lighter shaded peak located between about 4 and 6); results compared to genes associated with Crohn's Disease 'CD' (flatter peak between about 4 and 12), Schizophrenia 'Schizo' (light shaded sharp, high peak at about 2-3), LDL cholesterol 'LDL' (medium shaded sharp, high peak between 0 and 2), or Body Mass Index 'BMI' (smaller peak overlapping with the Schizo and LDL peaks located at about 2-3) abstracted from the NHGRI GWAS Catalog. FIG. 4C: Hierarchical clustering of based on expression of "pleiotropic" candidate gene associated with three or more autoimmune diseases across the murine immune cells. Boxes denote gene clusters enriched for specific disease associations discussed in the text. FIG. 4D: Functional, regulatory, conserved and literature-reported annotations for the 46 GWM or GWS lead SNPs reaching $P_{META}<1\times10^{-6}$. For each SNP, the shading of the associated pAIDs and the shaded bar at the bottom illustrates the strength of the association with the specific disease combination ($P_{META}$-value). The right side of the figure corresponds to the pAIDs identified as being associated with each lead SNP based on model search. Abbreviations: cpg: CPG islands; dgv: copy number variable regions; dnase: DNAse hypersensitivity I sites; eqtl: expression quantitative trail loci; gad: known genetic associations; gerp: conserved positions; mir: miRNAs; sift: functional mutations in SIFT; tfbs: transcription factor binding sites.

FIG. 5A: Quantification of pAID genetic sharing by genome-wide pairwise sharing test including SNPs within the extended MHC. Correlation plot of the pairwise pAID GPS test; the shading intensity and the size of the circle are proportional to the strength of the correlation as the negative base ten logarithms of the GPS test P-values.

FIG. 5B: Quantification of autoimmune disease genetic sharing by locus-specific pairwise sharing. Undirected weighted network (UWN) graph depicting results from the LPS test. Edge size represents the magnitude of the LPS test statistic; labeled nodes for each of the 17 autoimmune diseases are positioned based on a force-directed layout. Edges shown represent significant pairs after Bonferroni adjustment ($P_{adj}<0.05$). FIG. 5C: Protein-Protein Interaction network analysis of the top pAID associated protein candidates in STRING; Action view of protein interactions observed across the top 46 GWM ($P<1\times10^{-6}$) signals, of which 44 were mappable to corresponding proteins. Views are generated based on results for known and predicted protein interaction produced by STRING DB *Homo sapiens* database. The plots shown are results of the "action" view where the molecular actions (stimulatory, repressive or binding) are illustrated by the arrows. FIG. 5D: pAID associated genes are enriched in human immune tissues (KS test). Distribution of TGSEA enrichment scores (ES) values across 126 tissues derived from 1-sided Kolmogorov-Smirnov (KS) test statistic for pAID-associated genes (Center) with (Circles) and without (Triangles) the extended MHC 'extended MHC'. Known Crohn's Disease (Left) and Schizophrenia (Right) genes from the NHGRI GWAS Catalog are included as reference profiles. Tissues/cell types are classified as immune or non-immune and ranked left to right in each panel based on the magnitude of the KS test statistic. FIG. 5E: Differential enrichment of pAID-associated gene transcripts across immune cells based on cell lineage and developmental stage. Distribution of ES values for pAID-associated genes or adult/general autoimmune disease associated genes (compared to the remaining transcripts in the dataset) examined across all ImmGen cell types when classified by cell lineage and developmental stage, either including (Left) or excluding the extended MHC region (Right). Genes from adult cohorts were obtained from previously report association genes as noted in the Immunochip consortium database (available: immunobase "dot" org).

FIG. 6A: Protein-Protein Interaction network analysis in STRING. Evidence view of protein interactions observed for the (left) 27 ($P<1\times10^{-8}$) GWS loci, (center) 46 GWM ($P<1\times10^{-6}$) signals and (right) the interacting proteins in the JAK2 signaling cascade identified by the pAID meta-analysis using the PPI analysis module in webgestalt. Views are generated based on results for known and predicted protein-protein interactions identified using the STRING DB *homo sapiens* database. Plots show results of the "evidence" view such that each line demonstrates one source of PPI data. FIG. 6B: Protein-Protein Interaction network analysis in DAPPLE. Interactions identified using the protein network interaction tool Dapple. The input seeds are the 46 candidate GWM loci (inclusive of 200 kilobases up- and downstream of the lead SNPs). Seed scores Pdapple were used to color the protein nodes in the network plot. FIG. 6C: Biological pathways enriched for pAID-associated genes. Most significantly enriched pathways are identified. Input gene list from the GBAT was used to identify candidate biological pathways or biological processes important in pAIDs; pathways were manually annotated such that corresponding pathways that were named slightly differently across the respective databases could be directly compared and meta-analyzed. Each data point represents a test statistic (P- or q-value) obtained from DAVID (FDR, white circles), IPA (BH, black squares) or GSEA (BH, black circles) with annotation databases for a given "shared" pathway (ranked by their overall Fisher meta-analysis P-values on the x-axis). The area plot is bound by the Fisher's meta-analysis–log 10 (P-value) on the y-axis. The common pathways (found in all 3 databases) are annotated at top.

FIGS. 7A-7C. FIG. 7A: Top nine lead SNPs at which the direction of effect (DoE) observed across one or more pAIDs oppose that for the disease combination identified by model search. Abbreviations: SNP: rsID dbSNP 138; GENE: Candidate Gene Name (HGNC); REGION: Cytogenetic band; A1: alternative allele used in the logistic regression; pAIDs model: pAID(s) associated with this SNP based on the model search; BETA (SE) model: effect size and standard error of the SNP based on logistic regression combining cases from the diseases identified on the model search; pAID: the disease showing the opposite effect direction than that of the group of diseases identified by the subtype search; BETA (SE): z-score or effect size and standard error of the SNP for the disease found to have an opposite effect direction; P-value: disease-specific GWAS P-value. FIG. 7B: Quantification of pAID genetic sharing by genome-wide pairwise sharing test including (top) or excluding (bottom) the SNPs within the extended MHC. Correlation plot of the pairwise pAID GPS test; the shading intensity and the size of the circle are proportional to the strength of the correlation as the negative base ten logarithms of the GPS test P-values. FIG. 7C: Undirected weighted network (UWN) graph depicting results from the LPS test. Edge size represents the magnitude of the LPS test statistic; labeled nodes for each of the 17 autoimmune diseases are positioned based on a force-directed layout (Methods). Edges illustrating pairwise relationships reaching at least nominal significance based on the LPS test ($P<0.05$) are shown.

Figure 1A:
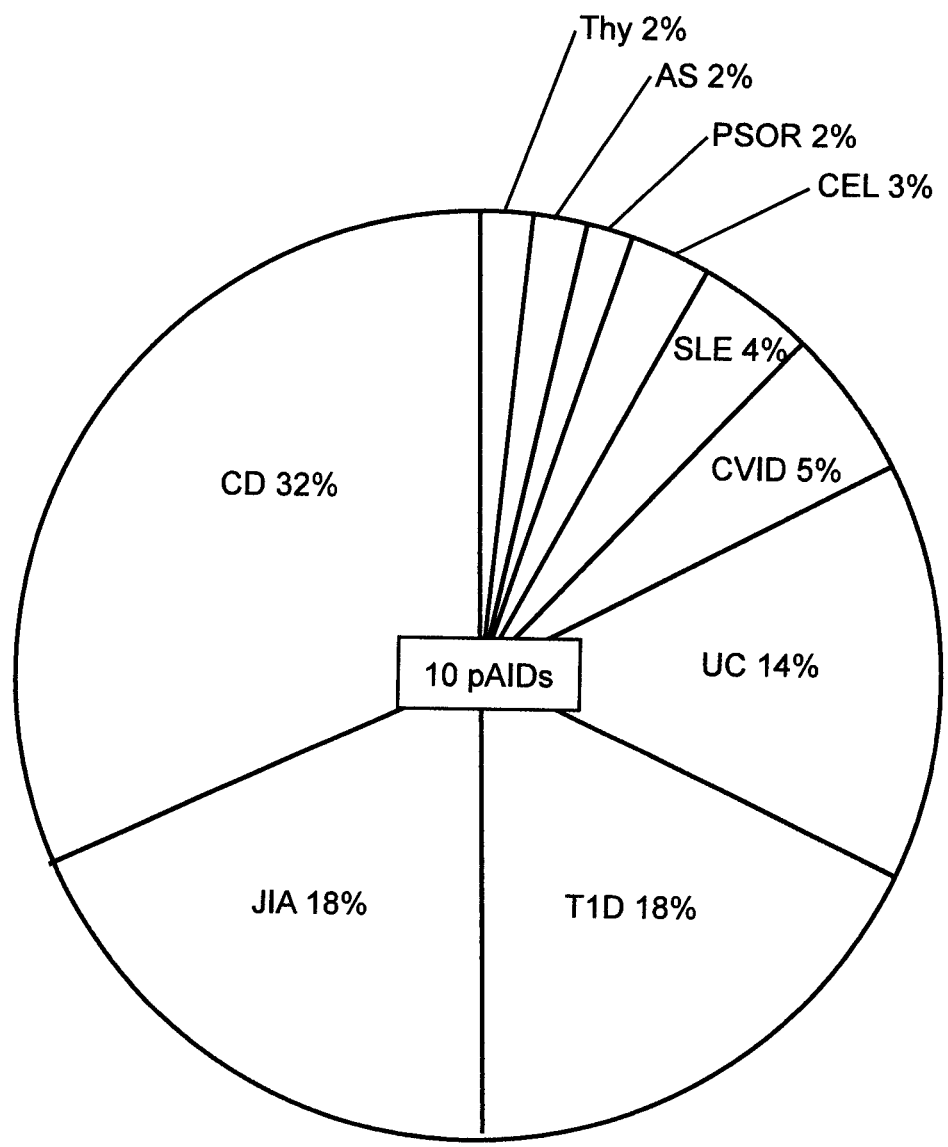
FIGS. 1A-1I. The ten pAID case cohorts and top pAID association loci identified.
Figure 1B:
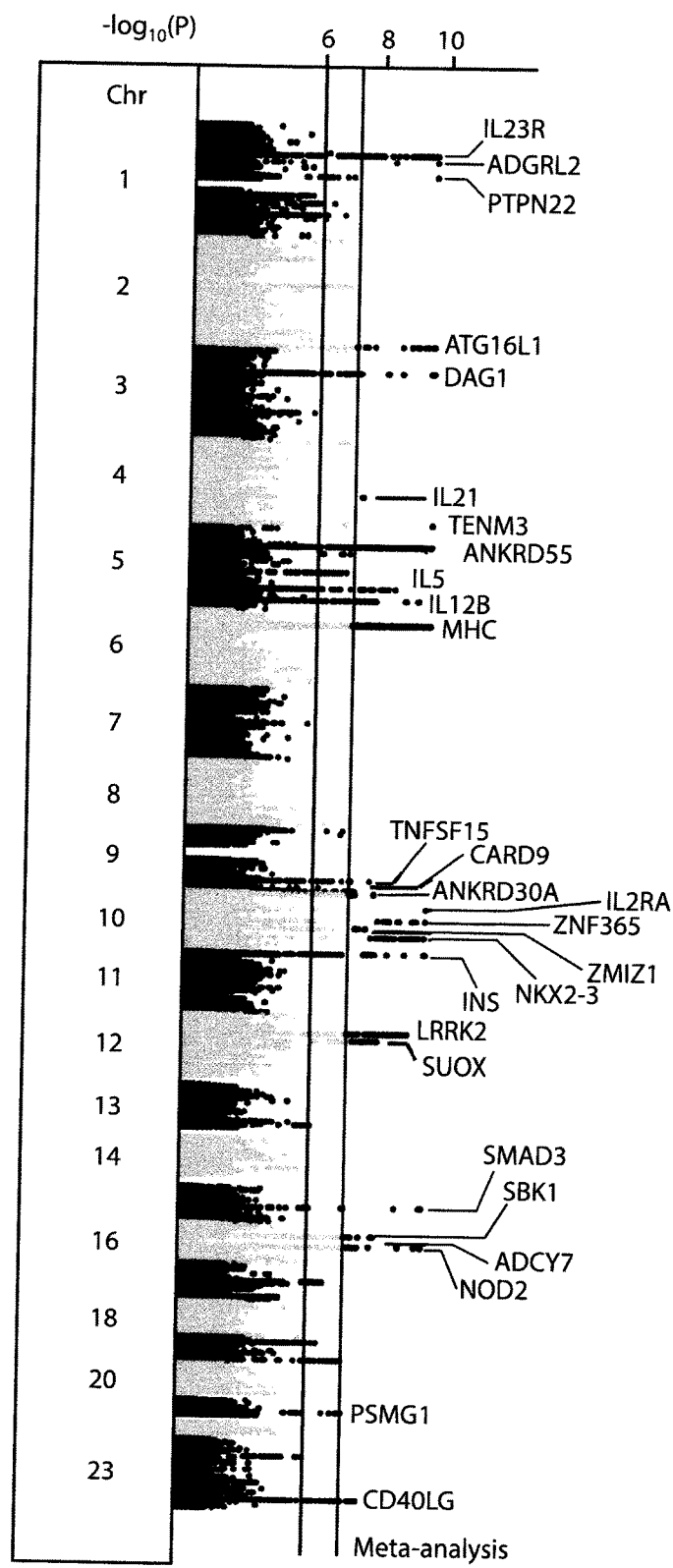

As noted earlier, color versions of certain figures included herein have also been published in Y. R. Li et al, *Nature Medicine* Aug. 24, 2015, online publication doi: 10.1038 "backslash" nm.3933, and in the supplemental materials for that publication, and those figures are incorporated by reference herein.

DETAILED DESCRIPTION OF THE INVENTION

Genome wide association studies (GWAS) have identified multiple susceptibility genes, including shared associations across clinically-distinct disease groups and autoimmune diseases. The present inventors performed an inverse chi-square meta-analysis across ten pediatric age-of-onset autoimmune diseases (pAIDs) in a case-control study including over 6,035 cases and 10,718 shared population-based controls. Twenty-seven genome-wide significant loci associated with one or more pAIDs were identified, mapping to in silico-replicated autoimmune-associated genes (including IL2RA) and novel, candidate loci with established immunoregulatory functions including LPHN2, TNM3, ANKRD30A, ADCY7, and CD40LG. The pAID-associated SNPs are functionally-enriched for DNAse-hypersensitivity sites, expression quantitative trait loci, micro-RNA binding sites and coding variants. Biologically-correlated, pAID-associated candidate gene-sets were also identified based on immune cell expression profiling, and show evidence of genetic sharing. Network and protein-interaction analyses demonstrated converging roles for the T helper type 1 ($T_H1$)/$T_H2$/$T_H17$, JAK-STAT, interferon and interleukin signaling pathways in multiple autoimmune diseases.

Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

An "Auto Immune Disease" is abbreviated AID herein and includes but is not limited to one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH). A "Pediatric Auto Immune Disease" is abbreviated pAID herein and includes but is not limited to each of the above diseases in a "pediatric" subject, which is defined herein as a subject under the age of 18. In contrast, an "adult" subject is 18 or older.

A "single nucleotide variation (SNV)," also interchangeably referred to as a "single nucleotide polymorphism (SNP)" herein, refers to a change in which a single base in the DNA differs from the usual base at that position. These single base changes are often called SNPs or "snips." Millions of SNP's have been cataloged in the human genome. Some SNPs such as that which causes sickle cell are responsible for disease. Other SNPs are normal variations in the genome.

"AID-associated SNP or AID-associated specific marker" or "AID-associated marker" is a SNP or marker that is associated with an increased risk of developing an AID and that is found at a lower frequency or is not generally found in normal subjects who do not have the AID. Such markers may include but are not limited to nucleic acids, proteins encoded thereby, or other small molecules. In some cases, the SNP or marker is an AID-associated SNP or AID-associated marker.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence. The term "genetic alteration" may also be applied to a protein and encompasses without limitation amino acid substitutions, insertions, and deletions. An "allelic variation" refers to the presence of an allele that differs from a wild-type or reference allele, i.e. one allele that has a genetic alteration in comparison to a wild-type or reference allele.

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

The term "solid matrix" or "solid support matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. In some embodiments, the matrix may be in the form of a chip.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation that may or may not be associated with pAID. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence is in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process includes the construction of a cDNA library from mRNA and isolation of distinct cDNA clones and yields an approximately $10^6$ fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence that hybridizes to any pAID specific marker nucleic acid, but does not hybridize to other nucleotides. Also polynucleotide that "specifically hybridizes" may hybridize only to an airway, colon, immune cell, dendritic, or other tissue specific marker, such as an pAID-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5\text{"}C + 16.6 \text{ Log }[Na+] + 0.41(\% \, G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57"C. The $T_m$ of a DNA duplex decreases by 1-1.5"C with every 1% decrease in homology. Thus, targets with greater than about 75% sequence identity would be observed using a hybridization temperature of 42"C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer or more nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNAs of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting mRNAs, for example, may be between 15-35 nucleotides in length, and more typically about 21 nucleotides in length.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together. When cloning a genetic region containing a duplication or a deletion, the skilled artisan is well aware that flanking sequences upstream and downstream of the affected region of a suitable length would be employed in the cloning process. Such vectors would have utility, for example in cell lines for studying the effects such alterations have on the encoded proteins.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the pAID specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the pAID specific marker encoding nucleic acid. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, which is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism" and "transgenic organism" refer to organisms that have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) that have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

A "patient" or "subject" as referred to herein may be either an adult (18 or older) or a pediatric subject (under 18). These two terms are generally used interchangeably herein. The patient or subject may be an individual who has been diagnosed with one or more AID, is undergoing AID treatment, or who is seeking a diagnosis of a medical condition due to symptoms of illness, as well as an individual who has not been diagnosed with an AID. For example, in cases where methods are performed to determine susceptibility to developing one or more AID, the subject being tested may be one who does not presently show symptoms of any AID, such as a healthy subject.

"Sample" or "patient sample" or "biological sample" generally refers to a sample that may be tested for a particular molecule, such as an AID specific marker molecule, such as a marker shown in the tables provided below. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule that exhibits the capacity to modulate the activity of the SNP containing nucleic acids described herein or their encoded proteins. Agents are evaluated for potential biological activity by inclusion in screening assays described herein below.

The term "diagnose" and similar terms such as "diagnosis" or "diagnosing" used when referring to the methods herein encompasses methods, for example, designed to assist in the diagnosis of an AID in conjunction with clinical observations, analysis of symptoms, or other tests for instance, or designed to confirm a diagnosis made based on such other factors or tests. For example, methods herein may be used in conjunction with analysis of symptoms and other tests to provide data that may help a physician to determine if a subject suffers from an AID and if so, which AID or combination AIDs the subject suffers from.

Methods for determining a susceptibility toward developing one or more AIDs are also encompassed herein. In that context, "susceptibility" toward developing an AID means, for example, that the subject is more likely to develop an AID than the population at large. For instance, a genetic alteration as described herein may be a risk factor toward developing an AID at some point in the subject's future.

"Treatment," as used herein, covers any administration or application of a therapeutic for a disease (also referred to herein as a "disorder" or a "condition") in a mammal, including a human, and includes inhibiting the disease or progression of the disease, inhibiting or slowing the disease or its progression, arresting its development, partially or fully relieving the disease, partially or fully relieving one or more symptoms of a disease, or restoring or repairing a lost, missing, or defective function; or stimulating an inefficient process.

The term "effective amount" or "therapeutically effective amount" refers to an amount of a drug effective for treatment of a disease or disorder in a subject, such as to partially or fully relieve one or more symptoms. In some embodiments, an effective amount refers to an amount effective, at dosages and for periods of time necessary, to achieve the desired therapeutic or prophylactic result.

An "interaction network" associated with a gene, such as a gene harboring a genetic alteration herein, means that gene as well as genes whose protein products either directly or indirectly bind to, activate, or deactivate the protein product of the gene in question. For example, the network includes genes coding for proteins that bind to the protein product of the gene in question. The network also includes genes coding for proteins that regulate expression, processing, secretion, or biological function of the protein product of the gene in question but that do not directly bind to that protein product.

Methods of Using AID-Associated SNVs for Diagnosing and Treating an AID

Methods of Detecting Genetic Alterations

In some embodiments a genetic alteration in one or more genes may be detected at the nucleic acid level. Any biological sample may be used, including, but not limited to, blood, urine, serum, gastric lavage, CNS fluid, any type of cell (such as brain cells, white blood cells, mononuclear cells) or body tissue. Any biological source material whereby DNA can be extracted may be used. Samples may be freshly collected, or samples may have been previously collected for any use/purpose and stored until the time of testing for genetic alterations. DNA that was previously purified for a different purpose may also be used.

Standard molecular biology methodologies such as quantitative polymerase chain reaction (PCR), droplet PCR, and TaqMan® probes (i.e., hydrolysis probes designed to increase the specificity of quantitative PCR), for example, coupled with sequencing, can be used to assess genetic alterations in a gene. Fluorescent in situ hybridization (FISH) probes may also be used to evaluate genetic alterations.

Various methods for determining genetic alterations are known, including the following below.

Single Nucleotide Variation (SNV)/Single Nucleotide Polymorphism (SNP) Genotyping Determining whether a patient has a genetic alteration in a gene may be done by SNV/SNP Genotyping, using a SNV/SNP genotyping array such as those commercially available from Illumina or Affymetrix. As noted above, a "single nucleotide variation (SNV)," also interchangeably referred to as a "single nucleotide polymorphism (SNP)" herein, refers to a change in which a single base in the DNA differs from the usual base at that position.

In SNV genotyping, SNVs can be determined by hybridizing complementary DNA probes to the SNV site. A wide range of platforms can be used with SNV genotyping tools to accommodate varying sample throughputs, multiplexing capabilities, and chemistries. In high-density SNV arrays, hundreds of thousands of probes are arrayed on a small chip, such that many SNVs can be interrogated simultaneously when target DNA is processed on the chip. By determining the amount of hybridization of target DNA in a sample to a probe (or redundant probes) on the array, specific SNV alleles can be determined. Use of arrays for SNV genotyping allows the large-scale interrogation of SNVs.

When analyzing CNVs, after SNVs have been analyzed, a computer program must be used to manipulate the SNV data to arrive at CNV data. PennCNV or a similar program can then be used to detect signal patterns across the genome and identify consecutive genetic markers with copy number changes. (See Wang K. and Bucan M. (June 2008) *Cold Spring Harb Protoc* Vol. 3(6); doi10: 1101/pdb.top46). PennCNV allows for kilobase-resolution detection of CNVs. (See Wang K, et al. (November 2007) *Genome Res.* 17(11): 1665-74).

In CNV analysis, the SNV genotyping data is compared with the behavior of normal diploid DNA. The software uses SNV genotyping data to determine the signal intensity data and SNV allelic ratio distribution and then uses these data to identify deviations from the normal diploid condition of DNA, indicative of the presence of a CNV. This is done in part by using the log R Ratio (LRR), which is a normalized measure of the total signal intensity for the two alleles of the SNV (Wang 2008). If the software detects regions of contiguous SNVs with intensity (LRR) trending below 0, this indicates a CNV deletion. If the software instead detects regions of contiguous SNVs with intensity (LRR) trending above 0, this indicates a CNV duplication. If no change in LRR is observed compared to the behavior of diploid DNA, the sequence is in the normal diploid state with no CNV present. The software also uses B allele frequency (BAF), a normalized measure of the allelic intensity ratio of two alleles that changes when alleles are lost or gained as with a CNV deletion or duplication. For example, a CNV deletion is indicated by both a decrease in LRR values and a lack of heterozygotes in BAF values. In contrast, a CNV duplication is indicated by both an increase in LRR values and a splitting of the heterozygous genotype BAF clusters into two distinct clusters. The software automates the calculation of LRR and BAF to detect CNV deletions and duplications for whole-genome SNV data. The simultaneous analysis of intensity and genotype data accurately defines the normal diploid state and determines CNVs.

Array platforms such as those from Illumina, Affymetrix, and Agilent may be used in SNV Genotyping. Custom arrays may also be designed and used based on the data described herein.

Comparative Genomic Hybridization

Comparative genomic hybridization (CGH) is another method that may be used to evaluate genetic alterations. CGH is a molecular cytogenetic method for analyzing genetic alterations in comparison to a reference sample using competitive fluorescence in situ hybridization (FISH). DNA is isolated from a patient and a reference source and independently labeled with fluorescent molecules (i.e., fluorophores) after denaturation of the DNA. Hybridization of the fluorophores to the resultant samples is compared along the length of each chromosome to identify chromosomal differences between the two sources. A mismatch of colors indicates a gain or loss of material in the test sample in a specific region, while a match of the colors indicates no difference in genetic alterations such as copy number between the test and reference samples at a particular region.

Sequencing Methods

Whole genome sequencing, whole exome sequencing, or targeted sequencing may also be used to analyze genetic alterations in multiple genes. Whole genome sequencing (also known as full genome sequencing, complete genome sequencing, or entire genome sequencing) involves sequencing of the full genome of a species, including genes that do or do not code for proteins. Whole exome sequencing, in contrast, is sequencing of only the protein-coding genes in the genome (approximately 1% of the genome). Targeted sequencing involves sequencing of only selected parts of the genome.

A wide range of techniques would be known to those skilled in the art to perform whole genome, whole exome, or targeted sequencing with DNA purified from a subject. Similar techniques could be used for different types of sequencing. Techniques used for whole genome sequencing include nanopore technology, fluorophore technology, DNA nanoball technology, and pyrosequencing (i.e., sequencing by synthesis). In particular, next-generation sequencing (NGS) involves sequencing of millions of small fragments of DNA in parallel followed by use of bioinformatics analyses to piece together sequencing data from the fragments.

As whole exome sequencing does not need to sequence as large an amount of DNA as whole genome sequencing, a wider range of techniques are may be used. Methods for whole exome sequencing include polymerase chain reaction methods, NGS methods, molecular inversion probes, hybrid capture using microarrays, in-solution capture, and classical Sanger sequencing. Targeted sequencing allows for providing sequence data for specific genes rather than whole genomes and can use any of the techniques used for other types of sequencing, including specialized microarrays containing materials for sequencing genes of interest. Proprietary methodologies, such as those from BioNano or OpGen, using genome mapping technology can also be used to evaluate genetic alterations.

AID-related SNV-containing nucleic acids, including but not limited to those listed in the Tables provided below may be used for a variety of purposes in accordance with the present invention. AID-associated SNV-containing DNA, RNA, or fragments thereof may be used as probes to detect the presence of and/or expression of AID specific markers. Methods in which AID specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting AID-associated SNVs or the proteins encoded thereby may be conducted on any type of biological sample, including but not limited to body fluids (including blood, urine, serum, gastric lavage), any type of cell (such as brain cells, white blood cells, mononuclear cells) or body tissue.

From the foregoing discussion, it can be seen that AID-associated SNV containing nucleic acids, vectors expressing the same, AID SNV containing marker proteins and anti-AID specific marker antibodies of the invention can be used to detect AID associated SNVs in body tissue, cells, or fluid, and alter AID SNV containing marker protein expression for purposes of assessing the genetic and protein interactions involved in the development of AID.

In most embodiments for screening for AID-associated SNVs, the AID-associated SNV containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify AID-associated SNV marker expression and accordingly, diagnose AID.

Associations of Particular Genetic Alterations with One or More AIDs

As described in the Examples, figures, and tables below, studies of the inventors on pediatric subjects identified 27 genome-wide significant (GWS) loci wherein genetic alterations are associated with presence of one or more pAID. In addition, there were 46 loci that reached at least genome-wide marginal significance (GWM) in associations with particular pAIDs. Thus, the present disclosure encompasses methods of identifying genetic alterations such as SNVs at these GWS and GWM loci, for example, to assist in determining appropriate treatments for AID patients with those genetic alterations or to diagnose one or more AIDs in patients, or to determine whether a subject is susceptible to developing one or more AIDs in the future.

For example, in some embodiments involving subjects with ankylosing spondylitis (AS), a method of detecting the presence of a genetic alteration, such as an SNV, is provided comprising obtaining a biological sample from an AS patient and detecting the presence of a genetic alteration in one or more of IL23R, TNM3, LRRK2, SBK1, IL2RA, ZMIZ1, IL21, or CARD9. (See Supplemental Table 1b.) Alternatively, in some embodiments a method is provided comprising obtaining a biological sample from a subject and detecting the presence of a genetic alteration in one or more of IL23R, TNM3, LRRK2, SBK1, IL2RA, ZMIZ1, IL21, or CARD9 in order to diagnose AS or determine if the subject has a propensity to develop AS. In some embodiments, genetic alterations in all of those genes are assessed. In some embodiments, one or more of those genes is not assessed. In some embodiments, genetic alterations in, for example, one or more of CRB1, GPR35, CYTL3, IL12B, 8q24.23, JAK2, FNBP1, or SMAD3 are also assessed. (See Table 2b.) In some embodiments, the detected genetic alteration is used to determine treatment options for the AS patient, for example, to administer a drug targeting a gene in the pathway of the altered gene. (See Tables 11 and 12 for agents targeting particular identified genes herein.) Thus, in some embodiments, the AS patient is administered a drug targeting the gene in which the genetic alteration is found. For example, the drug may target the pathway of that gene in order to influence the pathway in a way that compensates for the genetic alteration.

Similarly, in some embodiments involving subjects with psoriasis (PS), a method of detecting the presence of a genetic alteration, such as an SNV, is provided comprising obtaining a biological sample from a PS patient and detecting the presence of a genetic alteration in one or more of IL23R, PTPN22, TNM3, DAG1, ATG16L1, SUOX, SBK1, ADCY7, IL2RA, or ZMIZ1. (See Supplemental Table 1b.) Alternatively, in some embodiments a method is provided comprising obtaining a biological sample from a subject and detecting the presence of a genetic alteration in one or more of IL23R, PTPN22, TNM3, DAG1, ATG16L1, SUOX, SBK1, ADCY7, IL2RA, or ZMIZ1 in order to diagnose PS or determine if the subject has a propensity to develop PS. In some embodiments, genetic alterations in all of those genes are assessed. In some embodiments, one or more of those genes is not assessed. In some embodiments, genetic alterations in, for example, one or more of IL10, TSSC1, IL5, IL2RA, ADCY7, FUT2, and TNFRSF6B are also assessed. (See Table 2b.) In some embodiments, the detected genetic alteration is used to determine treatment options for the PS patient, for example, to administer a drug targeting a gene in the pathway of the altered gene. (See Tables 11 and 12 for agents targeting particular identified genes herein.) Thus, in some embodiments, the PS patient is administered a drug targeting the gene in which the genetic alteration is found.

In some embodiments involving subjects with celiac disease (CEL), a method of detecting the presence of a genetic alteration, such as an SNV, is provided comprising obtaining a biological sample from a CEL patient and detecting the presence of a genetic alteration in one or more of TNM3, DAG1, SBK1, IL2RA, C40LG, ZMIZ1, or IL21. (See Supplemental Table 1b.) Alternatively, in some embodiments a method is provided comprising obtaining a biological sample from a subject and detecting the presence of a genetic alteration in one or more of TNM3, DAG1, SBK1, IL2RA, C40LG, ZMIZ1, or IL21 in order to diagnose CEL or determine if the subject has a propensity to develop CEL. In some embodiments, genetic alterations in all of those genes are assessed. In some embodiments, one or more of those genes is not assessed. In some embodiments, genetic alterations in, for example, one or more of IL18R1, CYTL1, ERAP2, IL5, IL12B, 8q24.23, IKZF3, CD40LG, or RBMX are also assessed. (See Table 2b.) In some embodiments, the detected genetic alteration is used to determine treatment options for the CEL patient, for example, to administer a drug targeting a gene in the pathway of the altered gene. (See Tables 11 and 12 for agents targeting particular identified genes herein.) Thus, in some embodiments, the CEL patient is administered a drug targeting the gene in which the genetic alteration is found.

In some embodiments involving subjects with systemic lupus erythematosus (SLE), a method of detecting the presence of a genetic alteration, such as an SNV, is provided comprising obtaining a biological sample from an SLE patient and detecting the presence of a genetic alteration in one or both of PTPN22 or TNM3. (See Supplemental Table 1b.) Alternatively, in some embodiments a method is provided comprising obtaining a biological sample from a subject and detecting the presence of a genetic alteration in one or more of PTPN22 or TNM3 in order to diagnose SLE or determine if the subject has a propensity to develop SLE. In some embodiments, genetic alterations in all of those genes are assessed. In some embodiments, one or more of those genes is not assessed. In some embodiments, genetic alterations in, for example, one or more of IL10, TSSC1, GPR35, JAK2, ZNF365, TYK2, or TNFRSF6B are also assessed. (See Table 2b.) In some embodiments, the detected genetic alteration is used to determine treatment options for the SLE patient, for example, to administer a drug targeting a gene in the pathway of the altered gene. (See Tables 11 and 12 for agents targeting particular identified genes herein.) Thus, in some embodiments, the SLE patient is administered a drug targeting the gene in which the genetic alteration is found.

In some embodiments involving subjects with common variable immunodeficiency (CVID), a method of detecting the presence of a genetic alteration, such as an SNV, is provided comprising obtaining a biological sample from a CVID patient and detecting the presence of a genetic alteration in one or more of LPHN2, TNM3, or IL21. (See Supplemental Table 1b.) Alternatively, in some embodiments a method is provided comprising obtaining a biological sample from a subject and detecting the presence of a genetic alteration in one or more of LPHN2, TNM3, or IL21 in order to diagnose CVID or determine if the subject has a propensity to develop CVID. In some embodiments, genetic alterations in all of those genes are assessed. In some embodiments, one or more of those genes is not assessed. In some embodiments, genetic alterations in, for example, one or both of EFNB2 or IKZF3 are also assessed. (See Table 2b.) In some embodiments, the detected genetic alteration is used to determine treatment options for the CVID patient, for example, to administer a drug targeting a gene in the pathway of the altered gene. (See Tables 11 and 12 for agents targeting particular identified genes herein). Thus, in some embodiments, the CVID patient is administered a drug targeting the gene in which the genetic alteration is found.

In some embodiments involving subjects with ulcerative colitis (UC), a method of detecting the presence of a genetic alteration, such as an SNV, is provided comprising obtaining a biological sample from a UC patient and detecting the presence of a genetic alteration in one or more of IL23R, LPHN2, DAG1, PTGER4, SBK1, TNFSF15, CD40LG, IL21, CARD9, or PSMG1. (See Supplemental Table 1b.) Alternatively, in some embodiments a method is provided comprising obtaining a biological sample from a subject and detecting the presence of a genetic alteration in one or more of IL23R, LPHN2, DAG1, PTGER4, SBK1, TNFSF15, CD40LG, IL21, CARD9, or PSMG1 in order to diagnose UC or determine if the subject has a propensity to develop UC. In some embodiments, genetic alterations in all of those genes are assessed. In some embodiments, one or more of those genes is not assessed. In some embodiments, genetic alterations in, for example, one or more of IL10, TSSC1, IL18R1, GPR35, CYTL1, IL12B, JAK2, NKX2, SMAD3, ATXN2L, IKZF3, or TNFRSF6B are also assessed. (See Table 2b.) In some embodiments, the detected genetic alteration is used to determine treatment options for the UC patient, for example, to administer a drug targeting a gene in the pathway of the altered gene. (See Tables 11 and 12 for agents targeting particular identified genes herein.) Thus, in some embodiments, the UC patient is administered a drug targeting the gene in which the genetic alteration is found.

In some embodiments involving subjects with Type 1 diabetes (T1D), a method of detecting the presence of a genetic alteration, such as an SNV, is provided comprising obtaining a biological sample from a T1D patient and detecting the presence of a genetic alteration in one or more of PTPN22, INS, SUOX, IL2RA, or IL21. (See Supplemental Table 1b.) Alternatively, in some embodiments a method is provided comprising obtaining a biological sample from a subject and detecting the presence of a genetic alteration in one or more of PTPN22, INS, SUOX, IL2RA, or IL21 in order to diagnose T1D or determine if the subject has a propensity to develop T1D. In some embodiments, genetic alterations in all of those genes are assessed. In some embodiments, one or more of those genes is not assessed. In some embodiments, genetic alterations in, for example, one or more of CYTL1, 8q24.23, TYK2, or FUT2 are also assessed. (See Table 2b.) In some embodiments, the detected genetic alteration is used to determine treatment options for the T1D patient, for example, to administer a drug targeting a gene in the pathway of the altered gene. (See Tables 11 and 12 for agents targeting particular identified genes herein.) Thus, in some embodiments, the T1D patient is administered a drug targeting the gene in which the genetic alteration is found.

In some embodiments involving subjects with juvenile idiopathic arthritis (JIA), a method of detecting the presence of a genetic alteration, such as an SNV, is provided comprising obtaining a biological sample from a JIA patient and detecting the presence of a genetic alteration in one or more of LPHN2, PTPN22, TNM3, ANKRD30A, ANKRD55, IL2RA, CD40LG, or IL21. (See Supplemental Table 1b.) Alternatively, in some embodiments a method is provided comprising obtaining a biological sample from a subject and detecting the presence of a genetic alteration in one or more of LPHN2, PTPN22, TNM3, ANKRD30A, ANKRD55, IL2RA, CD40LG, or IL21 in order to diagnose J1A or determine if the subject has a propensity to develop JIA. In some embodiments, genetic alterations in all of those genes are assessed. In some embodiments, one or more of those genes is not assessed. In some embodiments, genetic alterations in, for example, one or more of CYTL1, ERAP2, 8q24.23, LURAP1L, FNBP1, EFNB2, IKZF3, TYK2, or RBMX are also assessed. (See Table 2b.) In some embodiments, the detected genetic alteration is used to determine treatment options for the JIA patient, for example, to administer a drug targeting a gene in the pathway of the altered gene. (See Tables 11 and 12 for agents targeting particular identified genes herein.) Thus, in some embodiments, the JIA patient is administered a drug targeting the gene in which the genetic alteration is found.

In some embodiments involving subjects with Crohn's disease (CD), a method of detecting the presence of a genetic alteration, such as an SNV, is provided comprising obtaining a biological sample from a CD patient and detecting the presence of a genetic alteration in one or more of IL23R, PTPN22, DAG1, ATG16L1, PTGER4, ANKRD55, LRRK2, SBK1, ADCY7, IL2RA, TNFSF15, CD40LG, ZMIZ1, IL21, CARD9, or PSMG1. (See Supplemental Table 1b.) Alternatively, in some embodiments a method is provided comprising obtaining a biological sample from a subject and detecting the presence of a genetic alteration in one or more of IL23R, PTPN22, DAG1, ATG16L1, PTGER4, ANKRD55, LRRK2, SBK1, ADCY7, IL2RA, TNFSF15, CD40LG, ZMIZ1, IL21, CARD9, or PSMG1 in order to diagnose CD or determine if the subject has a propensity to develop CD. In some embodiments, genetic alterations in all of those genes are assessed. In some embodiments, one or more of those genes is not assessed. In some embodiments, genetic alterations in, for example, one or more of CRB1, IL10, TSSC1, IL18R1, CYTL1, ERAP2, IL5, IL12B, 8q24.23, JAK2, FNBP1, ZNF365, NKX2, SMAD3, ATXN2L, NOD2, IKZF3, TYK2, FUT2, TNFRSF6B, or RBMX are also assessed. (See Table 2b.) In some embodiments, the detected genetic alteration is used to determine treatment options for the CD patient, for example, to administer a drug targeting a gene in the pathway of the altered gene. (See Tables 11 and 12 for agents targeting particular identified genes herein.) Thus, in some embodiments, the CD patient is administered a drug targeting the gene in which the genetic alteration is found.

In some embodiments involving subjects with alopecia areata (AA), a method of detecting the presence of a genetic alteration, such as an SNV, is provided comprising obtaining a biological sample from an AA patient and detecting the presence of a genetic alteration in one or both of IL2RA or IL21. (See Supplemental Table 1b.) Alternatively, in some embodiments a method is provided comprising obtaining a biological sample from a subject and detecting the presence of a genetic alteration in one or more of IL2RA or IL21 in order to diagnose AA or determine if the subject has a propensity to develop AA. In some embodiments, the detected genetic alteration is used to determine treatment options for the AA patient, for example, to administer a drug targeting a gene in the pathway of the altered gene. (See Tables 11 and 12 for agents targeting particular identified genes herein.) Thus, in some embodiments, the AA patient is administered a drug targeting the gene in which the genetic alteration is found.

In some embodiments involving subjects with multiple sclerosis (MS), a method of detecting the presence of a genetic alteration, such as an SNV, is provided comprising obtaining a biological sample from an MS patient and detecting the presence of a genetic alteration in one or more of PTGER4, ANKRD55, IL2RA, CD40LG, or ZMIZ1. (See Supplemental Table 1b.) Alternatively, in some embodiments a method is provided comprising obtaining a biological sample from a subject and detecting the presence of a genetic alteration in one or more of PTGER4, ANKRD55, IL2RA, CD40LG, or ZMIZ1 in order to diagnose MS or determine if the subject has a propensity to develop MS. In some embodiments, the detected genetic alteration is used to determine treatment options for the MS patient, for example, to administer a drug targeting a gene in the pathway of the altered gene. (See Tables 11 and 12 for agents targeting particular identified genes herein.) Thus, in some embodiments, the MS patient is administered a drug targeting the gene in which the genetic alteration is found.

In some embodiments involving subjects with primary sclerosing cholangitis (PSC), a method of detecting the presence of a genetic alteration, such as an SNV, is provided comprising obtaining a biological sample from a PSC patient and detecting the presence of a genetic alteration in one or both of IL2A or IL21. (See Supplemental Table 1b.) Alternatively, in some embodiments a method is provided comprising obtaining a biological sample from a subject and detecting the presence of a genetic alteration in one or more of IL2A or IL21 in order to diagnose PSC or determine if the subject has a propensity to develop PSC. In some embodiments, genetic alterations in all of those genes are assessed. In some embodiments, the detected genetic alteration is used to determine treatment options for the PSC patient, for example, to administer a drug targeting a gene in the pathway of the altered gene. (See Tables 11 and 12 for agents targeting particular identified genes herein.) Thus, in some embodiments, the PSC patient is administered a drug targeting the gene in which the genetic alteration is found.

In some embodiments involving subjects with rheumatoid arthritis (RA), a method of detecting the presence of a genetic alteration, such as an SNV, is provided comprising obtaining a biological sample from an RA patient and detecting the presence of a genetic alteration in one or more of PTPN22, ANKRD55, IL2RA, or IL21. (See Supplemental Table 1b.) Alternatively, in some embodiments a method is provided comprising obtaining a biological sample from a subject and detecting the presence of a genetic alteration in one or more of PTPN22, ANKRD55, IL2RA, or IL21 in order to diagnose RA or determine if the subject has a propensity to develop RA. In some embodiments, genetic alterations in all of those genes are assessed. In some embodiments, the detected genetic alteration is used to determine treatment options for the RA patient, for example, to administer a drug targeting a gene in the pathway of the altered gene. (See Tables 11 and 12 for agents targeting particular identified genes herein.) Thus, in some embodiments, the RA patient is administered a drug targeting the gene in which the genetic alteration is found.

In some embodiments involving subjects with vitiligo (VIT), a method of detecting the presence of a genetic alteration, such as an SNV, is provided comprising obtaining a biological sample from a VIT patient and detecting the presence of a genetic alteration in one or more of PTPN22 or IL2RA. (See Supplemental Table 1b.) Alternatively, in some embodiments a method is provided comprising obtaining a biological sample from a subject and detecting the presence of a genetic alteration in one or more of PTPN22 or IL2RA in order to diagnose VIT or determine if the subject has a propensity to develop VIT. In some embodiments, genetic alterations in all of those genes are assessed. In some embodiments, the detected genetic alteration is used to determine treatment options for the VIT patient, for example, to administer a drug targeting a gene in the pathway of the altered gene. (See Tables 11 and 12 for agents targeting particular identified genes herein.) Thus, in some embodiments, the VIT patient is administered a drug targeting the gene in which the genetic alteration is found.

In some embodiments involving subjects with thyroiditis (THY), a method of detecting the presence of a genetic alteration, such as an SNV, is provided comprising obtaining a biological sample from a THY patient and detecting the presence of a genetic alteration in one or more of PTPN22, TNM3, SBK1, IL2RA, or IL21. (See Supplemental Table 1b.) Alternatively, in some embodiments a method is provided comprising obtaining a biological sample from a subject and detecting the presence of a genetic alteration in one or more of PTPN22, TNM3, SBK1, IL2RA, or IL21 in order to diagnose THY or determine if the subject has a propensity to develop THY. In some embodiments, genetic alterations in all of those genes are assessed. In some embodiments, one or more of those genes is not assessed. In some embodiments, genetic alterations in, for example, one or more of IL18R1, CYTL1, FNBP1, IKZF3, TYK2, or TNFRSF6B are also assessed. (See Table 2b.) In some embodiments, the detected genetic alteration is used to determine treatment options for the THY patient, for example, to administer a drug targeting a gene in the pathway of the altered gene. (See Tables 11 and 12 for agents targeting particular identified genes herein.) Thus, in some embodiments, the THY patient is administered a drug targeting the gene in which the genetic alteration is found.

In some embodiments, samples from pediatric or adult patients diagnosed with one or more of AS, PS, CEL, SLE, CVID, UC, T1D, JIA, CD, AA, MS, primary biliary cirrhosis (PBC), primary sclerosing cholangitis (PSC), RA, Sjogren's syndrome (SJO), systemic sclerosis (SSC), vitiligo (VIT), or THY may be assessed for genetic alterations such as SNVs in one or more of IL23R, LPHN2, PTPN22, TNM3, ANKRD30A, INS, NOD2, DAG1, SMAD3, ATG16L1, ZNF365, PTGER4, NKX2 or 3, ANKRD55, IL12B, LRRK2, IL5, SUOX, SBK1, ADCY7, IL2RA, TNFSF15, CD40LG, ZMIZ1, IL21, CARD9, or PSMG1. (See Supplemental Table 1b.) In some embodiments, genetic alterations in all of those genes are assessed. In some embodiments, one or more of those genes is not assessed. In some embodiments, at least 5, such as at least 10, at least 15, or at least 20 of the above genes are assessed for genetic alterations. In some embodiments, samples from pediatric or adult subjects may be assessed for genetic alterations such as SNVs in one or more of IL23R, LPHN2, PTPN22, TNM3, ANKRD30A, INS, NOD2, DAG1, SMAD3, ATG16L1, ZNF365, PTGER4, NKX2 or 3, ANKRD55, IL12B, LRRK2, IL5, SUOX, SBK1, ADCY7, IL2RA, TNFSF15, CD40LG, ZMIZ1, IL21, CARD9, or PSMG1 in order to diagnose one or more AIDs or determine susceptibility to development of an AID. In some embodiments, genetic alterations in all of those genes are assessed. In some embodiments, one or more of those genes is not assessed. In some embodiments, at least 5, such as at least 10, at least 15, or at least 20 of the above genes are assessed for genetic alterations.

In some embodiments, samples from pediatric or adult patients diagnosed with one or more of AS, PS, CEL, SLE, CVID, UC, T1D, JIA, CD, AA, MS, primary biliary cirrhosis (PBC), primary sclerosing cholangitis (PSC), RA, Sjogren's syndrome (SJO), systemic sclerosis (SSC), vitiligo (VIT), or THY may be assessed for genetic alterations such as SNVs in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, or RBMX. (See Supplemental Table 1b.) In some embodiments, genetic alterations in all of those genes are assessed. In some embodiments, one or more of those genes is not assessed. In some embodiments, at least 5, such as at least 10, at least 15, at least 20, at least 25, at least 30, at least 35, or at least 40 of the above genes are assessed for genetic alterations. In some embodiments, samples from pediatric or adult subjects may be assessed for genetic alterations such as SNVs in one or more of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD9, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, CD40LG, or RBMX in order to diagnose or determine susceptibility to development of an AID. In some embodiments, genetic alterations in all of those genes are assessed.

In some embodiments, one or more of those genes is not assessed. In some embodiments, at least 5, such as at least 10, at least 15, at least 20, at least 25, at least 30, at least 35, or at least 40 of the above genes are assessed for genetic alterations.

In some of the above embodiments, samples from pediatric or adult patients diagnosed with one or more of AS, PS, CEL, SLE, CVID, US, T1D, JIA, CD, AA, MS, primary biliary cirrhosis (PBC), primary sclerosing cholangitis (PSC), RA, Sjogren's syndrome (SJO), systemic sclerosis (SSC), vitiligo (VIT), or THY may be assessed for genetic alterations such as SNVs in one or more of LPHN2, TNM3, ANKRD30A, ADCY7, or CD40LG. (See Supplemental Tables 1b and 1c.) In some embodiments, genetic alterations in all of those genes are assessed. In some embodiments, one or more of those genes is not assessed. In some embodiments, samples from pediatric or adult subjects may be assessed for genetic alterations such as SNVs in one or more of LPHN2, TNM3, ANKRD30A, ADCY7, or CD40LG in order to determine susceptibility to development of an AID. In some embodiments, genetic alterations in all of those genes are assessed. In some embodiments, one or more of those genes is not assessed.

In some embodiments, in order to diagnose, determine treatment for, or determine susceptibility towards either UC or PSC, genetic alterations in at least one of, such as 2, 3, 4, or all of, the following genes are also assessed: ICAM1, CD40, JAK2, TYK2, and IL12B. In some embodiments, in order to diagnose, determine treatment for, or determine susceptibility towards either MS or CEL, genetic alterations in at least one, 2, 3, or all of the following genes are assessed: IL19, IL20, STAT5A, and IL2RA. In some embodiments, in order to diagnose, determine treatment for, or determine susceptibility towards either SLE or PSC, genetic alterations in at least one, two, three, or all of the following genes are assessed: ILF3, CENPO, MEDI, and NCDA3. These genes may be screened, for instance, in addition to those associated with these diseases above.

Treatment of Subjects Harboring Genetic Alterations

In some embodiments, AID patients who are found to harbor one or more genetic alterations in the above genes may be directed to particular treatments that are targeted toward the pathway in which the products of the altered genes are included. Some embodiments herein include a method of first diagnosing AID in a patient through checking for one or more of the above genetic alterations or determining if a previously diagnosed AID patient has one or more of the above genetic alterations, and then, if such an alteration is present, providing a report with information about particular treatments that target the pathway associated with the product of the altered gene or genes. In some embodiments, the methods include administering such a treatment to the patient.

For example, Tables 11 and 12 herein list molecules that are on the U.S. market or in pre-clinical or clinical development that target particular genes or pathways.

For example, if an AID patient is found to have a genetic alteration in a gene in a particular pathway, such as in the CD40 pathway, such as an alteration in CD40LG, the patient may be directed to treatment with a therapeutic targeting that pathway, such as a CD40 inhibitor, such as an anti-CD40 antibody, an anti-CD40LG antibody, or other inhibitor of a CD40 pathway molecule. If an AID patient is found to have a genetic alteration, for example, in a gene in the JAK-STAT pathway, the patient may be directed to treatment with a therapeutic targeting the JAK-STAT pathway. If an AID patient is found to have a genetic alteration, for example, in a gene in the TNF superfamily such as in TNFSF15, the patient may be directed to treatment with a therapeutic targeting a TNF superfamily member pathway, such as a therapeutic targeting the pathway involving TNFSF15.

If an AID patient is found to have a genetic alteration, for example, in LRRK2, the patient may be directed to a therapeutic targeting LRRK2, such as those listed in Table 12. If an AID patient is found to have a genetic alteration, for example, in IL-21, the patient may be directed to a therapeutic targeting IL-21, such as those listed in Table 12. If an AID patient is found to have a genetic alteration, for example, in ADCY7, the patient may be directed to a therapeutic targeting ADCY7, such as those listed in Table 12. If an AID patient is found to have a genetic alteration, for example, in SMAD3, the patient may be directed to a therapeutic targeting SMAD3, such as that listed in Table 12. If an AID patient is found to have a genetic alteration, for example, in NOD2, the patient may be directed to a therapeutic targeting NOD2, such as those listed in Table 12. If an AID patient is found to have a genetic alteration, for example, in IL2RA, the patient may be directed to a therapeutic targeting IL2RA, such as those listed in Table 12.

Furthermore, some of the genes described herein encode proteins involved in the IL3, IL5, and/or GM-CSF signaling pathways, such as IL5, IL23R, INS, IL12B, ADCY7, IL2RA, and TNFSF15. Thus, if an AID patient is found to have a genetic alteration in one of these genes, the patient may be directed to a therapeutic targeting those pathways.

Otherwise, a patient may be directed to a treatment targeting a molecule that is within the interaction network of the gene harboring the genetic alteration. This may be a treatment targeting the altered gene (or its gene product) itself or targeting a molecule that binds to the product of the altered gene or that upregulates or downregulates the product of the altered gene or that upregulates or downregulates a protein that interacts with (e.g. binds, activates, or deactivates) the product of the altered gene.

As described in Example 1 below, the inventors have also discovered links between different pAID through common genetic etiologies. For example, several genetic alterations may be shared between subjects with J1A and CVID, e.g. alterations in LPHN2, TNM3, and IL21. Alterations in LPHN2 have also been observed in subjects with PSC, and thus, the methods herein may be used to identify subjects with J1A, CVID, and/or PSC who are at risk of developing one of these other AIDs. Alterations may be shared between subjects with J1A, T1D, and CEL, such as in IL2RA and IL21. Alterations may be shared between subjects with T1D and UC, such as in IL21, between CEL and UC, such as in DAG1, IL12B, SBK1, CD40LG, and IL21. Alterations may be shared between subjects with J1A and UC, such as in IL21. In these cases, methods of assessing genetic alterations in these genes may be performed in a patient diagnosed with one of these diseases in order to determine if the subject is susceptible to developing another AID such as one associated with the same genetic alterations.

Kits and Articles of Manufacture

This disclosure also encompasses kits and articles of manufacture, which may be used, for example, to test subjects for genetic alterations in one or more of the above genes. For example, in some embodiments, solid support matrices may be used containing reagents necessary to identify the genetic alterations, such as particular polynucleotide sequences that are capable of recognizing an SNV and/or CNV in one or more of the genes, such as an AID-associated SNV specific marker polynucleotide that could act as a probe to detect an SNV and/or CNV. In some embodiments, the solid support matrices may be in the form of chips. Any of the aforementioned products can be incorporated into a kit, which may contain an AID-associated SNV specific marker polynucleotide or one or more such markers immobilized on a solid support matrix such as a Gene Chip. A kit could also include molecules such as an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof, and a kit may also contain instructions for use.

In some embodiments, such a solid support or kit may be part of a system for carrying out one or more of the methods disclosed herein. For example, a solid support or kit with reagents needed to determine the presence of one or more genetic alterations discussed herein may be used for this portion of the methods herein.

Methods of Using AID-Associated SNVs for Development of Therapeutic Agents

Since the SNVs identified herein have been associated with the etiology of AID, methods for identifying agents that modulate the activity of the genes and their encoded products containing such SNVs may result in the generation of efficacious therapeutic agents for the treatment of this condition.

The chromosomal regions described herein contain protein coding regions which provide suitable targets for the rational design of therapeutic agents which modulate their activity. Small peptide molecules corresponding to these regions may be used to advantage in the design of therapeutic agents that may effectively modulate the activity of the encoded proteins.

Molecular modeling may facilitate the identification of specific organic molecules with capacity to bind to the active site of the proteins encoded by the SNV containing nucleic acids based on conformation or key amino acid residues required for function. A combinatorial chemistry approach may be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as airway smooth muscle cells, immune cells, dendritic cells, colon cells, etc.) that have a nonfunctional or altered AID associated gene. These host cell lines or cells are defective at the polypeptide level. The host cell lines or cells are grown in the presence of drug compound.

Host cells contemplated for use in the present invention include but are not limited to bacterial cells, fungal cells, insect cells, and any suitable type of mammalian cell. The AID-associated SNV encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); and yeast vectors such as YRP17, YIPS, and YEP24 (New England Biolabs, Beverly, Mass.), as well as pRS403 and pRS413 Stratagene Inc.); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, and *Saccharomyces* promoters such as the gal4 inducible promoter and the PGK constitutive promoter. In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the AID-associated SNVs of the present invention or functional fragments thereof provide a system in which to screen potential compounds or agents for the ability to modulate the development of AID. Thus, in one embodiment, the nucleic acid molecules of the invention may be used to create recombinant cell lines for use in assays to identify agents which modulate aspects of aberrant cytokine signaling associated with AID and/or aberrant bronchoconstriction. Also provided herein are methods to screen for compounds capable of modulating the function of proteins encoded by SNV containing nucleic acids.

Another approach entails the use of phage display libraries engineered to express fragment of the polypeptides encoded by the SNV containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs that have, e.g., improved polypeptide activity or stability or which act as inhibitors, agonists, antagonists, etc. of polypeptide activity. By virtue of the availability of SNV containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of AID-associated SNV containing nucleic acids enables the production of strains of laboratory mice carrying the AID-associated SNVs of the invention. Transgenic mice expressing the AID-associated SNV of the invention may provide a model system in which to examine the role of the protein encoded by the SNV containing nucleic acid in the development and progression towards AID. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. incorporation of genetically manipulated embryonic stem cells into an early embryo. Production of the transgenic mice described above will facilitate the molecular elucidation of the role that a target protein plays in various processes associated with the AID phenotypes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of AID-associated SNV containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated AID-associated SNV genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes that are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing AID-associated SNV containing nucleic acid as a targeted insertional cassette provides means to detect a successful insertion as visualized, for example, by acquisition of immunoreactivity to an antibody immunologically specific for the polypeptide encoded by AID-associated SNV nucleic acid and, therefore, facilitates screening/selection of ES cells with the desired genotype.

As used herein, a knock-in animal is one in which the endogenous murine gene, for example, has been replaced with human AID-associated SNV containing gene of the invention. Such knock-in animals provide an ideal model system for studying the development of pAID.

As used herein, the expression of a AID-associated SNV containing nucleic acid, fragment thereof, or an AID-associated SNV fusion protein can be targeted in a "tissue specific manner" or "cell type specific manner" using a vector in which nucleic acid sequences encoding all or a portion of an AID-associated SNV are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the AID-associated SNV of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; and a CMV promoter for the expression of transgenes in airway smooth muscle cells.

Methods of use for the transgenic mice of the invention are also provided herein. Transgenic mice into which a nucleic acid containing the AID-associated SNV or its encoded protein have been introduced are useful, for example, to develop screening methods to screen therapeutic agents to identify those capable of modulating the development of AID.

Pharmaceuticals and Further Methods of Treatment

The elucidation of the role played by the AID associated SNVs described herein in modulating the AID phenotypes may facilitate the development of further pharmaceutical compositions useful for treatment and diagnosis of AIDs including pAIDs. Such information may also enable new uses of existing pharmaceutical agents in combination for the treatment of AID. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, aerosolized, intramuscular, and intraperitoneal routes.

The invention includes a method of treating AID in a mammal. Preferably, the mammal is a human. An exemplary method entails administering to the mammal a pharmaceutically effective amount of AID siRNA. The siRNA may inhibit the expression of AID associated mRNA.

Specific siRNA preparations directed at inhibiting the expression of AID mRNA, as well as delivery methods are provided as a novel therapy to treat AID. SiRNA oligonucleotides directed to AID nucleic acids specifically hybridize with nucleic acids encoding AID genes and interfere with AID gene expression. The siRNA can be delivered to a patient in vivo either systemically or locally with carriers, as discussed below. The compositions of the invention may be used alone or in combination with other agents or genes encoding proteins to augment the efficacy of the compositions.

A "membrane permeant peptide sequence" refers to a peptide sequence able to facilitate penetration and entry of the AID inhibitor across the cell membrane. Exemplary peptides include without limitation, the signal sequence from Karposi fibroblast growth factor exemplified herein, the HIV tat peptide (Vives et al., J Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

In one embodiment of the invention siRNAs are delivered for therapeutic benefit. There are several ways to administer the siRNA of the invention in vivo to treat AID including, but not limited to, naked siRNA delivery, siRNA conjugation and delivery, liposome carrier-mediated delivery, polymer carrier delivery, nanoparticle compositions, plasmid-based methods, and the use of viruses.

siRNA composition of the invention can comprise a delivery vehicle, including liposomes, for administration to a subject, carriers and diluents and their salts, and/or can be present in pharmaceutically acceptable formulations. This can be necessary to allow the siRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995; Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

The frequency of administration of the siRNA to a patient will also vary depending on several factors including, but not limited to, the type and severity of the AID to be treated, the route of administration, the age and overall health of the individual, the nature of the siRNA, and the like. It is contemplated that the frequency of administration of the siRNA to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate siRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate siRNA to a patient according to the methods of the invention. The use of nanoparticles to deliver siRNAs, as well as cell membrane permeable peptide carriers that can be used are described in Crombez et al., Biochemical Society Transactions v35:p44 (2007).

The following examples are provided to illustrate certain embodiments of the invention. They are not intended to limit the invention in any way.

Example I

Identification of Genetic Markers for pAID

Autoimmune diseases affect 7-10% of individuals living in the Western Hemisphere[1], and represent a significant cause of chronic morbidity and disability. High rates of familial clustering and comorbidity across autoimmune diseases suggest that genetic predisposition underlies disease susceptibility. GWAS and immune-focused fine-mapping studies of autoimmune thyroiditis (AITD)[2], psoriasis (PSOR)[3], juvenile idiopathic arthritis (JIA)[4], primary biliary cirrhosis (PBC)[5], primary sclerosing cholangitis (PSC)[6], rheumatoid arthritis (RA)[7], celiac disease (CEL)[8], inflammatory bowel disease (IBD, which includes Crohn's Disease (CD) and ulcerative colitis (UC)[9]), and multiple sclerosis (MS)[10,11] have identified hundreds of autoimmune disease-associated single-nucleotide polymorphisms (SNVs) across the genome[12-14]. SNV associations in certain pan-autoimmune loci, such as PTPN22 c.1858C>T (rs2476601), are evident in independent GWAS across multiple autoimmune diseases[15-18], while others have been uncovered through large-scale meta-analyses (e.g. CEL/RA, T1D/CD) or through lookup of known loci from one disease in another (e.g. SLE)[19]. These studies demonstrate that over half of genome wide significant (GWS) autoimmune disease associations are shared by at least two distinct autoimmune diseases[20,21]. However, the degree to which common, shared genetic variations may similarly affect the risk of different pediatric age-of-onset autoimmune diseases (pAIDs) and whether these effects are heterogeneous have not been systematically examined at the genotype level across multiple diseases simultaneously.

To identify shared genetic etiologies underlying pAIDs and to illustrate how such associations may jointly or disparately affect pAID susceptibility, we performed a modified heterogeneity sensitive GWAS (hsGWAS) across ten common pAIDs. We modeled pAIDs as a heterogeneous phenotype, assigning each of the ten pAIDs as a disease subtype. By combining disease model-search[23], regional imputation, and disease model-specific association testing, we can maximize the power to identify risk variants shared across multiple autoimmune diseases in the context of phenotypic and genetic heterogeneity. Our study, including over 16,000 case-control individuals all genotyped on comparable platforms at The Children's Hospital of Philadelphia (CHOP), represents the largest pAID genetic association study performed to date.

Over hundred autoimmune disease loci have been reported in multiple independent GWAS studies of over a dozen pAIDs. Consistent with clinical observations that some pAIDs, such as THY, CEL and T1D, exhibit high rates of disease comorbidity, while others, such as CD and UC, have clear familial clustering, about half of all the GWS associations reported have been independently reported in at least one other autoimmune disease.

To address true genetic sharing across different autoimmune diseases, unbiased genome-wide approaches are needed as meta-analyses have mostly focused on known or candidate loci. However, a few studies have utilized genetic correlations to boost study power of genetic discovery and simultaneously investigated the genetic overlap across multiple autoimmune diseases affecting adults[60-65], similar to what we report in the present analysis for pAIDs. Indeed, given that most pAIDs are relatively rare, combining multiple diseases with expected genetic overlap to increase sample size, presents an intuitive approach addressing both discovery and replication, and far better powered than by directly merging cases in a classic GWAS.

Results

Shared Genetic Risk Associations Across Ten Pediatric Autoimmune Diseases

Figure 1C:
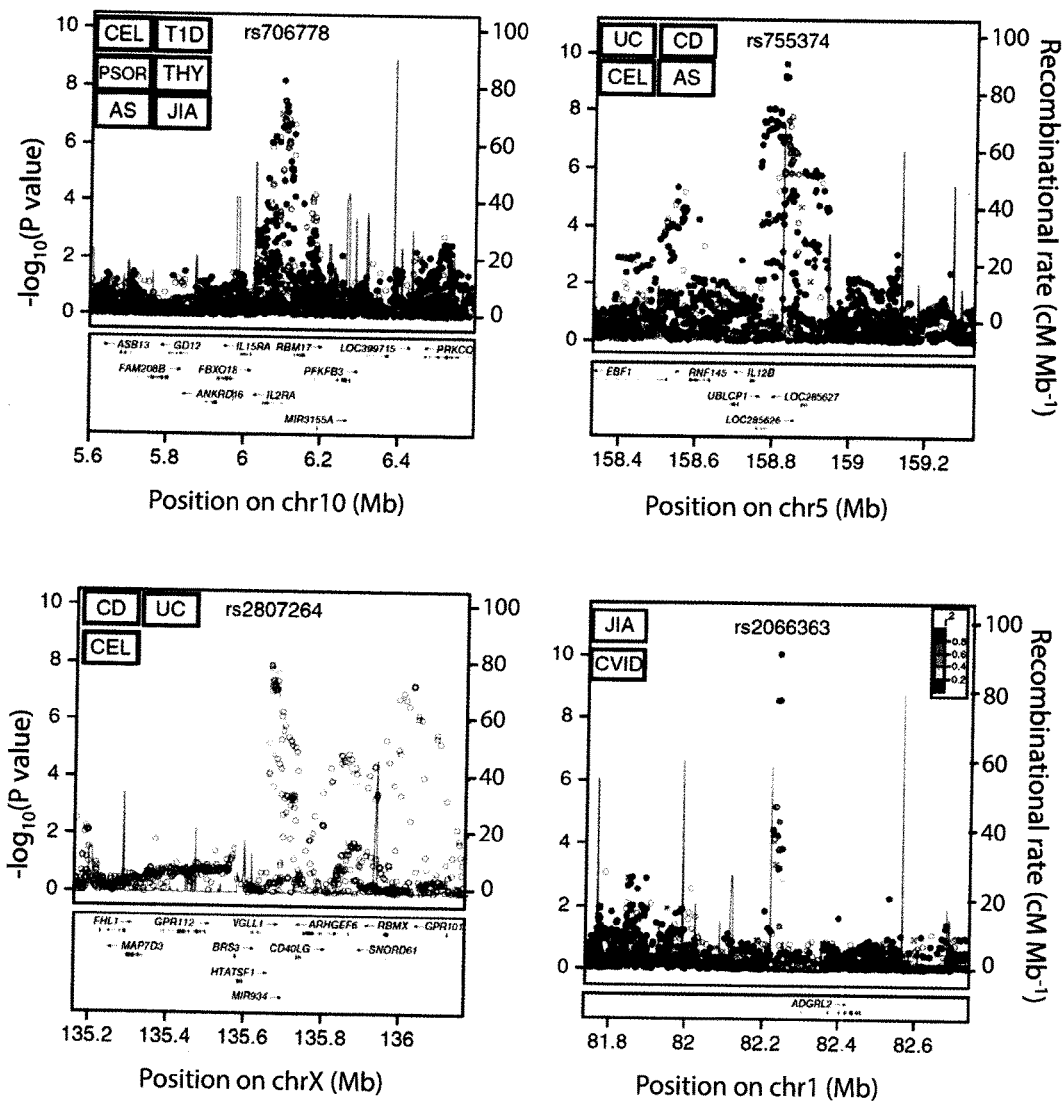
Figure 1D:
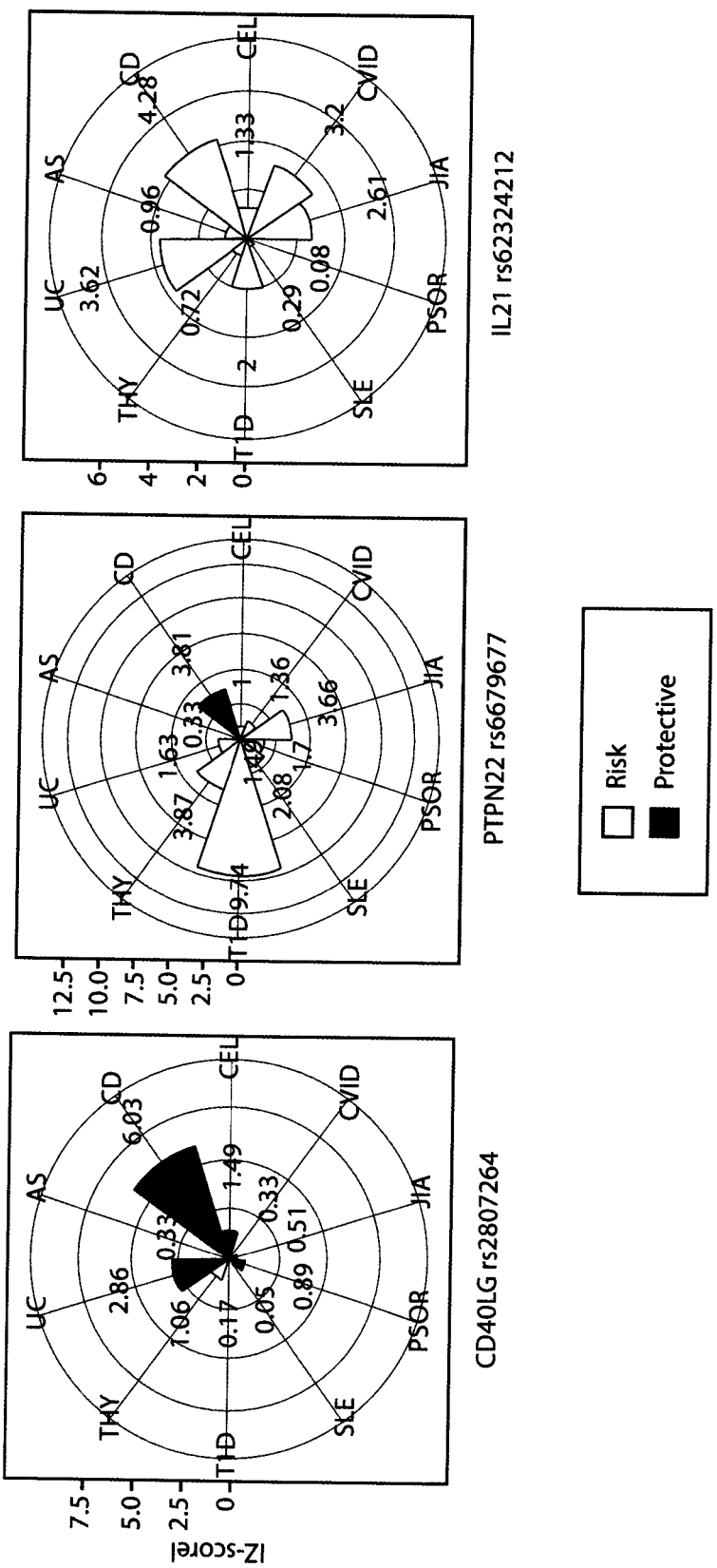
Figure 1E:
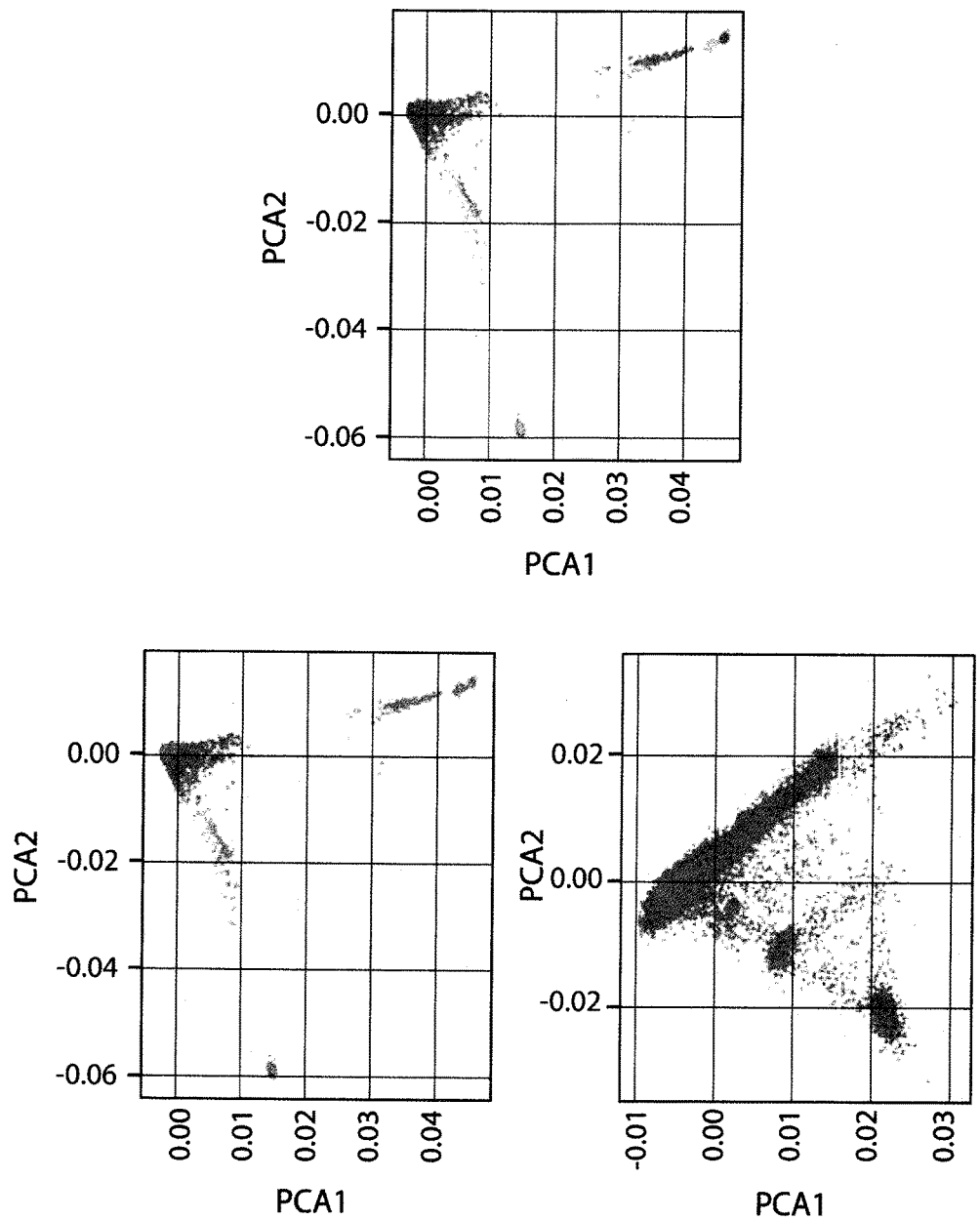

We performed whole-genome imputation on a combined cohort of over 6,035 pediatric cases across 10 clinically-distinct pAIDs (Supplementary Table 1a) and 10,718 population-based control subjects without prior history of autoimmune/immune-mediated disorders. We performed whole chromosome phasing and used the 1,000 Genomes Project Phase I Integrated cosmopolitan reference panel (1KGP-RP) for imputation as previously described (SHAPEIT and IMPUTE2)[22,23]. Only individuals of self-reported European ancestry, and confirmed by Principal Component Analysis (FIG. 1E), were included (See Methods). Rare (minor allele frequency [MAF]<1%) and poorly-imputed (INFO<0.8) SNVs were removed, leaving a total of 7,347,414 variants.

Figure 1F:
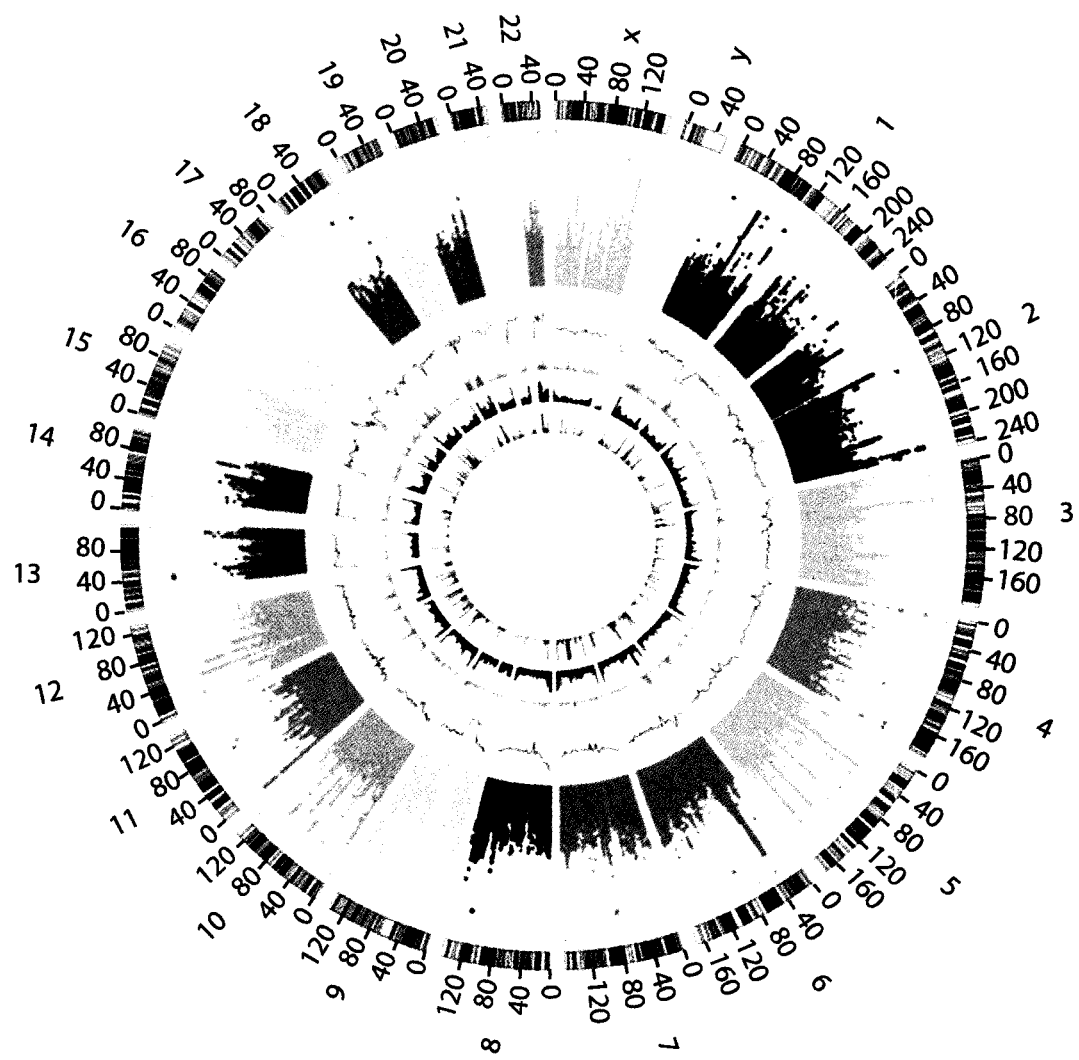
Figure 1G:
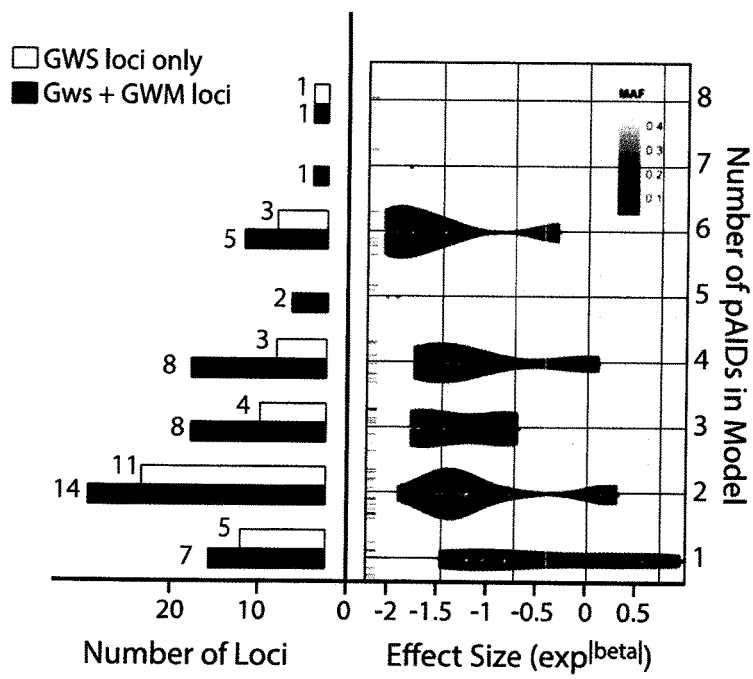
Figure 2B:
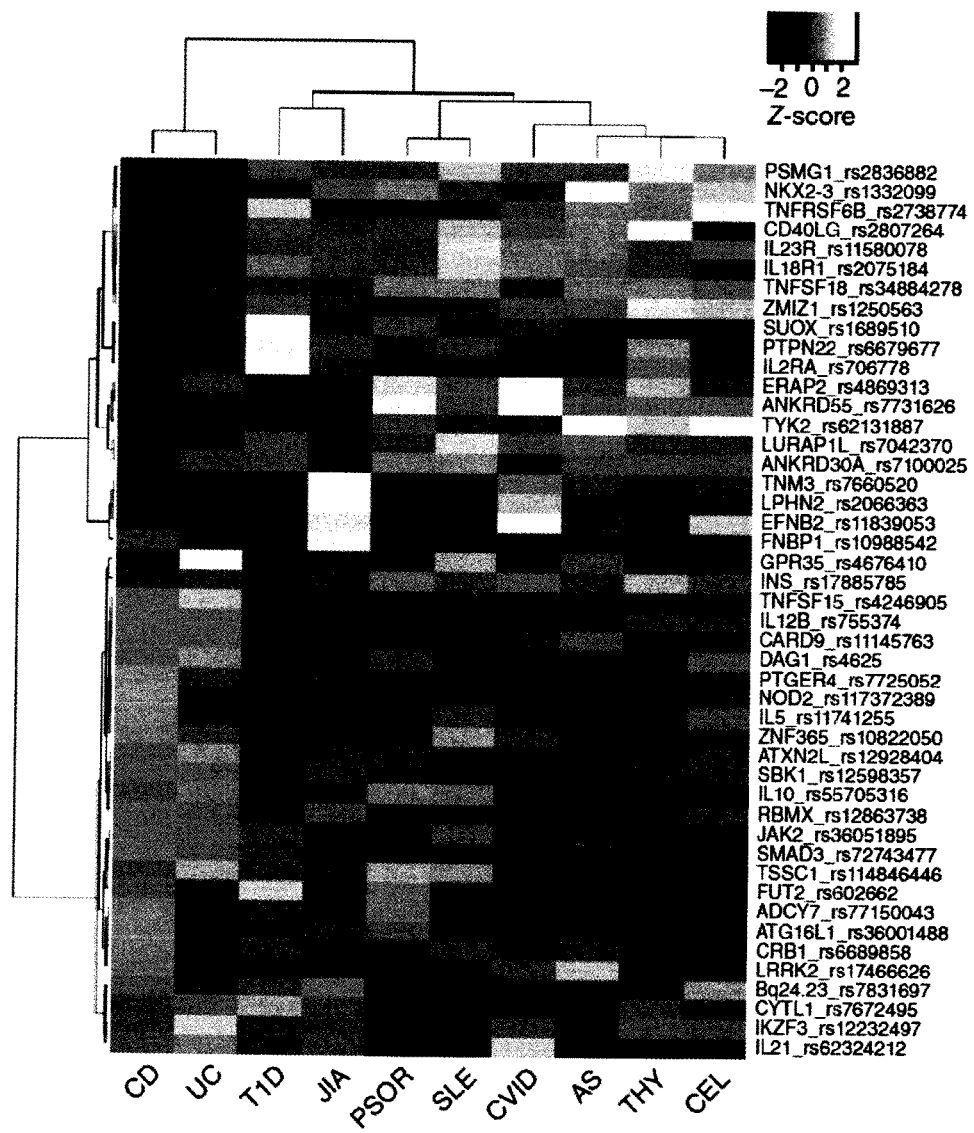
Figures 1, 2C:
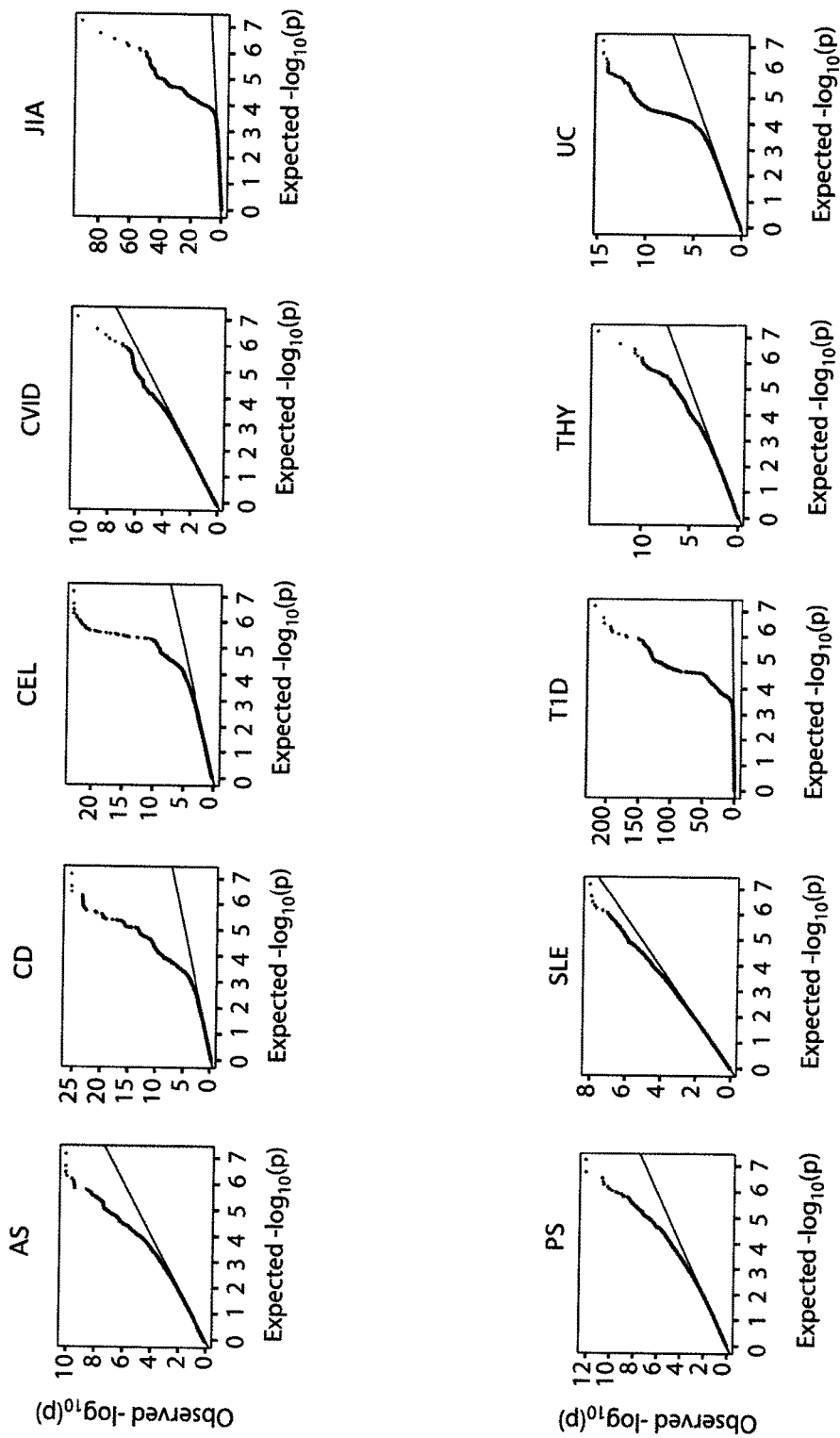
Figures 2, 2C:
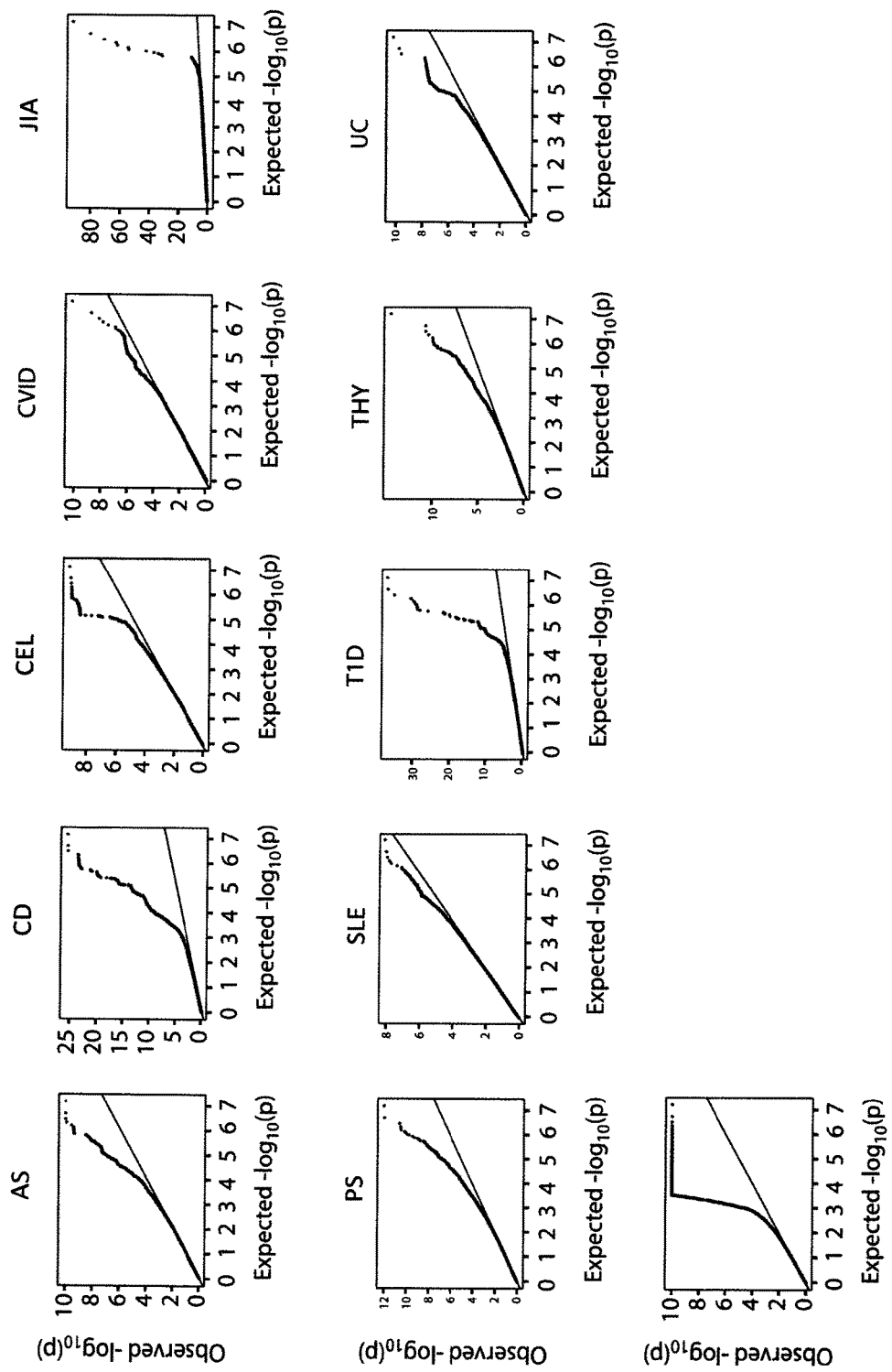

Whole-genome case-control association testing was performed using case samples from each of the ten pAID cases and the shared controls, additive logistic regression was applied using SNPTESTv2.5[24]. There was no evidence of genomic inflation. To identify shared pAID association loci, we performed an inverse chi-square meta-analysis, accounting for sample size variation and the use of a shared control across the ten pAIDs[25]. We identified 27 linkage disequilibrium (LD)-independent loci, consisting of associated SNPs with $r^2$>0.05 within a 1 Mb window where at least one lead SNP reached a conventionally-defined GWS threshold ($P<5\times10^{-8}$); See FIG. 1C and FIG. 1F. An additional 19 loci reached a marginally-significant (GWM) threshold at or below $P_{META}<1\times10^{-6}$, among which twelve map to previously-reported and seven to putatively novel autoimmune loci (FIG. 1 and Supplementary Table 2a).

We identified five novel GWS loci, including CD40LG ($P_{META}<8.38\times10^{-11}$), LPHN2 ($P_{META}<8.38\times10^{-11}$), TNM3 ($P_{META}<8.38\times10^{-11}$), ANKRD30A ($P_{META}<8.38\times10^{-11}$), and ADCY7 ($P_{META}<5.99\times10^{-9}$). For each lead association locus, we identified the corresponding combination of pAIDs contributing to the association signal, by enumerating all 1,023 unique disease combinations (e.g., one-disease: T1D, two diseases: T1D and SLE, or four diseases: UC, CD, CEL and SLE) and performing association testing to identify the disease combination that yields the maximum logistic regression Z-score (see Methods)[26]. With the exception of ANKRD30A, the remaining four putatively novel loci were jointly associated with at least two or more pAIDs; for example, CD40LG was shared by CEL, CD, and UC (FIG. 1 and Table 1). Among the 27 GWS lead SNPs, 22 were previously-reported as GWS for at least one of the associated pAIDs (i.e., the corresponding adult phenotypes) identified by our analysis (Supplementary Table 1b)[12,27]. The most widely shared locus, chr4q27: rs62324212 mapping to an intronic SNP in IL21 antisense RNA/and residing just upstream of IL21, was shared across all 10 diseases, three of which are novel (THY|AS|CVID). Among the previously known GWS loci in adult-onset or generalized autoimmune disease, we identified at least one novel pediatric age of onset autoimmune disease association for over 50% of them (Table 2d and Table 2c).

Figure 3A:
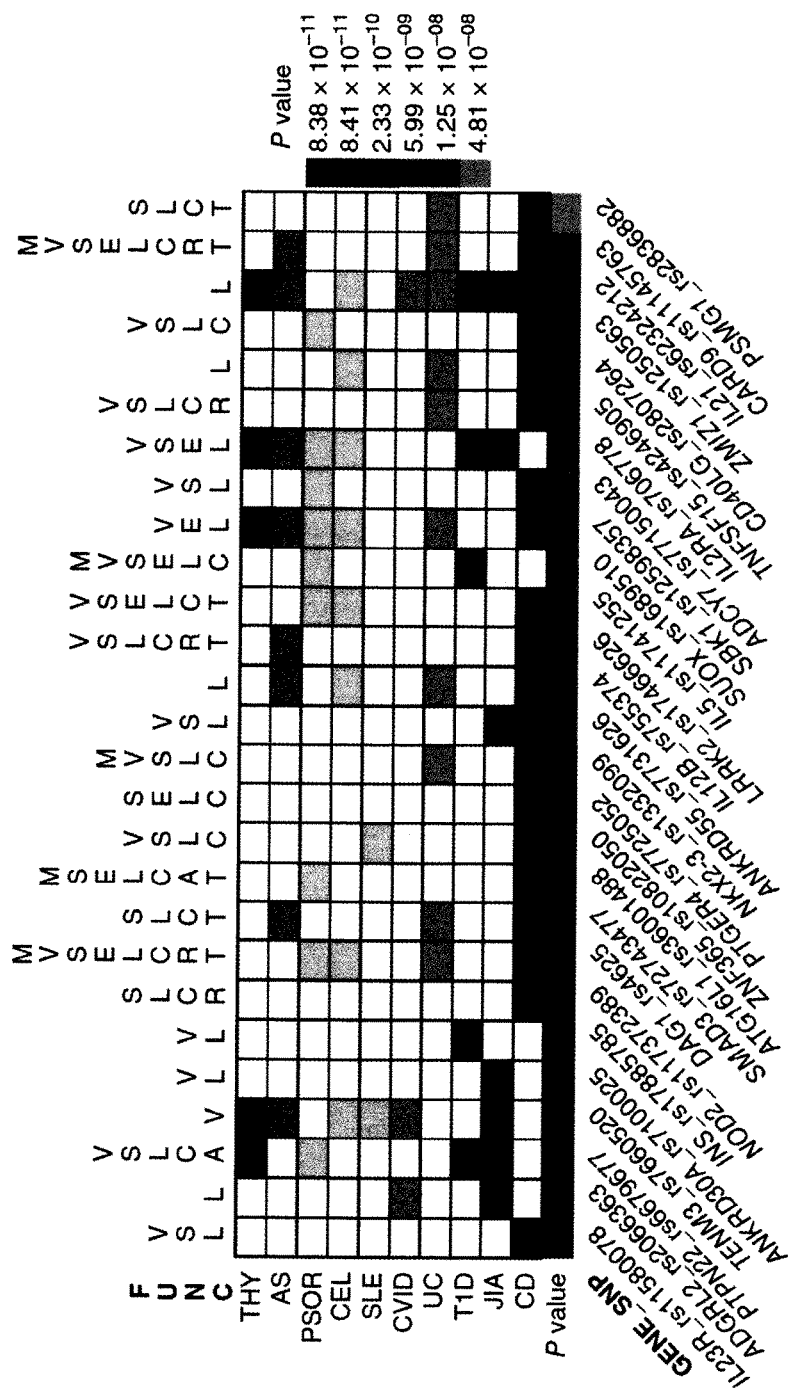
Figure 3B:
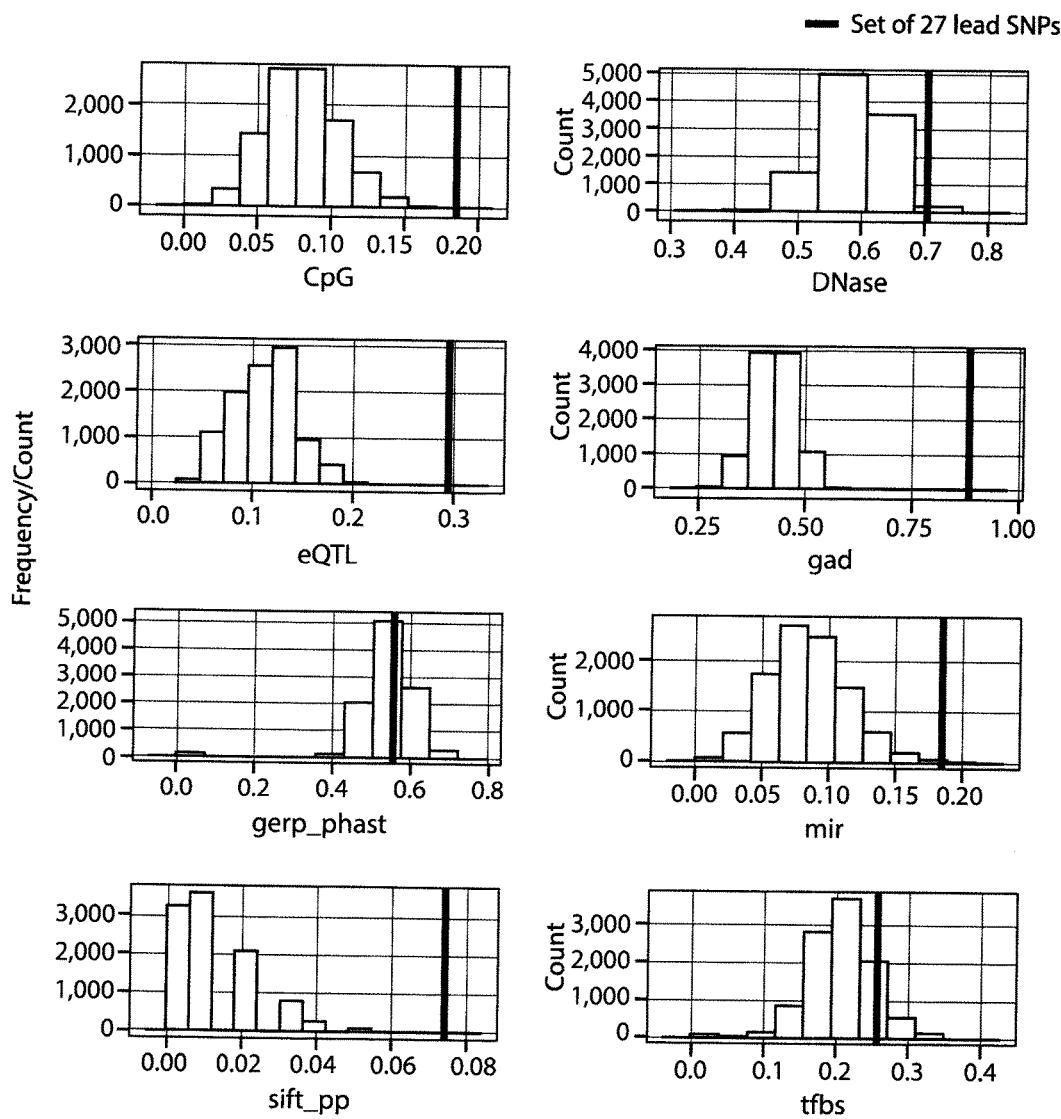
Figure 3C:
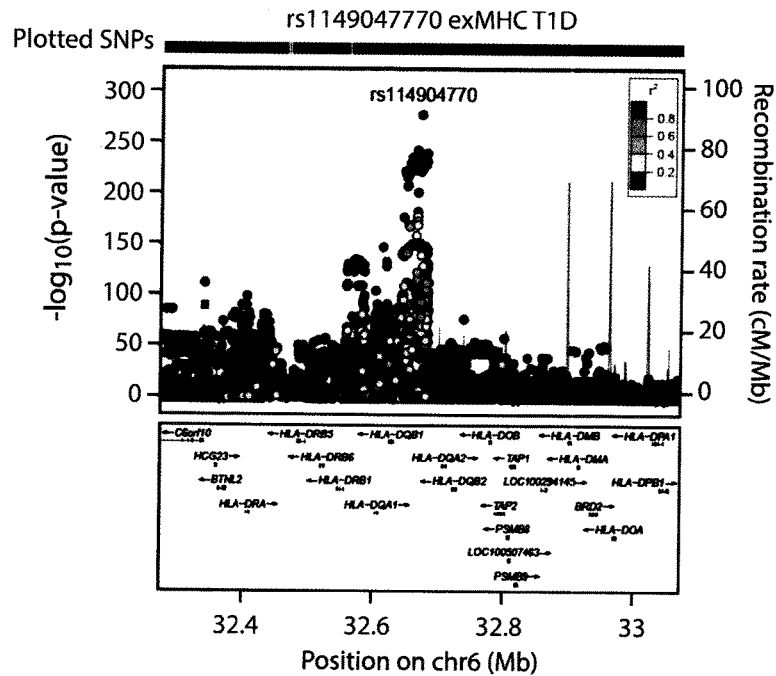
Figure 3D:
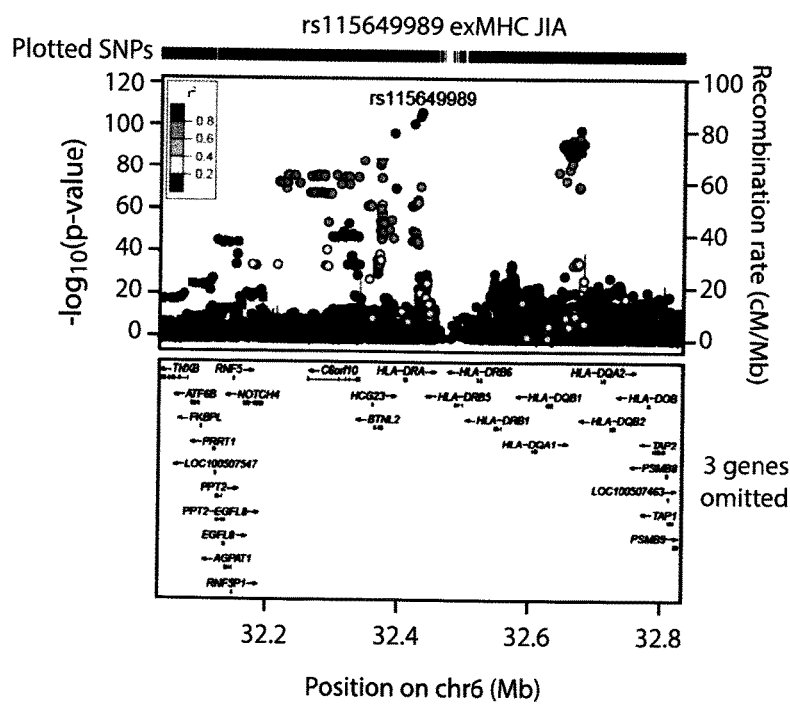

A number of the pAIDs are significantly associated with disease-specific signals mapping to or near the locus encoding HLA-DRB1. However, even the two most significant, LD-independent variants associated with T1D and JIA, respectively, were disease-specific (FIG. 3C), suggesting that the variants associated with a given disease are distinct. Although some of these associated signals are shared by at least one other autoimmune diseases, in no instance is a single signal associated with any of the diseases shared across all other diseases, further underscoring the complexity of signal sharing across the MHC (FIG. 3D).

Disease-Specific and Cross-Autoimmune Replication Support for the pAID Associated Loci We performed in silico analysis to test if the reported associations can be replicated in an independent dataset. We observed nominally significant replication support for four of the five putatively novel GWS loci, including three instances of disease-specific replication (Supplementary Table 1d). Among the replicated loci, chrXq26.3 (rs2807264) mapping within 70 Kb upstream of CD40LG, is notable, as we observe disease-specific replication in both UC ($P<4.66\times10^{-5}$) and CD ($P<5.81\times10^{4}$), as well as cross-autoimmune replication in AS ($P<9.54\times10^{-3}$). Although rs2807264 was not identified in our analysis as being associated with pediatric AS, it has been well-documented that adult-onset AS may be biologically a different disease with independent genetic etiologies.[28,29] A third disease-specific replication ($P<5.99\times10^{-6}$) was identified in CD for the chr16q12.1 (rs77150043) signal mapping to an intronic position in ADCY7. This latter instance and the replication of the CD40LG locus in UC were both significant, even following a very conservative Bonferonni adjustment for 156 tests ($P<3.21\times10^{4}$). A nominally significant pan-autoimmune replication signal ($P<1.69\times10^{-2}$) was also observed at chr1p31.1 (rs2066363) near LPHN2 in UC, and replication signal ($P<3.65\times10^{-3}$) was also observed at the chr4q35.1 locus (rs77150043) in PS (Supplementary Table 1d and Table 2e).

Figure 1H:
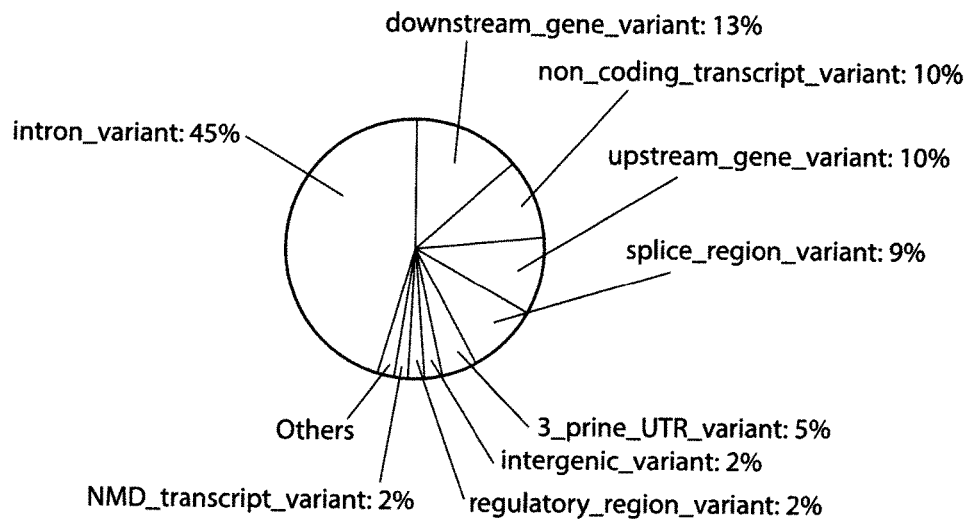
Figures 1I, 2A:
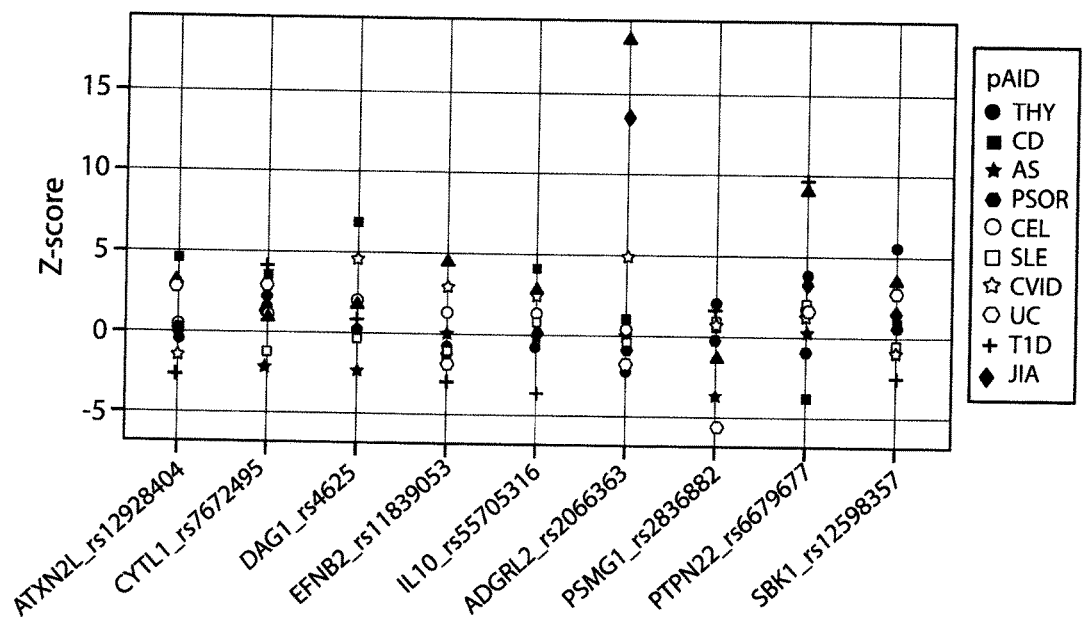
FIGS. 2A, 2B, 2C-1, and 2C-2. Pleiotropic loci with heterogeneous effect directions across pAIDs.

Sharing of pAID-Associated SNPs and Bidirectional Effects of Some SNPs on Disease-Specific Risk Of the 27 GWS loci, 81% (22) showed evidence of being shared among multiple pAIDs. These map to 77 unique SNP-pAID combinations, 44 of which have been previously reported at or near GWS ($P<1\times10^{-6}$), while 33 represent potentially novel disease association signals (Table 1 and Supplementary Table 1). While PTPN22 c.1858C>T (rs2476601) increases the risk for T1D, the variant is protective for CD[17,30-32]. We identified eight other instances ($P<0.05$) where the risk allele shared by the model pAID combination was associated with protection against another pAID (FIG. 2A and FIG. 7A).

TABLE 1

Twenty-seven independent loci reaching GWS ($P_{META} < 5 \times 10^{-8}$) after adjusting for the use of shared controls using an inverse chi-square meta-analysis across the pAIDs.

| CHR | POS(Mb) | SNP | REGION | GENE | A1 | MAF | $P_{META}$ | Known_P* | pAIDs |
|---|---|---|---|---|---|---|---|---|---|
| 1 | 67.7 | rs11580078 | 1p31.3 | IL23R | G | 0.43 | 8.4E−11 | 1.0E−146 | CD# |
| 1 | 82.2 | rs2066363 | 1p31.1 | LPHN2 | C | 0.34 | 8.4E−11 | novel | CVID\|JIA |
| 1 | 114.3 | rs6679677 | 1p13.2 | PTPN22 | A | 0.09 | 8.4E−11 | 1.1E−88 | THY#\|PS\|T1D#\|JIA# |
| 2 | 234.2 | rs36001488 | 2q37.1 | ATG16L1 | C | 0.48 | 8.4E−11 | 1.0E−12 | PS\|CD# |
| 3 | 49.6 | rs4625 | 3p21.31 | DAG1 | G | 0.31 | 8.4E−11 | 1.0E−47 | PS#\|CEL\|UC#\|CD# |
| 4 | 123.6 | rs62324212 | 4q27 | IL21 | A | 0.42 | 2.6E−08 | 1.0E−09 | THY\|AS\|CEL#\|CVID\|UC#\|T1D#\|JIA#\|CD# |
| 4 | 183.7 | rs7660520 | 4q35.1 | TNM3 | A | 0.26 | 8.4E−11 | novel | THY\|AS\|CEL\|SLE\|CVID\|JIA |
| 5 | 40.5 | rs7725052 | 5p13.1 | PTGER4 | C | 0.43 | 8.4E−11 | 1.4E−10 | CD# |
| 5 | 55.4 | rs7731626 | 5q11.2 | ANKRD55 | A | 0.39 | 1.4E−10 | 2.7E−11 | JIA\|CD# |
| 5 | 131.8 | rs11741255 | 5q31.1 | IL5 | A | 0.42 | 1.6E−09 | 1.4E−52 | PS#\|CEL\|CD# |
| 5 | 158.8 | rs755374 | 5q33.3 | IL12B | T | 0.32 | 2.3E−10 | 1.4E−42 | AS#\|CEL\|UC#\|CD# |
| 9 | 117.6 | rs4246905 | 9q32 | TNFSF15 | T | 0.28 | 9.5E−09 | 1.2E−17 | UC#\|CD# |
| 9 | 139.3 | rs11145763 | 9q34.3 | CARD9 | C | 0.40 | 3.3E−08 | 1.0E−06 | AS#\|UC#\|CD# |
| 10 | 6.1 | rs706778 | 10p15.1 | IL2RA | T | 0.41 | 6.3E−09 | 1.7E−12 | THY\|AS\|PS#\|CEL\|T1D#\|JIA# |
| 10 | 37.6 | rs7100025 | 10p11.21 | ANKRD30A | G | 0.34 | 8.4E−11 | novel | JIA |
| 10 | 64.4 | rs10822050 | 10q21.2 | ZNF365 | C | 0.39 | 8.4E−11 | 5.0E−17 | SLE\|CD# |
| 10 | 81.0 | rs1250563 | 10q22.3 | ZMIZ1 | C | 0.29 | 1.3E−08 | 1.1E−30 | PS#\|CD# |
| 10 | 101.3 | rs1332099 | 10q24.2 | NKX2-3 | T | 0.46 | 9.1E−11 | 1.0E−54 | UC#\|CD# |
| 11 | 2.2 | rs17885785 | 11p15.5 | INS | T | 0.20 | 8.4E−11 | 4.4E−48 | T1D# |
| 12 | 40.8 | rs17466626 | 12q12 | LRRK2 | G | 0.02 | 3.2E−10 | 3.0E−10 | AS\|CD# |
| 12 | 56.4 | rs1689510 | 12q13.2 | SUOX | C | 0.31 | 4.0E−09 | 1.1E−10 | PS#\|T1D# |
| 15 | 67.5 | rs72743477 | 15q22.33 | SMAD3 | G | 0.21 | 8.4E−11 | 2.7E−19 | AS\|UC\|CD# |
| 16 | 28.3 | rs12598357 | 16p11.2 | SBK1 | G | 0.39 | 4.4E−09 | 1.0E−08 | THY\|AS#\|PS\|CEL\|UC\|CD# |
| 16 | 50.3 | rs77150043 | 16q12.1 | ADCY7 | T | 0.23 | 6.0E−09 | novel | PS\|CD |
| 16 | 50.7 | rs117372389 | 16q12.1 | NOD2 | T | 0.02 | 8.4E−11 | 2.9E−69 | CD# |
| 21 | 40.5 | rs2836882 | 21q22.2 | PSMG1 | A | 0.27 | 4.8E−08 | 2.8E−14 | UC#\|CD# |
| 23 | 135.7 | rs2807264 | Xq26.3 | CD40LG | C | 0.21 | 1.3E−08 | novel | CEL\|UC\|CD |

CHR: chromosome;
SNP: dbSNP rsID;
POS (Mb): position in hg19;
REGION: Cytogenetic band;
A1: alternative allele;
MAF: minor allele frequency (controls);
GENE: candidate gene name (HNGC);
$P_{META}$: Meta-analysis P-value;
Known_P*: Lowest P-value from published association studies; "novel" denotes new loci (bolded) reaching GWS for the first time in the present study;
pAIDs: pAIDs associated with the locus; (#) denotes if the SNP-disease associated has been previously reported.

To integrate our results with experimental and predictive biological data, we curated four categories of SNP annotations: 1) functional: variants that are exonic or impact transcription, miRNA targets or tag copy-number polymorphic regions; 2) regulatory: transcription factor (TF)-binding sites and DNase hypersensitivity sites or eQTLs SNPs; 3) conserved: variants with evolutionarily-constrained positions or CpG islands; or 4) prior literature support: gene or locus previously reported to be associated with autoimmune diseases or immune function. Indeed, 100% of the GWS lead SNPs or their nearby LD proxies ($r^2 > 0.8$ based on 1KGP-RP within 500 Kb up- or downstream) belong to one or more of these categories (FIG. 3A). Nevertheless, the majority of the 27 GWS SNPs do not confer transcriptional consequences (51% are intronic variants, 28% are intergenic or up/downstream gene variants), suggesting that many of these SNPs are either tagging the true causal variants or impact disease risk through regulatory and/or epigenetic mechanisms (FIG. 3B).

To determine if the set of pAID-associated SNPs were enriched for specific annotation categories, we compared their annotation percentage with that of 10,000 simulated sets of SNPs with MAF>0.01 drawn from the 1KGP-RP, for each category. We found that pAID-associated SNPs are enriched for CpG islands ($P_{perm} < 1.0 \times 10^{-4}$), transcription-factor binding sites ($P_{perm} < 3.4 \times 10^{-3}$), and miRNA binding sites ($P_{perm} < 1.0 \times 10^{-4}$), among other findings of biological disease relevance (FIGS. 1H and 1I).

Figure 4C:
Figure 5A:
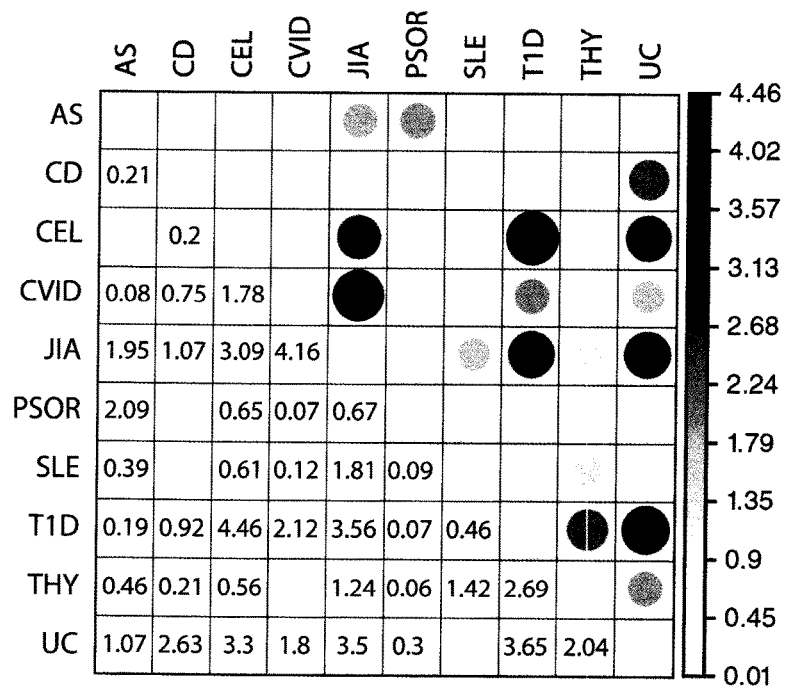
FIGS. 5A-5E: Genetic variants shared across the ten pAIDs reveal autoimmune disease networks.
Figure 5B:
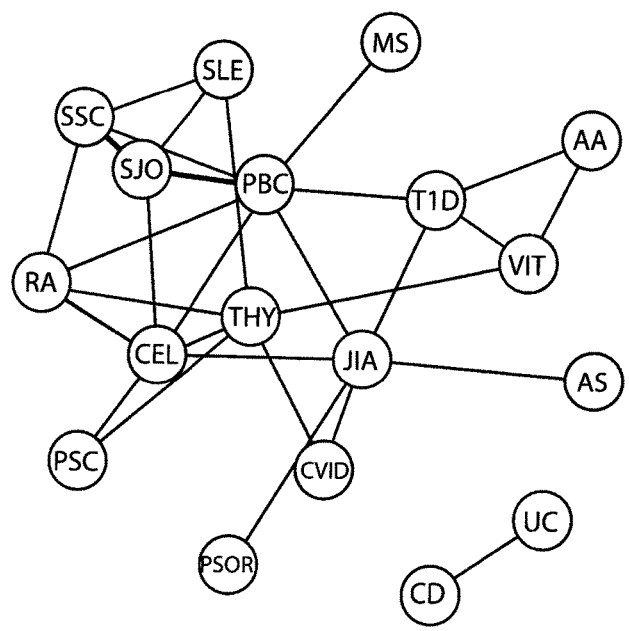
Figure 5C:
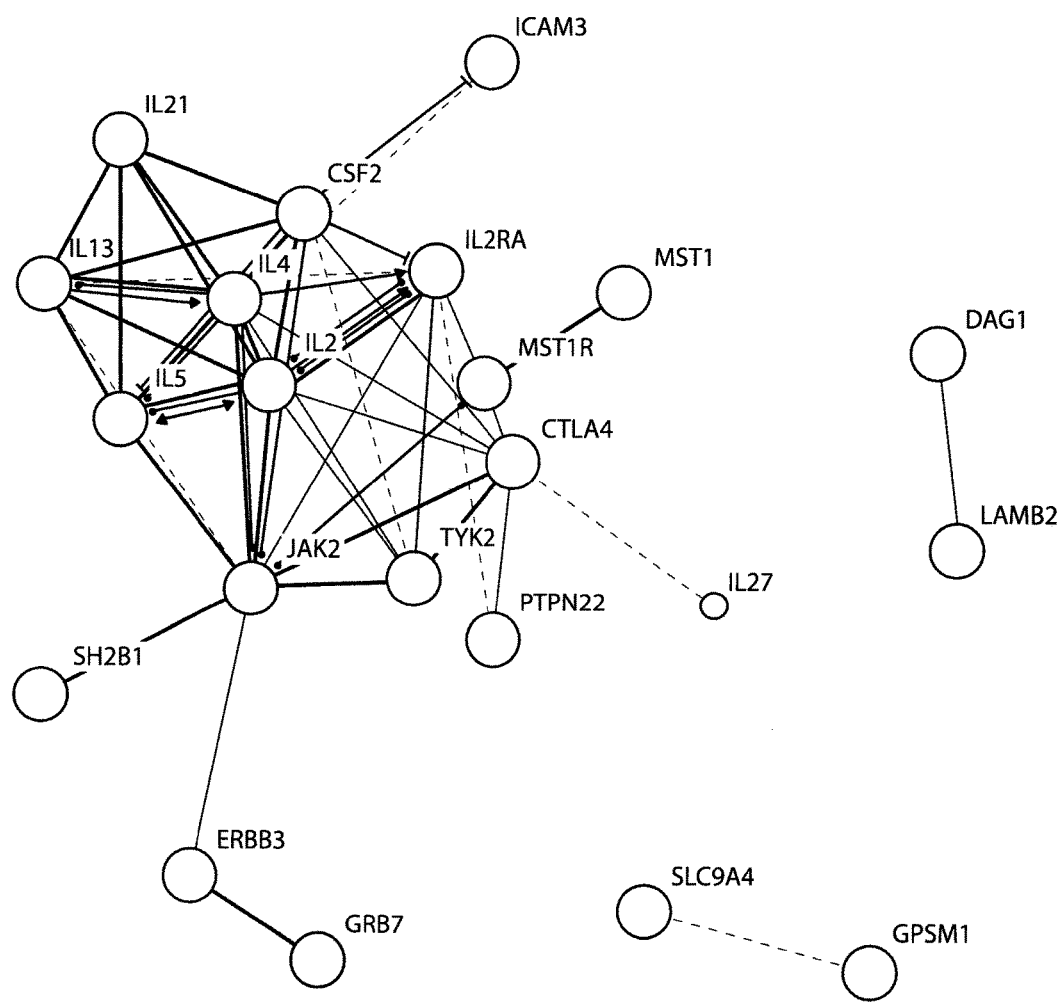
Figures 5D, 5E:
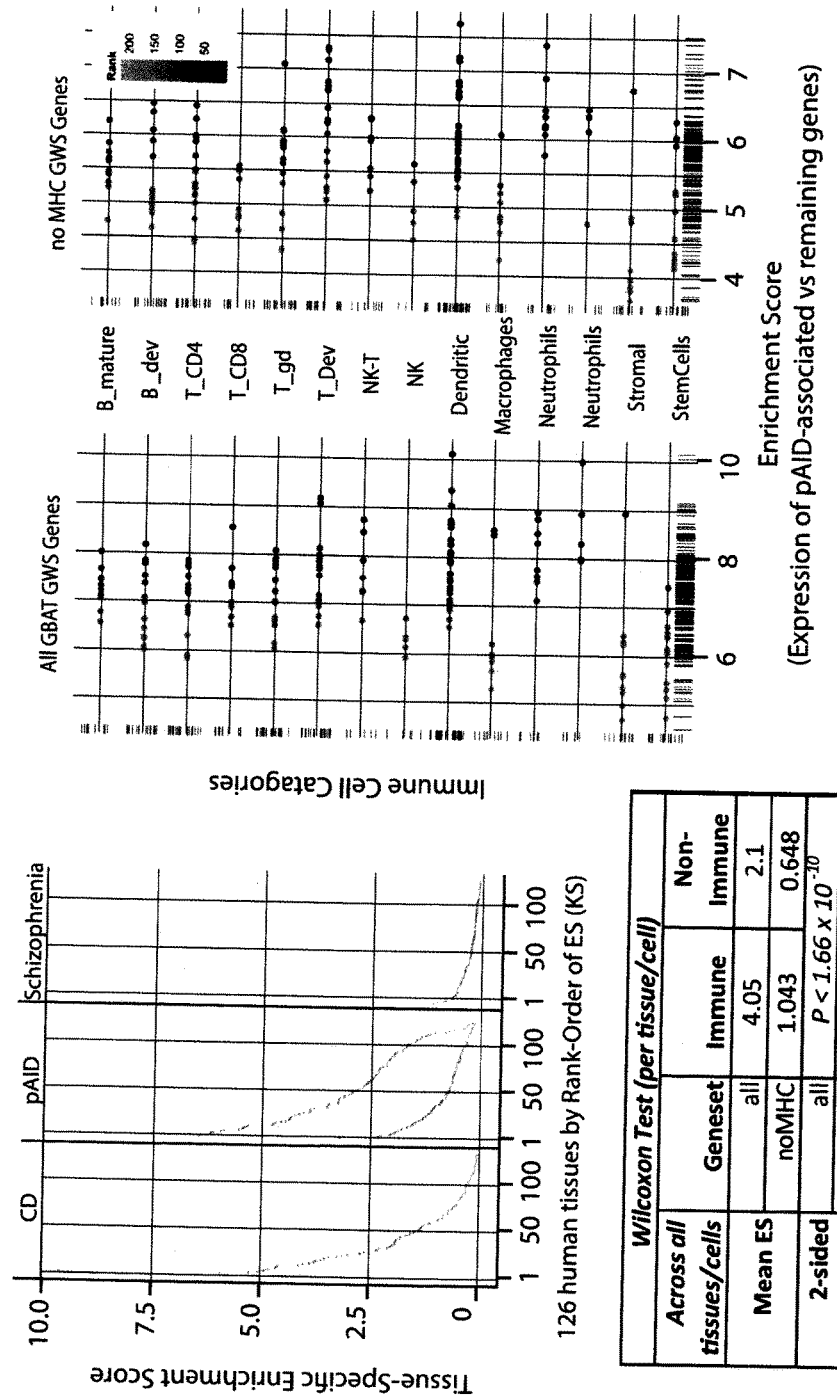

Candidate pAID Genes Share Expression Profiles Across Immune Cell Types and Tissues Recent studies show that gene-based association testing (GBAT) may boost the power of genetic discovery[33-35]. We performed GBAT (VEGAS[33]), using genome-wide summary-level $P_{META}$-values. We identified 182 significant pAID-associated genes (simulation-based $P_{sim} < 2.80 \times 10^{-6}$), based on a Bonferonni adjustment for ~17,500 protein-coding genes in the genome (Table 3a). To illustrate the biological relevance of this gene set, we examined their transcript levels in a human gene expression microarray dataset consisting of 12,000 genes and 126 tissue/cell types[36]. The distribution of pAID-associated gene expression was notably higher across immune (ES-I, =4.05) versus non-immune (ES-NI=2.10) tissues or cell types, based on a one-tailed Wilcoxon rank-sum test ($P < 1.66 \times 10^{-10}$). When all extended MHC genes were excluded, the average expression of pAID associated genes remained significantly higher ($P < 1.27 \times 10^{-7}$) across immune (ES-I=1.043) versus non-immune (ES-NI=0.648) cells/tissues. The immune-specific enrichment of pAID-associated gene transcripts was comparable to those observed in adult cohorts[12]; comparatively, schizophrenia-associated genes showed no such enrichment (FIG. 4A). Similar results were observed using the Kolmogorov-Smirnov (KS) test (FIG. 5D).

We examined the expression of pAID genes across a whole-transcriptome dataset comprising over 200 murine immune cell types isolated by flow cytometry (ImmGen[37]; see Methods and Table 3c). Genes associated with pAIDs demonstrated differential expression across immune cell types (FIG. 5E), and were more highly expressed as compared to genes associated with non-immune traits, similar to results observed from human tissue data (FIG. 4B). As the expression levels of these "pleiotropic" genes varied diversely across immune cell types, we performed agglomerative hierarchical clustering to identify sets of genes sharing similar profiles. Genes that belong to the same cluster (hence sharing similar expression profiles) were found to be enriched for association with a specific or multiple autoimmune diseases (see annotated clusters in FIG. 4C). For example, cluster 1 genes, including ICAM1, CD40, JAK2, TYK2 and IL12B, with known roles in immune effector cell activation and proliferation, were enriched for association with PSC, UC, and associated with both diseases ($P<6.82\times10^{-4}$; one-tailed Fisher's Exact test), and the expression of these genes was highest in a small subset of CD11b$^+$ lymphoid dendritic cells. These findings are consistent with the clinical observation that as many as 80% of patients diagnosed with PSC have been diagnosed with UC, and the risk of PSC is approximately 600-fold higher in patients with UC.[38,39] Cluster 2 genes include a number of cytokines and cytokine-response factors, including IL19, IL20, STAT5A, and IL2RA, which regulate effector T-cell activation, differentiation, and proliferation all of which were more broadly expressed, across mature natural killer (NK), NK-T and T cells as well as neutrophils. This cluster of genes is enriched for association with MS ($P<9.8\times10^{4}$), marginally with CEL ($P<0.062$), and both diseases ($P<3.41\times10^{4}$). Genes encoding nucleic acid binding proteins, including ILF3, CENPO, MEM, and NCOA3, are enriched in cluster 3. Genes in this cluster are jointly associated with SLE and PS ($P<0.03$), which is consistent with experimental and clinical data demonstrating that early defects in B[40,41] and T-cell[42-44] clonal selection may play an important role in the etiology of these diseases, respectively.

Quantification of Genetic Risk Factor Sharing Across pAIDs

Figure 7B:
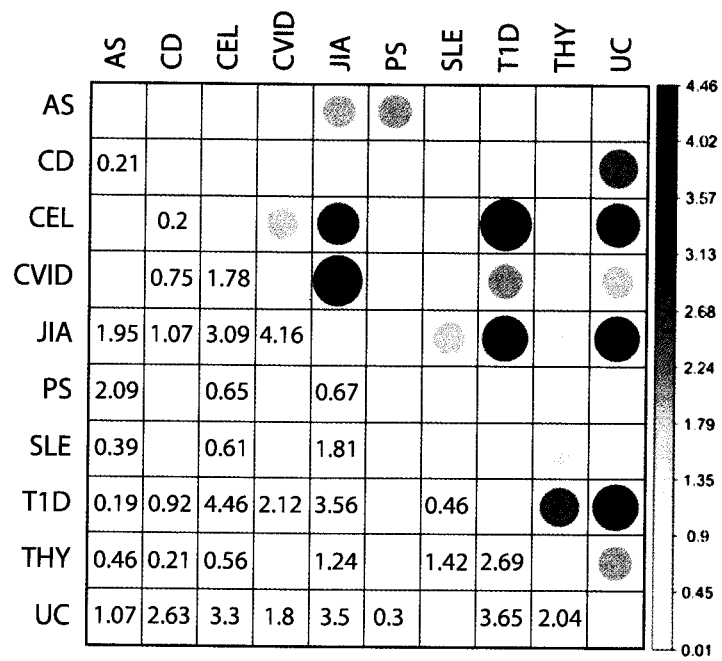
Figure 7B:
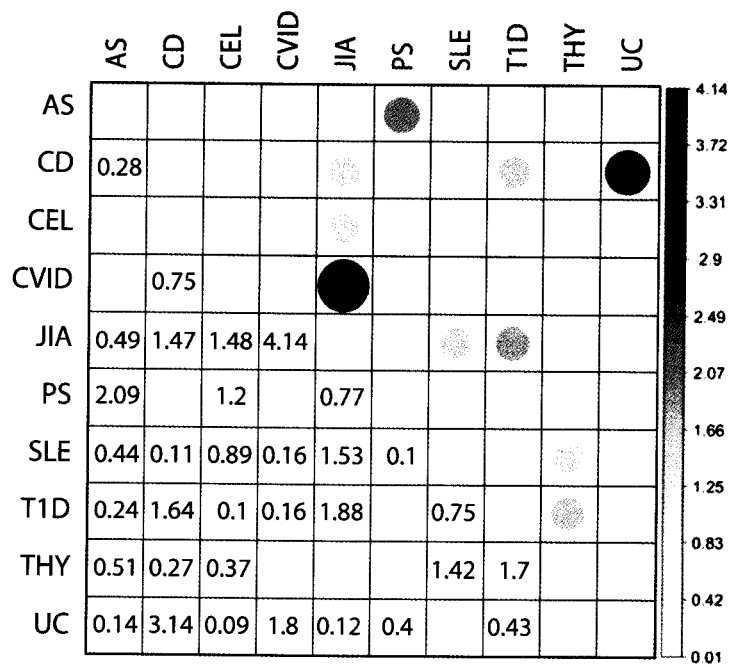
Figure 7C:
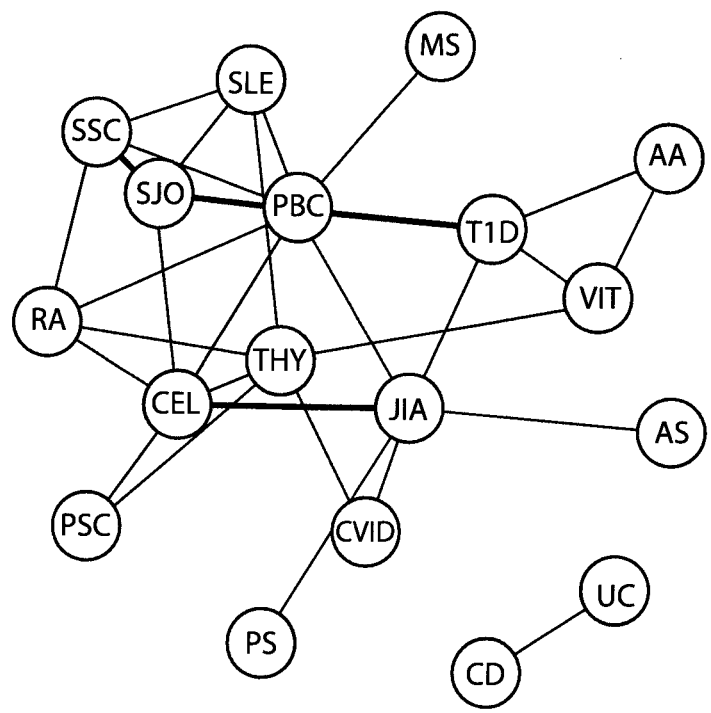
Figure 7C:
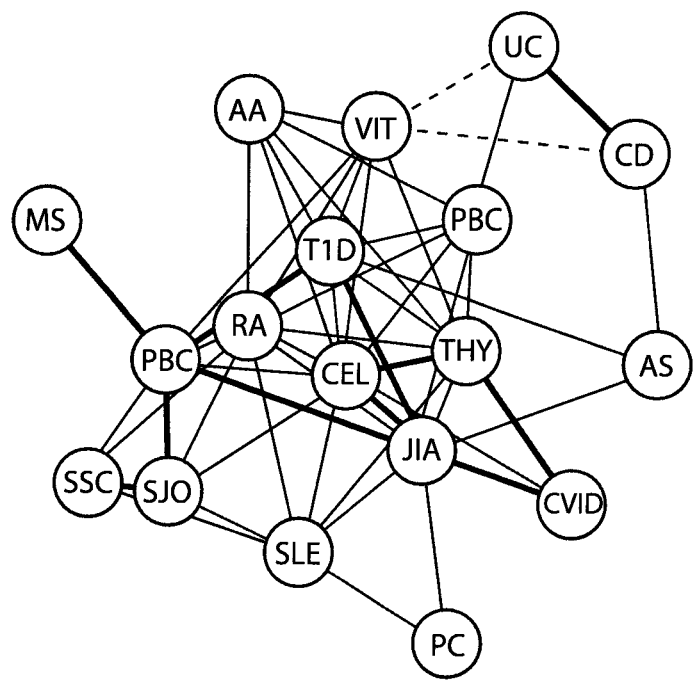

We developed a novel method to specifically examine genome-wide, pair-wise association signal sharing (GPS test) across the pAIDs (See Methods). Only data from the genotyped pAID cohort were used for this analysis. After Bonferroni adjustment for 45 pairwise combinations, the GPS test identified evidence of sharing between a number of pAID pairs noted in prior reports on autoimmune disease, including T1D-CEL ($P_{gps}<3.44\times10^{-5}$), T1D-THY ($P_{gps}<2.03\times10^{-3}$) UC-CD ($P_{gps}<2.36\times10^{-3}$), and AS-PS ($P_{gps}<8.15\times10^{-3}$). We also identified a strong GPS score for JIA-CVID$_{gps}$$<6.88\times10^{-5}$). Interestingly, the correlations between JIA-CVID ($P_{gps}<7.30\times10^{-5}$) and UC-CD ($P_{gps}<7.32\times10^{-a}$) were more significant following the exclusion of markers within the MHC region (FIG. 7B).

Finally, we examined evidence of sharing across the full range of autoimmune diseases using the immunobase (www.immunobase.org)[27]. We identified significant associations between UC-CD ($P<2.15\times10^{-4}$) and JIA-CVID ($P<1.44\times10^{-6}$), along with a number of novel pairwise relationships that include autoimmune diseases other than the ten cohorts unique to this study, such as that between SJO-SS ($P<1.30\times10^{-28}$) and PBC-SJO ($P<3.86\times10^{-12}$). We plotted those relationships that were significant following a Bonferroni adjustment for 153 pairwise tests using an undirected weighted network (FIG. 5B and Table 4). Collectively, these results support genetic sharing between the various autoimmune diseases and allow for further refinement of the shared signals potentially enabling targeted therapeutic interventions to be applied at multiple levels, such as the CD40L/CD40, JAK-STAT and the $TH_1$-$TH_2$/$TH_{17}$-interleukin signaling pathways.

Discussion

A major goal of this study was to identify shared genetic etiologies across pAIDs and illustrate how they jointly and disparately affect pAID susceptibility.

Knowledge of shared genetic etiologies may help pinpoint common therapeutic mechanisms, especially since certain pAIDs (e.g., THY, CEL and T1D) exhibit high rates of comorbidity and concordance in twins with others (e.g., CD and UC) being clustered in families[9,19,45,46]. Thus, among our primary objectives is to identify those patients who share genetic target(s) and identify therapeutic agents which may impact the activity of such genetic targets independent of patient disease classification and thereby develop new therapies, either de novo or through drug repositioning and develop them through studies on mutation positive patients. The goal is to identify therapeutic drug combinations which may act synergistically to alleviate symptoms of disease or inhibit progression to pAID.

Of the 27 pAID GWS association loci identified, 81% were shared by at least two pAIDs (Table 1 and Supplementary Table 1). Moreover, five of the 27 loci are novel signals not previously reported at GWS levels in association with autoimmune diseases, including chr1p31.1 (rs2066363) mapping near LPHN2, a gene that encodes a member of the latrophilin subfamily of G-protein coupled receptors that regulates exocytosis. While this signal associated with JIA and CVID, a microsatellite study of PBC in a Japanese cohort had identified an association signal to a 100 Kb region enclosing LPHN2.[47] Nominally significant replication support at this locus was identified in the adult UC cohort from the IBD consortium. Both JIA and CVID are among the six pAIDs (THY|AS|CEL|SLE|CVID|JIA) associated with the chr4q35.1 locus (rs7660520), which resides just downstream of TNM3 The observed association with a broad range of pAIDs may be related to eQTL signals in TNM3 SNPs that correlate with serum eosinophil counts[48] and IgG glycosylation rates, the latter reported by a landmark study showing a pleiotropic role for IgG glycosylation-associated SNPs in autoimmune disease risk susceptibility.[49] The third novel association was identified near chr10p11.21 (rs7100025) mapping to a transcription-factor ANKRD30A, a gene encoding an antigen recognized by CD8+ T-cell clones[50]. The fourth signal associated with the inflammatory disease PS and CD near chr16q12.1 (rs77150043). This intronic SNP in ADCY7, encodes a member of the adenylate cyclase (AC) enzyme family and is strongly expressed in peripheral leukocytes, spleen, thymus, and lung tissues[51] and supported by mouse data[52]. The fifth novel signal, rs34030418, mapping near CD40LG and associating with CEL|UC|CD, is the ligand of a prominent TNF superfamily receptor CD40[53,54]. CD40 ligand is a particularly compelling candidate as the locus encoding the CD40 receptor is an established GWAS locus in RA and MS, has been functionally studied in cell culture and animal models, and was the focus of a recent large-scale RA drug-screening effort[55].

A set of GWS candidate SNPs are enriched for miRNA and transcription factor (TF) binding sites. We performed a gene-set enrichment analysis[56] using GBAT, identifying 39 significant ($P_{BH}$<0.05) miRNAs, including as top candidates two well-known miRNA families miR-22 and miR-135a (Table 5a). The latter is shown to target IRS2, a regulator of insulin signaling and glucose uptake in a model systems[57]. Our candidate genes are enriched for targets of dozens of TFs, with the most prominent being SP1 ($P_{BH}$<2.30×10$^{-12}$), NFAT ($P_{BH}$<8.54×10$^{-9}$), and NFKB ($P_{BH}$<1.03×10$^{-8}$). See Table 5b.

Figure 6A:
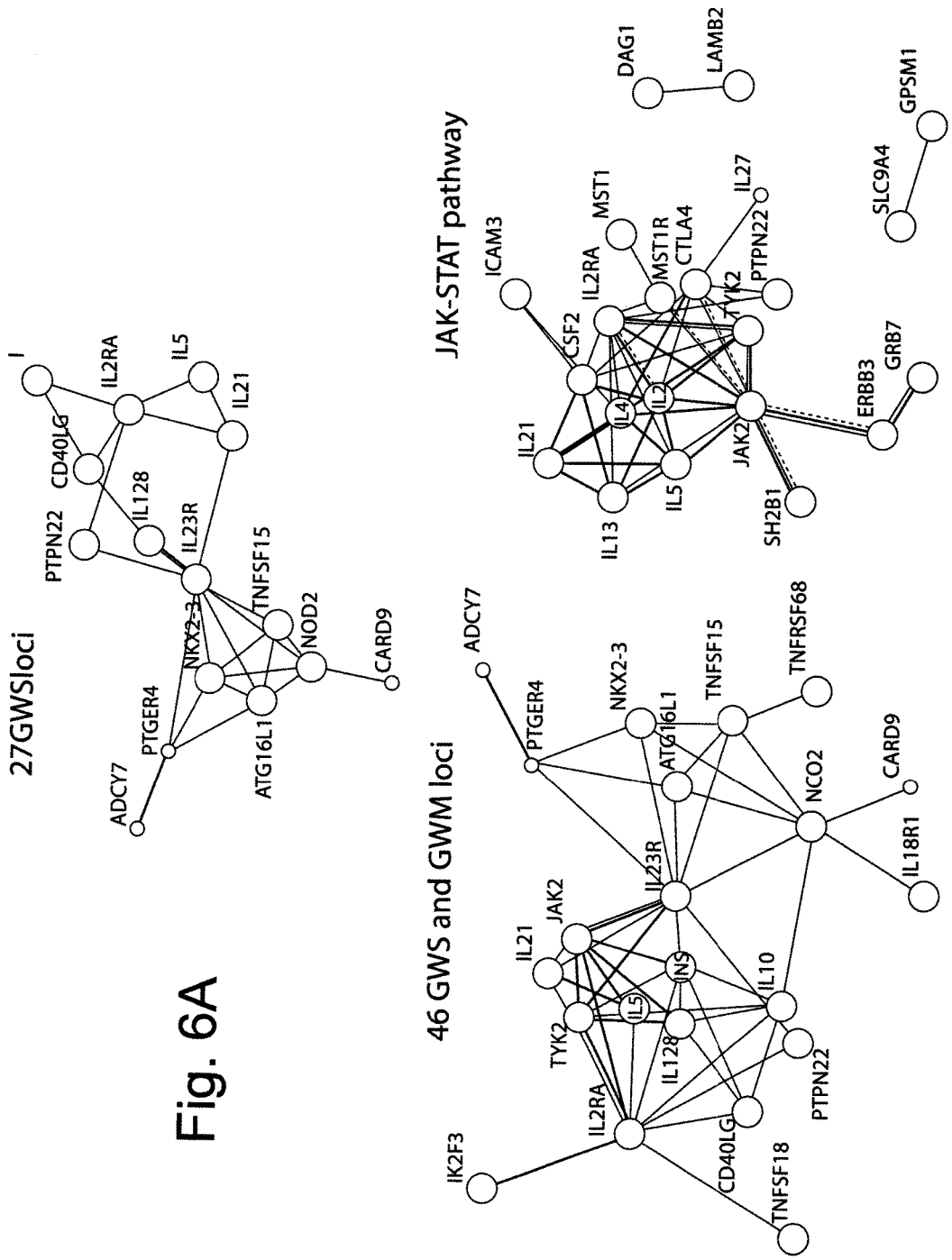
FIGS. 6A-6C.
Figure 6B:
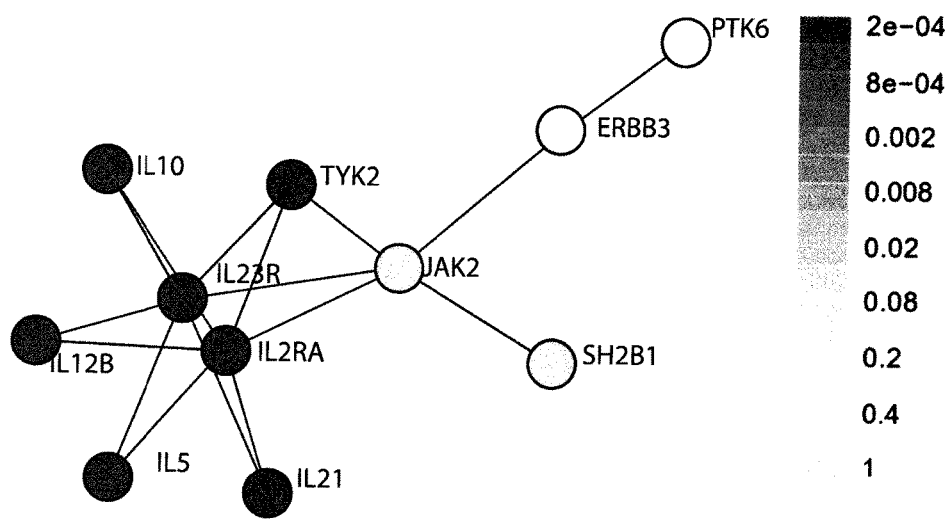

Using GBAT, we identified strong enrichment for proteins that act in cytokine signaling, antigen processing and presentation, T-cell activation, JAK-STAT activation, and $Th_1$, $Th_2$, and $Th_{17}$-associated cytokine signaling using DAVID[58], GSEA[36], IPA[59], and Pathway Commons[60], among others (Table 6). Of these, JAK2 signaling is particularly compelling ($P_{BH}$<6.93×10$^{-5}$; FIG. 6B) consistent the enrichment of known PPIs ($P_{STRING}$<1×10$^{-20}$) (FIG. 6). We also uncovered evidence supporting shared genetic susceptibility for disease pairs that not yet been well-established (e.g. JIA|CVID). The association between JIA and CVID is noteworthy, given that CVID actually represent a group of complex immunodeficiencies rather than a classic autoimmune disease. When we examined the overlap between CVID and all other pAIDs using both the GPS ($P_{adj}$<3.10×10$^{-s}$) and LPS ($P_{adj}$<1.47×10$^{-8}$) network analysis tests, we consistently observed overrepresentation of interaction between CVID and JIA (FIG. 5 and FIG. 7B). Our results show that over 70% (19) of the 27 GWS loci we identified were shared by at least three autoimmune diseases (Table 1), including both previously-reported (e.g., IL2RA [6], IL12B [4]) and novel signals (e.g., TNM3 [6], CD40LG [3]). Moreover, using TGSEA, we not only highlighted the expected enrichment of genes associated with CEL and SLE in $T\gamma_\delta$, $T_{CD4}$ and NK-T cells, but also identified interesting joint enrichment of genes associated with PSC and UC in a set of mature dendritic cells (FIG. 4C).

Many of the shared risk factors in pAIDs impact genes that encode for proteins which are established therapeutic targets, for example the anti-CD40L and anti-CD40 antibodies[54,55] and a number of the genes identified here have diverse biological effects and are currently in clinical development. Consequently, drug repurposing approaches may present feasible options in pAIDs, where these gene networks and pathways will be targeted in an expedited manner.

Methods

Affected subjects and controls were identified either directly as described in prior studies[61,62, 63,64,65,66,67,68,69,70] or from de-identified samples and associated electronic medical records (EMRs) in the genomics biorepository at The Children's Hospital of Philadelphia (CHOP). The predominant majority (>80%) of the included cases for IBD, T1D and CVID have been described in previous publications.

Details of each study population are outlined below. EMR searches were conducted with previously described algorithms based on phenotype mapping established using phenome-wide association study (PheWAS) ICD-9 code mapping tables[61,62,63,70] in consultation with qualified physician specialists for each disease cohort. All DNA samples were assessed for quality control (QC) and genotyped on the Illumina HumanHap550 or HumanHap610 platform at the Center for Applied Genomics (CAG) at CHOP. Note that the patient counts below refer to the total recruited sample size from which we excluded non-qualified samples or genotypes that did not pass QC criteria required for inclusion in the genetic analysis (for example, because of relatedness or poor genotyping rate).

The IBD cohort comprised 2,796 individuals between the ages of 2 and 17, of European ancestry, and with biopsy-proven disease, including 1,931 with CD and 865 with UC and excluding all patients with unclassified IBD. Affected individuals were recruited from multiple centers from four geographically discrete countries and were diagnosed before their 19th birthday according to standard IBD diagnostic criteria, as previously reported[63,65].

The T1D cohort consisted of 1,120 subjects from nuclear family trios (one affected child and two parents), including 267 independent Canadian T1D patients collected in pediatric diabetes clinics in Montreal, Toronto, Ottawa and Winnipeg and 203 T1D patients recruited at CHOP since September 2006. All patients were Caucasian by self-report and between 3 and 17 years of age, with a median age at onset of 7.9 years. All patients had been treated with insulin since diagnosis. Disease diagnosis was based on these clinical criteria, rather than on any laboratory tests.

The JIA cohort was recruited in the United States, Australia and Norway and comprised a total of 1,123 patients with onset of arthritis at less than 16 years of age. JIA diagnosis and JIA subtype were determined according to the International League of Associations for Rheumatology (ILAR) revised criteria[71] and confirmed using the JIA Calculator[72] (http://www.ra-researCh.org/JIAcalc/), an algorithm-based tool adapted from the ILAR criteria. Prior to standard QC procedures and exclusion of non-European ancestry, the JIA cohort comprised 464 subjects of self-reported European ancestry from Texas Scottish Rite Hospital for Children (Dallas, Tex., USA) and the Children's Mercy Hospitals and Clinics (Kansas City, Mo., USA); 196 subjects from CHOP; 221 subjects from the Murdoch Children's Research Institute (Royal Children's Hospital, Melbourne, Australia); and 504 subjects from Oslo University Hospital (Oslo, Norway).

The CVID study population consisted of 223 patients from Mount Sinai School of Medicine (MSSM; New York, N.Y., USA), 76 patients from University of Oxford, (London, England), 47 patients from CHOP, and 27 patients from University of South Florida (USF; Tampa, Fla., USA). The diagnosis in each case was validated against the ESID-PAGID diagnostic criteria, as previously described[73]. Although the diagnosis of CVID is most commonly made in young adults (ages 20-40), all of the CHOP and USF subjects had pediatric-age-of-onset disease, whereas the majority of the subjects from MSSM and Oxford had onset in young adulthood. We note that as the number of individuals with adult-onset CVID is so small (less than 5% of all cases presented) and all ten diseases studied here can present with pediatric age of onset, we elected to refer to the cohort material as pAID.

The balance of the pediatric subjects' (THY, AS, PSOR, CEL and SLE; a full list of phenotype abbreviations is provided in the Tables) samples were derived from our biorepository at CHOP, which includes more than 50,000 pediatric patients recruited and enrolled by CAG at CHOP (The Tables include details of genotyped subjects within the CAG pediatric biobank). These individuals were confirmed for diagnosis of THY, SPA, PSOR, CEL and SLE in the age range of 1-17 years at the time of diagnosis and were required to fulfill the clinical criteria for these respective disorders, as confirmed by a specialist. Only patients that upon EMR search were confirmed to have at least two or more in-person visits, at least one of which was with the specified ICD-9 diagnosis code(s), were pursued for clinical confirmation. We used ICD-9 codes previously identified and used for PheWASs or EMR-based GWASs and agreed upon by board-certified physicians[62,63].

Age- and gender-matched control subjects were identified from the CHOP-CAG biobank and selected by exclusion of any patient with any ICD-9 codes for disorders of autoimmunity or immunodeficiency[61] (http://icd9.chrisendres/). Research ethics boards of CHOP and other collaborating centers approved this study, and written informed consent was obtained from all subjects (or their legal guardians). Genomic DNA extraction and sample QC before and after genotyping were performed using standard methods as described previously[64]. All samples were genotyped at CAG on HumanHap550 and 610 BeadChip arrays (Illumina, CA). To minimize confounding due to population stratification, we included only individuals of European ancestry (as determined by both self-reported ancestry and principal-component analysis (PCA)) for the present study. Details of the PCA are provided below.

Genotyping, Imputation, Association Testing and QC.

Disease-Specific QC.

We merged the genotyping results from each disease-specific cohort with data from the shared controls before extracting the genotyping results from SNPs common to both Infinium HumanHap550 and 610 BeadChip array platforms and performing genotyping QC. SNPs with a low genotyping rate (<95%) or low MAF (<0.01) or those significantly departing from the expected Hardy-Weinberg equilibrium (HWE; $P<1\times10^{-6}$) were excluded. Samples with low overall genotyping call rates (<95%) or determined to be of outliers of European ancestry by PCA (>6.0 s.d. as identified by EIGENSTRAT[74]) were removed. In addition, one of each pair of related individuals as determined by identity-by-state analysis (PI_HAT>0.1875) was excluded, with cases preferentially retained where possible.

Merged-Cohort QC.

To prepare for whole-genome imputation across the entire study cohort, we combined case samples across the 10 pAIDs with the shared control samples. We repeated the genotyping and sample QC with the same criteria as described above, leaving a final set of ~486,000 common SNPs passing individual-cohort and merged-cohort QC. We again performed identity-by-state analysis and removed related samples (in order to remove related subjects that may have been recruited for different disease studies). We also repeated the PCA and removed population outliers. The final cohort, after the application of all QC metrics mentioned above, included a total of 6,035 patients representing ten pAIDs and 10,718 population-matched controls.

Note that because of the merged QC, compared with the sum of all ten disease-specific GWASs, the final case and control counts in the merged cohort were smaller than the "sum of all cases and controls" (Supplementary Table 1a). In addition, to avoid the potential for confounding due to the presence of duplicated samples, we assigned individuals fitting the diagnostic criteria for two or more pAIDs to whichever disease cohort had the smaller (or smallest) sample size. No subject was included twice. A total of 160 subjects in the study cohort fulfilled criteria for two or more diseases but were counted only once in our reported total of 6,035 unique subjects.

Whole-Genome Phasing and Imputation.

We used SHAPEIT[75] for whole-chromosome prephasing and IMPUTE2 (ref. 76) for imputation to the 1KGP-RP (https://mathgen.stats.ox.ac.uk/impute/impute v2.html, June 2014 haplotype release). For both, we used parameters suggested by the developers of the software and described elsewhere[75,76,77]. Imputation was done for each 5-Mb regional chunk across the genome, and data were subsequently merged for association testing. Prior to imputation, all SNPs were filtered using the criteria described above.

To verify the imputation accuracy, we validated randomly selected SNPs that reached a nominally significant P value after imputation. Because commercially designed genotyping probes were not readily available, we performed Sanger sequencing by designing primers to amplify and sequence the 200-bp region around the imputed SNP markers for two separate 96-well plates. We manually visualized and examined sequences and chromatograms using SeqTrace[78]. Results from this are presented in Supplementary Table 1e, showing >99% mean imputation accuracy.

In addition, a subset of the IBD and CVID subjects were subsequently genotyped on the Immunochip (Illumina) platform. We compared the genotype concordance of all pAID GWAS imputed SNPs that were directly genotyped on the Immunochip after performing sample and marker QC as described above. Results are shown in Supplementary Table 1f.

Disease-Specific Association Testing.

We performed whole-genome association testing using post-imputation genotype probabilities with the software SNPTEST (v2.5)[24]. We used logistic regression to estimate odds ratios and betas, 95% confidence intervals and P values for trend, using additive coding for genotypes (0, 1 or 2 minor alleles). For autosomal regions, we used a score test, whereas for regions on ChrX we used the ChrX-specific SNPTEST method Newml. QC was performed directly after association testing, excluding any SNPs with an INFO score of <0.80, HWE $P<1\times10^{-6}$, and MAF<0.01 (overall).

In all analyses, we adjusted for both gender and ancestry by conditioning on gender and the first ten principal components derived from EIGENSTRAT PCA[79]. The $\lambda_{GC}$ values for all cohorts were within acceptable limits; the highest was observed for the cohort with the largest case sample size, namely, CD ($\lambda_{GC}<1.07$), consistent with what was previously reported for this data set. In fact, we have previously reported on all the non-CHOP cases included in the present analysis in individual studies using CHOP controls and shown that these individual case-control analyses were well controlled for genomic[61,62,63,64,65,66,67,68,69,70]. A QQ plot is provided for each independent cohort in FIG. 2C-1.

Meta-Analysis to Identify Shared pAID Association Loci.

To identify association loci shared across pAIDs, we meta-analyzed the summary-level test statistics from each of the study cohorts after extracting those markers that passed post-association testing QC for all ten individual disease-specific analyses. To adjust for confounding due to the use of a shared or pooled control population, we applied a previously published method to perform an inverse weighted $\chi^2$ meta-analysis[80].

We LD-clumped the results of the meta-analysis (PLINK) and identified 27 LD-independent associations ($r^2<0.05$ within 500 kB up- or downstream of the lead or most strongly associated SNP) reaching a conventional genome-wide significance threshold of $P_{META}<5\times10^{-8}$. We observed that the calculated meta-analysis $\lambda_{GC}$ was less than 1.09. As recently discussed by de Bakker and colleagues and shown in a number of large-scale GWAS publications, $\lambda_{GC}$ is related to sample size. As discussed by Yang et al., $\lambda_{GC}$ depends on the relative contribution of variance due to population structure and true associations versus sampling variance: with no population structure or systematic error, inflation would still depend on heritability, genetic architecture and study sample size[82]. On the basis of de Bakker et al.'s recommendations, we also calculated a sample-size-adjusted $\lambda_{1000}$ by interpolating the $\lambda_{GC}$ that would have been expected if this study had included only 1,000 cases and 1,000 controls. We performed this only for the meta-analysis results, as the case and control counts for the meta-analysis were both significantly greater than 1,000 (Supplementary Table 1a).

Model Search to Identify pAIDs Associated with the Lead Signals.

The meta-analysis identified SNPs significantly associated with at least one pAID. To determine which pAIDs each SNP was most strongly associated with, we performed a model or 'disease-combination' search. For the lead SNP in each pAID-association locus, we searched for the pAID disease combination that, when the corresponding cases were merged in a mega-analysis, yielded the largest association test statistic.

To identify the disease phenotypes most likely contributing to each identified association signal, we applied the "h.types" method as implemented in the R statistical software package ASSET[83] to perform an exhaustive disease-subtype model search. Note that ASSET provides both a method for genotype-level association testing (h.types used in this study) and a summary-level modified fixed-effect meta-analysis approach ("h.traits") that allows for heterogeneity of SNP effects across different phenotypes. Both methods exhaustively enumerate each combination of phenotypes that are jointly considered, and therefore test a total of where r is the total number of disease subtypes assigned to cases (for example, ranging from one to ten pAIDs) and n is the total number of disease subtypes (i.e., ten pAIDs). Note that this reduces to $2^n-1$ (or 1,023 unique combinations here), as in this case we considered all possibilities of r across n of ten diseases. The ASSET algorithm iteratively tests each pAID case combination using logistic regression to determine whether there is an association between genotype counts and case status. For each SNP tested, the 'optimal' subtype model is the combination of pAIDs that, when tested against the shared controls in the logistic regression analysis produced the best test statistic after the DLM method had been used to correct for multiple testing across all subtype combinations.

Identification of Lead Associated Variants Showing Opposite Direction of Effect.

For each of the top 46 associating loci ($P_{META}<1\times10^{-6}$), we identified those loci for which the lead SNP had an effect direction (on the basis of logistic regression betas) opposite that reported for the disease combination identified by the subtype model search and whose corresponding association P value reached at least nominal significance (P<0.05). We identified nine instances.

Candidate Gene Prioritization.

To annotate the lead SNPs to candidate genes, we prioritized the mapping to candidate genes systematically in the following manner:
 1. If the SNP or locus was previously reported in autoimmune diseases at genome-wide significance, we provided the candidate gene symbol, where available, as identified in the GWAS Catalog or ImmunoBase.
 2. If an SNP was annotated as coding or fell within the coding DNA sequence (i.e., intronic or in the UTRs), we reported that gene as identified by the variant effect predictor (VEP).
 3. If the SNP was upstream, downstream, or intergenic, we prioritized the gene by using the best candidate gene identified with the network tool DAPPLE[86].
 4. If none of the above was feasible, we manually curated the most 'likely' gene on the basis of the observed LD block and evidence of prior association signals with autoimmune diseases or other immune-related phenotypes as presented in the dbSNP or GWAS catalog.

Functional or Biological Annotations and Enrichment Analysis Using Publicly Accessible Resources.

We annotated the lead pAID-associated SNPs using publicly available functional and biological databases and resources. We considered the top imputed lead SNP for each locus and, in addition, any of its near-perfect proxies (defined as $r^2>0.8$ within 500 kB up- or downstream) on the basis of the 1KGP-RP.

We included annotation, expression, interaction and network data from the following resources:
 1. Genomic mapping and annotation: SNAP[87], SNP-Nexus[88], Ensemble[89] and UCS[90].
 2. Regulatory annotations: EnCODE (TF-binding sites and DNase-hypersensitivity sites)[91], GTex[92] (eQTLs), and a published lymphoblastoid cell line eQTL data set[93].
 3. Functional annotations: SIFT, Polyphen[95], miRNA target site polymorphisms[96,97].
 4. Conservational or evolutionary predictions: GERP[98], PHAST++[99], CpG islands[100].
 5. Literature search: GAD[101], NHGRI GWAS catalog[102], dbGAP[103], or published Immunochip studies[104] (http://www.immunobase.org) for literature support.
 6. Gene expression and enrichment analysis: ImmGen[102] (murine) and whole-transcriptome analysis across 126 tissues[104] (human).
 7. Protein-protein interaction (PPI) database: DAPPLE[86], STRING[105].
 8. Pathway-based and gene set enrichment analysis: Gene Ontogeny[106], Webgestalt[107], Wikipathways[108], IPA[109], DAVID[110], GSEA[111] and Pathways Commons[112].
 9. Gene network analysis and visualization: DAPPLE[86] and VEP[85] to prioritize candidate causal genes and Grail[113] for text-mining of PubMed database for coassociations.

Figure 4D:
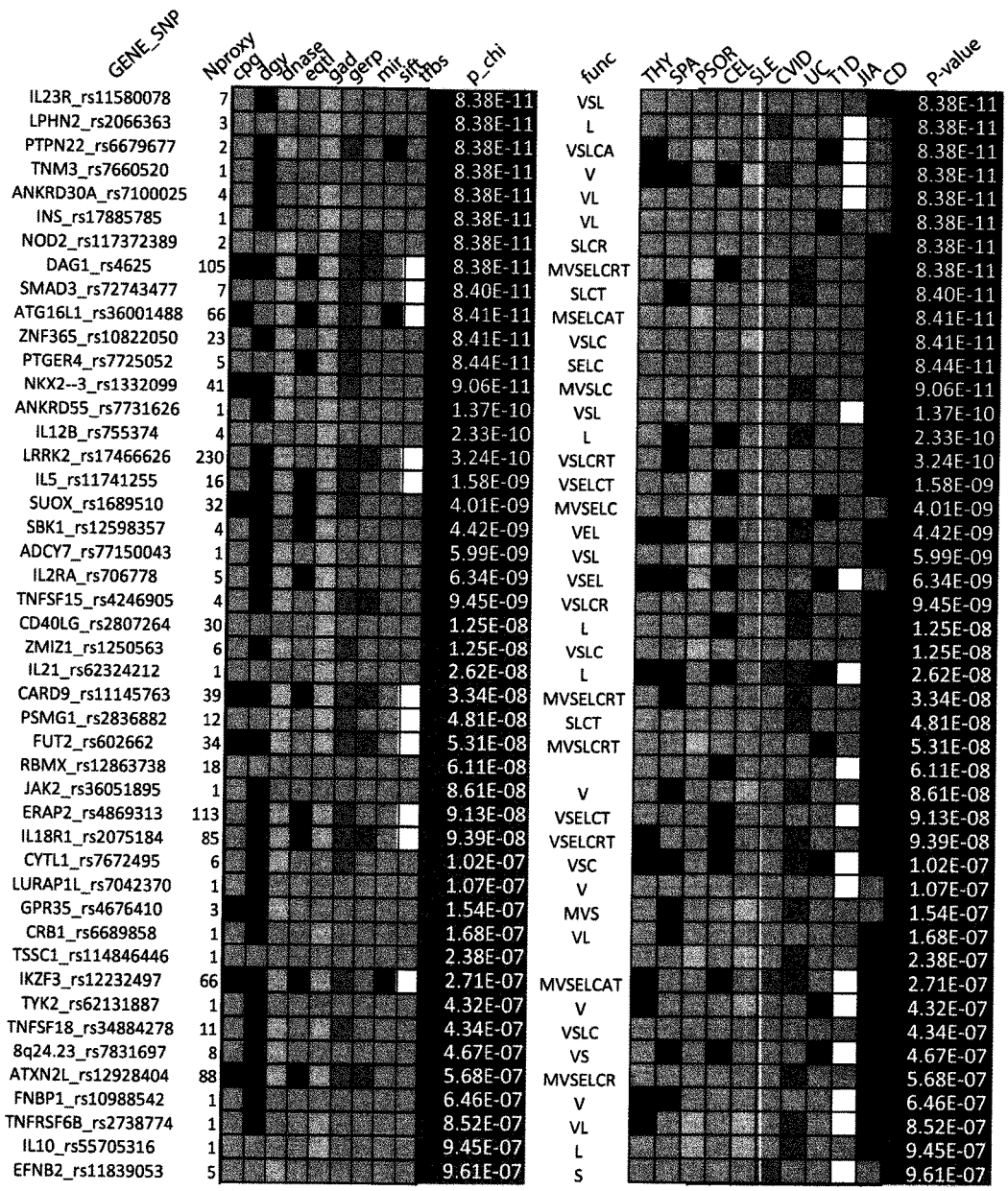

Functional and biological annotations (categories 1-5) for the 27 lead SNPs are illustrated in FIG. 3a; annotations are also provided for the 46 GWM loci in FIG. 4D. The following annotation types were used:
 1. Regulatory: EnCODE consensus TF-binding sites (T), DNase I hypersensitivity sites (S), or published eQTL signals (E)
 2. Functional: known mutations in PolyPhen or SIFT (A), experimentally validated (miRBASE 18.0) and predicted (mirSNP) miRNA target sites (R), or SNPs that tag regions containing common copy-number variation regions reported by the database of genomic variants (DGV) (V)
 3. Conserved: conserved nucleotide sequences based on GERP++/phastCon (C) or known CpG islands that correlate with epigenetic methylation patterns (M)
 4. Literature-supported: published association with immune or inflammatory diseases or immune-related endophenotypes from candidate studies or GWASs catalogued in the Genetic Association Database, NHGRI GWAS catalog, dbGAP, or Immunochip studies (L)

In addition to determining whether the 27 GWS pAID-associated SNPs were enriched for a given annotation type, we performed Monte Carlo simulations to resample 10,000 times the SNPs (MAF>0.01 in Europeans) from all SNPs in 1KGP-RP. As for the 27 lead SNPs, for each set of 100 randomly sampled SNPs, we expanded the list by first identifying all nearby SNPs in strong LD (i.e., LD proxies with $r^2>0.8$ within 500 kB up- or downstream) within the 1KGP-RP data set filtered for only SNPs with MAF>0.01 in the European population. We then annotated each original and any proxy SNPs as above for each major annotation category. We collapsed the information for all proxies identified for a given lead such that for any given category, if the lead SNP or any of its proxies were annotated, the lead SNP was marked as annotated. We then calculated the frequency of annotation for the 100 SNPs in each set. After sampling and annotating 100-SNP sets 10,000 times, we use the permutation-derived distribution of annotation percentages for each annotation type to calculate an enrichment P value such that where N is the number of permutations, f is the percentage of SNPs in the pAID set that are annotated and F is the distribution of the percentage of SNPs annotated across 10,000 sets of 100 SNPs resampled from the 1KGP-RP using only markers with MAF>0.01 in Europeans.

Hierarchical Clustering Based on Effect Size and Direction of Association.

We performed agglomerative hierarchical clustering across the top 27 independent loci using the directional Z-score obtained from logistic regression analysis in each of the ten disease-specific GWASs, defined as where beta is the effect size. The standardized and normalized Z-scores were used as inputs to the agglomerative hierarchical clustering. We used Ward's minimal-variance method to identify relatively consistent gene and locus cluster sizes.

Gene-Based Association Testing.

Given our interest in genetic overlap across pAIDs, we sought to identify genes associated with pAIDs in a disease-agnostic manner that was insensitive to locus and phenotypic heterogeneity. We used VEGAS[114], a set-based method, to perform GBAT. As input, we used the nominal $P_{META}$ values from the pooled, inverse $\chi^2$ meta-analysis for the ten pAIDs across the genome as the input summary statistics for VEGAS, without considering which specific diseases were identified in the model search analysis. We assigned SNPs to gene regions and performed $10^7$ simulations to estimate the gene-based P value as described in VEGAS's documentation. We used two thresholds: $P_{sim}<2.8\times10^{-6}$ to identify significant candidate genes, on the basis of a Bonferroni adjustment for approximately 17,500 genes tested, and a false discovery rate (FDR) of <2%, which corresponds to a q value of <0.0205, which was used only for pathway and gene set enrichment analysis.

Tissue-Specific Gene Set Enrichment Analysis.

With few exceptions, most genes that are known to have a causative role in autoimmune disease have been shown to regulate molecular or subcellular processes in immune or immune-related tissues. If candidate pAID-associated genes are relevant to autoimmune-disease biology, then expression of these genes would be expected to be, on average, higher across immune or immune-related tissues (as compared with expression in non-immune-related tissues). Thus, we compared the expression of candidate pAID-associated genes identified by GBAT with that of non-candidate genes in a variety of tissues.

We curated the expression of the transcriptome in a broad spectrum of human tissues using a publicly available data set consisting of summary-level, normalized gene expression levels for more than 12,000 unique genes across 126 tissues and/or cell types, including a large number of immune tissues and cells[104]. We downloaded the processed data set "mean expression data matrix."

Across the 126 unique tissues, we tested whether the median or cumulative distribution of expression of pAID-associated gene transcripts as identified by GBAT was higher than that of the remaining transcripts in the data set using a one-sided Wilcoxon rank test or a one-sided Kolmogorov-Smirnov (KS) test, respectively. We calculated a tissue-specific gene expression ES value, which is the $-\log_{10}$ (P value) obtained from comparing the relative enrichment in transcript expression of pAID-associated genes versus the transcripts of the remaining genes in the data set. The tests were done on a per-tissue basis to derive a set of KS and a set of Wilcoxon ES values. We performed this per tissue analysis (1) for the total set of pAID-associated genes from GBAT and (2) when genes across the extended MHC (chr6: 25-34 Mb) were excluded.

We performed the secondary immune-versus-non-immune comparative analysis by plotting the ES values obtained from either Wilcoxon or KS tests in descending rank order of the respective test statistics, as shown in FIG. 4a and FIGS. 5D and 5E for all 126 tissue types. In those figures each point represents a single tissue and is colored according to its classification as either immune (red) or non-immune (blue), as described previously[86].

To formally test whether the overall ES values were higher among immune tissues than among non-immune tissues, we performed both the Wilcoxon rank sum test and the KS test on the vector of per-tissue ES values, comparing those derived from immune and non-immune tissues. We found that the enrichment observed across immune tissues was specific and not general to any GWAS-identified signals. We repeated this analysis in two sets of candidate genes, one for CD and another for schizophrenia, by identifying all associated genes for the two phenotypes from the NHGRI GWAS Catalog.

Immune Cell Gene Set Enrichment Analysis.

Cells of the immune system are extremely diverse in function and gene expression. To more precisely assess the expression of pAID-associated genes, we examined the mRNA expression of pAID candidate genes across specific immune cell subtypes, as well as during different developmental time points.

ImmGen provides a publicly available, high-quality murine gene expression data set. The ImmGen data set consists of 226 murine immune cell types across different lineages at multiple developmental stages, sorted by FACS and assayed at least in triplicate. Standard QC and quantile-normalization methods were applied to the data set as described by ImmGen[102]. The total set of transcripts mapped to 14,624 homologs in the human transcriptome on the basis of genes annotated in the hg18/build36 of the human reference genome, which were used to query the gene expression data. Some of the cell types were derived from genetically altered animals, and the results from analysis of those cell types would have been difficult to interpret, so we removed those cell lines from the analysis. The complete list of cell types used in the analysis and the category to which we assigned each cell type for the categorical analysis are presented in Table 3c. A total of 176 unique cell lines remained for subsequent analyses using this data set.

As with the human data set, we calculated the ES values by comparing the expression of the pAID-associated candidate gene transcripts to that of the remaining transcripts assayed in the data set for each immune cell type examined. We plotted the distribution of relative gene expression ES values as a density plot across the range of ES values from all of the examined cell types available. We compared the results obtained using the full set of candidate pAID genes identified by GBAT or obtained when we excluded the genes within the extended MHC. To ensure that this was not simply a result of selection bias (as GWASs may be biased toward regions or genes across the genome that are better sampled or more densely genotyped), we compared the results to those obtained with the curated gene lists from the GWAS catalog (as above) for CD, schizophrenia, body mass index and LDL cholesterol.

To determine whether pAID-associated candidate genes are expressed at higher levels (relative to the rest of the genes in the transcriptome) in some immune cell types than in others, we defined immune cell types according to surface marker expression and tissue isolation details provided by ImmGen. Some categories were further divided into subcategories (for example, B and T cells) on the basis of developmental stage or lineage into a total of 16 non-overlapping cell-type categories. To compare the results across the cell-type categories, we plotted the distribution of ES value ranks for each cell type, binning the results according to the category each cell type belonged to (again, we performed the analysis either with or without the extended MHC region).

Expression Profiling of Pleiotropic Autoimmune Disease-Associated Genes Across Specific Immune Cell Types.

We profiled the expression of genes that had been identified in at least three autoimmune diseases in our subtype model search, previously published Immunochip fine-mapping studies, or a combination thereof (for example, identified as associated with JIA and UC in our analysis but previously identified as a candidate gene from an Immunochip analysis of alopecia areata). We identified 217 candidate pleiotropic genes, of which 191 could be mapped to unique gene transcripts within the ImmGen data sets.

We performed agglomerative hierarchical clustering with the matrix of gene expression levels from the 191 candidate gene transcripts using Ward's minimal-variance method across all 176 immune cell types. The genes and cell types shown in dendrograms are based on the results of unsupervised hierarchical clustering analysis and represent four major groups of cells and six major groups of genes.

We examined whether genes that were clustered on the basis of similar immune cell-expression profiles were likely to be associated with the same disease(s). Specifically, given a set of genes associated with one or more autoimmune diseases grouped in cluster i ($C_i$), we asked whether there is an increased likelihood (i.e., more so than expected by chance as compared with genes not found within this cluster) that these genes are also associated with disease j ($D_j$), such that where the expected probability of the values observed under the null is given by the hypergeometric distribution. As some of the cell counts were small and we were interested only in identifying instances where a>>b, c or d, we used a one-sided Fisher's exact test. We first tested each of the 18 autoimmune diseases across all identified clusters, declaring nominal and Bonferonni-adjusted significance at P<0.05 and P<5.6×10$^{-4}$, respectively. For any clusters where at least two diseases reached nominal or marginal significance, we also tested whether there was an overrepresentation of genes associated with both diseases at P<0.05.

PPI and Network Analysis.

DAPPLE[86]: PPIs among the set of either 27 GWS or 46 GWM candidate regions were identified; the input seeds were defined as the 100-kB sequences up- and downstream of the most significantly associated SNP (based on hg19) in each candidate region. Other input parameters included 50-kB regulatory region length, a common interactor binding degree cutoff of 2, and the following specified known genes: IL23R, PTPN22, INS, NOD2, DAG1, SMAD3, ATG16L1, ZNF365, PTGER4, NKX2-3, ANKRD55 and IL12B. We performed 10,000 permutations to accurately calculate enrichment network statistics. Seed scores $P_{dapple}$ were used to color the protein nodes in the network plot.

Figure 6C:
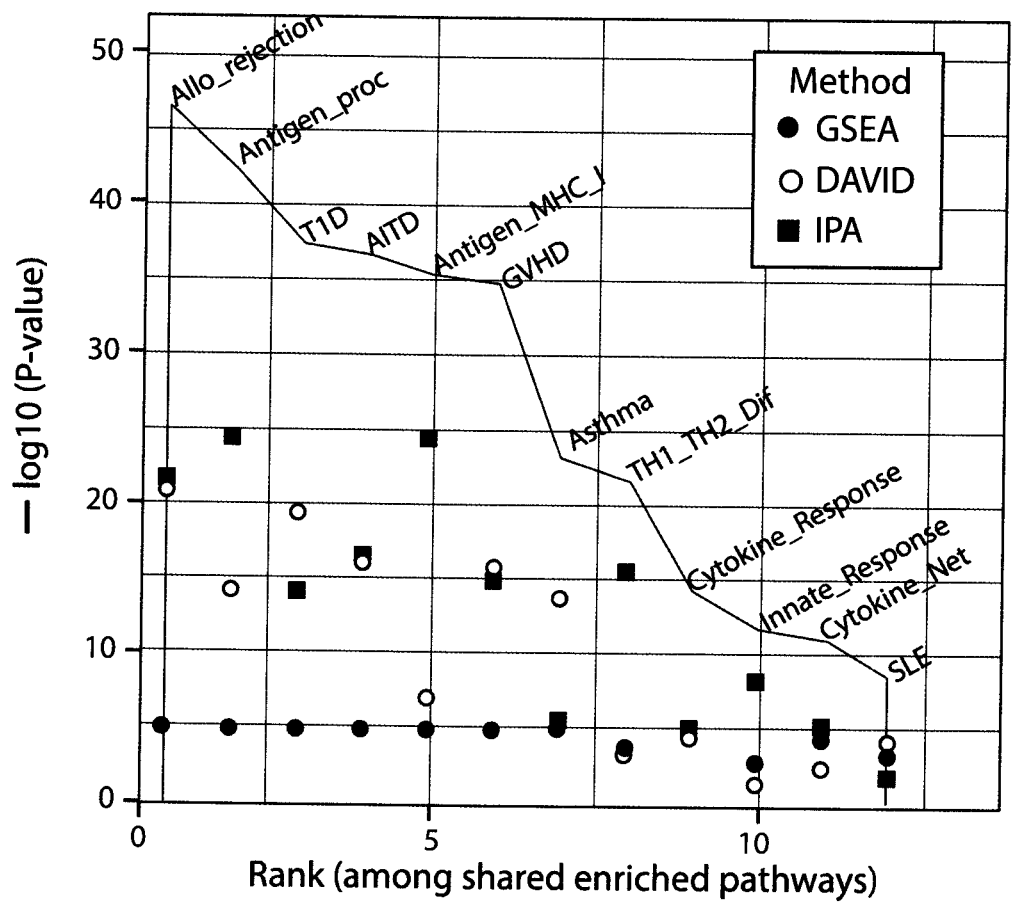

STRING[105]: We used the *Homo sapiens* PPI database to query one of three lists: (1) the GWS loci, (2) GWS and GWM loci or (3) the list of genes identified by GBAT shown to be enriched for key proteins in the JAK-STAT pathway. We assessed and reported the evidence of PPI enrichment on the basis of these queries as compared to the results expected for the rest of the genes in the human genome. We generated network plots for the directly connected protein candidates (FIGS. 6A-6C represents the "evidence" plot option).

Pathway and Gene Set Enrichment Analysis.

Webgestalt[107]: For pathway and gene set analysis, we used the web-based tool Webgestalt to examine evidence of shared TF binding, miRNA target-binding sites, and enrichment in specific Gene Ontology and Pathway Commons categories. The inputs for this analysis included all lead genes (FDR<2%) from the GBAT (similar to that for the other pathway annotation databases below for consistency).

DAVID[110]: We used the bioinformatics web tool DAVID (v6.7, available at http://david.abcc.nciferf.gov) for functional-annotation analysis of the significant genes. Significant genes with FDR<2% in VEGAS, the gene-based association analysis, were used as input for DAVID. DAVID performed overrepresentation analysis of functional-annotation terms on the basis of hypergeometric testing and adjusted for multiple testing. To compare the results of this analysis with results obtained via other methods, we used BioCarta, KEGG pathways and GO BP FAT as gene set definition files.

IPA[109]: We used IPA software (http://www.ingenuity.com/) for canonical pathway and network analysis. We inputted all the significant genes in the VEGAS output (FDR<2%) for IPA analysis. In the IPA core analysis, we selected the Ingenuity Knowledge Base (Genes Only) as the reference set, including both direct and indirect relationships. We used the filter setting of relationships in human and experimentally observed only. Information regarding canonical pathways was obtained from IPA output.

GSEA[115,116]: We conducted gene set enrichment analysis with the software GSEA (http://www.broadinstitute.org/gsea) using as input the pre-ranked gene list generated on the basis of the −log(P value) from VEGAS using all genes. We selected the following settings for our analysis: number of permutations, 5,000; enrichment statistic, weighted; maximum size of gene set, 500; minimum size of gene set, 15; and with normalization.

Interdisease Genetic Sharing Analysis.

To examine the degree of overlap in genetic risk susceptibility between any two autoimmune diseases, we developed and/or implemented the following statistical measures to quantify interdisease genetic sharing:

1. LPS test, optimized to evaluate whether two pAIDs share more loci in common than would be expected to occur by chance; the score 'penalizes' disease pairs if many of the loci are disease specific. The test is helpful if only data on whether diseases share specific candidate genes or association loci in common are known.
2. GPS test, optimized to assess the correlation between the set of association test statistics observed genome-wide across any two pAIDs. This test is valuable because it is independent of the gene sets chosen and thus does not require the use of any arbitrary method to define a significance 'threshold' of input data.

LPS Analysis.

To quantify the similarity between any two diseases $D_1$ and $D_2$ on the basis of the degree to which $D_1$ and $D_2$ share independent genetic risk associations (i.e., loci, SNPs or candidate genes), we considered the following model.

We began with a list of candidate genes, association loci or LD-independent SNPs $n_r$, identified as having reached a predefined GWAS significance threshold (e.g., GWS or GWM) across one or more SNPs from $n_r$, for a set of diseases with expected or hypothesized sharing (i.e., all autoimmune diseases in this study and those reported on by the Immunochip studies catalogued by ImmunoBase[83]).

For any two diseases $D_1$ and $D_2$, a given candidate gene or SNP $x_i$ could be uniquely classified in one of four ways: associated with $D_1$ and $D_2$ ($n_{11}$), associated only with $D_1$ ($n_{12}$) or $D_2$ ($n_{21}$), or associated with neither $D_1$ nor $D_2$ ($n_{22}$). For any given list of TOP associations (i.e., $n_r$), the distribution across the four possible categories can be tabulated as follows:

| Locus $x_i$ | $D_2$ (yes) | $D_2$ (no) |
| --- | --- | --- |
| $D_1$ (yes) | $n_{11}$ | $n_{12}$ |
| $D_1$ (no) | $n_{21}$ | $n_{22}$ | where $n_{11}+n_{12}+n_{21}+n_{22}=n_r$, and $D_1$ (yes) or (no) means the SNP $x_i$ is or is not associated with that marker, respectively. The probability $P_x$ that an SNP $x_i$ from the list $n_r$ is associated with either $D_1$ or $D_2$ can be expressed as:

$$P_1 = \frac{n_{11}+n_{12}}{n_r} \text{ (for } D_1\text{)}$$

$$P_2 = \frac{n_{12}+n_{21}}{n_r} \text{ (for } D_2\text{)}$$

for any two pAIDs $D_1$ and $D_2$.

Thus, the frequency at which $x_i$ should truly be associated with two distinct disease subtypes is given by $n_r(P_1 P_2)$, and the observed number of overlapping associations is represented by $n_{11}$. Therefore, under the null hypothesis $H_0$, for a given pair of diseases $D_1$ and $D_2$, the variance of the difference between the numbers of expected and observed associations of all those tested ($n_T$) shared by both $D_1$ and $D_2$ should follow a normal distribution.

$$z = \frac{n_{11} - n_r(P_1 P_2)}{\sqrt{n_r(P_1 P_2)(1 - P_1 P_2)}} \sim N(0, 1)$$

We used the one-sided Z-test to examine whether the degree of overlap was significantly greater than expected, assuming a normal distribution under the null hypothesis that $D_1$ and $D_2$ do not share more associations than they would by chance. We used a Bonferroni adjustment to correct for 45 pairwise disease-combination tests.

GPS Analysis.

The GPS test determines whether two pAIDs are genetically related. For the ith SNP, let $X_i=1$ if the SNP is truly associated with one disease, and let $X_i=0$ otherwise. Similarly, define $Y_i$ as the indicator of whether the SNP is associated with the other disease in the pair. We can therefore consider the diseases to be genetically related if there are more SNPs with $(X_i,Y_i)=(1,1)$ than would be expected to occur by chance. This amounts to testing the independence of $X_i$ and $Y_i$.

However, we do not directly observe $X_i$ and $Y_i$ and instead observe P values $U_i$ and $V_i$, which come from the two GWAS studies for the two diseases. When $X_i=1$, the P value $U_i$ will tend to be small, and otherwise $U_i$ will be uniformly distributed; the same is true of $Y_i$ and $V_i$. If $U_i$ and $V_i$ are independent, then $X_i$ and $Y_i$ must be as well. We can therefore test for genetic relatedness by testing whether the P values are dependent.

Most existing methods may not take advantage of the availability of the full genome data set for testing genetic sharing using $U_i$ and $V_i$. To address this limitation, we developed a novel, threshold-free method to detect genetic relatedness. Our test statistic is defined by $$D = \sup_{u,v} \sqrt{\frac{n}{\ln n}} \frac{|F_{uv}(u,v) - F_u(u)F_v(v)|}{\sqrt{F_u(u)F_v(v) - F_u(u)^2 F_v(v)^2}}$$

where n is the total number of SNPs, $F_{uv}(u,v)$ is the empirical bivariate distribution function of $(U_i,V_i)$, and $F_u(u)$ and $F_v(v)$ are the empirical univariate distribution functions of $U_i$ and $V_i$, respectively. Intuitively, the numerator of D is motivated by the fact that if $U_i$ and $V_i$ are truly independent, their bivariate distribution is equal to the product of their univariate distributions. The denominator of D makes the test capable of detecting even very weak correlations. Under the null hypothesis of no genetic sharing, it can be shown that D is approximately distributed like the inverse square root of a standard exponential random variable. This gives us an analytic expression for calculating P values. Note that no significance threshold is required.

The asymptotic null distribution of D is derived under the assumption that the genetic markers examined across the genome are statistically independent. We therefore pruned the SNPs for each pair of diseases before applying our test. We conducted inverse $\chi^2$ meta-analyses separately for each pair of diseases and pruned the resulting P values using a threshold of $r^2<0.5$ within a 500-kB up- and downstream region. This left about 800,000 SNPs for each disease pair analyzed. The use of more stringent $r^2$ thresholds (for example, $r^2<0.3$ or 0.2) gave comparable results.

Undirected Weighted Cyclic Network Visualization of Results from the Locus-Specific Sharing Test.

In graphic representations, pairwise relationships between autoimmune diseases (nodes) are represented by edges, whose weights are determined by the magnitude of the LPS test statistic (R statistical software package q-graph). Specifically, the width and density of the edges are the standardized transformations of the test statistic, and the colors denote whether the direction of the test statistic is positive (blue, meaning more sharing than expected) or negative (red, meaning less sharing than expected). Although graphs are constructed from all 45 pairwise interactions, for simplicity and improved visualization, we showed only those edges that represented a pairwise interaction that reached a Bonferroni-adjusted or nominal (FIG. 7) significance threshold (P<0.05). The nodes are positioned on the basis of a force-directed layout based on the Fruchterman-Reingold algorithm.

In Silico Replication of Novel pAID-Association Loci Using Previously Published Autoimmune Disease Cohort Data Sets.

Replication set I: The following data sets were used in the first replication set: CASP[117], CIDR Celiac Disease[118], NIDDK Crohn's Disease[119], Wellcome Trust Case Control Consortium (WT) Crohn's Disease and Type 1 Diabetes[120], WT Ulcerative Colitis[121] and WT Ankylosing Spondylitis[122]. These data sets were obtained via dbGaP or the Wellcome Trust Case Control Consortium. In order to maximize the power, we sought replication for each of the 12 significant SNPs in all of the seven available data sets. Full results are summarized in Table 2e.

Each data set was subjected to strict QC filtering as follows: we removed individuals that were inferred to be related on the basis of genetic data, individuals with >10% missing data, individuals with a reported sex that did not match the observed heterozygosity rates on chromosome X, and individuals not of European ancestry.

We further removed variants with >10% missingness, variants not in HWE, variants with missingness significantly correlated to phenotype, and variants with MAF<0.005. Variants to be replicated that were not observed in the original data set were imputed using IMPUTE2 (ref. 123) and the 1KGP-RP haplotype data[124]. Markers across the X chromosome, which were previously considered by most of these studies, were reanalyzed using the WAS toolset[125,126]. Replication-association analysis was carried out by logistic regression implemented in PLINK[127]. The first ten principal components calculated using EIGENSOFT[128] were added as covariates for all data sets except CASP, where no population stratification was observed.

Replication set II: The second replication set consisted of the following data sets: Rheumatoid Arthritis meta-analysis[129], IBDG Ulcerative Colitis meta-analysis[130], IBDG Crohn's Disease meta-analysis[131], Systemic Lupus Erythematosus GWAS, and SLEGEN[133]. Individuals from these data sets were of European ancestry. Summary statistics from the original studies were publicly available and were used for the replication analysis. Details regarding QC procedures and association analysis can be obtained from the original studies[129,130,131,132,133].

LD-based replication for replication sets I and II: We further assessed replication in SNPs that were in LD with the significant SNPs in the discovery set. For each associated SNP, a list of SNPs in LD ($r^2 > 0.5$) within 500 kb of the original SNP was obtained from SNAP[87] using the 1KGP-RP.

List of Tables as Described and Referred to within the Main Text or Methods

Supplementary Table 1:

The 10 study cohorts and leading 27 GWS loci associated with pediatric autoimmune diseases.

(a) The 10 pAID cohorts and common controls. The ratio of female to male subjects (F:M), and the genomic inflation factor (.lamda.GC) for each cohort and from the inverse chi-square meta-analysis calculated either with and without (exMHC) markers in the Major Histocompatibility Region (MHC) region. .lamda.GC adjusted for an expected study cohort of 1000 cases and 1000 controls (.lamda.1000).

(b) Autoimmune diseases associated with the 27 GWS candidate genes. Novel loci are denoted with an asterisk; underlined circles or Xs denotes instances of in silico replication in an independent dataset.

(c) In silico replication for the five putatively novel GWS loci. Abbreviations: CHR: chromosome; SNP: rsID dbSNP 138; POS: position in hg19; GENE: Candidate Gene Name (HGNC); REGION: Cytogenetic band; P META: disease-specific GWAS logistic regression P-value; P_REP: Disease-specific replication P-value in the specified dataset; AI-D: replication cohort autoimmune disease (d) Summary statistics tabulating key attributes across respective categories for the set of 27 GWS loci (See text for details). Abbreviations: Num: Number; prey: previously (e) Sanger validation results for five randomly-selected imputed SNPs (f) Imputation concordance for select samples genotyped on the Immunochip.

SUPPLEMENTAL TABLE 1a

The 10 pAID cohorts and 27 genome-wide significant loci identified in this study

| Ab | pAID | Count | F:M | GIF | GIF |
|---|---|---|---|---|---|
| THY | Thyroiditis | 97 | 0.76 | 1.016 | 1.018 |
| AS | Ankylosing Spondylitis | 107 | 0.55 | 1.014 | 1.013 |
| PS | Psoriasis | 100 | 0.58 | 1.012 | 1.010 |
| CEL | Celiac Disease | 173 | 0.63 | 1.018 | 1.016 |
| SLE | Systemic Lupus Erythematosus | 254 | 0.88 | 1.017 | 1.018 |
| CVID | Common Variable | 308 | 0.54 | 1.010 | 1.010 |
| UC | Ulcerative Colitis | 865 | 0.54 | 1.023 | 1.019 |
| T1D | Type 1 Diabetes | 1086 | 0.49 | 1.047 | 1.044 |
| JIA | Juvenile Idiopathic Arthritis | 1123 | 0.69 | 0.988 | 0.982 |
| CD | Crohn's Disease | 1922 | 0.42 | 1.069 | 1.069 |
| CTRL | Non-AID Ascertained Controls | 10718 | 0.48 | — | — |
| average | Across 10 case-control | 6035 | 0.46 | 1.021 | 1.020 |
| merge | studies | | | $1.096^e$ $1.012^f$ | $1.089^e$ $1.011^f$ |
| Meta | Inverse chi-sq meta-analysis | | | $1.085^e$ $1.011^f$ | $1.078^e$ $1.010^f$ |

SUPPLEMENTAL TABLE 1b

The 10 pAID cohorts and 27 genome-wide significant loci identified in this study

| | AS | PS | CEL | SLE | CVID | US | T1D | JIA | CD | AA | MS | PBC | PSC | RA | SJO | SSC | VIT | THY |
|---|---|---|---|---|---|---|---|---|---|---|---|---|---|---|---|---|---|---|
| IL23R | X | X | O | O | O | X | O | O | X | O | O | O | O | O | O | O | O | O |
| LPHN2* | O | O | O | O | X | <u>O</u> | O | X | O | O | O | O | O | O | O | O | O | O |
| PTPN22 | O | X | O | X | O | O | X | X | X | O | O | O | O | X | O | O | X | X |
| TNM3* | X | <u>O</u> | X | X | X | O | O | X | O | O | O | O | O | O | O | O | O | X |
| ANKRD30A* | O | O | O | O | O | O | O | X | O | O | O | O | O | O | O | O | O | O |
| INS | O | O | O | O | O | O | X | O | O | O | O | O | O | O | O | O | O | O |

SUPPLEMENTAL TABLE 1b-continued

The 10 pAID cohorts and 27 genome-wide significant loci identified in this study

| | AS | PS | CEL | SLE | CVID | US | T1D | JIA | CD | AA | MS | PBC | PSC | RA | SJO | SSC | VIT | THY |
|---|---|---|---|---|---|---|---|---|---|---|---|---|---|---|---|---|---|---|
| NOD2 | | | | | | | | | | | | | | | | | | |
| DAG1 | O | X | X | O | O | X | O | O | X | O | O | O | O | O | O | O | O | O |
| SMAD3 | | | | | | | | | | | | | | | | | | |
| ATG16L1 | O | X | O | O | O | O | O | O | X | O | O | O | O | O | O | O | O | O |
| ZNF365 | | | | | | | | | | | | | | | | | | |
| PTGER4 | O | O | O | O | O | X | O | O | X | O | X | O | O | O | O | O | O | O |
| NKX2-3 | | | | | | | | | | | | | | | | | | |
| ANKRD55 | O | O | O | O | O | O | O | X | X | O | X | O | O | X | O | O | O | O |
| IL128 | | | | | | | | | | | | | | | | | | |
| LRRK2 | X | O | O | O | O | O | O | O | X | O | O | O | O | O | O | O | O | O |
| IL5 | | | | | | | | | | | | | | | | | | |
| SUOX | O | X | O | O | O | O | X | O | O | O | O | O | O | O | O | O | O | O |
| SBK1 | X | X | X | O | O | X | O | O | X | O | O | O | O | O | O | O | O | X |
| ADCY7* | O | X | O | O | O | O | O | O | <u>X</u> | O | O | O | O | O | O | O | O | O |
| IL2RA | X | X | X | O | O | O | X | X | X | X | X | O | X | X | O | O | X | X |
| TNFSF15 | O | O | O | O | O | X | O | O | X | O | O | O | O | O | O | O | O | O |
| CD40LG* | O | O | X | O | O | X | O | <u>O</u> | X | O | <u>O</u> | O | O | O | O | O | O | O |
| ZMIZ1 | X | X | X | O | O | O | O | O | X | O | X | O | O | O | O | O | O | O |
| IL21 | X | O | X | O | X | X | X | X | X | X | O | X | X | O | O | O | O | X |
| CARD9 | X | O | O | O | O | X | O | O | X | O | O | O | O | O | O | O | O | O |
| PSMG1 | O | O | O | O | O | X | O | O | X | O | O | O | O | O | O | O | O | O |

SUPPLEMENTAL TABLE 1c

The 10 pAID cohorts and 27 genome-wide significant loci identified in this study

| REGION | SNP | GENE | P_META | P_REP | AI-D |
|---|---|---|---|---|---|
| 1p31.1 | rs2066363 | LPHN2 | 8.38E-11 | 1.69E-02 | UC |
| 4q35.1 | rs7660520 | TNM3 | 8.38E-11 | 3.65E-03 | PS |
| 16q12.1 | rs77150043 | ADCY7 | 5.99E-09 | 4.98E-04 | CD |
| Xq26.3 | rs2807264 | CD40LG | 1.25E-08 | 4.66E-05 | UC |
| Xq26.3 | rs2807264 | CD40LG | 1.25E-08 | 9.54E-03 | AS |
| Xq26.3 | rs2807264 | CD40LG | 1.25E-08 | 5.81E-04 | CD |

SUPPLEMENTAL TABLE 1d

The 10 pAID cohorts and 27 genome-wide significant loci identified in this study

| Category Description | Count |
|---|---|
| Total SNP-pAID pairs identified | 77 |
| Num of Pairs prev known | 44 |
| Num of Pairs novelly reported | 33 |
| Novel loci (no prev reported AI disease) | 5 |
| Loci assoc with 2 or more pAIDs | 22 |
| Loci assoc with at least one novel pAID | 16 |
| Pleiotropic Loci (>3 diseases) | 11 |

SUPPLEMENTARY TABLE 1e

Imputation concordance for imputed SNPs assessed by Sanger Sequencing across random samples

| Alleles correct (per sample) | rs13089824 | rs11691517 | rs9833463 | rs13288173 | rs1932990 |
|---|---|---|---|---|---|
| Not assessed* | 2 | 3 | 3 | 0 | 0 |
| 0 | 0 | 2 | 0 | 1 | 0 |
| 1 | 1 | 5 | 2 | 1 | 0 |
| 2 | 189 | 180 | 187 | 190 | 192 |
| Total alleles | | | | | |
| correct | 379 | 365 | 376 | 381 | 384 |
| Percent correct | 99.74% | 97.59% | 99.47% | 99.22% | 100.00% |

| Mean Accuracy | Min Accuracy | Max Accuracy | Stdev Accuracy |
|---|---|---|---|
| 99.20% | 97.59% | 100.00% | 0.95% |

SUPPLEMENTARY TABLE 1f

Imputation concordance for samples that were also directly genotyped on the immunochip platform; CVID (269 subjects)

| min maf | max maf | All Overlapping SNPs | % Concordance all | Imputed Overlapping | % Imputation Concordance |
|---|---|---|---|---|---|
| 0.01 | 0.05 | 520 | 99.77% | 482 | 99.76% |
| 0.05 | 0.10 | 800 | 99.76% | 688 | 99.73% |
| 0.10 | 0.20 | 1127 | 99.72% | 917 | 99.67% |
| 0.20 | 0.30 | 1005 | 99.74% | 818 | 99.68% |
| 0.30 | 0.40 | 849 | 99.67% | 686 | 99.60% |
| 0.40 | 0.50 | 855 | 99.71% | 690 | 99.66% |
| 0.01 | 0.50 | 5225 | 99.73% | 4340 | 99.68% |
| IBD (281 subjects) | | | | | |
| 0.01 | 0.05 | 560 | 99.77% | 518 | 99.76% |
| 0.05 | 0.10 | 873 | 99.77% | 752 | 99.74% |
| 0.10 | 0.20 | 1254 | 99.71% | 1023 | 99.66% |
| 0.20 | 0.30 | 1106 | 99.68% | 904 | 99.63% |
| 0.30 | 0.40 | 920 | 99.62% | 744 | 99.56% |
| 0.40 | 0.50 | 942 | 99.57% | 762 | 99.50% |
| 0.01 | 0.50 | 5730 | 99.68% | 4765 | 99.64% |

**Note that the total overlapping SNPs are those after QC filtering for both platforms and samples to keep SNPs with minor allele freq >0.01, individual missingness <0.05, genotyping rate >0.95 and hardy-weinberg >1e−06

***The imputed columns excluded snps that were directly genotyped on both platforms from the analysis; to strictly assess imputation concordane with ichip genotypes

TABLE 2a

The 46 pAID association loci reaching GWM significance ($P\_META < 1 \times 10^{-6}$).

| CHR | POS(Mb) | SNP | REGION | GENE | Al | MAFCASE | MAFCTRL | $P_{META}$ | Known_P* | pAIDs |
|---|---|---|---|---|---|---|---|---|---|---|
| 1 | 67.7 | rs11580078 | 1p31.3 | IL23R | G | 0.35 | 0.43 | 8.4E-11 | 1.0E-146 | CD# |
| 1 | 82.2 | rs2066363 | 1p31.1 | LPHN2 | C | 0.16 | 0.34 | 8.4E-11 | novel | CVID\|JIA |
| 1 | 114.3 | rs6679677 | 1p13.2 | PTPN22 | A | 0.15 | 0.09 | 8.4E-11 | 1.1E-88 | THY#\|PS\|T1D#\|JIA# |
| 1 | 172.8 | rs34884278 | 1q24.3 | TNFSF18 | C | 0.35 | 0.30 | 4.3E-07 | 1.4E-10 | CD# |
| 1 | 197.4 | rs6689858 | 1q31.3 | CR61 | C | 0.33 | 0.29 | 1.7E-07 | 4.3E-12 | AS\|CD# |
| 1 | 206.9 | rs55705316 | 1q32.1 | IL10 | G | 0.16 | 0.14 | 9.5E-07 | 1.9E-09 | PS\|SLE#\|UC#\|CD# |
| 2 | 2.9 | rs114846446 | 2p25.3 | TSSC1 | A | 0.02 | 0.01 | 2.4E-07 | novel | PS\|SLE\|UC\|CD# |
| 2 | 103.1 | rs2075184 | 2q11.1 | IL18R1 | T | 0.26 | 0.23 | 9.4E-08 | 1.2E-16 | THY\|CEL#\|UC\|CD# |
| 2 | 234.2 | rs36001488 | 2q37.1 | ATG16L1 | C | 0.40 | 0.48 | 8.4E-11 | 1.0E-12 | PS\|CD# |
| 2 | 241.6 | rs4676410 | 2q37.3 | GPR35 | A | 0.24 | 0.19 | 1.5E-07 | 2.2E-20 | AS#\|SLE\|UC# |
| 3 | 49.6 | rs4625 | 3p21.31 | DAG1 | G | 0.37 | 0.31 | 8.4E-11 | 1.0E-47 | PS#\|CEL\|UC#\|CD# |
| 4 | 5.0 | rs7672495 | 4p16.2 | CYTL1 | C | 0.21 | 0.18 | 1.0E-07 | novel | THY\|AS\|CEL\|UC\|T1D\|JIA\|CD |
| 4 | 123.6 | rs62324212 | 4q27 | IL21 | A | 0.46 | 0.42 | 2.6E-08 | 1.0E-09 | THY\|AS\|CEL#\|CVID\|UC#\|T1D#\|JIA#\|CD# |
| 4 | 183.7 | rs7660520 | 4q35.1 | TNM3 | A | 0.35 | 0.26 | 8.4E-11 | novel | THY\|AS\|CEL\|SLE\|CVID\|JIA |
| 5 | 40.5 | rs7725052 | 5p13.1 | PTGER4 | C | 0.37 | 0.43 | 8.4E-11 | 1.4E-10 | CD# |
| 5 | 55.4 | rs7731626 | 5q11.2 | ANKRD55 | A | 0.34 | 0.39 | 1.4E-06 | 2.7E-11 | JIA#\|CD# |
| 5 | 96.2 | rs4869313 | 5q15 | ERAP2 | T | 0.46 | 0.42 | 9.1E-08 | 1.9E-20 | CEL\|JIA#\|CD# |
| 5 | 131.8 | rs11741255 | 5q31.1 | IL5 | A | 0.47 | 0.42 | 1.6E-09 | 1.4E-52 | PS#\|CEL\|CD# |
| 5 | 158.8 | rs755374 | 5q33.3 | IL12B | T | 0.37 | 0.32 | 2.3E-10 | 1.4E-42 | AS\|CEL\|UC#\|CD# |
| 8 | 138.1 | rs7831697 | 8q24.23 | 8q24.23 | G | 0.28 | 0.25 | 4.7E-07 | novel | AS\|CEL\|T1D\|JIA\|CD |
| 9 | 5.0 | rs36051895 | 9p24.1 | JAK2 | T | 0.33 | 0.29 | 8.6E-08 | 1.4E-31 | AS\|SLE\|UC#\|CD# |
| 9 | 12.8 | rs7042370 | 9p23 | LURAP1L | T | 0.52 | 0.43 | 1.1E-07 | novel | JIA |
| 9 | 117.6 | rs4246905 | 9q32 | TNFSF15 | T | 0.24 | 0.28 | 9.5E-49 | 1.2E-17 | UC#\|CD# |
| 9 | 132.7 | rs10988542 | 9q34.11 | FNBP1 | C | 0.11 | 0.08 | 6.5E-07 | novel | THY\|AS\|JIA\|CD |
| 9 | 139.3 | rs11145763 | 9q34.3 | CARD9 | C | 0.44 | 0.40 | 3.3E-08 | 1.0E-06 | AS#\|UC#\|CD# |
| 10 | 6.1 | rs706778 | 10p15.1 | IL2RA | T | 0.46 | 0.41 | 6.3E-09 | 1.7E-12 | THY\|AS\|PS#\|CEL\|T1D#\|JIA# |
| 10 | 37.6 | rs7100025 | 10p11.21 | ANKRD30A | G | 0.59 | 0.34 | 8.4E-11 | novel | JIA |
| 10 | 64.4 | rs10822050 | 10q21.2 | ZNF365 | C | 0.45 | 0.39 | 8.4E-11 | 5.0E-17 | SLE\|CD# |
| 10 | 81.0 | rs1250563 | 10q22.3 | ZMIZ1 | C | 0.24 | 0.29 | 1.3E-08 | 1.1E-30 | PS#\|CD# |
| 10 | 101.3 | rs1332099 | 10q24.2 | NKX2-3 | T | 0.52 | 0.46 | 9.1E-11 | 1.0E-54 | UC#\|CD# |
| 11 | 2.2 | rs17885785 | 11p15.5 | INS | T | 0.10 | 0.20 | 8.4E-11 | 4.4E-48 | T1D# |
| 12 | 40.8 | rs17466626 | 12q12 | LRRK2 | G | 0.05 | 0.02 | 3.2E-10 | 3.0E-10 | AS\|CD# |
| 12 | 56.4 | rs1689510 | 12q13.2 | SUOX | C | 0.39 | 0.31 | 4.0E-09 | 1.1E-10 | PS#\|T1D# |
| 13 | 107.1 | rs11839053 | 13q33.3 | EFNB2 | C | 0.04 | 0.02 | 9.6E-07 | novel | CVID\|JIA |
| 15 | 67.5 | rs72743477 | 15q22.33 | SMAD3 | G | 0.26 | 0.21 | 8.4E-11 | 2.7E-19 | AS\|UC\|CD# |
| 16 | 28.3 | rs12598357 | 16p11.2 | SBK1 | G | 0.42 | 0.39 | 4.4E-09 | 1.0E-08 | THY\|AS#\|PS\|CEL\|UC\|CD# |
| 16 | 28.8 | rs12928404 | 16p11.2 | ATXN2L | C | 0.41 | 0.38 | 5.7E-07 | 1.0E-08 | UC\|CD# |
| 16 | 50.3 | rs77150043 | 16q12.1 | ADCY7 | T | 0.28 | 0.23 | 6.0E-09 | novel | PS\|CD |
| 16 | 50.7 | rs117372389 | 16q12.1 | NOD2 | T | 0.04 | 0.02 | 8.4E-11 | 2.9E-69 | CD# |
| 17 | 38.0 | rs12232497 | 17q12 | IKZF3 | C | 0.49 | 0.45 | 2.7E-07 | 1.0E-07 | THY\|CEL\|CVID\|UC#\|JIA\|CD# |
| 19 | 10.6 | rs62131887 | 19p13.2 | TYK2 | T | 0.25 | 0.28 | 4.3E-07 | 1.0E-10 | THY\|SLE\|T1D#\|JIA#\|CD# |
| 19 | 49.2 | rs602662 | 19q13.33 | FUT2 | G | 0.45 | 0.49 | 5.3E-08 | 1.0E-15 | PS\|T1D#\|CD# |
| 20 | 62.3 | rs2738774 | 20q13.33 | TNFRSF6B | A | 0.29 | 0.32 | 8.5E-07 | 1.1E-23 | THY\|PS\|SLE\|UC#\|JIA\|CD# |
| 21 | 40.5 | rs2836882 | 21q22.2 | PSMG1 | A | 0.23 | 0.27 | 4.8E-08 | 2.8E-14 | UC#\|CD# |
| 23 | 135.7 | rs2807264 | Xq26.3 | CD40LG | C | 0.25 | 0.21 | 1.3E-08 | novel | CEL\|UC\|CD |
| 23 | 136.0 | rs12863738 | Xq26.3 | RBMX | T | 0.20 | 0.17 | 6.1E-08 | novel | CEL\|JIA\|CD |

Abbreviations in table: CHR: chromosome; SNP: dbSNP rsID; POS (Mb): position in hg19; REGION: Cytogenetic band; Al: alternative allele; MAF: minor allele frequency (all, cases or controls; cases refer to the subjects from diseases indicated in the pAID columns); GENE: candidate gene name (HNGC); PMETA: Meta-analysis P-value of the lead SNP(s); Known-P*: Lowest P-value previously reported by any published autoimmune disease GWAS based on annotations in the GWAS Catalog or published Immunochip studies; "novel" denotes new loci (bolded) reaching GWS for the first time in the present study; pAIDs: combination of pAIDs identified as being associated with the locus based on model search; (#) denotes if the SNP has been previously reported as being associated with a given disease at GWS.

TABLE 2b

Previously-reported associations with the top 46 loci in the GWAS Catalog and Immunochip datasets.

| SNP | AA | AS | CD | CeD | IBD | JIA | MS | NAR | PBC | PSC | PS | RA | SJO | SLE | SSC | T1D | THY | UC | VIT | GWAS Catalog |
|---|---|---|---|---|---|---|---|---|---|---|---|---|---|---|---|---|---|---|---|---|
| rs11580078 |  | O | O |  | O |  |  |  |  |  |  |  |  |  |  |  |  | O |  | CD\|2E-7\|CD\|1E-8\|CD\|3E-12\|IBD\|4E-13 |
| rs2066363 |  |  |  |  |  |  |  |  |  |  |  |  |  |  |  |  |  |  |  | NA |
| rs6679677 |  | O |  |  | O |  |  |  |  |  |  | O |  | X |  | O | O |  | X | T1D\|1E-40\|T1D\|5E-26\|T1D\|8E-24\|IBD\|2E-15\|RA\|6E-25\|RA\|6E-42\|CD\|2E-15\|HTHY\|3E-13 |
| rs7660520 |  |  |  |  |  |  |  |  |  |  |  |  |  |  |  |  |  |  |  | NA |
| rs7100025 |  |  |  |  |  |  |  |  |  |  |  |  |  |  |  |  |  |  |  | NA |
| rs17885785 |  |  |  |  |  |  |  |  |  |  |  |  |  |  |  | O |  |  |  | T1D\|5E-196 |
| rs117372389 |  | O | O |  |  |  |  |  |  |  |  |  |  |  |  |  |  |  |  | NA |
| rs4625 |  | O | O |  |  | O | O |  |  |  |  |  |  |  |  |  |  | O |  | CD\|4E-8\|CD\|5E-8\|UC\|7E-9\|UC\|2E-17\|CD\|1E-12\|CD\|6E-17\|IBD\|1E-47\|PSC\|1E-16\|UC\|4E-9 |
| rs72743477 |  | O | O |  |  |  |  |  |  |  |  |  |  |  |  |  |  |  |  | CD\|3E-19\|IBD\|6E-16 |
| rs36001488 |  | O | O |  |  |  |  |  |  |  |  |  |  |  |  |  |  |  |  | CD\|5E-14\|IBD\|4E-70\|CD\|4E-70\|CD\|2E-32\|CD\|1E-12\|CD\|3E-6\|CD\|1E-13\|CD\|5E-9\|CD\|7E-41 |
| rs10822050 |  |  | O |  | O |  |  |  |  |  |  |  |  |  |  |  |  | O |  | ADER\|6E-20\|CD\|4E-20 |
| rs7725052 |  |  | O | O | O |  |  |  |  |  |  |  |  |  |  |  |  | X |  | AS\|3E-7 |
| rs1332099 | X | O | O |  |  |  |  |  |  |  |  |  |  |  |  |  |  | O |  | CD\|2E-20\|IBD\|1E-54\|CD\|6E-8\|CD\|4E-10\|UC\|2E-6\|UC\|8E-21\|UC\|2E-7\|CD\|3E-16\|UC\|1E-8 |
| rs7731626 |  | X | X | X | X |  |  |  |  |  |  | O |  |  |  |  |  |  |  | NA |
| rs755374 | O | X |  | O |  |  |  |  |  |  | O |  |  |  |  |  |  | O |  | UC\|1E-21\|IBD\|1E-42 |
| rs17466626 |  |  | O |  | O |  |  |  |  |  |  |  |  |  |  |  |  |  |  | CD\|3E-10\|CD\|6E-21\|IBD\|6E-29 |
| rs11741255 |  |  | O |  | O | X |  |  |  |  | X |  |  |  |  |  |  | X |  | IBD\|1E-52\|CD\|2E-18\|CD\|1E-7\|CD\|1E-20 |
| rs1689510 | X |  |  |  |  |  |  |  |  |  | O | X |  |  |  | O |  |  | X | VIT\|8E-12\|T1D\|9E-10\|AA\|3E-8\|AST\|2E-13\|T1D\|5E-18\|VIT\|3E-14\|T1D\|1E-11\|T1D\|3E-16\|T1D\|2E-20\|T1D\|3E-27\|T1D\|2E-25 |
| rs12598357 |  | X | O |  | O |  |  |  |  |  |  |  |  |  |  | X |  |  |  | CD\|2E-11\|IBD\|1E-21\|T1D\|3E-13\|T1D\|1E-8\|IBD\|2E-9 |
| rs77150043 |  |  |  |  |  |  |  |  |  |  |  |  |  |  |  |  |  |  |  | NA |
| rs706778 | X | X | X | X | O |  |  |  |  | O | O | X |  |  |  | O | X |  | X | RA\|1E-11\|MS\|3E-11\|AA\|2E-12 |
| rs4246905 |  |  | O |  | O |  |  |  |  |  |  |  |  |  |  |  |  | O |  | CD\|1E-15\|IBD\|3E-32\|UC\|6E-12\|LEP\|3E-21\|CD\|3E-10\|IBD\|3E-8 |

TABLE 2b-continued

Previously-reported associations with the top 46 loci in the GWAS Catalog and Immunochip datasets.

| SNP | AA | AS | CD | CeD | IBD | JIA | MS | NAR | PBC | PSC | PS | RA | SJO | SLE | SSC | T1D | THY | UC | VIT | GWAS Catalog |
|---|---|---|---|---|---|---|---|---|---|---|---|---|---|---|---|---|---|---|---|---|
| rs2807264 | | | | | | | | | | | | | | | | | | | | NA |
| rs1250563 | | X | O | O | O | | O | | | X | | | | | | | | | | IBD\|3E-18\|CD\|7E-14\|PSOR\|7E-14\|MS\|4E-7\|MS\|2E-6\|IBD\|6E-9\|MS\|6E-9\|CD\|1E-30 |
| rs62324212 | X | | X | O | X | X | | | X | X | X | | | | | X | | X | | NA |
| rs11145763 | | X | O | | O | | | | | | | | | | | | | O | | UC\|3E-19\|IBD\|4E-56\|CD\|4E-6\|UC\|5E-8\|CD\|1E-36\|UC\|7E-6\|AS\|1E-6 |
| rs2836882 | | O | X | | O | | | | O | O | | | | | | | | O | | AS\|8E-20\|UC\|2E-22\|IBD\|4E-12\|IBD\|5E-48 |
| rs602662 | | | O | | X | | | | | | | | | | | O | | | | IBD\|1E-15\|CD\|1E-15\|CD\|2E-8\|CD\|7E-12 |
| rs12863738 | | | | | | | | | | | | | | | | | | | | NA |
| rs36051895 | | | O | | O | | | | | | | | | | | | | O | | UC\|1E-6\|UC\|2E-25\|CD\|1E-13\|IBD\|8E-45\|CD\|3E-9 |
| rs4869313 | | O | X | | X | X | | | | | O | | | | | | | | | CD\|1E-10\|IBD\|6E-13 |
| rs2075184 | | | O | O | O | | | | | | | | | | | | | | | ADER\|8E-18\|CeD\|4E-9\|CD\|2E-12\|CeD\|1E-15\|IBD\|3E-20 |
| rs7672495 | | | | | | | | | | | | | | | | | | | | NA |
| rs7042370 | | | | | | | | | | | | | | | | | | | | NA |
| rs4676410 | | X | X | | O | | | | | | | | | | | | | O | | UC\|2E-9\|PSC\|2E-9\|IBD\|3E-21 |
| rs6689858 | | X | | | X | | | X | | | | | | | | | | X | | NA |
| rs114846446 | | | | | | | | | | | | | | | | | | | | NA |
| rs12232497 | | | O | | O | X | | | X | | | X | | | | X | | O | | IBD\|4E-38\|PBC\|8E-6\|SLE\|7E-6\|PBC\|4E-9\|SSC\|7E-6\|PBC\|2E-9\|T1D\|2E-6\|UC\|5E-11\|CD\|5E-9\|RA\|9E-7\|CD\|2E-9\|UC\|1E-7\|AST\|1E-7\|UC\|3E-8\|AST\|2E-16\|T1D\|6E-13\|AST\|9E-11\|AST\|1E-8 |
| rs62131887 | | X | O | | O | X | O | | X | | O | O | | | | X | | X | | NA |
| rs34884278 | | | O | X | X | | | | | | | | | | | | | | | CD\|2E-15\|CD\|2E-9\|IBD\|6E-22\|CD\|6E-22 |
| rs7831697 | | | | | | | | | | | | | | | | | | | | NA |
| rs12928404 | X | O | | O | | | | | | | | | | | | X | | | | CD\|2E-11\|IBD\|1E-21\|T1D\|3E-13\|T1D\|1E-8\|IBD\|2E-9 |
| rs10988542 | | | | | | | | | | | | | | | | | | | | NA |
| rs2738774 | | | O | | O | X | | | | | | | | | | | | X | | NA |
| rs55705316 | | | O | | O | | | | | | | | | X | | X | | O | | UC\|6E-17\|UC\|1E-8\|CD\|2E-14\|UC\|1E-12\|T1D\|5E-10\|T1D\| |

TABLE 2b-continued

Previously-reported associations with the top 46 loci in the GWAS Catalog and Immunochip datasets.

| SNP | AA | AS | CD | CeD | IBD | JIA | MS | NAR | PBC | PSC | PS | RA | SJO | SLE | SSC | T1D | THY | UC | VIT | GWAS Catalog |
|---|---|---|---|---|---|---|---|---|---|---|---|---|---|---|---|---|---|---|---|---|
| rs11839053 | | | | | | | | | | | | | | | | | | | | 2E-9\|IBD\|<br>7E-42\|UC\|1E-12\|<br>UC\|8E-8<br>NA |

Table 2c: Detailed information for the lead loci with evidence of directions of effect heterogeneity across pAIDs. Abbreviations: SNP: rsID dbSNP 138; GENE: Candidate Gene Name (HGNC); REGION: Cytogenetic band; A1: alternative allele used in the logistic regression; pAIDs model: pAID(s) associated with this SNP based on the model search; BETA (SE) model: effect size and standard error of the SNP based on logistic regression combining cases from the diseases identified on the model search; pAID: the disease showing the opposite effect direction than that of the group of diseases identified by the subtype search; BETA (SE): effect size and standard error of the SNP for the disease found to have an opposite effect direction; P-value: disease-specific GWAS P-value.

TABLE 2c

| CHR | POS | REGION | SNP | GENE | A1 | MAF | HWE | P | INFO | BETA(SE) | pAID | BETA(SE) model | pAIDs model |
|---|---|---|---|---|---|---|---|---|---|---|---|---|---|
| 1 | 82237577 | 1p31.1 | rs2066363 | LPHN2 | C | 0.34 | 0.004 | 0.026 | 1.00 | −0.49(0.17) | CD | 0.68(0.05) | CVID\|JIA |
| 1 | 114303808 | 1p13.2 | rs6679677 | PTPN22 | C | 0.08 | 0.855 | 1.40E−04 | 0.99 | −0.13(0.05) | CD | 0.59(0.06) | THY\|PS\|T1D\|JIA |
| 1 | 206933517 | 1q32.1 | rs55705316 | IL10 | T | 0.14 | 0.715 | 2.88E−04 | 0.91 | −0.13(0.05) | T1D | 0.21(0.04) | PS\|SLE\|UC\|CD |
| 3 | 49572140 | 3p21.31 | rs4625 | DAG1 | A | 0.31 | 0.472 | 0.019 | 1.00 | −0.08(0.04) | AS | 0.25(0.03) | PS\|CEL\|UC\|CD |
| 4 | 4992367 | 4p16.2 | rs7672495 | CYTL1 | T | 0.18 | 0.162 | 0.042 | 0.96 | 0.34(0.17) | PS | 0.18(0.03) | THY\|AS\|CEL\|UC\|T1D\|JIA\|CD |
| 13 | 107063042 | 13q33.3 | rs11839053 | EFNB2 | T | 0.02 | 0.074 | 4.61E−03 | 0.93 | −0.35(0.15) | T1D | 0.76(0.15) | CVID\|JIA |
| 16 | 28340945 | 16p11.2 | rs12598357 | SBK1 | A | 0.39 | 0.257 | 0.013 | 0.90 | −0.26(0.07) | T1D | 0.18(0.03) | THY\|AS\|PS\|CEL\|UC\|CD |
| 16 | 28847246 | 16p11.2 | rs12928404 | ATXN2L | T | 0.38 | 0.325 | 8.94E−03 | 0.99 | −0.25(0.07) | T1D | 0.17(0.03) | UC\|CD |
| 21 | 40466570 | 21q22.2 | rs2836882 | PSMG1 | G | 0.27 | 0.112 | 0.038 | 0.98 | −0.38(0.18) | THY | −0.21(0.04) | UC\|CD |

TABLE 2d

Key summary attributes tabulated for the set of 27 GWS and 46 GWM lead loci

| Category Description | GWSGWM | GWS | GWM only |
|---|---|---|---|
| Total SNP-pAID pairs identified | 146 | 77 | 69 |
| Num of Pairs prev known | 67 | 44 | 23 |
| Num of Pairs novelly reported | 79 | 33 | 46 |
| Novel loci (no prev reported AI disease) | 12 | 5 | 7 |
| Loci assoc with 2 or more pAIDs | 39 | 22 | 17 |
| Loci assoc with at least one novel pAID | 34 | 16 | 18 |
| Pleiotropic Loci (>3 diseases) | 25 | 11 | 14 |

TABLE 2e

In silico replication results for the 12 putatively novel pAID associated loci reaching PMETA $< 1 \times 10^{-6}$.

| CHR | SNP | POS | REGION | P_META | AI - - - D | DATASET | P_REP | METHOD | GENE | GWS |
|---|---|---|---|---|---|---|---|---|---|---|
| 1 | rs2066363 | 82237577 | 1p31.1 | 8.38E−11 | UC | IBDG_UC | 1.69E−02 | SUM | LPHN2 | GWS |
| 4 | rs7660520 | 183745321 | 4q35.1 | 8.38E−11 | PS | CASP | 3.65E−03 | IMP | TNM3 | GWS |
| 8 | rs7831697 | 138136304 | 8q24.23 | 4.67E−07 | RA | RA_meta | 1.02E−02 | SUM | 8q24.23 | GWM |
| 9 | rs7042370 | 12785073 | 9p23 | 1.07E−07 | CD | NIDDK_IBD | 2.69E−02 | IMP | LURAP1L | GWM |
| 16 | rs77150043 | 50304249 | 16q12.1 | 5.99E−09 | CD | NIDDK_IBD | 4.98E−04 | IMP | ADCY7 | GWS |
| 23 | rs2807264 | 135665778 | Xq26.3 | 1.25E−08 | UC | WT2_UC | 4.66E−05 | IMP | CD40LG | GWS |
| 23 | rs2807264 | 135665778 | Xq26.3 | 1.25E−08 | AS | WT2_AS | 9.54E−03 | IMP | CD40LG | GWS |

TABLE 2e-continued

In silico replication results for the 12 putatively novel pAID associated loci reaching PMETA < 1 × 10$^{-6}$.

| CHR | SNP | POS | REGION | P_META | AI - - - D | DATASET | P_REP | METHOD | GENE | GWS |
|---|---|---|---|---|---|---|---|---|---|---|
| 23 | rs2807264 | 135665778 | Xq26.3 | 1.25E−08 | CD | WT_CD | 5.81E−04 | IMP | CD40LG | GWS |
| 23 | rs12863738 | 136032127 | Xq26.3 | 6.11E−08 | UC | WT2_UC | 1.78E−03 | IMP | RBMX | GWM |
| 23 | rs12863738 | 136032127 | Xq26.3 | 6.11E−08 | CeD | CIDR_Celiac | 3.72E−02 | IMP | RBMX | GWM |

Table 3a: Significantly associated genes identified by Gene Based Association Testing (GBAT) Abbreviations: CHR: chromosome; nSNP: number of SNPs mapped to this gene; Start/Stop: gene start or stop position in build hg19; GENE: Candidate Gene Name (HGNC); PGBAT: P-value of the gene association test based on simulations; PBest SNP: Most significant Meta-analysis P-value of the SNPs mapping to this gene; DATASET: Best.SNP: lead SNP in the region with the lowest P-value; Test: Test statistic of the GBAT; q_value: FDR q-value.

TABLE 3a

| Chr | Gene | nSNPs | Start | Stop | Test | Pvalue | Best.SNP | SNP.pvalue | q - - - value |
|---|---|---|---|---|---|---|---|---|---|
| 1 | C1orf141 | 124 | 67330446 | 67366808 | 1212. | <1.00E−06 | rs11209008 | 5.88E−10 | 0.00E+00 |
| 1 | IL23R | 146 | 67404756 | 67498238 | 2343. | <1.00E−06 | rs11209026 | 8.38E−11 | 0.00E+00 |
| 1 | IL12RB2 | 122 | 67545634 | 67635171 | 995.1 | 2.00E−06 | rs10889677 | 1.53E−10 | 1.94E−04 |
| 2 | ATG16L1 | 142 | 233382495 | 233869059 | 2064. | <1.00E−06 | rs3792108 | 8.41E−11 | 0.00E+00 |
| 2 | SAG | 133 | 23388104 | 233920440 | 1668. | <1.00E−06 | rs3792108 | 8.41E−11 | 0.00E+00 |
| 3 | USP4 | 63 | 49289997 | 49352519 | 866.6 | <1.00E−06 | rs6809216 | 8.39E−11 | 0.00E+00 |
| 3 | GPX1 | 39 | 49369612 | 49370795 | 690.2 | <1.00E−06 | rs6809216 | 8.39E−11 | 0.00E+00 |
| 3 | RHOA | 60 | 49371582 | 49424530 | 1309. | <1.00E−06 | rs11711485 | 8.38E−11 | 0.00E+00 |
| 3 | TCTA | 40 | 49424642 | 49428913 | 969.7 | <1.00E−06 | rs11711485 | 8.38E−11 | 0.00E+00 |
| 3 | AMT | 40 | 49429214 | 49435016 | 969.8 | <1.00E−06 | rs11711485 | 8.38E−11 | 0.00E+00 |
| 3 | NICN1 | 41 | 49434769 | 49441761 | 1046. | <1.00E−06 | rs11711485 | 8.38E−11 | 0.00E+00 |
| 3 | DAG1 | 65 | 49482568 | 49548052 | 1345. | <1.00E−06 | rs4625 | 8.38E−11 | 0.00E+00 |
| 3 | BSN | 113 | 49566925 | 49683986 | 2144. | <1.00E−06 | rs4625 | 8.38E−11 | 0.00E+00 |
| 3 | APEH | 69 | 49686438 | 49695938 | 1426. | <1.00E−06 | rs9882740 | 8.43E−11 | 0.00E+00 |
| 3 | MST1 | 66 | 49696391 | 49701099 | 1351. | <1.00E−06 | rs9882740 | 8.43E−11 | 0.00E+00 |
| 3 | RNF123 | 73 | 49701993 | 49733966 | 1540. | <1.00E−06 | rs9882740 | 8.43E−11 | 0.00E+00 |
| 3 | AMIGO3 | 53 | 49729968 | 49732127 | 1079. | <1.00E−06 | rs3197999 | 8.43E−11 | 0.00E+00 |
| 3 | GMPPB | 52 | 49733935 | 49736388 | 1036. | <1.00E−06 | rs3197999 | 8.43E−11 | 0.00E+00 |
| 3 | IHPK1 | 72 | 49736731 | 49798977 | 1289. | <1.00E−06 | rs3197999 | 8.43E−11 | 0.00E+00 |
| 3 | LOC389118 | 37 | 49810668 | 49812272 | 535.9 | <1.00E−06 | rs6802890 | 5.53E−07 | 0.00E+00 |
| 3 | C3orf54 | 39 | 49815690 | 49817467 | 535.0 | 1.00E−06 | rs6802890 | 5.53E−07 | 9.99E−05 |
| 3 | UBA7 | 44 | 49817641 | 49826395 | 576.8 | <1.00E−06 | rs6802890 | 5.53E−07 | 0.00E+00 |
| 3 | CAMKV | 48 | 49870425 | 49882373 | 581.2 | 1.00E−06 | rs6775384 | 5.64E−07 | 9.99E−05 |
| 5 | LOC441108 | 193 | 13177457 | 131825958 | 1867. | <1.00E−06 | rs11741255 | 1.58E−09 | 0.00E+00 |
| 5 | IRF1 | 132 | 13184668 | 131854326 | 1539. | <1.00E−06 | rs11741255 | 1.58E−09 | 0.00E+00 |
| 6 | GABBR1 | 65 | 29677983 | 29708941 | 725.1 | <1.00E−06 | rs396660 | 1.39E−08 | 0.00E+00 |
| 6 | MOG | 69 | 29732787 | 29748128 | 758.3 | <1.00E−06 | rs396660 | 1.39E−08 | 0.00E+00 |
| 6 | ZFP57 | 96 | 29748238 | 29756866 | 979.6 | <1.00E−06 | rs396660 | 1.39E−08 | 0.00E+00 |
| 6 | HLA - - - F | 107 | 29799095 | 29803052 | 1013. | <1.00E−06 | rs396660 | 1.39E−08 | 0.00E+00 |
| 6 | HLA - - - G | 37 | 29902734 | 29906878 | 350.6 | <1.00E−06 | rs2975033 | 5.93E−09 | 0.00E+00 |
| 6 | HLA - - - A29.1 | 49 | 30018304 | 30085130 | 483.8 | <1.00E−06 | rs9366752 | 2.12E−09 | 0.00E+00 |
| 6 | HLA - - - A | 32 | 30018309 | 30021633 | 366.6 | <1.00E−06 | rs2256919 | 2.90E−07 | 0.00E+00 |
| 6 | HCG9 | 38 | 30050870 | 30054156 | 406.4 | <1.00E−06 | rs2256919 | 2.90E−07 | 0.00E+00 |
| 6 | ZNRD1 | 56 | 30137014 | 30140665 | 456.3 | <1.00E−06 | rs9366752 | 2.12E−09 | 0.00E+00 |
| 6 | PPP1R11 | 54 | 30142910 | 30146087 | 450.2 | <1.00E−06 | rs9366752 | 2.12E−09 | 0.00E+00 |
| 6 | RNF39 | 57 | 30146021 | 30151607 | 482.4 | <1.00E−06 | rs9366752 | 2.12E−09 | 0.00E+00 |
| 6 | TRIM31 | 61 | 30178652 | 30188846 | 572.6 | <1.00E−06 | rs9366752 | 2.12E−09 | 0.00E+00 |
| 6 | TRIM40 | 49 | 30212488 | 30224491 | 525.2 | <1.00E−06 | rs2021723 | 1.64E−07 | 0.00E+00 |
| 6 | TRIM10 | 37 | 30227702 | 30236690 | 344.0 | <1.00E−06 | rs2021723 | 1.64E−07 | 0.00E+00 |
| 6 | TRIM15 | 26 | 30238961 | 30248452 | 244.4 | <1.00E−06 | rs2021723 | 1.64E−07 | 0.00E+00 |
| 6 | MUC21 | 44 | 31059463 | 31065654 | 410.8 | <1.00E−06 | rs13210132 | 4.47E−08 | 0.00E+00 |
| 6 | C6orf15 | 198 | 31186311 | 31188311 | 1877. | <1.00E−06 | rs1265098 | 8.40E−11 | 0.00E+00 |
| 6 | PSORS1C1 | 210 | 31130601 | 31215816 | 2023. | <1.00E−06 | rs1265098 | 8.40E−11 | 0.00E+00 |
| 6 | CDSN | 203 | 31190848 | 31196202 | 1943. | <1.00E−06 | rs1265098 | 8.40E−11 | 0.00E+00 |
| 6 | PSORS1C2 | 205 | 31213289 | 31215106 | 1976. | <1.00E−06 | rs1265098 | 8.40E−41 | 0.00E+00 |
| 6 | CCHCR1 | 212 | 31218194 | 31233994 | 2059.7 | <1.00E−06 | rs1265098 | 8.40E−11 | 0.00E+00 |
| 6 | TCF19 | 206 | 31234281 | 31239971 | 2021.6 | <1.00E−06 | rs1265098 | 8.40E−11 | 0.00E+00 |
| 6 | POU5F1 | 172 | 31240092 | 31246430 | 1549.0 | <1.00E−06 | rs1265098 | 8.40E−11 | 0.00E+00 |
| 6 | HCG27 | 48 | 31273577 | 31279724 | 556.5 | <1.00E−06 | rs887464 | 1.66E−07 | 0.00E+00 |
| 6 | HLA - - - C | 59 | 31344507 | 31347834 | 703.9 | <1.00E−06 | rs2395471 | 3.50E−10 | 0.00E+00 |
| 6 | HLA - - - B | 61 | 31429627 | 31432968 | 1148.9 | <1.00E−06 | rs2596560 | 8.38E−11 | 0.00E+00 |
| 6 | MICA | 68 | 31479349 | 31491069 | 1330.9 | <1.00E−06 | rs2596560 | 8.38E−11 | 0.00E+00 |
| 6 | HCP5 | 114 | 31538937 | 31541461 | 2395.3 | <1.00E−06 | rs2516403 | 8.42E−11 | 0.00E+00 |
| 6 | MICB | 146 | 31573833 | 31586880 | 2843.6 | <1.00E−06 | rs2516403 | 8.42E−11 | 0.00E+00 |
| 6 | MCCD1 | 150 | 31604717 | 31605987 | 3011.4 | <1.00E−06 | rs2516403 | 8.42E−11 | 0.00E+00 |
| 6 | BAT1 | 157 | 31605974 | 31618204 | 3054.4 | <1.00E−06 | rs2516403 | 8.42E−11 | 0.00E+00 |
| 6 | ATP6V1G2 | 148 | 31620218 | 31622606 | 2873.6 | <1.00E−06 | rs2516403 | 8.42E−11 | 0.00E+00 |
| 6 | NFKBIL1 | 142 | 31623350 | 31634585 | 2732.6 | <1.00E−06 | rs2516403 | 8.42E−11 | 0.00E+00 |
| 6 | LTA | 88 | 31648071 | 31650077 | 1418.8 | <1.00E−06 | rs1799964 | 1.72E−10 | 0.00E+00 |

TABLE 3a-continued

| Chr | Gene | nSNPs | Start | Stop | Test | Pvalue | Best.SNP | SNP.pvalue | q - - - value |
|---|---|---|---|---|---|---|---|---|---|
| 6 | TNF | 87 | 31651328 | 31654091 | 1393.7 | <1.00E−06 | rs1799964 | 1.72E−10 | 0.00E+00 |
| 6 | LTB | 84 | 31656314 | 31658181 | 1360.6 | <1.00E−06 | rs1799964 | 1.72E−10 | 0.00E+00 |
| 6 | LST1 | 87 | 31661949 | 31664665 | 1480.1 | <1.00E−06 | rs1046089 | 8.38E−11 | 0.00E+00 |
| 6 | NCR3 | 90 | 31664650 | 31668741 | 1551.6 | <1.00E−06 | rs1046089 | 8.38E−11 | 0.00E+00 |
| 6 | AIF1 | 64 | 31691011 | 31692777 | 1277.2 | <1.00E−06 | rs1046089 | 8.38E−11 | 0.00E+00 |
| 6 | BAT2 | 62 | 31696428 | 31713533 | 1224.1 | <1.00E−06 | rs1046089 | 8.38E−11 | 0.00E+00 |
| 6 | BAT3 | 39 | 31714783 | 31728456 | 848.7 | <1.00E−06 | rs1046089 | 8.38E−11 | 0.00E+00 |
| 6 | APOM | 26 | 31731649 | 31733966 | 681.5 | <1.00E−06 | rs1046089 | 8.38E−11 | 0.00E+00 |
| 6 | C6orf47 | 25 | 31734053 | 31736528 | 662.0 | <1.00E−06 | rs1046089 | 8.38E−11 | 0.00E+00 |
| 6 | BAT4 | 28 | 31737840 | 31741142 | 708.4 | <1.00E−06 | rs1046089 | 8.38E−11 | 0.00E+00 |
| 6 | CSNK2B | 29 | 31741635 | 31745822 | 739.0 | <1.00E−06 | rs1046089 | 8.38E−11 | 0.00E+00 |
| 6 | LY6G5B | 29 | 31746706 | 31748206 | 746.3 | <1.00E−06 | rs1046089 | 8.38E−11 | 0.00E+00 |
| 6 | LY6G5C | 28 | 31752439 | 31756120 | 738.4 | <1.00E−06 | rs1046089 | 8.38E−11 | 0.00E+00 |
| 6 | BAT5 | 42 | 31762714 | 31779067 | 1082.1 | <1.00E−06 | rs1144708 | 8.38E−11 | 0.00E+00 |
| 6 | LY6G6F | 42 | 31782662 | 31786351 | 1063.2 | <1.00E−06 | rs1144708 | 8.38E−11 | 0.00E+00 |
| 6 | LY6G6D | 45 | 31791111 | 31793560 | 1053.2 | <1.00E−06 | rs1144708 | 8.38E−11 | 0.00E+00 |
| 6 | LY6G6C | 45 | 31794403 | 31797489 | 1053.2 | <1.00E−06 | rs1144708 | 8.38E−11 | 0.00E+00 |
| 6 | C6orf25 | 44 | 31799139 | 31800830 | 1073.0 | <1.00E−06 | rs1144708 | 8.38E−11 | 0.00E+00 |
| 6 | DDAH2 | 43 | 31802795 | 31806018 | 1071.8 | <1.00E−06 | rs1144708 | 8.38E−11 | 0.00E+00 |
| 6 | CLIC1 | 42 | 31806336 | 31812320 | 1035.7 | <1.00E−6 | rs1144708 | 8.38E−11 | 0.00E+00 |
| 6 | MSH5 | 50 | 31815752 | 31838431 | 1200.7 | <1.00E−06 | rs1144708 | 8.38E−11 | 0.00E+00 |
| 6 | C6orf26 | 47 | 31838751 | 31840603 | 1127.0 | <1.00E−06 | rs1144708 | 8.38E−11 | 0.00E+00 |
| 6 | C6orf27 | 49 | 31841349 | 31853087 | 1187.4 | <1.00E−06 | rs1144708 | 8.38E−11 | 0.00E+00 |
| 6 | VARS | 50 | 31853275 | 31871691 | 1225.4 | <1.00E−06 | rs1144708 | 8.38E−11 | 0.00E+00 |
| 6 | LSM2 | 38 | 31873152 | 31882722 | 937.5 | <1.00E−06 | rs2227956 | 8.38E−11 | 0.00E+00 |
| 6 | HSPA1L | 31 | 31885374 | 31890814 | 667.0 | <1.00E−06 | rs2227956 | 8.38E−11 | 0.00E+00 |
| 6 | HSPA1A | 22 | 31891269 | 31893698 | 505.0 | <1.00E−06 | rs2227956 | 8.38E−11 | 0.00E+00 |
| 6 | HSPA1B | 42 | 31903490 | 31906010 | 699.4 | <1.00E−06 | rs2227956 | 8.38E−11 | 0.00E+00 |
| 6 | C6orf48 | 47 | 31910671 | 31915520 | 772.3 | <1.00E−06 | rs2227956 | 8.38E−11 | 0.00E+00 |
| 6 | NEU1 | 48 | 31934807 | 31938688 | 765.7 | <1.00E−06 | rs2227956 | 8.38E−11 | 0.00E+00 |
| 6 | SLC44A4 | 47 | 31938948 | 31954071 | 701.6 | <1.00E−06 | rs497309 | 8.38E−11 | 0.00E+00 |
| 6 | EHMT2 | 59 | 31955515 | 31973443 | 904.6 | <1.00E−06 | rs497309 | 8.38E−11 | 0.00E+00 |
| 6 | ZBTB12 | 66 | 31975372 | 31977748 | 990.4 | <1.00E−06 | rs1270942 | 8.38E−11 | 0.00E+00 |
| 6 | C2 | 65 | 32003472 | 32021427 | 1204.0 | <1.00E−06 | rs1270942 | 8.38E−11 | 0.00E+00 |
| 6 | CFB | 54 | 32021699 | 32027840 | 1012.7 | <1.00E−06 | rs1270942 | 8.38E−11 | 0.00E+00 |
| 6 | RDBP | 53 | 32027842 | 32034843 | 1000.9 | <1.00E−06 | rs1270942 | 8.38E−11 | 0.00E+00 |
| 6 | SKIV2L | 52 | 32034559 | 32045511 | 976.3 | <1.00E−06 | rs1270942 | 8.38E−11 | 0.00E+00 |
| 6 | DOM3 | 52 | 32045566 | 32048011 | 976.3 | <1.00E−06 | rs1270942 | 8.38E−11 | 0.00E+00 |
| 6 | STK19 - - - 1 | 52 | 32047624 | 32057202 | 976.3 | <1.00E−06 | rs1270942 | 8.38E−11 | 0.00E+00 |
| 6 | C4A - - - 1 | 52 | 32057812 | 32078435 | 1008.3 | <1.00E−06 | rs1270942 | 8.38E−11 | 0.00E+00 |
| 6 | C4B - - - 1 | 52 | 32057812 | 32078436 | 1008.3 | <1.00E−06 | rs1270942 | 8.38E−11 | 0.00E+00 |
| 6 | STK19 - - - 2 | 26 | 32089495 | 32089939 | 640.1 | <1.00E−06 | rs1150758 | 8.38E−11 | 0.00E+00 |
| 6 | C4A - - - 2 | 50 | 32090549 | 32111173 | 1117.4 | <1.00E−06 | rs1150754 | 8.38E−11 | 0.00E+00 |
| 6 | C4B - - - 2 | 50 | 32090549 | 32111174 | 1117.4 | <1.00E−06 | rs1150754 | 8.38E−11 | 0.00E+00 |
| 6 | CYP21A2 | 43 | 32114060 | 32117398 | 870.5 | <1.00E−06 | rs1150754 | 8.38E−11 | 0.00E+00 |
| 6 | TNXB | 69 | 32116910 | 32185129 | 1562.9 | <1.00E−06 | rs1150752 | 8.38E−11 | 0.00E+00 |
| 6 | CREBL1 | 53 | 32191022 | 32203995 | 1228.9 | <1.00E−06 | rs1150752 | 8.38E−11 | 0.00E+00 |
| 6 | FKBPL | 43 | 32204461 | 32206045 | 1075.6 | <1.00E−06 | rs1150752 | 8.38E−11 | 0.00E+00 |
| 6 | PRRT1 | 32 | 32224117 | 32227698 | 850.9 | <1.00E−06 | rs1269852 | 8.38E−11 | 0.00E+00 |
| 6 | PPT2 | 29 | 32229278 | 32239430 | 759.7 | <1.00E−06 | rs1269852 | 8.38E−11 | 0.00E+00 |
| 6 | EGFL8 | 21 | 32240382 | 32244040 | 542.0 | <1.00E−06 | rs3134603 | 8.38E−11 | 0.00E+00 |
| 6 | A6PAT1 | 36 | 32243966 | 32253820 | 892.6 | <1.00E−06 | rs2267644 | 8.38E−11 | 0.00E+00 |
| 6 | RNF5 | 36 | 32254139 | 32256548 | 892.6 | <1.00E−06 | rs2267644 | 8.38E−11 | 0.00E+00 |
| 6 | AGER | 39 | 32256723 | 32260001 | 953.1 | <1.00E−06 | rs2267644 | 8.38E−11 | 0.00E+00 |
| 6 | PBX2 | 42 | 32260487 | 32265941 | 1000.9 | <1.00E−06 | rs2267644 | 8.38E−11 | 0.00E+00 |
| 6 | GPSM3 | 48 | 32266520 | 32271278 | 1124.8 | <1.00E−06 | rs2267644 | 8.38E−11 | 0.00E+00 |
| 6 | NOTCH4 | 55 | 32270597 | 32299822 | 1373.4 | <1.00E−06 | rs2267644 | 8.38E−11 | 0.00E+00 |
| 6 | C6orf10 | 70 | 32368452 | 32447634 | 2440.6 | <1.00E−06 | rs10947262 | 8.38E−11 | 0.00E+00 |
| 6 | BTNL2 | 53 | 32470490 | 32482878 | 1992.5 | <1.00E−06 | rs10947262 | 8.38E−11 | 0.00E+00 |
| 6 | HLA - - - DRA | 36 | 32515624 | 32520802 | 1388.6 | <1.00E−06 | rs10947262 | 8.38E−11 | 0.00E+00 |
| 6 | HLA - - - | 27 | 32654524 | 32665540 | 997.6 | <1.00E−06 | rs17425622 | 8.38E−11 | 0.00E+00 |
| 6 | HLA - - - | 46 | 32713160 | 32719407 | 1745.9 | <1.00E−06 | rs1063355 | 8.38E−11 | 0.00E+00 |
| 6 | HLA - - - | 44 | 32735634 | 32742444 | 1461.6 | <1.00E−06 | rs1063355 | 8.38E−11 | 0.00E+00 |
| 6 | HLA - - - | 52 | 32817140 | 32823199 | 1401.6 | <1.00E−06 | rs10807113 | 8.38E−11 | 0.00E+00 |
| 6 | HLA - - - DOB | 206 | 32888517 | 32892803 | 5053.7 | <1.00E−06 | rs1015166 | 8.38E−11 | 0.00E+00 |
| 6 | TAP2 | 206 | 32897587 | 32914525 | 4945.3 | <1.00E−06 | rs1015166 | 8.38E−11 | 0.00E+00 |
| 6 | PSMB8 | 200 | 32916471 | 32920690 | 4794.5 | <1.00E−06 | rs1015166 | 8.38E−11 | 0.00E+00 |
| 6 | TAP1 | 202 | 32920963 | 32929726 | 4879.4 | <1.00E−06 | rs1015166 | 8.38E−11 | 0.00E+00 |
| 6 | PSMB9 | 195 | 32929915 | 32935606 | 4766.9 | <1.00E−06 | rs1015166 | 8.38E−11 | 0.00E+00 |
| 6 | HLA - - - DMB | 55 | 33010392 | 33016795 | 734.5 | <1.00E−06 | rs241407 | 8.38E−11 | 0.00E+00 |
| 6 | HLA - - - DMA | 58 | 33024372 | 33028831 | 669.0 | <1.00E−06 | rs3101942 | 8.38E−11 | 0.00E+00 |
| 6 | BRD2 | 125 | 33044414 | 33057260 | 1382.2 | <1.00E−06 | rs9501239 | 8.40E−11 | 0.00E+00 |
| 6 | HLA - - - DOA | 103 | 33079937 | 33085367 | 1125.6 | <1.00E−06 | rs378571 | 5.98E−10 | 0.00E+00 |
| 6 | HLA - - - DPA1 | 44 | 33140771 | 33149356 | 778.8 | <1.00E−06 | rs2301226 | 8.38E−11 | 0.00E+00 |
| 6 | HLA - - - DPB1 | 47 | 33151737 | 33162954 | 824.8 | <1.00E−06 | rs2301226 | 8.38E−11 | 0.00E+00 |
| 6 | COL11A2 | 94 | 33238446 | 33268223 | 958.9 | 1.00E−06 | rs4713610 | 1.76E−09 | 9.99E−05 |
| 6 | WDR46 | 26 | 33354862 | 33364969 | 330.6 | 2.00E−06 | rs3106189 | 1.14E−06 | 1.94E−04 |
| 9 | TNFSF15 | 113 | 11659143 | 116608229 | 1270.5 | <1.00E−06 | rs4246905 | 9.45E−09 | 0.00E+00 |

TABLE 3a-continued

| Chr | Gene | nSNPs | Start | Stop | Test | Pvalue | Best.SNP | SNP.pvalue | q - - - value |
|---|---|---|---|---|---|---|---|---|---|
| 9 | GPSM1 | 75 | 13834872 | 138372493 | 1011.5 | <1.00E−06 | rs10870077 | 3.36E−08 | 0.00E+00 |
| 9 | DNL | 83 | 13837617 | 138378062 | 1077.0 | 1.00E−06 | rs10870077 | 3.36E−08 | 9.99E−05 |
| 9 | CARD9 | 92 | 13837822 | 138387939 | 1173.8 | <1.00E−06 | rs10870077 | 3.36E−08 | 0.00E+00 |
| 9 | SNAPC4 | 118 | 13838984 | 138412710 | 1427.1 | <1.00E−06 | rs10870077 | 3.36E−08 | 0.00E+00 |
| 9 | SDCCAG3 | 120 | 13841619 | 138424875 | 1435.4 | 1.00E−06 | rs10870077 | 3.36E−08 | 9.99E−05 |
| 9 | PMPCA | 116 | 13842493 | 138438034 | 1444.6 | <1.00E−06 | rs10870077 | 3.36E−08 | 0.00E+00 |
| 9 | INPP5E | 108 | 13844289 | 138454077 | 1154.8 | <1.00E−06 | rs4567159 | 5.36E−08 | 0.00E+00 |
| 9 | SEC16A | 114 | 13845436 | 138497328 | 1033.0 | 1.00E−06 | rs4266763 | 6.08E−08 | 9.99E−05 |
| 10 | IL2RA | 183 | 6093511 | 6144278 | 978.1 | <1.00E−06 | rs706778 | 6.34E−09 | 0.00E+00 |
| 10 | NKX2 - - - 3 | 155 | 10128267 | 101286270 | 2039.1 | <1.00E−06 | rs1332099 | 9.06E−11 | 0.00E+00 |
| 11 | IGF2 | 98 | 2106922 | 2127409 | 1110.8 | <1.00E−06 | rs3842727 | 8.38E−11 | 0.00E+00 |
| 11 | IGF2AS | 79 | 2118312 | 2126470 | 1061.4 | <1.00E−06 | rs3842727 | 8.38E−11 | 0.00E+00 |
| 11 | INS - - - IGF2 | 107 | 2124431 | 2139015 | 1257.6 | <1.00E−06 | rs3842727 | 8.38E−11 | 0.00E+00 |
| 11 | INS | 101 | 2137584 | 2139015 | 1253.3 | <1.00E−06 | rs3842727 | 8.38E−11 | 0.00E+00 |
| 11 | TH | 125 | 2141734 | 2149611 | 1376.9 | <1.00E−06 | rs3842727 | 8.38E−11 | 0.00E+00 |
| 12 | LRRK2 | 605 | 38905079 | 39049353 | 4273.4 | <1.00E−06 | rs17466626 | 3.24E−10 | 0.00E+00 |
| 12 | SILV | 47 | 54634155 | 54646093 | 377.6 | <1.00E−06 | rs772921 | 6.01E−09 | 0.00E+00 |
| 12 | CDK2 | 47 | 54646822 | 54652835 | 411.1 | <1.00E−06 | rs772921 | 6.01E−09 | 0.00E+00 |
| 12 | RAB5B | 51 | 54654128 | 54674755 | 502.5 | <1.00E−06 | rs772921 | 6.01E−09 | 0.00E+00 |
| 12 | SUOX | 46 | 54677309 | 54685576 | 502.1 | <1.00E−06 | rs772921 | 6.01E−09 | 0.00E+00 |
| 12 | IKZF4 | 49 | 54700955 | 54718486 | 670.2 | <1.00E−06 | rs772921 | 6.01E−09 | 0.00E+00 |
| 12 | RPS26 | 34 | 54721952 | 54724274 | 468.8 | <1.00E−06 | rs772921 | 6.01E−09 | 0.00E+00 |
| 12 | LOC728937 | 34 | 54722190 | 54724271 | 468.8 | <1.00E−06 | rs772921 | 6.01E−09 | 0.00E+00 |
| 12 | ERBB3 | 45 | 54760158 | 54783395 | 423.0 | <1.00E−06 | rs705704 | 1.24E−08 | 0.00E+00 |
| 15 | SMAD3 | 255 | 65145248 | 65274587 | 1367.5 | <1.00E−06 | rs17228058 | 8.85E−11 | 0.00E+00 |
| 16 | LOC390688 | 1 | 28332524 | 28333958 | 27.6 | <1.00E−06 | rs149299 | 1.49E−07 | 0.00E+00 |
| 16 | LOC440350- | 12 | 28376192 | 28389260 | 302.6 | <1.00E−06 | rs151181 | 7.45E−08 | 0.00E+00 |
| 16 | CLN3 | 19 | 28396100 | 28411124 | 449.3 | <1.00E−06 | rs12446550 | 6.39E−08 | 0.00E+00 |
| 16 | APOB48R | 26 | 28413493 | 28417783 | 552.9 | <1.00E−06 | rs12446550 | 6.39E−08 | 0.00E+00 |
| 16 | IL27 | 28 | 28418183 | 28425656 | 595.2 | <1.00E−06 | rs12446550 | 6.39E−08 | 0.00E+00 |
| 16 | NUPR1 | 45 | 28456162 | 28457996 | 821.3 | <1.00E−06 | rs12446550 | 6.39E−08 | 0.00E+00 |
| 16 | CCDC101 | 51 | 28472757 | 28510610 | 854.1 | <1.00E−06 | rs12446550 | 6.39E−08 | 0.00E+00 |
| 16 | SULT1A2 | 41 | 28510766 | 28515892 | 642.4 | <1.00E−06 | rs3859172 | 7.54E−08 | 0.00E+00 |
| 16 | SULT1A1 | 32 | 28524416 | 28542367 | 496.5 | <1.00E−06 | rs1968752 | 8.74E−08 | 0.00E+00 |
| 16 | LOC440350- | 8 | 28563411 | 28576505 | 167.4 | <1.00E−06 | rs1968752 | 8.74E−08 | 0.00E+00 |
| 16 | ATXN2L | 32 | 28741914 | 28756059 | 677.2 | 2.00E−06 | rs8049439 | 4.40E−07 | 1.94E−04 |
| 16 | TUFM | 35 | 28761232 | 28765230 | 721.6 | 1.00E−06 | rs8049439 | 4.40E−07 | 9.99E−05 |
| 16 | SH2B1 | 44 | 28782814 | 28793027 | 862.8 | 2.00E−06 | rs8049439 | 4.40E−07 | 1.94E−04 |
| 16 | ATP2A1 | 46 | 28797309 | 28823331 | 810.0 | 1.00E−06 | rs12928404 | 5.68E−07 | 9.99E−05 |
| 16 | RABEP2 | 45 | 28823242 | 28844033 | 601.1 | 2.00E−06 | rs8055782 | 7.91E−07 | 1.94E−04 |
| 16 | SNX20 | 73 | 49264386 | 49272667 | 1228.7 | <1.00E−06 | rs11649521 | 8.38E−11 | 0.00E+00 |
| 16 | NOD2 | 82 | 49288550 | 49324488 | 1509.8 | <1.00E−06 | rs11649521 | 8.38E−11 | 0.00E+00 |
| 16 | CYLD | 144 | 49333461 | 49393347 | 1889.9 | <1.00E−06 | rs11649521 | 8.38E−11 | 0.00E+00 |
| 17 | ZPBP2 | 68 | 35277980 | 35287675 | 892.7 | <1.00E−06 | rs12232497 | 2.71E−07 | 0.00E+00 |
| 19 | LOC126147 | 64 | 53856475 | 53868076 | 634.9 | 1.00E−06 | rs602662 | 5.31E−08 | 9.99E−05 |

TABLE 3b

Expression of genes associated with pAIDs are enriched in immune tissues. Mean ES-values and P-values of the TGSEA Wilcoxon rank sum test results for the pAID-associated gene set.

| Across all tissues/cells | GBAT GWS Genes | Wilcoxon Test (per tissue/cell) | | KS Test (per tissue/cell) | |
|---|---|---|---|---|---|
| | | Immune | Non-Immune | Immune | Non-Immune |
| Mean ES values | all | 2.982 | 1.089 | 3.06 | 1.277 |
| | noMHC | 0.448 | 0.099 | 0.561 | 0.068 |
| 2-sided KS Test (P-value) | all | 3.96E−14 | | 5.04E−12 | |
| | noMHC | 1.33E−14 | | 3.47E−13 | |
| 2-sided Wilcoxon Test (P-value) | all | 4.99E−17 | | 3.20E−15 | |
| | noMHC | 1.77E−15 | | 7.25E−15 | |

TABLE 3c

ImmGen (murine) cell lines included by cell lineage and developmental stage.

| Immgen Catalog Name | Type | Plot_name | Organ |
|---|---|---|---|
| SC LT34F BM | StemCell | StemCell 1 | BM |
| SC_LTSL_BM | StemCell | StemCell_2 | BM |
| SC_STSL_BM | StemCell | StemCell_3 | BM |
| SC_LTSL_FL | StemCell | StemCell_4 | FL |

TABLE 3c-continued

ImmGen (murine) cell lines included by cell lineage and developmental stage.

| Immgen Catalog Name | Type | Plot_name | Organ |
|---|---|---|---|
| SC_STSL_FL | StemCell | StemCell_5 | FL |
| SC_MPP34F_BM | StemCell | StemCell_6 | BM |
| SC_ST34F_BM | StemCell | StemCell_7 | BM |
| SC_CMP_BM | StemCell | StemCell_8 | BM |
| SC_MEP_BM | StemCell | StemCell_9 | BM |
| SC_GMP_BM | StemCell | StemCell_10 | BM |
| SC_CDP_BM | StemCell | StemCell_11 | BM |
| SC_MDP_BM | StemCell | StemCell_12 | BM |
| DC_4._Sp | DC | Dendritic_15 | SPL |
| DC_8._Sp | DC | Dendritic_16 | SPL |
| DC_8.4.11b._Sp | DC | Dendritic_17 | SPL |
| DC_8.4.11b._Sp.1 | DC | Dendritic_18 | SPL |
| DC_pDC_8._Sp | DC | Dendritic_19 | SPL |
| DC_pDC_8._Sp.1 | DC | Dendritic_20 | SPL |
| DC_4._SLN | DC | Dendritic_21 | LN |
| DC_8._SLN | DC | Dendritic_22 | LN |
| DC_8.4.11b._SLN | DC | Dendritic_23 | LN |
| DC_8.4.11b._SLN.1 | DC | Dendritic_24 | LN |
| DC_pDC_8._SLN | DC | Dendritic_25 | LN |
| DC_IIhilang.103.11b._SLN | DC | Dendritic_26 | LN |
| DC_IIhilang.103.11b._SLN | DC | Dendritic_27 | LN |
| DC_IIhilang.103.11blo_SLN.1 | DC | Dendritic_28 | LN |
| DC_IIhilang.103.11b._SLN.1 | DC | Dendritic_29 | LN |
| DC_4._MLN | DC | Dendritic_30 | MLN |
| DC_8._MLN | DC | Dendritic_31 | MLN |
| DC_8.4.11b._MLN | DC | Dendritic_32 | MLN |
| DC_8.4.11b._MLN.1 | DC | Dendritic_33 | MLN |
| DC_pDC_8._MLM | DC | Dendritic_34 | MLN |
| DC_LC_Sk | DC | Dendritic_35 | Skin |
| DC_103.11b._Lv | DC | Dendritic_36 | LV |
| DC_103.11b._Lv.1 | DC | Dendritic_37 | LV |
| DC_103.11b._LuLN | DC | Dendritic_38 | LuLN |
| DC_103.11b._LuLN.1 | DC | Dendritic_39 | LuLN |
| DC_103.11b.24.Lu | DC | Dendritic_40 | Lu |
| DC_103.11b._Lu | DC | Dendritic_41 | Lu |
| DC_103.11b._PolyIC_Lu | DC | Dendritic_42 | Lu |
| DC_103.11b._PolyIC_Lu.1 | DC | Dendritic_43 | Lu |
| DC_103.11b.F4.80lo_Kd | DC | Dendritic_44 | kidney |
| DC_103.11b._SI | DC | Dendritic_45 | sm intest |
| DC_103.11b._SI.1 | DC | Dendritic_46 | sm intest |
| Mo_6C.II._BM | Monocytes | Monocytes_49 | BM |
| Mo_6C.II._BM.1 | Monocytes | Monocytes_50 | BM |
| Mo_6C.II._BI | Monocytes | Monocytes_51 | BI |
| Mo_6C.II._BI.1 | Monocytes | Monocytes_52 | BI |
| Mo_6C.II._BI.2 | Monocytes | Monocytes_53 | BI |
| Mo_6C.II._BI.3 | Monocytes | Monocytes_54 | BI |
| Mo_6C.IIint_BI | Monocytes | Monocytes_55 | BI |
| Mo_6C.II._LN | Monocytes | Monocytes_56 | LN |
| MLP_BM | StemCell | StemCell_57 | BM |
| MLP_FL | StemCell | StemCell_58 | FL |
| proB_CLP_BM | B_Dev | B_Dev_59 | BM |
| proB_FrA_BM | B_Dev | B_Dev_60 | BM |
| proB_FrBC_BM | B_Dev | B_Dev_61 | BM |
| preB_FrC_BM | B_Dev | B_Dev_62 | BM |
| preB_FrD_BM | B_Dev | B_Dev_63 | BM |
| B_FrE_BM | B_Dev | B_Dev_64 | BM |
| proB_CLP_FL | B_Dev | B_Dev_65 | FL |
| proB_FrA_FL | B_Dev | B_Dev_66 | FL |
| proB_FrBC_FL | B_Dev | B_Dev_67 | FL |
| pre-B_FrD_PL | B_Dev | B_Dev_68 | FL |
| B_FrE_FL | B_Dev | B_Dev_69 | FL |
| B_T1_Sp | B_Dev | B_Dev_70 | SPL |
| B_T2_Sp | B_Dev | B_Dev_71 | SPL |
| B_T3_Sp | B_Dev | B_Dev_72 | SPL |
| B_Fo_Sp | B_Mature | B_Mature_73 | SPL |
| B_GC_Sp | B_Mature | B_Mature_74 | SPL |
| B_MZ_Sp | B_Mature | B_Mature_75 | SPL |
| B1a_Sp | B_Mature | B_Mature_76 | SPL |
| B_FrF_BM | B_Mature | B_Mature_77 | BM |
| B_Fo_MLN | B_Mature | B_Mature_78 | MLN |
| B_Fo_LN | B_Mature | B_Mature_79 | LN |
| B_Fo_PC | B_Mature | B_Mature_80 | PerC |
| B1b_PC | B_Mature | B_Mature_81 | PerC |
| B1a_PC | B_Mature | B_Mature_82 | PerC |
| MF_BM | Macrophages | Macrophages_83 | BM |

TABLE 3c-continued

ImmGen (murine) cell lines included by cell lineage and developmental stage.

| Immgen Catalog Name | Type | Plot_name | Organ |
|---|---|---|---|
| MF_RP_Sp | Macrophages | Macrophages_84 | SPL |
| MF_Lu | Macrophages | Macrophages_85 | Lu |
| MF_103.11b.24._Lu | Macrophages | Macrophages_86 | Lu |
| MF_II.480lo_PC | Macrophages | Macrophages_87 | PC |
| MF_103.11b._SI | Macrophages | Macrophages_88 | SI |
| MF_11cloSer_SI | Macrophages | Macrophages_89 | SI |
| MF_II.480hi_PC | Macrophages | Macrophages_92 | PC |
| MF_Microglia_CNS | Macrophages | Macrophages_93 | CNS |
| BEC_SLN | Stromal | Stromal_213 | SLN |
| St_31.38.44_SLN | Stromal | Stromal_214 | SLN |
| GN_BM | Neutrop | Neutrophils_9 | BM |
| GN_BI | Neutrop | Neutrophils_9 | BI |
| GN_Arth_BM | Neutrophils | Neutrophils_100 | BM |
| GN_Arth_SynF | Neutrophils | Neutrophils_101 | SynF |
| GN_UrAc_PC | Neutrophils | Neutrophils_102 | PC |
| NK_Sp | NK | NK_104 | SPL |
| NK_46CI._Sp | NK | NK_105 | SPL |
| NK_49CI._Sp.1 | NK | NK_106 | SPL |
| NK_49H._Sp | NK | NK_107 | SPL |
| NK_49H._Sp.1 | NK | NK_108 | SPL |
| preT_ETP_Th | T_Dev | T_Dev_116 | Th |
| preT_ETP.2A_Th | T_Dev | T_Dev_117 | Th |
| preT_DN2_Th | T_Dev | T_Dev_118 | Th |
| preT_DN2A_Th | T_Dev | T_Dev_119 | Th |
| preT_DN2B_Th | T_Dev | T_Dev_120 | Th |
| preT_DN2.3_Th | T_Dev | T_Dev_121 | Th |
| preT_DN3A_Th | T_Dev | T_Dev_122 | Th |
| preT_DN3B_Th | T_Dev | T_Dev_123 | Th |
| preT_DN3.4_Th | T_Dev | T_Dev_124 | Th |
| T_DN4_Th | T_Dev | T_Dev_125 | Th |
| T_ISP_Th | T_Dev | T_Dev_126 | Th |
| T_DP_Th | T_Dev | T_Dev_127 | Th |
| T_DPbl_Th | T_Dev | T_Dev_128 | Th |
| T_DPsm_Th | T_Dev | T_Dev_129 | Th |
| T_DP69._Th | T_Dev | T_Dev_130 | Th |
| T_4.8int_Th | T_Dev | T_Dev_131 | Th |
| T_4SP69._Th | T_CD4 | T_CD4_132 | Th |
| T_4SP24int_Th | T_CD4 | T_CD4_133 | Th |
| T_4SP24._Th | T_CD4 | T_CD4_134 | Th |
| T_4int8._Th | T_Dev | T_Dev_135 | Th |
| T_8SP69._Th | T_CD8 | T_CD8_136 | Th |
| T_8SP24int_Th | T_CD8 | T_CD8_137 | Th |
| T_8SP24._Th | T_CD8 | T_CD8_138 | Th |
| T_4Nve_Sp | T_CD4 | T_CD4_139 | SPL |
| T_4Mem_Sp | T_CD4 | T_CD4_140 | SPL |
| T_4Mem44h62l_Sp | T_CD4 | T_CD4_141 | SPL |
| T_4Nve_LN | T_CD4 | T_CD4_142 | LN |
| T_4Mem_LN | T_CD4 | T_CD4_143 | LN |
| T_4Mem44h62l_LN | T_CD4 | T_CD4_144 | LN |
| T_4Nve_PP | T_CD4 | T_CD4_145 | PP |
| T_4Nve_MLN | T_CD4 | T_CD4_146 | MLN |
| T_4_LN_BDC | T_CD4 | T_CD4_147 | BDC |
| T_4_PLN_BDC | T_CD4 | T_CD4_148 | BDC |
| T_4_Pa_BDC | T_CD4 | T_CD4_149 | BDC |
| T_4FP3._Sp | T_CD4 | T_CD4_150 | SPL |
| T_4FP3.25._Sp | T_CD4 | T_CD4_151 | SPL |
| T_4FP3.25._AA | T_CD4 | T_CD4_152 | AA |
| T_4FP3.25._LN | T_CD4 | T_CD4_153 | LN |
| T_8Nve_Sp | T_CD8 | T_CD8_154 | SPL |
| T_8Mem_Sp | T_CD8 | T_CD8_155 | SPL |
| T_8Nve_LN | T_CD8 | T_CD8_156 | LN |
| T_8Mem_LN | T_CD8 | T_CD8_157 | LN |
| T_8Nve_PP | T_CD8 | T_CD8_158 | PP |
| T_8Nve_MLN | T_CD8 | T_CD8_159 | MLN |
| NKT_44.NK1_1._Th | NK_T | NK_T_176 | Th |
| NKT_44.NK1_1._Th.1 | NK_T | NK_T_177 | Th |
| NKT_44.NK1_1._Th.2 | NK_T | NK_T_178 | Th |
| NKT_4._Sp | NK_T | NK_T_179 | SPL |
| NKT_4._Sp.1 | NK_T | NK_T_180 | SPL |
| NKT_4._Lv | NK_T | NK_T_181 | Lv |
| NKT_4._Lv.1 | NK_T | NK_T_182 | Lv |
| Tgd_Th | T_gd | T_gd_183 | Th |
| Tgd_vg2.24ahi_Th | T_gd | T_gd_186 | Th |
| Tgd_vg2.24ahi_e17_Th | T_gd | T_gd_187 | Th |
| Tgd_vg3.24ahi_e17_Th | T_gd | T_gd_188 | Th |

TABLE 3c-continued

ImmGen (murine) cell lines included by cell lineage and developmental stage.

| Immgen Catalog Name | Type | Plot_name | Organ |
|---|---|---|---|
| Tgd_vg5.24ahi_Th | T_gd | T_gd_189 | Th |
| Tgd_vg1.vd6.24alo_Th | T_gd | T_gd_190 | Th |
| Tgd_vg1.vd6.24alo_Th.1 | T_gd | T_gd_191 | Th |
| Tgd_vg2.24alo_Th | T_gd | T_gd_192 | Th |
| Tgd_vg3.24alo_e17_Th | T_gd | T_gd_193 | Th |
| Tgd_Sp | T_gd | T_gd_194 | SPL |
| Tgd_vg2._Sp | T_gd | T_gd_195 | SPL |
| Tgd_vg2._act_Sp | T_gd | T_gd_196 | SPL |
| Tgd_vg2._Sp.1 | T_gd | T_gd_197 | SPL |
| Tgd_vg2._act_Sp.1 | T_gd | T_gd_198 | SPL |
| Tgd_vg5._IEL | T_gd | T_gd_201 | IEL |
| Tgd_vg5._IEL.1 | T_gd | T_gd_202 | IEL |
| Tgd_vg5._act_IEL | T_gd | T_gd_203 | IEL |
| Tgd_vg5._act_IEL.1 | T_gd | T_gd_204 | IEL |
| Ep_MEChi_Th | Stromal | Stromal_205 | Th |
| Fi_MTS15._Th | Stromal | Stromal_206 | Th |
| Fi_Sk | Stromal | Stromal_207 | Skin |
| FRC_MLN | Stromal | Stromal_208 | MLN |
| FRC_SLN | Stromal | Stromal_209 | SLN |
| LEC_MLN | Stromal | Stromal_210 | MLN |
| LEC_SLN | Stromal | Stromal_211 | SLN |
| BEC_MLN | Stromal | Stromal_212 | MLN |
| BEC_SLN | Stromal | Stromal_213 | SLN |
| St_31.38.44._SLN | Stroma | Stromal_214 | SLN |

TABLE 4a

Significant pAID pairs identified by genome-wide pairwise sharing analysis.

| pAIDs | GPS P-value | MHC removed GPS P-value |
|---|---|---|
| CEL-T1D | 3.44E−05 | 8.02E−01 |
| CVID-JIA | 6.88E−05 | 7.30E−05 |
| UC-T1D | 2.26E−04 | 3.73E−01 |
| T1D-JIA | 2.76E−04 | 1.31E−02 |
| UC-JIA | 3.15E−04 | 9.83E−01 |
| CEL-UC | 4.99E−04 | 8.17E−01 |
| CD-UC | 2.36E−03 | 7.32E−04 |
| CEL-JIA | 8.19E−04 | 3.28E−02 |

TABLE 4b

Significant autoimmune disease pairs identified by locus-specific pairwise sharing analysis.

| Pair | Zstat | P-value | Adj P-value |
|---|---|---|---|
| SJO-SSC | 11.53 | 9.05E−31 | 1.38E−28 |
| PBC-SJO | 7.62 | 2.52E−14 | 3.86E−12 |
| T1D-JIA | 5.75 | 9.13E−09 | 1.40E−06 |
| CEL-JIA | 5.74 | 9.40E−09 | 1.44E−06 |
| CVID-JIA | 5.67 | 1.47E−08 | 2.25E−06 |
| MS-PBC | 5.33 | 1.01E−07 | 1.54E−05 |
| CEL-THY | 5.25 | 1.49E−07 | 2.28E−05 |
| T1D-PBC | 5.21 | 1.88E−07 | 2.88E−05 |
| CVID-THY | 5.12 | 3.08E−07 | 4.71E−05 |
| PBC-SSC | 5.10 | 3.36E−07 | 5.14E−05 |
| JIA-PBC | 4.90 | 9.46E−07 | 1.45E−04 |
| UC-CD | 4.82 | 1.41E−06 | 2.15E−04 |
| CEL-RA | 4.67 | 2.98E−06 | 4.56E−04 |
| CEL-PSC | 4.51 | 6.50E−06 | 9.94E−04 |
| SLE-THY | 4.51 | 6.59E−06 | 1.01E−03 |
| SLE-SJO | 4.50 | 6.65E−06 | 1.02E−03 |
| PSC-THY | 4.40 | 1.09E−05 | 1.66E−03 |
| T1D-VIT | 4.38 | 1.18E−05 | 1.81E−03 |
| SLE-SSC | 4.19 | 2.75E−05 | 4.20E−03 |
| PS-JIA | 4.15 | 3.39E−05 | 5.19E−03 |
| VIT-THY | 4.10 | 4.12E−05 | 6.31E−03 |
| AS-JIA | 4.09 | 4.30E−05 | 6.58E−03 |
| T1D-AA | 3.89 | 9.96E−05 | 1.52E−02 |
| CEL-PBC | 3.88 | 1.06E−04 | 1.63E−02 |
| CEL-SJO | 3.78 | 1.59E−04 | 2.43E−02 |
| RA-THY | 3.74 | 1.87E−04 | 2.86E−02 |
| PBC-RA | 3.68 | 2.30E−04 | 3.51E−02 |
| AA-VIT | 3.66 | 2.56E−04 | 3.92E−02 |

**Note
that due to limited data available across the MHC, candidate genes in the extended MHC were not included in this analysis

TABLE 5

MicroRNA target (a) and transcription factor (b) consensus binding site target gene set enrichment analysis.

| Target Seq (Known TF) | TF_ID | Enrichment Statistics |
|---|---|---|
| hsa_GGGCGGR_V$SP1_Q6 | DB_ID = 2452 | C = 2891; O = 45; E = 11.93; R = 3.77; rawP = 5.42e−15; adjP = 2.30e−12 |
| hsa_TGGAAA_V$NFAT_Q4_01 | DB_ID = 2437 | C = 1871; O = 31; E = 7.72; R = 4.01; rawP = 4.02e−11; adjP = 8.54e−09 |
| hsa_V$NFKB_C | DB_ID = 1992 | C = 262; O = 13; E = 1.08; R = 12.02; rawP = 8.64e−11; adjP = 1.03e−08 |
| hsa_CTTTGT_V$LEF1_Q2 | DB_ID = 2428 | C = 1939; O = 31; E = 8.00; R = 3.87; rawP = 9.71e−11; adjP = 1.03e−08 |
| hsa_RYTTCCTG_V$ETS2_B | DB_ID = 2415 | C = 1074; O = 21; E = 4.43; R = 4.74; rawP = 4.47e−09; adjP = 3.80e−07 |
| hsa_V$TEF1_Q6 | DB_ID = 2212 | C = 222; O = 10; E = 0.92; R = 10.91; rawP = 3.42e−08; adjP = 2.42e−06 |

TABLE 5-continued

MicroRNA target (a) and transcription factor (b) consensus binding site target gene set enrichment analysis.

| Target Seq (Known TF) | TF_ID | Enrichment Statistics |
|---|---|---|
| hsa_TTANTCA_UNKNOWN | DB_ID = 2372 | C = 937; O = 18; E = 3.87; R = 4.65; rawP = 7.91e−08; adjP = 4.80e−06 |
| hsa_V$NFKAPPAB_01 | DB_ID = 1874 | C = 250; O = 10; E = 1.03; R = 9.69; rawP = 1.04e−07; adjP = 5.53e−06 |
| hsa_V$MYOD_Q6_01 | DB_ID = 2305 | C = 254; O = 10; E = 1.05; R = 9.54; rawP = 1.20e−07; adjP = 5.67e−06 |
| hsa_CAGCTG_V$AP4_Q5 | DB_ID = 2403 | C = 1502; O = 22; E = 6.20; R = 3.55; rawP = 2.99e−07; adjP = 1.27e−05 |
| hsa_V$GATA1_02 | DB_ID = 1930 | C = 241; O = 9; E = 0.99; R = 9.05; rawP = 8.12e−07; adjP = 3.14e−05 |
| hsa_V$NFAT_Q6 | DB_ID = 2050 | C = 245; O = 9; E = 1.01; R = 8.90; rawP = 9.31e−07; adjP = 3.30e−05 |
| hsa_V$AML1_01 | DB_ID = 2032 | C = 261; O = 9; E = 1.08; R = 8.35; rawP = 1.57e−06; adjP = 4.65e−05 |
| hsa_V$AML1_Q6 | DB_ID = 2244 | C = 261; O = 9; E = 1.08; R = 8.35; rawP = 1.57e−06; adjP = 4.65e−05 |
| hsa_GGGTGGRR_V$PAX4_03 | DB_ID = 2445 | C = 1278; O = 19; E = 5.27; R = 3.60; rawP = 1.64e−06; adjP = 4.65e−05 |
| hsa_GGGAGGRR_V$MAZ_Q6 | DB_ID = 2430 | C = 2250; O = 26; E = 9.29; R = 2.80; rawP = 2.08e−06; adjP = 5.53e−05 |
| hsa_TGAYRTCA_V$ATF3_Q6 | DB_ID = 2406 | C = 531; O = 12; E = 2.19; R = 5.48; rawP = 2.45e−06; adjP = 6.12e−05 |
| hsa_V$AHR_Q5 | DB_ID = 2263 | C = 209; O = 8; E = 0.86; R = 9.27; rawP = 2.80e−06; adjP = 6.61e−05 |
| hsa_CAGGTG_V$E12_Q6 | DB_ID = 2409 | C = 2450; O = 27; E = 10.11; R = 2.67; rawP = 3.14e−06; adjP = 6.67e−05 |
| hsa_TCCCRNNRTGC_UNKNOWN | DB_ID = 2364 | C = 211; O = 8; E = 0.87; R = 9.19; rawP = 3.01e−06; adjP = 6.67e−05 |
| hsa_GATAAGR_V$GATA_C | DB_ID = 2419 | C = 290; O = 9; E = 1.20; R = 7.52; rawP = 3.71e−06; adjP = 7.51e−05 |
| hsa_YGCGYRCGC_UNKNOWN | DB_ID = 2389 | C = 314; O = 9; E = 1.30; R = 6.94; rawP = 7.04e−06; adjP = 0.0001 |
| hsa_TATAAA_V$TATA_01 | DB_ID = 2456 | C = 1276; O = 18; E = 5.27; R = 3.42; rawP = 6.41e−06; adjP = 0.0001 |
| hsa_AACTTT_UNKNOWN | DB_ID = 1851 | C = 1859; O = 22; E = 7.67; R = 2.87; rawP = 9.45e−06; adjP = 0.0001 |
| hsa_V$ISRE_01 | DB_ID = 2029 | C = 246; O = 8; E = 1.02; R = 7.88; rawP = 9.26e−06; adjP = 0.0001 |
| hsa_V$YY1_Q6 | DB_ID = 2268 | C = 238; O = 8; E = 0.98; R = 8.14; rawP = 7.28e−06; adjP = 0.0001 |
| hsa_V$NRF1_Q6 | DB_ID = 2193 | C = 245; O = 8; E = 1.01; R = 7.91; rawP = 8.99e−06; adjP = 0.0001 |
| hsa_CACGTG_V$MYC_Q2 | DB_ID = 2434 | C = 1015; O = 16; E = 4.19; R = 3.82; rawP = 5.48e−06; adjP = 0.0001 |
| hsa_V$COREBINDINGFACTOR_Q6 | DB_ID = 2221 | C = 266; O = 8; E = 1.10; R = 7.29; rawP = 1.63e−05; adjP = 0.0002 |
| hsa_ACTAYRNNNCCCR_UNKNOWN | DB_ID = 1928 | C = 444; O = 10; E = 1.83; R = 5.46; rawP = 1.77e−05; adjP = 0.0002 |
| hsa_TTGTTT_V$FOXO4_01 | DB_ID = 2416 | C = 2037; O = 23; E = 8.41; R = 2.74; rawP = 1.24e−05; adjP = 0.0002 |
| hsa_V$USF_C | DB_ID = 1999 | C = 275; O = 8; E = 1.14; R = 7.05; rawP = 2.07e−05; adjP = 0.0003 |
| hsa_V$EGR_Q6 | DB_ID = 2283 | C = 273; O = 8; E = 1.13; R = 7.10; rawP = 1.96e−05; adjP = 0.0003 |
| hsa_V$CREB_Q4_01 | DB_ID = 2294 | C = 209; O = 7; E = 0.86; R = 8.11; rawP = 2.81e−05; adjP = 0.0004 |
| hsa_GCANCTGNY_V$MYOD_Q6 | DB_ID = 2435 | C = 913; O = 14; E = 3.77; R = 3.72; rawP = 2.91e−05; adjP = 0.0004 |
| hsa_TGGNNNNNNKCCAR_UNKNOWN | DB_ID = 2368 | C = 411; O = 9; E = 1.70; R = 5.31; rawP = 5.81e−05; adjP = 0.0006 |
| hsa_V$NFKB_Q6_01 | DB_ID = 2259 | C = 231; O = 7; E = 0.95; R = 7.34; rawP = 5.30e−05; adjP = 0.0006 |
| hsa_TGACGTCA_V$ATF3_Q6 | DB_ID = 2405 | C = 230; O = 7; E = 0.95; R = 7.37; rawP = 5.16e−05; adjP = 0.0006 |
| hsa_TGTTTGY_V$HNF3_Q6 | DB_ID = 2423 | C = 733; O = 12; E = 3.03; R = 3.97; rawP = 5.91e−05; adjP = 0.0006 |
| hsa_V$ZF5_01 | DB_ID = 2217 | C = 234; O = 7; E = 0.97; R = 7.25; rawP = 5.75e−05; adjP = 0.0006 |
| hsa_YTTCCNNNGGAMR_UNKNOWN | DB_ID = 2398 | C = 52; O = 4; E = 0.21; R = 18.64; rawP = 6.51e−05; adjP = 0.0007 |
| hsa_V$USF2_Q6 | DB_ID = 2224 | C = 249; O = 7; E = 1.03; R = 6.81; rawP = 8.48e−05; adjP = 0.0007 |
| hsa_GTGACGY_V$E4F1_Q6 | DB_ID = 2412 | C = 646; O = 11; E = 2.67; R = 4.13; rawP = 8.54e−05; adjP = 0.0007 |
| hsa_V$MYC_Q2 | DB_ID = 2274 | C = 182; O = 6; E = 0.75; R = 7.99; rawP = 0.0001; adjP = 0.0007 |
| hsa_V$CREBP1_Q2 | DB_ID = 1970 | C = 254; O = 7; E = 1.05; R = 6.68; rawP = 9.60e−05; adjP = 0.0007 |
| hsa_V$YY1_01 | DB_ID = 1879 | C = 245; O = 7; E = 1.01; R = 6.92; rawP = 7.67e−05; adjP = 0.0007 |
| hsa_V$TAL1BETAE47_01 | DB_ID = 1882 | C = 246; O = 7; E = 1.02; R = 6.89; rawP = 7.86e−05; adjP = 0.0007 |
| hsa_V$HMGIY_Q6 | DB_ID = 2243 | C = 248; O = 7; E = 1.02; R = 6.84; rawP = 8.27e−05; adjP = 0.0007 |
| hsa_RCGCANGCGY_V$NRF1_Q6 | DB_ID = 2441 | C = 894; O = 13; E = 3.69; R = 3.52; rawP = 9.60e−05; adjP = 0.0007 |
| hsa_RACCACAR_V$AML_Q6 | DB_ID = 2401 | C = 255; O = 7; E = 1.05; R = 6.65; rawP = 9.83e−05; adjP = 0.0007 |
| hsa_V$AREB6_03 | DB_ID = 2080 | C = 253; O = 7; E = 1.04; R = 6.70; rawP = 9.36e−05; adjP = 0.0007 |
| hsa_V$AML_Q6 | DB_ID = 2253 | C = 261; O = 7; E = 1.08; R = 6.50; rawP = 0.0001; adjP = 0.0007 |
| hsa_V$HOXA4_Q2 | DB_ID = 2183 | C = 266; O = 7; E = 1.10; R = 6.38; rawP = 0.0001; adjP = 0.0007 |
| hsa_V$FXR_Q3 | DB_ID = 2177 | C = 113; O = 5; E = 0.47; R = 10.72; rawP = 0.0001; adjP = 0.0007 |
| hsa_V$ELF1_Q6 | DB_ID = 2240 | C = 238; O = 7; E = 0.98; R = 7.13; rawP = 6.39e−05; adjP = 0.0007 |
| hsa_V$IRF7_01 | DB_ID = 2110 | C = 250; O = 7; E = 1.03; R = 6.78; rawP = 8.69e−05; adjP = 0.0007 |
| hsa_V$CREBP1CJUN_01 | DB_ID = 1867 | C = 258; O = 7; E = 1.06; R = 6.57; rawP = 0.0001; adjP = 0.0007 |
| hsa_V$TAL1BETAITF2_01 | DB_ID = 1887 | C = 253; O = 7; E = 1.04; R = 6.70; rawP = 9.36e−05; adjP = 0.0007 |
| hsa_V$CREB_01 | DB_ID = 1865 | C = 261; O = 7; E = 1.08; R = 6.50; rawP = 0.0001; adjP = 0.0007 |
| hsa_V$GATA1_04 | DB_ID = 1932 | C = 242; O = 7; E = 1.00; R = 7.01; rawP = 7.10e−05; adjP = 0.0007 |
| hsa_GCTNWTTGK_UNKNOWN | DB_ID = 2247 | C = 299; O = 7; E = 1.23; R = 5.67; rawP = 0.0003; adjP = 0.0021 |
| hsa_MGGAAGTG_V$GABP_B | DB_ID = 2418 | C = 744; O = 11; E = 3.07; R = 3.58; rawP = 0.0003; adjP = 0.0021 |
| hsa_SYATTGTG_UNKNOWN | DB_ID = 2360 | C = 231; O = 6; E = 0.95; R = 6.29; rawP = 0.0004; adjP = 0.0027 |
| hsa_V$NFKAPPAB65_01 | DB_ID = 1871 | C = 235; O = 6; E = 0.97; R = 6.19; rawP = 0.0005; adjP = 0.0033 |
| hsa_V$STAT5A_01 | DB_ID = 2112 | C = 243; O = 6; E = 1.00; R = 5.98; rawP = 0.0005; adjP = 0.0033 |
| hsa_V$HNF4_DR1_Q3 | DB_ID = 2249 | C = 257; O = 6; E = 1.06; R = 5.66; rawP = 0.0007; adjP = 0.0036 |
| hsa_V$HNF_Q6 | DB_ID = 2331 | C = 257; O = 6; E = 1.06; R = 5.66; rawP = 0.0007; adjP = 0.0036 |
| hsa_V$NFKB_Q6 | DB_ID = 1984 | C = 254; O = 6; E = 1.05; R = 5.72; rawP = 0.0007; adjP = 0.0036 |
| hsa_V$STAT_Q6 | DB_ID = 2262 | C = 258; O = 6; E = 1.06; R = 5.63; rawP = 0.0007; adjP = 0.0036 |
| hsa_V$ICSBP_Q6 | DB_ID = 2210 | C = 246; O = 6; E = 1.02; R = 5.91; rawP = 0.0006; adjP = 0.0036 |
| hsa_V$CP2_01 | DB_ID = 1889 | C = 258; O = 6; E = 1.06; R = 5.63; rawP = 0.0007; adjP = 0.0036 |
| hsa_V$TATA_01 | DB_ID = 2025 | C = 255; O = 6; E = 1.05; R = 5.70; rawP = 0.0007; adjP = 0.0036 |
| hsa_V$STAT_01 | DB_ID = 2003 | C = 248; O = 6; E = 1.02; R = 5.86; rawP = 0.0006; adjP = 0.0036 |
| hsa_V$TAL1ALPHAE47_01 | DB_ID = 1883 | C = 249; O = 6; E = 1.03; R = 5.84; rawP = 0.0006; adjP = 0.0036 |
| hsa_V$TST1_01 | DB_ID = 1937 | C = 256; O = 6; E = 1.06; R = 5.68; rawP = 0.0007; adjP = 0.0036 |
| hsa_V$CREL_01 | DB_ID = 1872 | C = 255; O = 6; E = 1.05; R = 5.70; rawP = 0.0007; adjP = 0.0036 |
| hsa_V$GATA4_Q3 | DB_ID = 2178 | C = 246; O = 6; E = 1.02; R = 5.91; rawP = 0.0006; adjP = 0.0036 |

TABLE 5-continued

MicroRNA target (a) and transcription factor (b) consensus binding site target gene set enrichment analysis.

| Target Seq (Known TF) | TF_ID | Enrichment Statistics |
|---|---|---|
| hsa_V$PAX2_02 | DB_ID = 2139 | C = 255; O = 6; E = 1.05; R = 5.70; rawP = 0.0007; adjP = 0.0036 |
| hsa_V$MAX_01 | DB_ID = 1924 | C = 258; O = 6; E = 1.06; R = 5.63; rawP = 0.0007; adjP = 0.0036 |
| hsa_V$PXR_Q2 | DB_ID = 2328 | C = 254; O = 6; E = 1.05; R = 5.72; rawP = 0.0007; adjP = 0.0036 |
| hsa_V$MYCMAX_01 | DB_ID = 1923 | C = 252; O = 6; E = 1.04; R = 5.77; rawP = 0.0007; adjP = 0.0036 |
| hsa_V$HSF2_01 | DB_ID = 1951 | C = 248; O = 6; E = 1.02; R = 5.86; rawP = 0.0006; adjP = 0.0036 |
| hsa_V$AREB6_02 | DB_ID = 2079 | C = 253; O = 6; E = 1.04; R = 5.75; rawP = 0.0007; adjP = 0.0036 |
| hsa_V$NFAT_Q4_01 | DB_ID = 2310 | C = 264; O = 6; E = 1.09; R = 5.51; rawP = 0.0008; adjP = 0.0040 |
| hsa_V$CREB_Q2 | DB_ID = 1968 | C = 262; O = 6; E = 1.08; R = 5.55; rawP = 0.0008; adjP = 0.0040 |
| hsa_V$NMYC_01 | DB_ID = 1875 | C = 269; O = 6; E = 1.11; R = 5.40; rawP = 0.0009; adjP = 0.0044 |
| hsa_WGGAATGY_V$TEF1_Q6 | DB_ID = 2458 | C = 370; O = 7; E = 1.53; R = 4.58; rawP = 0.0009; adjP = 0.0044 |
| hsa_V$HAND1E47_01 | DB_ID = 2002 | C = 274; O = 6; E = 1.13; R = 5.31; rawP = 0.0010; adjP = 0.0048 |
| hsa_V$ATF_B | DB_ID = 2056 | C = 186; O = 5; E = 0.77; R = 6.51; rawP = 0.0011; adjP = 0.0051 |
| hsa_RGAGGAARY_V$PU1_Q6 | DB_ID = 2447 | C = 495; O = 8; E = 2.04; R = 3.92; rawP = 0.0011; adjP = 0.0051 |
| hsa_V$TATA_C | DB_ID = 1998 | C = 279; O = 6; E = 1.15; R = 5.21; rawP = 0.0011; adjP = 0.0051 |
| hsa_GTCNYYATGR_UNKNOWN | DB_ID = 2335 | C = 108; O = 4; E = 0.45; R = 8.97; rawP = 0.0011; adjP = 0.0051 |
| hsa_V$MAZ_Q6 | DB_ID = 2189 | C = 189; O = 5; E = 0.78; R = 6.41; rawP = 0.0012; adjP = 0.0054 |
| hsa_V$FXR_IR1_Q6 | DB_ID = 2252 | C = 110; O = 4; E = 0.45; R = 8.81; rawP = 0.0012; adjP = 0.0054 |
| hsa_V$ETF_Q6 | DB_ID = 2208 | C = 113; O = 4; E = 0.47; R = 8.58; rawP = 0.0013; adjP = 0.0058 |
| hsa_CTGCAGY_UNKNOWN | DB_ID = 2137 | C = 756; O = 10; E = 3.12; R = 3.20; rawP = 0.0013; adjP = 0.0058 |
| hsa_GGAMTNNNNNTCCY_UNKNOWN | DB_ID = 2269 | C = 117; O = 4; E = 0.48; R = 8.28; rawP = 0.0014; adjP = 0.0061 |
| hsa_V$RREB1_01 | DB_ID = 2028 | C = 204; O = 5; E = 0.84; R = 5.94; rawP = 0.0016; adjP = 0.0067 |
| hsa_RACTNNRTTTNC_UNKNOWN | DB_ID = 2347 | C = 121; O = 4; E = 0.50; R = 8.01; rawP = 0.0016; adjP = 0.0067 |
| hsa_CAGGTA_V$AREB6_01 | DB_ID = 2404 | C = 780; O = 10; E = 3.22; R = 3.11; rawP = 0.0016; adjP = 0.0067 |
| hsa_CTTTGA_V$LEF1_Q2 | DB_ID = 2427 | C = 1208; O = 13; E = 4.99; R = 2.61; rawP = 0.0016; adjP = 0.0067 |
| hsa_V$IRF2_01 | DB_ID = 1881 | C = 125; O = 4; E = 0.52; R = 7.75; rawP = 0.0018; adjP = 0.0075 |
| hsa_GCCATNTTG_V$YY1_Q6 | DB_ID = 2459 | C = 419; O = 7; E = 1.73; R = 4.05; rawP = 0.0019; adjP = 0.0078 |
| hsa_V$EVI1_02 | DB_ID = 1894 | C = 129; O = 4; E = 0.53; R = 7.51; rawP = 0.0021; adjP = 0.0086 |
| hsa_V$LBP1_Q6 | DB_ID = 2185 | C = 220; O = 5; E = 0.91; R = 5.51; rawP = 0.0023; adjP = 0.0093 |
| hsa_RGAANNTTC_V$HSF1_01 | DB_ID = 2425 | C = 441; O = 7; E = 1.82; R = 3.85; rawP = 0.0025; adjP = 0.0100 |
| hsa_GATTGGY_V$NFY_Q6_01 | DB_ID = 2440 | C = 1141; O = 12; E = 4.71; R = 2.55; rawP = 0.0029; adjP = 0.0115 |
| hsa_V$NKX61_01 | DB_ID = 2090 | C = 236; O = 5; E = 0.97; R = 5.13; rawP = 0.0031; adjP = 0.0122 |
| hsa_V$STAT5B_01 | DB_ID = 2113 | C = 239; O = 5; E = 0.99; R = 5.07; rawP = 0.0032; adjP = 0.0123 |
| hsa_V$TBP_01 | DB_ID = 2125 | C = 239; O = 5; E = 0.99; R = 5.07; rawP = 0.0032; adjP = 0.0123 |
| hsa_V$YY1_02 | DB_ID = 1886 | C = 239; O = 5; E = 0.99; R = 5.07; rawP = 0.0032; adjP = 0.0123 |
| hsa_V$E2F1_Q3 | DB_ID = 2095 | C = 240; O = 5; E = 0.99; R = 5.05; rawP = 0.0033; adjP = 0.0125 |
| hsa_V$E2A_Q2 | DB_ID = 2279 | C = 241; O = 5; E = 0.99; R = 5.03; rawP = 0.0034; adjP = 0.0128 |
| hsa_V$CMYB_01 | DB_ID = 1849 | C = 244; O = 5; E = 1.01; R = 4.96; rawP = 0.0035; adjP = 0.0128 |
| hsa_V$FOXO3_01 | DB_ID = 2131 | C = 243; O = 5; E = 1.00; R = 4.99; rawP = 0.0035; adjP = 0.0128 |
| hsa_V$GATA1_03 | DB_ID = 1931 | C = 243; O = 5; E = 1.00; R = 4.99; rawP = 0.0035; adjP = 0.0128 |
| hsa_V$ATF3_Q6 | DB_ID = 2156 | C = 245; O = 5; E = 1.01; R = 4.94; rawP = 0.0036; adjP = 0.0131 |
| hsa_AAAYWAACM_V$HFH4_01 | DB_ID = 2421 | C = 250; O = 5; E = 1.03; R = 4.85; rawP = 0.0039; adjP = 0.0137 |
| hsa_V$OCT1_05 | DB_ID = 1960 | C = 250; O = 5; E = 1.03; R = 4.85; rawP = 0.0039; adjP = 0.0137 |
| hsa_V$PAX4_03 | DB_ID = 2066 | C = 249; O = 5; E = 1.03; R = 4.87; rawP = 0.0039; adjP = 0.0137 |
| hsa_V$AR_01 | DB_ID = 2133 | C = 153; O = 4; E = 0.63; R = 6.33; rawP = 0.0038; adjP = 0.0137 |
| hsa_V$CP2_02 | DB_ID = 2316 | C = 253; O = 5; E = 1.04; R = 4.79; rawP = 0.0041; adjP = 0.0139 |
| hsa_V$MYB_Q6 | DB_ID = 1971 | C = 253; O = 5; E = 1.04; R = 4.79; rawP = 0.0041; adjP = 0.0139 |
| hsa_V$HLF_01 | DB_ID = 2030 | C = 253; O = 5; E = 1.04; R = 4.79; rawP = 0.0041; adjP = 0.0139 |
| hsa_V$P53_DECAMER_Q2 | DB_ID = 2245 | C = 253; O = 5; E = 1.04; R = 4.79; rawP = 0.0041; adjP = 0.0139 |
| hsa_V$ATF_01 | DB_ID = 1856 | C = 256; O = 5; E = 1.06; R = 4.73; rawP = 0.0043; adjP = 0.0142 |
| hsa_V$IRF1_Q6 | DB_ID = 2241 | C = 254; O = 5; E = 1.05; R = 4.77; rawP = 0.0042; adjP = 0.0142 |
| hsa_V$SREBP_Q3 | DB_ID = 2261 | C = 256; O = 5; E = 1.06; R = 4.73; rawP = 0.0043; adjP = 0.0142 |
| hsa_V$AP4_01 | DB_ID = 1850 | C = 256; O = 5; E = 1.06; R = 4.73; rawP = 0.0043; adjP = 0.0142 |
| hsa_V$ZIC1_01 | DB_ID = 2106 | C = 257; O = 5; E = 1.06; R = 4.71; rawP = 0.0044; adjP = 0.0144 |
| hsa_RTAAACA_V$FREAC2_01 | DB_ID = 2417 | C = 907; O = 10; E = 3.74; R = 2.67; rawP = 0.0046; adjP = 0.0145 |
| hsa_V$E12_Q6 | DB_ID = 2206 | C = 260; O = 5; E = 1.07; R = 4.66; rawP = 0.0046; adjP = 0.0145 |
| hsa_YATTNATC_UNKNOWN | DB_ID = 2385 | C = 370; O = 6; E = 1.53; R = 3.93; rawP = 0.0045; adjP = 0.0145 |
| hsa_TAANNYSGCG_UNKNOWN | DB_ID = 2361 | C = 80; O = 3; E = 0.33; R = 9.09; rawP = 0.0045; adjP = 0.0145 |
| hsa_V$NF1_Q6 | DB_ID = 1982 | C = 259; O = 5; E = 1.07; R = 4.68; rawP = 0.0046; adjP = 0.0145 |
| hsa_V$OSF2_Q6 | DB_ID = 2228 | C = 261; O = 5; E = 1.08; R = 4.64; rawP = 0.0047; adjP = 0.0146 |
| hsa_WCTCNATGGY_UNKNOWN | DB_ID = 2377 | C = 81; O = 3; E = 0.33; R = 8.97; rawP = 0.0047; adjP = 0.0146 |
| hsa_V$MYCMAX_02 | DB_ID = 1927 | C = 263; O = 5; E = 1.09; R = 4.61; rawP = 0.0049; adjP = 0.0148 |
| hsa_V$HNF4_01 | DB_ID = 1938 | C = 264; O = 5; E = 1.09; R = 4.59; rawP = 0.0049; adjP = 0.0148 |
| hsa_V$HEB_Q6 | DB_ID = 2209 | C = 263; O = 5; E = 1.09; R = 4.61; rawP = 0.0049; adjP = 0.0148 |
| hsa_V$TCF1P_Q6 | DB_ID = 2198 | C = 263; O = 5; E = 1.09; R = 4.61; rawP = 0.0049; adjP = 0.0148 |
| hsa_V$ARP1_01 | DB_ID = 1954 | C = 165; O = 4; E = 0.68; R = 5.87; rawP = 0.0050; adjP = 0.0149 |
| hsa_V$HSF1_01 | DB_ID = 1949 | C = 265; O = 5; E = 1.09; R = 4.57; rawP = 0.0050; adjP = 0.0149 |
| hsa_SGCGSSAAA_V$E2F1DP2_01 | DB_ID = 2410 | C = 167; O = 4; E = 0.69; R = 5.80; rawP = 0.0052; adjP = 0.0152 |
| hsa_V$NF1_Q6_01 | DB_ID = 2282 | C = 267; O = 5; E = 1.10; R = 4.54; rawP = 0.0052; adjP = 0.0152 |
| hsa_V$VDR_Q6 | DB_ID = 2325 | C = 268; O = 5; E = 1.11; R = 4.52; rawP = 0.0053; adjP = 0.0154 |
| hsa_V$IK1_01 | DB_ID = 1902 | C = 274; O = 5; E = 1.13; R = 4.42; rawP = 0.0058; adjP = 0.0168 |
| hsa_TGACATY_UNKNOWN | DB_ID = 2365 | C = 652; O = 8; E = 2.69; R = 2.97; rawP = 0.0059; adjP = 0.0169 |
| hsa_V$AP2REP_01 | DB_ID = 2122 | C = 176; O = 4; E = 0.73; R = 5.51; rawP = 0.0063; adjP = 0.0180 |
| hsa_TGANTCA_V$AP1_C | DB_ID = 2402 | C = 1104; O = 11; E = 4.56; R = 2.41; rawP = 0.0064; adjP = 0.0181 |
| hsa_YGACNNYACAR_UNKNOWN | DB_ID = 2387 | C = 94; O = 3; E = 0.39; R = 7.73; rawP = 0.0070; adjP = 0.0197 |
| hsa_STTTCRNTTT_V$IRF_Q6 | DB_ID = 2426 | C = 186; O = 4; E = 0.77; R = 5.21; rawP = 0.0076; adjP = 0.0213 |
| hsa_V$HFH3_01 | DB_ID = 2043 | C = 189; O = 4; E = 0.78; R = 5.13; rawP = 0.0080; adjP = 0.0222 |

TABLE 5-continued

MicroRNA target (a) and transcription factor (b) consensus binding site target gene set enrichment analysis.

| Target Seq (Known TF) | TF_ID | Enrichment Statistics |
|---|---|---|
| hsa_ACTWSNACTNY_UNKNOWN | DB_ID = 1939 | C = 102; O = 3; E = 0.42; R = 7.13; rawP = 0.0088; adjP = 0.0243 |
| hsa_V$FOXD3_01 | DB_ID = 1934 | C = 196; O = 4; E = 0.81; R = 4.94; rawP = 0.0091; adjP = 0.0250 |
| hsa_TTCYRGAA_UNKNOWN | DB_ID = 2374 | C = 325; O = 5; E = 1.34; R = 3.73; rawP = 0.0115; adjP = 0.0313 |
| hsa_CCANNAGRKGGC_UNKNOWN | DB_ID = 2038 | C = 113; O = 3; E = 0.47; R = 6.43; rawP = 0.0116; adjP = 0.0314 |
| hsa_TTCYNRGAA_V$STAT5B_01 | DB_ID = 2455 | C = 328; O = 5; E = 1.35; R = 3.69; rawP = 0.0119; adjP = 0.0318 |
| hsa_V$AR_02 | DB_ID = 2317 | C = 40; O = 2; E = 0.17; R = 12.11; rawP = 0.0119; adjP = 0.0318 |
| hsa_V$HNF3B_01 | DB_ID = 1935 | C = 217; O = 4; E = 0.90; R = 4.47; rawP = 0.0128; adjP = 0.0340 |
| hsa_V$CREB_Q2_01 | DB_ID = 2293 | C = 219; O = 4; E = 0.90; R = 4.43; rawP = 0.0132; adjP = 0.0346 |
| hsa_TCANNTGAY_V$SREBP1_01 | DB_ID = 2453 | C = 466; O = 6; E = 1.92; R = 3.12; rawP = 0.0132; adjP = 0.0346 |
| hsa_WTGAAAT_UNKNOWN | DB_ID = 2379 | C = 609; O = 7; E = 2.51; R = 2.78; rawP = 0.0137; adjP = 0.0357 |
| hsa_V$E2F1_Q6 | DB_ID = 2097 | C = 228; O = 4; E = 0.94; R = 4.25; rawP = 0.0151; adjP = 0.0383 |
| hsa_V$E2F1DP1_01 | DB_ID = 2231 | C = 231; O = 4; E = 0.95; R = 4.20; rawP = 0.0157; adjP = 0.0383 |
| hsa_V$E2F1DP1RB_01 | DB_ID = 2235 | C = 228; O = 4; E = 0.94; R = 4.25; rawP = 0.0151; adjP = 0.0383 |
| hsa_V$GRE_C | DB_ID = 1990 | C = 124; O = 3; E = 0.51; R = 5.86; rawP = 0.0149; adjP = 0.0383 |
| hsa_V$MZF1_01 | DB_ID = 1899 | C = 231; O = 4; E = 0.95; R = 4.20; rawP = 0.0157; adjP = 0.0383 |
| hsa_V$E2F_Q4 | DB_ID = 2092 | C = 231; O = 4; E = 0.95; R = 4.20; rawP = 0.0157; adjP = 0.0383 |
| hsa_V$E2F_Q6 | DB_ID = 2094 | C = 229; O = 4; E = 0.95; R = 4.23; rawP = 0.0153; adjP = 0.0383 |
| hsa_V$E2F4DP2_01 | DB_ID = 2234 | C = 231; O = 4; E = 0.95; R = 4.20; rawP = 0.0157; adjP = 0.0383 |
| hsa_V$E2F_02 | DB_ID = 1870 | C = 231; O = 4; E = 0.95; R = 4.20; rawP = 0.0157; adjP = 0.0383 |
| hsa_V$E2F1DP2_01 | DB_ID = 2232 | C = 231; O = 4; E = 0.95; R = 4.20; rawP = 0.0157; adjP = 0.0383 |
| hsa_V$ATF1_Q6 | DB_ID = 2205 | C = 230; O = 4; E = 0.95; R = 4.21; rawP = 0.0155; adjP = 0.0383 |
| hsa_V$NKX3A_01 | DB_ID = 2109 | C = 232; O = 4; E = 0.96; R = 4.18; rawP = 0.0160; adjP = 0.0389 |
| hsa_V$PAX4_02 | DB_ID = 2065 | C = 233; O = 4; E = 0.96; R = 4.16; rawP = 0.0162; adjP = 0.0391 |
| hsa_V$CDPCR1_01 | DB_ID = 1912 | C = 130; O = 3; E = 0.54; R = 5.59; rawP = 0.0169; adjP = 0.0399 |
| hsa_CTAWWWATA_V$RSRFC4_Q2 | DB_ID = 2448 | C = 358; O = 5; E = 1.48; R = 3.38; rawP = 0.0168; adjP = 0.0399 |
| hsa_V$E2F4DP1_01 | DB_ID = 2233 | C = 236; O = 4; E = 0.97; R = 4.11; rawP = 0.0169; adjP = 0.0399 |
| hsa_V$SOX9_B1 | DB_ID = 2076 | C = 236; O = 4; E = 0.97; R = 4.11; rawP = 0.0169; adjP = 0.0399 |
| hsa_V$MEIS1_01 | DB_ID = 2085 | C = 237; O = 4; E = 0.98; R = 4.09; rawP = 0.0171; adjP = 0.0400 |
| hsa_V$FOXO1_02 | DB_ID = 2129 | C = 238; O = 4; E = 0.98; R = 4.07; rawP = 0.0173; adjP = 0.0400 |
| hsa_V$GATA3_01 | DB_ID = 1892 | C = 238; O = 4; E = 0.98; R = 4.07; rawP = 0.0173; adjP = 0.0400 |
| hsa_V$CACBINDINGPROTEIN_Q6 | DB_ID = 2219 | C = 238; O = 4; E = 0.98; R = 4.07; rawP = 0.0173; adjP = 0.0400 |
| hsa_V$NKX62_Q2 | DB_ID = 2140 | C = 239; O = 4; E = 0.99; R = 4.06; rawP = 0.0176; adjP = 0.0404 |
| hsa_V$SP1_Q6_01 | DB_ID = 2307 | C = 240; O = 4; E = 0.99; R = 4.04; rawP = 0.0178; adjP = 0.0405 |
| hsa_V$HNF1_C | DB_ID = 1991 | C = 240; O = 4; E = 0.99; R = 4.04; rawP = 0.0178; adjP = 0.0405 |
| hsa_V$NFY_C | DB_ID = 1993 | C = 241; O = 4; E = 0.99; R = 4.02; rawP = 0.0181; adjP = 0.0409 |
| hsa_GGGNNTTTCC_V$NFKB_Q6_01 | DB_ID = 2439 | C = 134; O = 3; E = 0.55; R = 5.42; rawP = 0.0183; adjP = 0.0412 |
| hsa_V$MYOD_Q6 | DB_ID = 1973 | C = 244; O = 4; E = 1.01; R = 3.97; rawP = 0.0188; adjP = 0.0418 |
| hsa_V$STAT1_03 | DB_ID = 2147 | C = 244; O = 4; E = 1.01; R = 3.97; rawP = 0.0188; adjP = 0.0418 |
| hsa_V$NERF_Q2 | DB_ID = 2163 | C = 245; O = 4; E = 1.01; R = 3.96; rawP = 0.0191; adjP = 0.0421 |
| hsa_V$SREBP1_Q6 | DB_ID = 2242 | C = 245; O = 4; E = 1.01; R = 3.96; rawP = 0.0191; adjP = 0.0421 |
| hsa_V$IRF1_01 | DB_ID = 1880 | C = 247; O = 4; E = 1.02; R = 3.92; rawP = 0.0196; adjP = 0.0427 |
| hsa_V$ETS_Q4 | DB_ID = 2255 | C = 247; O = 4; E = 1.02; R = 3.92; rawP = 0.0196; adjP = 0.0427 |
| hsa_WCAANNNYCAG_UNKNOWN | DB_ID = 2376 | C = 248; O = 4; E = 1.02; R = 3.91; rawP = 0.0198; adjP = 0.0429 |
| hsa_V$AP2_Q3 | DB_ID = 2275 | C = 249; O = 4; E = 1.03; R = 3.89; rawP = 0.0201; adjP = 0.0431 |
| hsa_V$STAT1_02 | DB_ID = 2143 | C = 249; O = 4; E = 1.03; R = 3.89; rawP = 0.0201; adjP = 0.0431 |
| hsa_V$PBX1_01 | DB_ID = 1907 | C = 250; O = 4; E = 1.03; R = 3.88; rawP = 0.0204; adjP = 0.0436 |
| hsa_TGACAGNY_V$MEIS1_01 | DB_ID = 2432 | C = 819; O = 8; E = 3.38; R = 2.37; rawP = 0.0210; adjP = 0.0444 |
| hsa_V$AP4_Q6_01 | DB_ID = 2304 | C = 252; O = 4; E = 1.04; R = 3.85; rawP = 0.0209; adjP = 0.0444 |
| hsa_V$USF_Q6 | DB_ID = 1976 | C = 255; O = 4; E = 1.05; R = 3.80; rawP = 0.0217; adjP = 0.0454 |
| hsa_V$ETS1_B | DB_ID = 2057 | C = 255; O = 4; E = 1.05; R = 3.80; rawP = 0.0217; adjP = 0.0454 |
| hsa_V$AP2_Q6 | DB_ID = 1978 | C = 256; O = 4; E = 1.06; R = 3.79; rawP = 0.0220; adjP = 0.0456 |
| hsa_V$ZID_01 | DB_ID = 1901 | C = 256; O = 4; E = 1.06; R = 3.79; rawP = 0.0220; adjP = 0.0456 |
| hsa_V$NFY_Q6 | DB_ID = 1974 | C = 258; O = 4; E = 1.06; R = 3.76; rawP = 0.0225; adjP = 0.0464 |
| hsa_V$GFI1_01 | DB_ID = 2023 | C = 260; O = 4; E = 1.07; R = 3.73; rawP = 0.0231; adjP = 0.0467 |
| hsa_V$PAX4_01 | DB_ID = 2064 | C = 261; O = 4; E = 1.08; R = 3.71; rawP = 0.0234; adjP = 0.0467 |
| hsa_V$PR_01 | DB_ID = 2318 | C = 147; O = 3; E = 0.61; R = 4.94; rawP = 0.0233; adjP = 0.0467 |
| hsa_V$NFY_Q6_01 | DB_ID = 2260 | C = 261; O = 4; E = 1.08; R = 3.71; rawP = 0.0234; adjP = 0.0467 |
| hsa_V$STAT4_01 | DB_ID = 2150 | C = 261; O = 4; E = 1.08; R = 3.71; rawP = 0.0234; adjP = 0.0467 |
| hsa_V$LMO2COM_01 | DB_ID = 2034 | C = 260; O = 4; E = 1.07; R = 3.73; rawP = 0.0231; adjP = 0.0467 |
| hsa_V$NKX25_02 | DB_ID = 2014 | C = 260; O = 4; E = 1.07; R = 3.73; rawP = 0.0231; adjP = 0.0467 |
| hsa_V$GATA_C | DB_ID = 1989 | C = 263; O = 4; E = 1.09; R = 3.68; rawP = 0.0240; adjP = 0.0476 |
| hsa_YTAAYNGCT_UNKNOWN | DB_ID = 2396 | C = 149; O = 3; E = 0.61; R = 4.88; rawP = 0.0241; adjP = 0.0476 |
| hsa_V$ER_Q6_01 | DB_ID = 2290 | C = 264; O = 4; E = 1.09; R = 3.67; rawP = 0.0243; adjP = 0.0478 |
| hsa_SCGGAAGY_V$ELK1_02 | DB_ID = 2413 | C = 1176; O = 10; E = 4.85; R = 2.06; rawP = 0.0247; adjP = 0.0479 |
| hsa_V$CEBP_01 | DB_ID = 1958 | C = 266; O = 4; E = 1.10; R = 3.64; rawP = 0.0249; adjP = 0.0479 |
| hsa_V$AP2_Q6_01 | DB_ID = 2292 | C = 265; O = 4; E = 1.09; R = 3.66; rawP = 0.0246; adjP = 0.0479 |
| hsa_V$EGR1_01 | DB_ID = 2017 | C = 266; O = 4; E = 1.10; R = 3.64; rawP = 0.0249; adjP = 0.0479 |
| hsa_V$CEBP_Q2_01 | DB_ID = 2288 | C = 265; O = 4; E = 1.09; R = 3.66; rawP = 0.0246; adjP = 0.0479 |
| hsa_V$CREB_Q4 | DB_ID = 1969 | C = 267; O = 4; E = 1.10; R = 3.63; rawP = 0.0252; adjP = 0.0480 |
| hsa_V$AREB6_01 | DB_ID = 2078 | C = 267; O = 4; E = 1.10; R = 3.63; rawP = 0.0252; adjP = 0.0480 |
| hsa_V$EFC_Q6 | DB_ID = 2175 | C = 268; O = 4; E = 1.11; R = 3.62; rawP = 0.0255; adjP = 0.0484 |
| hsa_V$AP4_Q5 | DB_ID = 1966 | C = 270; O = 4; E = 1.11; R = 3.59; rawP = 0.0261; adjP = 0.0493 |

TABLE 6a

PPI and biological pathways (wikipathways and pathways commons) gene set enrichment analysis.

| PPI set from Webgestalt | Set ID | Enrichment Statistics |
|---|---|---|
| Hsapiens_Module_866 | DB_ID = 866 | C = 19; O = 5; E = 0.19; R = 25.94; rawP = 1.05e−06; adjP = 6.93e−05 |
| Hsapiens_Module_596 | DB_ID = 596 | C = 36; O = 5; E = 0.37; R = 13.69; rawP = 2.96e−05; adjP = 0.0007 |
| Hsapiens_Module_17 | DB_ID = 17 | C = 6; O = 3; E = 0.06; R = 49.28; rawP = 2.01e−05; adjP = 0.0007 |
| Hsapiens_Module_287 | DB_ID = 287 | C = 115; O = 7; E = 1.17; R = 6.00; rawP = 0.0002; adjP = 0.0026 |
| Hsapiens_Module_25 | DB_ID = 25 | C = 1871; O = 35; E = 18.98; R = 1.84; rawP = 0.0002; adjP = 0.0026 |
| Hsapiens_Module_669 | DB_ID = 669 | C = 6; O = 2; E = 0.06; R = 32.85; rawP = 0.0015; adjP = 0.0165 |
| Hsapiens_Module_845 | DB_ID = 845 | C = 24; O = 3; E = 0.24; R = 12.32; rawP = 0.0018; adjP = 0.0170 |
| Hsapiens_Module_94 | DB_ID = 94 | C = 9; O = 2; E = 0.09; R = 21.90; rawP = 0.0035; adjP = 0.0289 |
| Hsapiens_Module_110 | DB_ID = 110 | C = 212; O = 7; E = 2.15; R = 3.25; rawP = 0.0059; adjP = 0.0433 |
| Hsapiens_Module_203 | DB_ID = 203 | C = 341; O = 9; E = 3.46; R = 2.60; rawP = 0.0081; adjP = 0.0486 |
| Hsapiens_Module_951 | DB_ID = 951 | C = 13; O = 2; E = 0.13; R = 15.16; rawP = 0.0074; adjP = 0.0486 |

TABLE 6b

Wikipathways modules enriched for pAID associated candidate genes

| PPI set | Set ID | Enrichment Statistics |
|---|---|---|
| Inflammatory Response Pathway | WP = 453 | C = 32; O = 6; E = 0.13; R = 45.43; rawP = 3.77e−09; adjP = 2.15e−07 |
| Cytokines and Inflammatory Response | WP = 530 | C = 67; O = 6; E = 0.28; R = 21.70; rawP = 3.68e−07; adjP = 1.05e−05 |
| Th1-Th2 | WP = 1722 | C = 7; O = 3; E = 0.03; R = 103.84; rawP = 2.39e−06; adjP = 4.54e−05 |
| AGE-RAGE pathway | WP = 2324 | C = 76; O = 5; E = 0.31; R = 15.94; rawP = 1.65e−05; adjP = 0.0002 |
| IL-12 SIGNALING PATHWAY | WP = 2111 | C = 11; O = 3; E = 0.05; R = 66.08; rawP = 1.11e−05; adjP = 0.0002 |
| IL-4 signaling pathway | WP = 395 | C = 59; O = 4; E = 0.24; R = 16.43; rawP = 0.0001; adjP = 0.0008 |
| Senescence and Autophagy | WP = 615 | C = 120; O = 5; E = 0.50; R = 10.10; rawP = 0.0001; adjP = 0.0008 |
| Arylamine metabolism | WP = 694 | C = 9; O = 2; E = 0.04; R = 53.84; rawP = 0.0006; adjP = 0.0043 |
| Allograft rejection | WP = 2328 | C = 119; O = 4; E = 0.49; R = 8.14; rawP = 0.0015; adjP = 0.0095 |
| IL-6 signaling pathway | WP = 364 | C = 58; O = 3; E = 0.24; R = 12.53; rawP = 0.0018; adjP = 0.0103 |
| Sulfation Biotransformation Reaction | WP = 692 | C = 17; O = 2; E = 0.07; R = 28.50; rawP = 0.0022; adjP = 0.0114 |
| Kit receptor signaling pathway | WP = 304 | C = 66; O = 3; E = 0.27; R = 11.01; rawP = 0.0026; adjP = 0.0123 |
| Epithelium TarBase | WP = 2002 | C = 340; O = 6; E = 1.40; R = 4.28; rawP = 0.0030; adjP = 0.0132 |
| Leptin signaling pathway | WP = 2034 | C = 81; O = 3; E = 0.33; R = 8.97; rawP = 0.0047; adjP = 0.0191 |
| Folate Metabolism | WP = 176 | C = 29; O = 2; E = 0.12; R = 16.71; rawP = 0.0064; adjP = 0.0197 |
| Apoptosis | WP = 254 | C = 92; O = 3; E = 0.38; R = 7.90; rawP = 0.0066; adjP = 0.0197 |
| Androgen receptor signaling pathway | WP = 138 | C = 91; O = 3; E = 0.38; R = 7.99; rawP = 0.0064; adjP = 0.0197 |
| Integrated Pancreatic Cancer Pathway | WP = 2256 | C = 181; O = 4; E = 0.75; R = 5.35; rawP = 0.0069; adjP = 0.0197 |
| DNA damage response (only ATM dependent) | WP = 710 | C = 89; O = 3; E = 0.37; R = 8.17; rawP = 0.0061; adjP = 0.0197 |
| Oncostatin M Signaling Pathway | WP = 2358 | C = 85; O = 3; E = 0.35; R = 8.55; rawP = 0.0053; adjP = 0.0197 |
| NOD pathway | WP = 1433 | C = 39; O = 2; E = 0.16; R = 12.42; rawP = 0.0114; adjP = 0.0309 |
| TSLP Signaling Pathway | WP = 2203 | C = 49; O = 2; E = 0.20; R = 9.89; rawP = 0.0175; adjP = 0.0399 |
| IL-5 signaling pathway | WP = 127 | C = 47; O = 2; E = 0.19; R = 10.31; rawP = 0.0162; adjP = 0.0399 |
| Interleukin-11 Signaling Pathway | WP = 2332 | C = 49; O = 2; E = 0.20; R = 9.89; rawP = 0.0175; adjP = 0.0399 |
| Adipogenesis | WP = 236 | C = 130; O = 3; E = 0.54; R = 5.59; rawP = 0.0169; adjP = 0.0399 |
| Alpha 6 Beta 4 signaling pathway | WP = 244 | C = 50; O = 2; E = 0.21; R = 9.69; rawP = 0.0182; adjP = 0.0399 |
| IL-2 Signaling pathway | WP = 49 | C = 53; O = 2; E = 0.22; R = 9.14; rawP = 0.0203; adjP = 0.0429 |
| IL-3 Signaling Pathway | WP = 286 | C = 54; O = 2; E = 0.22; R = 8.97; rawP = 0.0211; adjP = 0.0430 |

TABLE 6c

Pathways commons modules enriched for pAID associated candidate genes

| Pathway | Set ID | Enrichment Statistics |
|---|---|---|
| EGF receptor (ErbB1) signaling pathway | DB_ID = 1550 | C = 1288; O = 36; E = 5.32; R = 6.77; rawP = 8.38e−20; adjP = 6.92e−19 |
| ErbB receptor signaling network | DB_ID = 1573 | C = 1312; O = 37; E = 5.42; R = 6.83; rawP = 1.78e−20; adjP = 6.92e−19 |
| Beta1 integrin cell surface interactions | DB_ID = 1517 | C = 1351; O = 37; E = 5.58; R = 6.64; rawP = 4.69e−20; adjP = 6.92e−19 |

TABLE 6c-continued

Pathways commons modules enriched for pAID associated candidate genes

| Pathway | Set ID | Enrichment Statistics |
|---|---|---|
| Urokinase-type plasminogen activator (uPA) and uPAR-mediated signaling | DB_ID = 1519 | C = 1288; O = 36; E = 5.32; R = 6.77; rawP = 8.38e−20; adjP = 6.92e−19 |
| PDGFR-beta signaling pathway | DB_ID = 1540 | C = 1288; O = 36; E = 5.32; R = 6.77; rawP = 8.38e−20; adjP = 6.92e−19 |
| Insulin Pathway | DB_ID = 1466 | C = 1288; O = 36; E = 5.32; R = 6.77; rawP = 8.38e−20; adjP = 6.92e−19 |
| EGFR-dependant Endothelin signaling events | DB_ID = 1603 | C = 1289; O = 36; E = 5.32; R = 6.77; rawP = 8.59e−20; adjP = 6.92e−19 |
| Arf6 trafficking events | DB_ID = 1615 | C = 1288; O = 36; E = 5.32; R = 6.77; rawP = 8.38e−20; adjP = 6.92e−19 |
| IFN-gamma pathway | DB_ID = 1529 | C = 1296; O = 36; E = 5.35; R = 6.73; rawP = 1.02e−19; adjP = 6.92e−19 |
| PAR1-mediated thrombin signaling events | DB_ID = 1531 | C = 1299; O = 36; E = 5.36; R = 6.71; rawP = 1.10e−19; adjP = 6.92e−19 |
| Thrombin/protease-activated receptor (PAR) pathway | DB_ID = 1552 | C = 1300; O = 36; E = 5.37; R = 6.71; rawP = 1.13e−19; adjP = 6.92e−19 |
| GMCSF-mediated signaling events | DB_ID = 1461 | C = 1292; O = 36; E = 5.33; R = 6.75; rawP = 9.26e−20; adjP = 6.92e−19 |
| Signaling events mediated by Hepatocyte Growth Factor Receptor (c-Met) | DB_ID = 1491 | C = 1293; O = 36; E = 5.34; R = 6.75; rawP = 9.49e−20; adjP = 6.92e−19 |
| Internalization of ErbB1 | DB_ID = 1509 | C = 1288; O = 36; E = 5.32; R = 6.77; rawP = 8.38e−20; adjP = 6.92e−19 |
| IGF1 pathway | DB_ID = 1482 | C = 1291; O = 36; E = 5.33; R = 6.76; rawP = 9.03e−20; adjP = 6.92e−19 |
| Signaling events mediated by focal adhesion kinase | DB_ID = 1574 | C = 1288; O = 36; E = 5.32; R = 6.77; rawP = 8.38e−20; adjP = 6.92e−19 |
| Integrin family cell surface interactions | DB_ID = 1499 | C = 1378; O = 38; E = 5.69; R = 6.68; rawP = 1.07e−20; adjP = 6.92e−19 |
| Syndecan-1-mediated signaling events | DB_ID = 1454 | C = 1300; O = 36; E = 5.37; R = 6.71; rawP = 1.13e−19; adjP = 6.92e−19 |
| Arf6 signaling events | DB_ID = 1554 | C = 1288; O = 36; E = 5.32; R = 6.77; rawP = 8.38e−20; adjP = 6.92e−19 |
| Nectin adhesion pathway | DB_ID = 1472 | C = 1295; O = 36; E = 5.34; R = 6.74; rawP = 9.98e−20; adjP = 6.92e−19 |
| Class I PI3K signaling events | DB_ID = 1553 | C = 1288; O = 36; E = 5.32; R = 6.77; rawP = 8.38e−20; adjP = 6.92e−19 |
| mTOR signaling pathway | DB_ID = 1571 | C = 1288; O = 36; E = 5.32; R = 6.77; rawP = 8.38e−20; adjP = 6.92e−19 |
| Class I PI3K signaling events mediated by Akt | DB_ID = 1648 | C = 1288; O = 36; E = 5.32; R = 6.77; rawP = 8.38e−20; adjP = 6.92e−19 |
| TRAIL signaling pathway | DB_ID = 1480 | C = 1328; O = 37; E = 5.48; R = 6.75; rawP = 2.66e−20; adjP = 6.92e−19 |
| Plasma membrane estrogen receptor signaling | DB_ID = 1556 | C = 1301; O = 36; E = 5.37; R = 6.70; rawP = 1.16e−19; adjP = 6.92e−19 |
| IL3-mediated signaling events | DB_ID = 1564 | C = 1295; O = 36; E = 5.34; R = 6.74; rawP = 9.98e−20; adjP = 6.92e−19 |
| Signaling events mediated by VEGFR1 and VEGFR2 | DB_ID = 1516 | C = 1296; O = 36; E = 5.35; R = 6.73; rawP = 1.02e−19; adjP = 6.92e−19 |
| PDGF receptor signaling network | DB_ID = 1497 | C = 1293; O = 36; E = 5.34; R = 6.75; rawP = 9.49e−20; adjP = 6.92e−19 |
| S1P1 pathway | DB_ID = 1594 | C = 1288; O = 36; E = 5.32; R = 6.77; rawP = 8.38e−20; adjP = 6.92e−19 |
| Arf6 downstream pathway | DB_ID = 1585 | C = 1288; O = 36; E = 5.32; R = 6.77; rawP = 8.38e−20; adjP = 6.92e−19 |
| Glypican 1 network | DB_ID = 1492 | C = 1299; O = 36; E = 5.36; R = 6.71; rawP = 1.10e−19; adjP = 6.92e−19 |
| IL5-mediated signaling events | DB_ID = 1627 | C = 1292; O = 36; E = 5.33; R = 6.75; rawP = 9.26e−20; adjP = 6.92e−19 |
| ErbB1 downstream signaling | DB_ID = 1602 | C = 1288; O = 36; E = 5.32; R = 6.77; rawP = 8.38e−20; adjP = 6.92e−19 |
| Alpha9 beta1 integrin signaling events | DB_ID = 1578 | C = 1305; O = 36; E = 5.39; R = 6.68; rawP = 1.28e−19; adjP = 7.20e−19 |
| VEGF and VEGFR signaling network | DB_ID = 1575 | C = 1304; O = 36; E = 5.38; R = 6.69; rawP = 1.25e−19; adjP = 7.20e−19 |
| Endothelins | DB_ID = 1619 | C = 1307; O = 36; E = 5.39; R = 6.67; rawP = 1.34e−19; adjP = 7.33e−19 |
| LKB1 signaling events | DB_ID = 1649 | C = 1308; O = 36; E = 5.40; R = 6.67; rawP = 1.38e−19; adjP = 7.35e−19 |
| Sphingosine 1-phosphate (S1P) pathway | DB_ID = 1635 | C = 1311; O = 36; E = 5.41; R = 6.65; rawP = 1.48e−19; adjP = 7.67e−19 |
| Glypican pathway | DB_ID = 1459 | C = 1338; O = 36; E = 5.52; R = 6.52; rawP = 2.85e−19; adjP = 1.44e−18 |
| Proteoglycan syndecan-mediated signaling events | DB_ID = 1637 | C = 1345; O = 36; E = 5.55; R = 6.48; rawP = 3.37e−19; adjP = 1.66e−18 |

TABLE 6c-continued

Pathways commons modules enriched for pAID associated candidate genes

| Pathway | Set ID | Enrichment Statistics |
|---|---|---|
| IL12-mediated signaling events | DB_ID = 1633 | C = 113; O = 14; E = 0.47; R = 30.02; rawP = 4.76e−17; adjP = 2.29e−16 |
| AP-1 transcription factor network | DB_ID = 1565 | C = 623; O = 24; E = 2.57; R = 9.33; rawP = 1.80e−16; adjP = 8.44e−16 |
| Integrin-linked kinase signaling | DB_ID = 1546 | C = 656; O = 24; E = 2.71; R = 8.86; rawP = 5.67e−16; adjP = 2.60e−15 |
| CDC42 signaling events | DB_ID = 1488 | C = 757; O = 24; E = 3.12; R = 7.68; rawP = 1.32e−14; adjP = 5.91e−14 |
| Regulation of CDC42 activity | DB_ID = 1456 | C = 770; O = 24; E = 3.18; R = 7.55; rawP = 1.90e−14; adjP = 8.32e−14 |
| Calcineurin-regulated NFAT-dependent transcription in lymphocytes | DB_ID = 1502 | C = 49; O = 9; E = 0.20; R = 44.50; rawP = 5.05e−13; adjP = 2.16e−12 |
| IL23-mediated signaling events | DB_ID = 1628 | C = 66; O = 9; E = 0.27; R = 33.04; rawP = 8.57e−12; adjP = 3.59e−11 |
| IL1-mediated signaling events | DB_ID = 1500 | C = 234; O = 13; E = 0.97; R = 13.46; rawP = 2.12e−11; adjP = 8.70e−11 |
| Regulation of nuclear SMAD2/3 signaling | DB_ID = 1611 | C = 305; O = 14; E = 1.26; R = 11.12; rawP = 4.48e−11; adjP = 1.73e−10 |
| Regulation of cytoplasmic and nuclear SMAD2/3 signaling | DB_ID = 1440 | C = 305; O = 14; E = 1.26; R = 11.12; rawP = 4.48e−11; adjP = 1.73e−10 |
| TGF-beta receptor signaling | DB_ID = 1510 | C = 305; O = 14; E = 1.26; R = 11.12; rawP = 4.48e−11; adjP = 1.73e−10 |
| ALK1 signaling events | DB_ID = 1612 | C = 321; O = 14; E = 1.32; R = 10.57; rawP = 8.78e−11; adjP = 3.33e−10 |
| ALK1 pathway | DB_ID = 1583 | C = 324; O = 14; E = 1.34; R = 10.47; rawP = 9.93e−11; adjP = 3.69e−10 |
| Regulation of p38-alpha and p38-beta | DB_ID = 1536 | C = 164; O = 11; E = 0.68; R = 16.25; rawP = 1.03e−10; adjP = 3.76e−10 |
| Role of Calcineurin-dependent NFAT signaling in lymphocytes | DB_ID = 1587 | C = 95; O = 9; E = 0.39; R = 22.95; rawP = 2.46e−10; adjP = 8.81e−10 |
| TNF receptor signaling pathway | DB_ID = 1600 | C = 299; O = 13; E = 1.23; R = 10.53; rawP = 4.38e−10; adjP = 1.54e−09 |
| p38 MAPK signaling pathway | DB_ID = 1549 | C = 189; O = 11; E = 0.78; R = 14.10; rawP = 4.70e−10; adjP = 1.62e−09 |
| Immune System | DB_ID = 522 | C = 532; O = 16; E = 2.20; R = 7.29; rawP = 8.90e−10; adjP = 3.02e−09 |
| IL27-mediated signaling events | DB_ID = 1463 | C = 26; O = 6; E = 0.11; R = 55.91; rawP = 9.76e−10; adjP = 3.26e−09 |
| BMP receptor signaling | DB_ID = 1644 | C = 226; O = 11; E = 0.93; R = 11.79; rawP = 3.10e−09; adjP = 1.00e−08 |
| IL12 signaling mediated by STAT4 | DB_ID = 1533 | C = 31; O = 6; E = 0.13; R = 46.89; rawP = 3.07e−09; adjP = 1.00e−08 |
| Validated transcriptional targets of AP1 family members Fra1 and Fra2 | DB_ID = 1592 | C = 136; O = 9; E = 0.56; R = 16.03; rawP = 6.05e−09; adjP = 1.92e−08 |
| CXCR4-mediated signaling events | DB_ID = 1593 | C = 192; O = 10; E = 0.79; R = 12.62; rawP = 8.61e−09; adjP = 2.69e−08 |
| IL2-mediated signaling events | DB_ID = 1558 | C = 115; O = 8; E = 0.47; R = 16.85; rawP = 2.92e−08; adjP = 8.99e−08 |
| Glucocorticoid receptor regulatory network | DB_ID = 1577 | C = 80; O = 7; E = 0.33; R = 21.20; rawP = 4.47e−08; adjP = 1.35e−07 |
| Glucocorticoid receptor signaling | DB_ID = 1569 | C = 85; O = 7; E = 0.35; R = 19.95; rawP = 6.82e−08; adjP = 2.04e−07 |
| TCR signaling in naïve CD4+ T cells | DB_ID = 1624 | C = 135; O = 8; E = 0.56; R = 14.36; rawP = 1.02e−07; adjP = 3.00e−07 |
| Calcium signaling in the CD4+ TCR pathway | DB_ID = 1639 | C = 29; O = 5; E = 0.12; R = 41.77; rawP = 1.24e−07; adjP = 3.59e−07 |
| Hemostasis | DB_ID = 64 | C = 376; O = 11; E = 1.55; R = 7.09; rawP = 5.43e−07; adjP = 1.55e−06 |
| JNK signaling in the CD4+ TCR pathway | DB_ID = 1586 | C = 42; O = 5; E = 0.17; R = 28.84; rawP = 8.51e−07; adjP = 2.36e−06 |
| Ras signaling in the CD4+ TCR pathway | DB_ID = 1520 | C = 42; O = 5; E = 0.17; R = 28.84; rawP = 8.51e−07; adjP = 2.36e−06 |
| Cytokine Signaling in Immune system | DB_ID = 1120 | C = 193; O = 8; E = 0.80; R = 10.04; rawP = 1.55e−06; adjP = 4.24e−06 |
| Signaling events mediated by TCPTP | DB_ID = 1514 | C = 92; O = 6; E = 0.38; R = 15.80; rawP = 2.41e−06; adjP = 6.42e−06 |
| Signaling by Interleukins | DB_ID = 1129 | C = 92; O = 6; E = 0.38; R = 15.80; rawP = 2.41e−06; adjP = 6.42e−06 |
| Interleukin-3,5 and GM-CSF signaling | DB_ID = 1132 | C = 29; O = 4; E = 0.12; R = 33.42; rawP = 6.15e−06; adjP = 1.59e−05 |
| IL4-mediated signaling events | DB_ID = 1588 | C = 62; O = 5; E = 0.26; R = 19.54; rawP = 6.05e−06; adjP = 1.59e−05 |
| Factors involved in megakaryocyte development and platelet production | DB_ID = 109 | C = 119; O = 5; E = 0.49; R = 10.18; rawP = 0.0001; adjP = 0.0002 |
| Developmental Biology | DB_ID = 11 | C = 433; O = 9; E = 1.79; R = 5.04; rawP = 8.63e−05; adjP = 0.0002 |
| p75(NTR)-mediated signaling | DB_ID = 1551 | C = 178; O = 6; E = 0.73; R = 8.17; rawP = 0.0001; adjP = 0.0002 |
| 3-phosphoinositide degradation | DB_ID = 1390 | C = 19; O = 3; E = 0.08; R = 38.26; rawP = 6.38e−05; adjP = 0.0002 |

TABLE 6c-continued

Pathways commons modules enriched for pAID associated candidate genes

| Pathway | Set ID | Enrichment Statistics |
|---|---|---|
| Signaling events mediated by PTP1B | DB_ID = 1591 | C = 52; O = 4; E = 0.21; R = 18.64; rawP = 6.51e−05; adjP = 0.0002 |
| Interleukin-2 signaling | DB_ID = 1128 | C = 28; O = 3; E = 0.12; R = 25.96; rawP = 0.0002; adjP = 0.0005 |
| IL2 signaling events mediated by STAT5 | DB_ID = 1442 | C = 28; O = 3; E = 0.12; R = 25.96; rawP = 0.0002; adjP = 0.0005 |
| Signaling events regulated by Ret tyrosine kinase | DB_ID = 1566 | C = 69; O = 4; E = 0.28; R = 14.05; rawP = 0.0002; adjP = 0.0005 |
| NOD1/2 Signaling Pathway | DB_ID = 1145 | C = 26; O = 3; E = 0.11; R = 27.96; rawP = 0.0002; adjP = 0.0005 |
| IL2 signaling events mediated by PI3K | DB_ID = 1634 | C = 67; O = 4; E = 0.28; R = 14.46; rawP = 0.0002; adjP = 0.0005 |
| a6b1 and a6b4 Integrin signaling | DB_ID = 1622 | C = 35; O = 3; E = 0.14; R = 20.77; rawP = 0.0004; adjP = 0.0009 |
| amb2 Integrin signaling | DB_ID = 1568 | C = 41; O = 3; E = 0.17; R = 17.73; rawP = 0.0007; adjP = 0.0016 |
| Nucleotide-binding domain, leucine rich repeat containing receptor (NLR) signaling pathways | DB_ID = 1144 | C = 43; O = 3; E = 0.18; R = 16.90; rawP = 0.0008; adjP = 0.0018 |
| LPA receptor mediated events | DB_ID = 1481 | C = 100; O = 4; E = 0.41; R = 9.69; rawP = 0.0008; adjP = 0.0018 |
| E-cadherin signaling in the nascent adherens junction | DB_ID = 1544 | C = 275; O = 6; E = 1.14; R = 5.29; rawP = 0.0010; adjP = 0.0021 |
| Stabilization and expansion of the E-cadherin adherens junction | DB_ID = 1469 | C = 275; O = 6; E = 1.14; R = 5.29; rawP = 0.0010; adjP = 0.0021 |
| IL6-mediated signaling events | DB_ID = 1445 | C = 47; O = 3; E = 0.19; R = 15.47; rawP = 0.0010; adjP = 0.0021 |
| E-cadherin signaling events | DB_ID = 1617 | C = 280; O = 6; E = 1.16; R = 5.19; rawP = 0.0011; adjP = 0.0023 |
| Regulation of beta-cell development | DB_ID = 35 | C = 109; O = 4; E = 0.45; R = 8.89; rawP = 0.0011; adjP = 0.0023 |
| FoxO family signaling | DB_ID = 1557 | C = 49; O = 3; E = 0.20; R = 14.83; rawP = 0.0011; adjP = 0.0023 |
| KitReceptor | DB_ID = 1658 | C = 54; O = 3; E = 0.22; R = 13.46; rawP = 0.0015; adjP = 0.0030 |
| Endogenous TLR signaling | DB_ID = 1645 | C = 57; O = 3; E = 0.24; R = 12.75; rawP = 0.0017; adjP = 0.0034 |
| CD40/CD40L signaling | DB_ID = 1479 | C = 58; O = 3; E = 0.24; R = 12.53; rawP = 0.0018; adjP = 0.0036 |
| TCR signaling in naïve CD8+ T cells | DB_ID = 1521 | C = 129; O = 4; E = 0.53; R = 7.51; rawP = 0.0021; adjP = 0.0041 |
| Regulation of retinoblastoma protein | DB_ID = 1623 | C = 66; O = 3; E = 0.27; R = 11.01; rawP = 0.0026; adjP = 0.0051 |
| Regulation of Telomerase | DB_ID = 1507 | C = 68; O = 3; E = 0.28; R = 10.69; rawP = 0.0028; adjP = 0.0054 |
| Adaptive Immune System | DB_ID = 515 | C = 243; O = 5; E = 1.00; R = 4.99; rawP = 0.0035; adjP = 0.0067 |
| N-cadherin signaling events | DB_ID = 1494 | C = 251; O = 5; E = 1.04; R = 4.83; rawP = 0.0040; adjP = 0.0075 |
| Signaling events mediated by PRL | DB_ID = 1651 | C = 23; O = 2; E = 0.09; R = 21.07; rawP = 0.0040; adjP = 0.0075 |
| Integration of energy metabolism | DB_ID = 812 | C = 83; O = 3; E = 0.34; R = 8.76; rawP = 0.0050; adjP = 0.0093 |
| Transmembrane transport of small molecules | DB_ID = 937 | C = 379; O = 6; E = 1.56; R = 3.84; rawP = 0.0051; adjP = 0.0094 |
| Ca-dependent events | DB_ID = 493 | C = 27; O = 2; E = 0.11; R = 17.95; rawP = 0.0056; adjP = 0.0102 |
| Negative regulators of RIG-I/MDA5 signaling | DB_ID = 1121 | C = 28; O = 2; E = 0.12; R = 17.31; rawP = 0.0060; adjP = 0.0108 |
| S1P3 pathway | DB_ID = 1526 | C = 29; O = 2; E = 0.12; R = 16.71; rawP = 0.0064; adjP = 0.0114 |
| Insulin-mediated glucose transport | DB_ID = 1576 | C = 29; O = 2; E = 0.12; R = 16.71; rawP = 0.0064; adjP = 0.0114 |
| Notch-mediated HES/HEY network | DB_ID = 1457 | C = 94; O = 3; E = 0.39; R = 7.73; rawP = 0.0070; adjP = 0.0120 |
| Transport of inorganic cations/anions and amino acids/oligopeptides | DB_ID = 940 | C = 94; O = 3; E = 0.39; R = 7.73; rawP = 0.0070; adjP = 0.0120 |
| Noncanonical Wnt signaling pathway | DB_ID = 1535 | C = 182; O = 4; E = 0.75; R = 5.32; rawP = 0.0070; adjP = 0.0120 |
| Notch signaling pathway | DB_ID = 1625 | C = 94; O = 3; E = 0.39; R = 7.73; rawP = 0.0070; adjP = 0.0120 |
| Signaling by Aurora kinases | DB_ID = 1525 | C = 98; O = 3; E = 0.40; R = 7.42; rawP = 0.0079; adjP = 0.0133 |
| Interferon Signaling | DB_ID = 1123 | C = 98; O = 3; E = 0.40; R = 7.42; rawP = 0.0079; adjP = 0.0133 |
| Regulation of gene expression in beta cells | DB_ID = 61 | C = 99; O = 3; E = 0.41; R = 7.34; rawP = 0.0081; adjP = 0.0134 |
| Innate Immune System | DB_ID = 1094 | C = 190; O = 4; E = 0.78; R = 5.10; rawP = 0.0081; adjP = 0.0134 |
| EPO signaling pathway | DB_ID = 1555 | C = 34; O = 2; E = 0.14; R = 14.25; rawP = 0.0087; adjP = 0.0143 |
| Canonical NF-kappaB pathway | DB_ID = 1450 | C = 35; O = 2; E = 0.14; R = 13.84; rawP = 0.0092; adjP = 0.0149 |
| PLK1 signaling events | DB_ID = 1483 | C = 104; O = 3; E = 0.43; R = 6.99; rawP = 0.0093; adjP = 0.0149 |
| Signal transduction by L1 | DB_ID = 27 | C = 35; O = 2; E = 0.14; R = 13.84; rawP = 0.0092; adjP = 0.0149 |
| Wnt signaling network | DB_ID = 1435 | C = 200; O = 4; E = 0.83; R = 4.85; rawP = 0.0097; adjP = 0.0154 |
| Polo-like kinase signaling events in the cell cycle | DB_ID = 1528 | C = 109; O = 3; E = 0.45; R = 6.67; rawP = 0.0105; adjP = 0.0165 |
| Glypican 3 network | DB_ID = 1471 | C = 206; O = 4; E = 0.85; R = 4.70; rawP = 0.0107; adjP = 0.0167 |
| ErbB2/ErbB3 signaling events | DB_ID = 1443 | C = 38; O = 2; E = 0.16; R = 12.75; rawP = 0.0108; adjP = 0.0168 |
| Syndecan-4-mediated signaling events | DB_ID = 1604 | C = 209; O = 4; E = 0.86; R = 4.64; rawP = 0.0113; adjP = 0.0173 |
| PLC beta mediated events | DB_ID = 487 | C = 39; O = 2; E = 0.16; R = 12.42; rawP = 0.0114; adjP = 0.0173 |
| p75 NTR receptor-mediated signalling | DB_ID = 252 | C = 39; O = 2; E = 0.16; R = 12.42; rawP = 0.0114; adjP = 0.0173 |
| Platelet homeostasis | DB_ID = 66 | C = 40; O = 2; E = 0.17; R = 12.11; rawP = 0.0119; adjP = 0.0178 |
| G-protein mediated events | DB_ID = 488 | C = 40; O = 2; E = 0.17; R = 12.11; rawP = 0.0119; adjP = 0.0178 |
| Axon guidance | DB_ID = 20 | C = 219; O = 4; E = 0.90; R = 4.43; rawP = 0.0132; adjP = 0.0196 |

TABLE 6c-continued

Pathways commons modules enriched for pAID associated candidate genes

| Pathway | Set ID | Enrichment Statistics |
|---|---|---|
| FOXA2 and FOXA3 transcription factor networks | DB_ID = 1511 | C = 43; O = 2; E = 0.18; R = 11.27; rawP = 0.0137; adjP = 0.0200 |
| Signal Transduction | DB_ID = 331 | C = 1231; O = 11; E = 5.08; R = 2.17; rawP = 0.0137; adjP = 0.0200 |
| Posttranslational regulation of adherens junction stability and dissassembly | DB_ID = 1512 | C = 231; O = 4; E = 0.95; R = 4.20; rawP = 0.0157; adjP = 0.0226 |
| Presenilin action in Notch and Wnt signaling | DB_ID = 1621 | C = 46; O = 2; E = 0.19; R = 10.53; rawP = 0.0156; adjP = 0.0226 |
| Interferon gamma signaling | DB_ID = 1124 | C = 47; O = 2; E = 0.19; R = 10.31; rawP = 0.0162; adjP = 0.0231 |
| Alpha6Beta4Integrin | DB_ID = 1660 | C = 48; O = 2; E = 0.20; R = 10.10; rawP = 0.0169; adjP = 0.0240 |
| Signaling mediated by p38-alpha and p38-beta | DB_ID = 1524 | C = 50; O = 2; E = 0.21; R = 9.69; rawP = 0.0182; adjP = 0.0256 |
| Regulation of nuclear beta catenin signaling and target gene transcription | DB_ID = 1547 | C = 135; O = 3; E = 0.56; R = 5.38; rawP = 0.0186; adjP = 0.0260 |
| SLC-mediated transmembrane transport | DB_ID = 943 | C = 248; O = 4; E = 1.02; R = 3.91; rawP = 0.0198; adjP = 0.0275 |
| Platelet activation, signaling and aggregation | DB_ID = 56 | C = 139; O = 3; E = 0.57; R = 5.23; rawP = 0.0201; adjP = 0.0277 |
| Opioid Signalling | DB_ID = 486 | C = 53; O = 2; E = 0.22; R = 9.14; rawP = 0.0203; adjP = 0.0278 |
| Signalling by NGF | DB_ID = 254 | C = 143; O = 3; E = 0.59; R = 5.08; rawP = 0.0217; adjP = 0.0293 |
| Metabolism | DB_ID = 634 | C = 824; O = 8; E = 3.40; R = 2.35; rawP = 0.0217; adjP = 0.0293 |
| C-MYC pathway | DB_ID = 1467 | C = 149; O = 3; E = 0.61; R = 4.88; rawP = 0.0241; adjP = 0.0323 |
| ATF-2 transcription factor network | DB_ID = 1485 | C = 59; O = 2; E = 0.24; R = 8.21; rawP = 0.0249; adjP = 0.0331 |
| Fc-epsilon receptor I signaling in mast cells | DB_ID = 1496 | C = 61; O = 2; E = 0.25; R = 7.94; rawP = 0.0264; adjP = 0.0347 |
| Coregulation of Androgen receptor activity | DB_ID = 1506 | C = 61; O = 2; E = 0.25; R = 7.94; rawP = 0.0264; adjP = 0.0347 |
| Canonical Wnt signaling pathway | DB_ID = 1542 | C = 155; O = 3; E = 0.64; R = 4.69; rawP = 0.0267; adjP = 0.0348 |
| Validated targets of C-MYC transcriptional repression | DB_ID = 1444 | C = 63; O = 2; E = 0.26; R = 7.69; rawP = 0.0281; adjP = 0.0364 |
| Aurora A signaling | DB_ID = 1646 | C = 64; O = 2; E = 0.26; R = 7.57; rawP = 0.0289; adjP = 0.0372 |
| Signaling by SCF-KIT | DB_ID = 472 | C = 66; O = 2; E = 0.27; R = 7.34; rawP = 0.0306; adjP = 0.0391 |
| Downstream signaling in naï ve CD8+ T cells | DB_ID = 1455 | C = 67; O = 2; E = 0.28; R = 7.23; rawP = 0.0314; adjP = 0.0394 |
| BCR signaling pathway | DB_ID = 1513 | C = 67; O = 2; E = 0.28; R = 7.23; rawP = 0.0314; adjP = 0.0394 |
| RIG-I/MDA5 mediated induction of IFN-alpha/beta pathways | DB_ID = 1115 | C = 67; O = 2; E = 0.28; R = 7.23; rawP = 0.0314; adjP = 0.0394 |
| Cell surface interactions at the vascular wall | DB_ID = 467 | C = 72; O = 2; E = 0.30; R = 6.73; rawP = 0.0359; adjP = 0.0448 |
| Downstream signal transduction | DB_ID = 467 | C = 75; O = 2; E = 0.31; R = 6.46; rawP = 0.0386; adjP = 0.0478 |
| Syndecan-2-mediated signaling events | DB_ID = 1581 | C = 77; O = 2; E = 0.32; R = 6.29; rawP = 0.0405; adjP = 0.0496 |
| Interferon alpha/beta signaling | DB_ID = 1122 | C = 77; O = 2; E = 0.32; R = 6.29; rawP = 0.0405; adjP = 0.0496 |

Table 7a and Table 7b: Network statistics obtained from the PPI analysis in Dapple (a) and String (b). For Dapple, provided are the number of Exp (Expected), Obs (Observed), and permutation-derived P-values for the network statistic measures of connectivity. For String, O (observed) and E (expected) interactions and enrichment P-values (against a genome background) for candidate proteins encoded by (A) the GWS loci, (B) GWS and GWM loci, and (C) pAID candidate genes overlapping those in the JAK-STAT pathway.

B

| String | 27 GWS | 46 GWM | JAK-STAT PPI |
|---|---|---|---|
| Proteins Considered | 27 | 44 | 30 |
| N interactions | 26 | 48 | 50 |
| E interactions | 4.05 | 9.22 | 4.92 |
| P-value | 3.24E−13 | <1.00E−20 | <1.00E−20 |

A

| | Dapple | | | | | |
|---|---|---|---|---|---|---|
| | 27 GWS Loci (P < 5E−08) | | | 46 GWM Loci (P < 1E−06) | | |
| Network Statistics | Obs | Exp | P - - - value | Obs | Exp | P - - - value |
| Direct Edges Count | 8 | 3.47 | 1.73E−02 | 15 | 5.10 | 2.0E−04 |
| Seed Direct Degrees Mean | 1.78 | 1.15 | 2.23E−02 | 1.76 | 1.19 | 1.9E−02 |
| Seed Indirect Degrees Mean | 25.33 | 17.44 | 7.86E−02 | 22.16 | 17.20 | 1.2E−01 |
| CI Degrees Mean | 2.39 | 2.26 | 1.33E−01 | 2.53 | 2.30 | 7.4E−02 |

TABLE 7c

Significant pathways and biological processes enriched for pAID genes shared across DAVID, IPA, and GSEA. Biological pathways showing significant enrichment for candidate pAID associated genes identified by GBAT. Points correspond to P-values of each individual pathway database analysis method and are plotted in rank order as well as surrounded by gray boundary whose ordinate value corresponds to the Fisher meta-analysis score of the three pathways databases.

| Pathway | Full Pathway Name | GSEA | IPA | DAVID | P_Fisher | Stat |
|---|---|---|---|---|---|---|
| Allo_rejection | Allograft rejection | 1.00E−05 | 2.00E−22 | 1.10E−21 | 2.61E−47 | 219.47 |
| T1D | Type I diabetes mellitus | 1.00E−05 | 7.94E−15 | 3.39E−20 | 2.88E−38 | 177.62 |
| AITD | Autoimmune thyroid disease | 1.00E−05 | 2.00E−17 | 8.12E−17 | 1.72E−37 | 174.03 |
| GVHD | Graft - - - versus - - - host disease | 1.00E−05 | 1.00E−15 | 1.72E−16 | 1.77E−35 | 164.70 |
| Antigen_proc | Antigen processing and presentation | 1.00E−05 | 3.16E−25 | 5.77E−15 | 2.08E−43 | 201.43 |
| Asthma | Asthma | 1.00E−05 | 2.14E−06 | 1.94E−14 | 3.54E−24 | 112.28 |
| Antigen_MHC_I | Antigen processing and presentation of peptide antigen via MHC class I | 1.00E−05 | 3.16E−25 | 7.80E−08 | 2.57E−36 | 168.59 |
| Cytokine_Response | Cytokines and Inflammatory Response | 1.00E−05 | 6.03E−06 | 1.74E−05 | 7.05E−15 | 68.98 |
| SLE | Systemic lupus erythematosus | 4.83E−04 | 1.05E−02 | 6.16E−05 | 1.69E−09 | 43.77 |
| TH1_TH2_Dif | Th1/Th2 Differentiation | 1.60E−04 | 2.51E−16 | 4.50E−04 | 1.49E−22 | 104.74 |
| Cytokine_Net | Cytokine Network | 4.44E−05 | 6.03E−06 | 3.71E−03 | 6.00E−12 | 55.28 |
| Innate_Response | Positive regulation of innate immune response | 1.46E−03 | 4.79E−09 | 3.77E−02 | 1.63E−12 | 57.93 |

TABLE 8

List of phenotype abbreviations.

| Abbreviation | Phenotype |
|---|---|
| THY | Thyroiditis |
| AS | Spondyloarthropathy |
| PS | Psoriasis |
| CEL | Celiac Disease |
| SLE | Systemic Lupus Erythematosus |
| CVID | Common Variable Immunodeficiency |
| UC | Ulcerative Colitis |
| T1D | Type 1 Diabetes |
| JIA | Juvenile Idiopathic Arthritis |
| CD | Crohns Disease |
| INF | Inflammation |
| BEH | Behect's Disease |
| MG | Myasthenia Gravis |
| PBC | Primary Biliary Cirrhosis |
| LEP | Leprosy |
| CRP | C-Reactive Proteins |
| VIT | Vitiligo |
| SCH | Schizophrenia |
| AST | Asthma |
| AUT | Autism |
| ALZ | Alzheimer's |
| END | Endometriosis |
| BPD | Bipolar Disorder |
| ALL | Acute lymphocytic leukemia |
| CLL | Chronic lymphocytic leukemia |
| LEL | Liver Enzyme Levels |
| PSC | Primary Sclerosing cholangitis |
| REN | Renal Function Traits/Chronic Kidney Disease |
| DER | Dermatitis |
| ADER | Atopic Dermatitis |
| D-NPH | Diabetic Nephropathy |
| NPH | Nephropathy |
| GRV | Grave's |
| AA | Alopecia areata |
| POS | Polycystic ovarian syndrome |
| HEMO | Hemoglobin |
| CJD | Creutzfeldt-Jakob disease |
| EPI | Epilepsy |
| RLS | Restless Leg Syndrome |
| TOU | Tourette syndrome |
| SAR | Sarcoidosis |
| CF | Cystic Fibrosis |
| VAS | Vasculitis |
| URL | Urate Levels |
| ANTC | Anticoagulant Levels |
| BIL | Billirubin Levels |
| RES | Resistin levels |
| EOS | Eosinophil Levels |
| APA | antiphospholipid antibodies |
| INS | Insulin |
| BAS | Basophils |
| CFCDNA | Circulating Free Cell DNA |
| GDM | Gestational Diabetes |
| ADPT | Adiponectin |
| FIB | Fibrinogen |
| PAN | Pancreatitis |
| DUD | Dupuytren's disease |
| NEU | Neutrophil |
| MNT | Monocytes |
| GLI | Glioma |
| NLUP | Neonatal Lupus |
| LYM | Lymphocytes |
| S-INF-A | secreted IFN-alpha |
| MPN | Myeloproliferative neoplasms |
| CAM | Cell Adhesion Molecule |
| HepC | Hepatitis C |
| AIDS | autoimmune deficiency syndrome |
| PAG | Pagat's Disease |
| MYLO | Myloma |
| GHEM | glycohemoglobin |
| GAU | Gaucher disease |
| CRC | Colorectal Cancer Hematocrit/ |
| GLA | Heme/Hemostatic Factors/ Glaucoma |
| SS | Systemic Sclerosis |
| ALS | Amyotrophic lateral sclerosis |
| MYO | Myopia |
| KAW | Kawasaki |
| PRI | Prion disease |
| KEL | Keloid |
| MET | Metabolite Levels |
| BAR | Barrett's esophagus |
| CKD | Chronic kidney disease |
| HLM | Hodgkin's Lymphoma |
| TSH | Thyroid Stimulating Hormone |
| NA | None Available |
| PAR | Parkinson's Disease |
| HEM | Hematological phenotypes |
| WTM | Wilms Tumor |
| SCO | Scoliosis |

TABLE 9a

Genotyped subjects in the CHOP Biorepository eligible for this study.

|  | Total | male | female |
|---|---|---|---|
| RACE |  |  |  |
| WHITE | 13918 | 7567 | 6351 |
| BLACK OR AFRICAN AMERICAN | 10179 | 5136 | 5043 |
| OTHER | 1718 | 929 | 789 |
| ASIAN | 433 | 208 | 225 |
| AMERICAN INDIAN/ESKIMO/ ALASKA NATIVE | 23 | 11 | 12 |
| REFUSED | 20 | 14 | 6 |
| INDIAN | 9 | 5 | 4 |
| NATIVE HAWAIIAN/ PACIFIC ISLANDER | 8 | 4 | 4 |
| Total | 26308 | 13874 | 12434 |
| AGE (at recruitment) |  |  |  |
| 18 | 1044 | 457 | 587 |
| 17 | 1277 | 558 | 719 |
| 16 | 1515 | 679 | 836 |
| 15 | 1490 | 696 | 794 |
| 14 | 1465 | 724 | 741 |
| 13 | 1453 | 719 | 734 |
| 12 | 1269 | 648 | 621 |
| 11 | 1205 | 619 | 586 |
| 10 | 1163 | 623 | 540 |
| 9 | 1179 | 640 | 539 |
| 8 | 1188 | 660 | 528 |
| 7 | 1097 | 623 | 474 |
| 6 | 1013 | 584 | 429 |
| 5 | 1188 | 661 | 527 |
| 4 | 1496 | 866 | 630 |
| 3 | 1996 | 1128 | 868 |
| 2 | 2117 | 1206 | 911 |
| 1 | 2514 | 1389 | 1125 |
| 0 | 643 | 398 | 245 |
| Total | 26312 | 13878 | 12434 |

TABLE 9b

ICD9 diagnosis and search terms used to initially filter subjects based on CHOP EMRs.

| pAID | ICD9 Search Terms and Codes ICD9 Search Terms and Codes |
|---|---|
| THY | %Chronic%Thyroiditis%|%Grave%|%Hashimoto%| 242.0%|245.0%|245.2% |
| SPA | %Ankyl%Spond%litis%|%Spondyloarthropathy%|720%| 720% |
| PSOR | %Psoriasis%|696.10% |
| CEL | %Celiac%|579.00% |
| SLE | %Systemic%Lupus%Erythematosus%|710.0% |
| CVID | %Variable%Immunodefi%|279.06% |
| UC | %Ulcerative%Colitis%|556% |
| T1D | %Type%1%Diabetes%|250._1%|250._3% |
| JIA | %Enthe%rthritis%|%Idiop%rthritis%|%Juvenile%rthritis%| %Mono%rthritis%|%Oligo%rthritis%|%Poly%rthritis%| %Psor%rthritis%|%Rheum%rthritis%|%System%Arthritis%| 714%|716.2%|716.5%|716.6%|716.8%|716.9% |
| CD | %Crohn%|555% |

NOTE:
ICD9 codes used for EPIC-SQL case identification by patient diagnosis [% = wildcard (0 or more characters), _ = wildcard (exactly 1 character)]

References for Example I

1. Cooper, G. S., Bynum, M. L. & Somers, E. C. Recent insights in the epidemiology of autoimmune diseases: improved prevalence estimates and understanding of clustering of diseases. J. Autoimmun. 33, 197-207 (2009).
2. Cooper, J. D. et al. Seven newly identified loci for autoimmune thyroid disease. Hum. Mol. Genet. 21, 5202-5208 (2012).
3. Tsoi, L. C. et al. Identification of 15 new psoriasis susceptibility loci highlights the role of innate immunity. Nat. Genet. 44, 1341-1348 (2012).
4. Hinks, A. et al. Dense genotyping of immune-related disease regions identifies 14 new susceptibility loci for juvenile idiopathic arthritis. Nat. Genet. 45, 664-669 (2013).
5. Liu, J. Z. et al. Dense fine-mapping study identifies new susceptibility loci for primary biliary cirrhosis. Nat. Genet. 44, 1137-1141(2012).
6. Liu, J. Z. et al. Dense genotyping of immune-related disease regions identifies nine new risk loci for primary sclerosing cholangitis. Nat. Genet. 45, 670-675 (2013).
7. Eyre, S. et al. High-density genetic mapping identifies new susceptibility loci for rheumatoid arthritis. Nat. Genet. 44, 1336-1340 (2012).
8. Zhernakova, A. et al. Meta-analysis of genome-wide association studies in celiac disease and rheumatoid arthritis identifies fourteen non-HLA shared loci. PLoS Genet. 7, e1002004 (2011).
9. Jostins, L. et al. Host-microbe interactions have shaped the genetic architecture of inflammatory bowel disease. Nature 491, 119-124 (2012).
10. International Multiple Sclerosis Genetics Consortium. et al. Genetic risk and a primary role for cell-mediated immune mechanisms in multiple sclerosis. Nature 476, 214-219 (2011).
11. Beecham, A. H. et al. Analysis of immune-related loci identifies 48 new susceptibility variants for multiple sclerosis. Nat. Genet. 45, 1353-1360 (2013).
12. National Human Genome Research Institute Published Genome-Wide Associations through Aug. 1, 2014. NHGRI GWAS Catalog https://www.genome.gov/ 26525384 (2014).
13. Welter, D. et al. The NHGRI GWAS Catalog, a curated resource of SNP-trait associations. Nucleic Acids Res. 42, D1001-D1006 (2014).
14. Cortes, A. & Brown, M. A. Promise and pitfalls of the Immunochip. Arthritis Res. Ther. 13, 101 (2011).
15. Hakonarson, H. et al. A genome-wide association study identifies KIAA0350 as a type 1 diabetes gene. Nature 448, 591-594 (2007).
16. Hinks, A. et al. Association between the PTPN22 gene and rheumatoid arthritis and juvenile idiopathic arthritis in a UK population: further support that PTPN22 is an autoimmunity gene. Arthritis Rheum. 52, 1694-1699 (2005).
17. Smyth, D. J. et al. Shared and distinct genetic variants in type 1 diabetes and celiac disease. N. Engl. J. Med. 359, 2767-2777 (2008).
18. Harley, J. B. et al. Genome-wide association scan in women with systemic lupus erythematosus identifies susceptibility variants in ITGAM, PXK, KIAA1542 and other loci. Nat. Genet. 40, 204-210 (2008).
19. Ramos, P. S. et al. A comprehensive analysis of shared loci between systemic lupus erythematosus (SLE) and sixteen autoimmune diseases reveals limited genetic overlap. PLoS Genet. 7, e1002406 (2011).
20. Cotsapas, C. et al. Pervasive sharing of genetic effects in autoimmune disease. PLoS Genet. 7, e1002254 (2011).
21. Cotsapas, C. & Hafler, D. A. Immune-mediated disease genetics: the shared basis of pathogenesis. Trends Immunol. 34, 22-26 (2013).

22. Howie, B., Fuchsberger, C., Stephens, M., Marchini, J. & Abecasis, G. R. Fast and accurate genotype imputation in genome-wide association studies through prephasing. Nat. Genet. 44, 955-959 (2012).
23. Delaneau, O., Coulonges, C. & Zagury, J.-F. Shape-IT: new rapid and accurate algorithm for haplotype inference. BMC Bioinformatics 9, 540 (2008).
24. Marchini, J. SNPTEST (v2.5) https://mathgen.stats.ox-.ac.uk/genetics_software/snptest/snptest.html (2007).
25. Zaykin, D. V. & Kozbur, D. O. P-value based analysis for shared controls design in genome-wide association studies. Genet. Epidemiol. 34, 725-738 (2010).
26. Bhattacharjee, S. et al. A subset-based approach improves power and interpretation for the combined analysis of genetic association studies of heterogeneous traits. Am. J. Hum. Genet. 90, 821-835 (2012).
27. Institute for Systems Biology and Juvenile Diabetes Research Foundation-Wellcome Trust Diabetes and Inflammation Laboratory. ImmunoBase http://www.immunobase.org (2013).
28. Gensler, L. S. et al. Clinical, radiographic and functional differences between juvenile-onset and adult-onset ankylosing spondylitis: results from the PSOAS cohort. Ann. Rheum. Dis. 67, 233-237 (2008).
29. Lin, Y.-C., Liang, T.-H., Chen, W.-S. & Lin, H.-Y. Differences between juvenile-onset ankylosing spondylitis and adult-onset ankylosing spondylitis. J. Chin. Med. Assoc. 72, 573-580 (2009).
30. Anaya, J.-M., Gómez, L. & Castiblanco, J. Is there a common genetic basis for autoimmune diseases? Clin. Dev. Immunol. 13, 185-195 (2006).
31. De Jager, P. L. et al. Evaluating the role of the 620W allele of protein tyrosine phosphatase PTPN22 in Crohn's disease and multiple sclerosis. Eur. J. Hum. Genet. 14, 317-321 (2006).
32. Zhernakova, A. et al. Differential association of the PTPN22 coding variant with autoimmune diseases in a Dutch population. Genes Immun. 6, 459-461 (2005).
33. Liu, J. Z. et al. A versatile gene-based test for genome-wide association studies. Am. J. Hum. Genet. 87, 139-145 (2010).
34. Li, M.-X., Gui, H.-S., Kwan, J. S. H. & Sham, P. C. GATES: a rapid and powerful gene-based association test using extended Simes procedure. Am. J. Hum. Genet. 88, 283-293 (2011).
35. Huang, H., Chanda, P., Alonso, A., Bader, J. S. & Arking, D. E. Gene-based tests of association. PLoS Genet. 7, e1002177 (2011).
36. Benita, Y. et al. Gene enrichment profiles reveal T-cell development, differentiation, and lineage-specific transcription factors including ZBTB25 as a novel NF-AT repressor. Blood 115, 5376-5384 (2010).
37. Heng, T. S. P. & Painter, M. W. The Immunological Genome Project: networks of gene expression in immune cells. Nat. Immunol. 9, 1091-1094 (2008).
38. Olsson, R. et al. Prevalence of primary sclerosing cholangitis in patients with ulcerative colitis. Gastroenterology 100, 1319-1323 (1991).
39. Feld, J. J. & Heathcote, E. J. Epidemiology of autoimmune liver disease. J. Gastroenterol. Hepatol. 18, 1118-1128 (2003).
40. Yurasov, S. et al. Defective B cell tolerance checkpoints in systemic lupus erythematosus. J. Exp. Med. 201, 703-711 (2005).
41. Cappione, A. et al. Germinal center exclusion of autoreactive B cells is defective in human systemic lupus erythematosus. J. Clin. Invest. 115, 3205-3216 (2005).
42. Evenou, J.-P. et al. The potent protein kinase C-selective inhibitor AEB071 (sotrastaurin) represents a new class of immunosuppressive agents affecting early T-cell activation. J. Pharmacol. Exp. Ther. 330, 792-801 (2009).
43. Jegasothy, B. V. Tacrolimus (FK 506)—a new therapeutic agent for severe recalcitrant psoriasis. Arch. Dermatol. 128, 781-785 (1992).
44. Nograles, K. E. & Krueger, J. G. Anti-cytokine therapies for psoriasis. Exp. Cell Res. 317, 1293-1300 (2011).
45. Ergür, A. T. et al. Celiac disease and autoimmune thyroid disease in children with type 1 diabetes mellitus: clinical and HLA-genotyping results. J. Clin. Res. Pediatr. Endocrinol. 2, 151-154 (2010).
46. Eyre, S. et al. Overlapping genetic susceptibility variants between three autoimmune disorders: rheumatoid arthritis, type 1 diabetes and coeliac disease. Arthritis Res. Ther. 12, R175 (2010).
47. Joshita, S. et al. A2BP1 as a novel susceptible gene for primary biliary cirrhosis in Japanese patients. Hum. Immunol. 71, 520-524 (2010).
48. Pruitt, K., Brown, G., Tatusova, T. & Maglott, D. The Reference Sequence (RefSeq) database http://proxy.library.upenn.edu:2084/books/NBK21091/(2012).
49. Lauc, G. et al. Loci associated with N-glycosylation of human immunoglobulin G show pleiotropy with autoimmune diseases and haematological cancers. PLoS Genet. 9, e1003225 (2013).
50. Jäger, D. et al. Humoral and cellular immune responses against the breast cancer antigen NY-BR-1: definition of two HLA-A2 restricted peptide epitopes. Cancer Immun. 5, 11 (2005).
51. Ludwig, M.-G. & Seuwen, K. Characterization of the human adenylyl cyclase gene family: cDNA, gene structure, and tissue distribution of the nine isoforms. J. Recept. Signal Transduct. Res. 22, 79-110 (2002).
52. Jiang, L. I., Sternweis, P. C. & Wang, J. E. Zymosan activates protein kinase A via adenylyl cyclase VII to modulate innate immune responses during inflammation. Mol. Immunol. 54, 14-22 (2013).
53. Anderson, D. M. et al. A homologue of the TNF receptor and its ligand enhance T-cell growth and dendritic-cell function. Nature 390, 175-179 (1997).
54. Miyashita, T. et al. Bidirectional regulation of human B cell responses by CD40-CD40 ligand interactions. J. Immunol. 158, 4620-4633 (1997).
55. Li, G. et al. Human genetics in rheumatoid arthritis guides a high-throughput drug screen of the CD40 signaling pathway. PLoS Genet. 9, e1003487 (2013).
56. Wang, J., Duncan, D., Shi, Z. & Zhang, B. WEB-based GEne SeT AnaLysis Toolkit (WebGestalt): update 2013. Nucleic Acids Res. 41, W77-W83 (2013).
57. Agarwal, P., Srivastava, R., Srivastava, A. K., Ali, S. & Datta, M. miR-135a targets IRS2 and regulates insulin signaling and glucose uptake in the diabetic gastrocnemius skeletal muscle. Biochim. Biophys. Acta 1832, 1294-1303 (2013).
58. Huang, D. W. et al. The DAVID Gene Functional Classification Tool: a novel biological module-centric algorithm to functionally analyze large gene lists. Genome Biol. 8, R183 (2007).
59. Ingenuity Systems. Ingenuity Pathway Analysis http://www.ingenuity.com/products/ipa (2015).
60. Cerami, E. G. et al. Pathway Commons, a web resource for biological pathway data. Nucleic Acids Res. 39, D685-D690 (2011).

61. Denny, J. C. et al. PheWAS: demonstrating the feasibility of a phenome-wide scan to discover gene-disease associations. Bioinformatics 26, 1205-1210 (2010).
62. Ritchie, M. D. et al. Robust replication of genotype-phenotype associations across multiple diseases in an electronic medical record. Am. J. Hum. Genet. 86, 560-572 (2010).
63. Liao, K. P. et al. Associations of autoantibodies, autoimmune risk alleles, and clinical diagnoses from the electronic medical records in rheumatoid arthritis cases and non-rheumatoid arthritis controls. Arthritis Rheum. 65, 571-581 (2013).
64. Hakonarson, H. et al. A genome-wide association study identifies KIAA0350 as a type 1 diabetes gene. Nature 448, 591-594 (2007).
65. Imielinski, M. et al. Common variants at five new loci associated with early-onset inflammatory bowel disease. Nat. Genet. 41, 1335-1340 (2009).
66. Kugathasan, S. et al. Loci on 20q13 and 21q22 are associated with pediatric-onset inflammatory bowel disease. Nat. Genet. 40, 1211-1215 (2008).
67. Orange, J. S. et al. Genome-wide association identifies diverse causes of common variable immunodeficiency. J. Allergy Clin. Immunol. 127, 1360-1367.e6 (2011).
68. Behrens, E. M. et al. Association of the TRAF1-C5 locus on chromosome 9 with juvenile idiopathic arthritis. Arthritis Rheum. 58, 2206-2207 (2008).
69. Grant, S. F. et al. Association of the BANK 1 R61H variant with systemic lupus erythematosus in Americans of European and African ancestry. Appl. Clin. Genet. 2, 1-5 (2009).
70. Liao, K. P. et al. Electronic medical records for discovery research in rheumatoid arthritis. Arthritis Care Res. (Hoboken) 62, 1120-1127 (2010).
71. Petty, R. E. et al. International League of Associations for Rheumatology classification of juvenile idiopathic arthritis: second revision, Edmonton, 2001. J. Rheumatol. 31, 390-392 (2004).
72. Behrens, E. M. et al. Evaluation of the presentation of systemic onset juvenile rheumatoid arthritis: data from the Pennsylvania Systemic Onset Juvenile Arthritis Registry (PASOJAR). J. Rheumatol. 35, 343-348 (2008).
73. Conley, M. E., Notarangelo, L. D. & Etzioni, A. Diagnostic criteria for primary immunodeficiencies. Representing PAGID (Pan-American Group for Immunodeficiency) and ESID (European Society for Immunodeficiencies). Clin. Immunol. 93, 190-197 (1999).
74. Price, A. L. et al. Principal components analysis corrects for stratification in genome-wide association studies. Nat. Genet. 38, 904-909 (2006).
75. Delaneau, O., Coulonges, C. & Zagury, J.-F. Shape-IT: new rapid and accurate algorithm for haplotype inference. BMC Bioinformatics 9, 540 (2008).
76. Howie, B. N., Donnelly, P. & Marchini, J. A flexible and accurate genotype imputation method for the next generation of genome-wide association studies. PLoS Genet. 5, e1000529 (2009).
77. Howie, B., Marchini, J. & Stephens, M. Genotype imputation with thousands of genomes. G3 (Bethesda) 1, 457-470 (2011).
78. Stucky, B. J. SeqTrace: a graphical tool for rapidly processing DNA sequencing chromatograms. J. Biomol. Tech. 23, 90-93 (2012).
79. Price, A. L. et al. Principal components analysis corrects for stratification in genome-wide association studies. Nat. Genet. 38, 904 (2006).
80. Zaykin, D. V. & Kozbur, D. O. P-value based analysis for shared controls design in genome-wide association studies. Genet. Epidemiol. 34, 725-738 (2010).
81. De Bakker, P. I. et al. Practical aspects of imputation-driven meta-analysis of genome-wide association studies. Hum. Mol. Genet. 17, R122-R128 (2008).
82. Yang, J., Lee, S. H., Goddard, M. E. & Visscher, P. M. GCTA: a tool for genome-wide complex trait analysis. Am. J. Hum. Genet. 88, 76-82 (2011).
83. Institute for Systems Biology and Juvenile Diabetes Research Foundation-Wellcome Trust Diabetes and Inflammation Laboratory. ImmunoBase http://www.imunobase.org (2013).
84. NHGRI. Published GWAS through Aug. 1, 2014. NHGRI GWA Catalog http://www.genome.gov/multimedia/illustrations/GWAS_2011_3.pdf (2014).
85. McLaren, W. et al. Deriving the consequences of genomic variants with the Ensembl API and SNP Effect Predictor. Bioinformatics 26, 2069-2070 (2010).
86. Rossin, E. J. et al. Proteins encoded in genomic regions associated with immune-mediated disease physically interact and suggest underlying biology. PLoS Genet. 7, e1001273 (2011).
87. Johnson, A. D. et al. SNAP: a web-based tool for identification and annotation of proxy SNPs using HapMap. Bioinformatics 24, 2938 (2008).
88. Chelala, C., Khan, A. & Lemoine, N. R. SNPnexus: a web database for functional annotation of newly discovered and public domain single nucleotide polymorphisms. Bioinformatics 25, 655-661 (2009).
89. Cunningham, F. et al. Ensembl 2015. Nucleic Acids Res. 43, D662-D669 (2015).
90. Kent, W. J. et al. The human genome browser at UCSC. Genome Res. 12, 996 (2002).
91. Boyle, A. P. et al. Annotation of functional variation in personal genomes using RegulomeDB. Genome Res. 22, 1790-1797 (2012).
92. National Institutes of Health Genotype-Tissue Expression (GTEx) http://proxy.library.upenn.edu:2328/GTEx/index (2015).
93. Liang, L. et al. A cross-platform analysis of 14,177 expression quantitative trait loci derived from lymphoblastoid cell lines. Genome Res. 23, 716-726 (2013).
94. Kumar, P., Henikoff, S. & Ng, P. C. Predicting the effects of coding non-synonymous variants on protein function using the SIFT algorithm. Nat. Protoc. 4, 1073-1081 (2009).
95. Adzhubei, I., Jordan, D. M. & Sunyaev, S. R. Predicting functional effect of human missense mutations using PolyPhen-2. Curr. Protoc. Hum. Genet. Chapter 7, Unit 7.20 (2013).
96. Liu, C. et al. MirSNP, a database of polymorphisms altering miRNA target sites, identifies miRNA-related SNPs in GWAS SNPs and eQTLs. BMC Genomics 13, 661 (2012).
97. Griffiths-Jones, S., Grocock, R. J., van Dongen, S., Bateman, A. & Enright, A. J. miRBase: microRNA sequences, targets and gene nomenclature. Nucleic Acids Res. 34, D140-D144 (2006).
98. Davydov, E. V. et al. Identifying a high fraction of the human genome to be under selective constraint using GERP. PLoS Comput. Biol. 6, e1001025 (2010).
99. Nguyen, D.-Q. et al. Reduced purifying selection prevails over positive selection in human copy number variant evolution. Genome Res. 18, 1711-1723 (2008).

100. Bird, A. P. CpG-rich islands and the function of DNA methylation. Nature 321, 209-213 (1986).
101. Becker, K. G., Barnes, K. C., Bright, T. J. & Wang, S. A. The genetic association database. Nat. Genet. 36, 431-432 (2004).
102. Heng, T. S. P. & Painter, M. W. The Immunological Genome Project: networks of gene expression in immune cells. Nat. Immunol. 9, 1091-1094 (2008).
103. Mailman, M. D. et al. The NCBI dbGaP database of genotypes and phenotypes. Nat. Genet. 39, 1181-1186 (2007).
104. Benita, Y. et al. Gene enrichment profiles reveal T-cell development, differentiation, and lineage-specific transcription factors including ZBTB25 as a novel NF-AT repressor. Blood 115, 5376-5384 (2010).
105. Franceschini, A. et al. STRING v9.1: protein-protein interaction networks, with increased coverage and integration. Nucleic Acids Res. 41, D808-D815 (2013).
106. Ashburner, M. et al. Gene ontology: tool for the unification of biology. The Gene Ontology Consortium. Nat. Genet. 25, 25-29 (2000).
107. Wang, J., Duncan, D., Shi, Z. & Zhang, B. WEB-based GEne SeT AnaLysis Toolkit (WebGestalt): update 2013. Nucleic Acids Res. 41, W77-W83 (2013).
108. Kelder, T. et al. WikiPathways: building research communities on biological pathways. Nucleic Acids Res. 40, D1301-D1307 (2012).
109. Ingenuity Systems Ingenuity Pathway Analysis http://www.ingenuity.corn/products/ipa (2015).
110. Huang, D. W. et al. The DAVID Gene Functional Classification Tool: a novel biological module-centric algorithm to functionally analyze large gene lists. Genome Biol. 8, R183 (2007).
111. Wang, K., Li, M. & Bucan, M. Pathway-based approaches for analysis of genomewide association studies. Am. J. Hum. Genet. 81, 1278-1283 (2007).
112. Cerami, E. G. et al. Pathway Commons, a web resource for biological pathway data. Nucleic Acids Res. 39, D685-D690 (2011).
113. Raychaudhuri, S. et al. Identifying relationships among genomic disease regions: predicting genes at pathogenic SNP associations and rare deletions. PLoS Genet. 5, e1000534 (2009).
114. Liu, J. Z. et al. A versatile gene-based test for genome-wide association studies. Am. J. Hum. Genet. 87, 139-145 (2010).
115. Subramanian, A. et al. Gene set enrichment analysis: a knowledge-based approach for interpreting genome-wide expression profiles. Proc. Natl. Acad. Sci. USA 102, 15545-15550 (2005).
116. Mootha, V. K. et al. PGC-1alpha-responsive genes involved in oxidative phosphorylation are coordinately downregulated in human diabetes. Nat. Genet. 34, 267-273 (2003).
117. Nair, R. P. et al. Genome-wide scan reveals association of psoriasis with IL-23 and NF-κB pathways. Nat. Genet. 41, 199-204 (2009).
118. Ahn, R. et al. Association analysis of the extended MHC region in celiac disease implicates multiple independent susceptibility loci. PLoS ONE 7, e36926 (2012).
119. Duerr, R. H. et al. A genome-wide association study identifies IL23R as an inflammatory bowel disease gene. Science 314, 1461-1463 (2006).
120. Wellcome Trust Case Control Consortium. et al. Genome-wide association study of 14,000 cases of seven common diseases and 3,000 shared controls. Nature 447, 661-678 (2007).
121. Barrett, J. C. et al. Genome-wide association study of ulcerative colitis identifies three new susceptibility loci, including the HNF4A region. Nat. Genet. 41, 1330-1334 (2009).
122. Evans, D. M. et al. Interaction between ERAP1 and HLA-B27 in ankylosing spondylitis implicates peptide handling in the mechanism for HLA-B27 in disease susceptibility. Nat. Genet. 43, 761-767 (2011).
123. Marchini, J. et al. A new multipoint method for genome-wide association studies by imputation of genotypes. Nat. Genet. 39, 906-913 (2007).
124. Abecasis, G. R. et al. An integrated map of genetic variation from 1,092 human genomes. Nature 491, 56-65 (2012).
125. Gao, F. et al. WAS: a software toolset for genetic data analysis and association studies of the X chromosome. bioRxiv doi:10.1101/009795.
126. Chang, D. et al. Accounting for eXentricities: analysis of the X chromosome in GWAS reveals X-linked genes implicated in autoimmune diseases. PLoS One 9, e113684 (2014).
127. Purcell, S. et al. PLINK: a tool set for whole-genome association and population-based linkage analyses. Am. J. Hum. Genet. 81, 559-575 (2007).
128. Patterson, N., Price, A. L. & Reich, D. Population structure and eigenanalysis. PLoS Genet. 2, e190 (2006).
129. Stahl, E. A. et al. Genome-wide association study meta-analysis identifies seven new rheumatoid arthritis risk loci. Nat. Genet. 42, 508-514 (2010).
130. Anderson, C. A. et al. Meta-analysis identifies 29 additional ulcerative colitis risk loci, increasing the number of confirmed associations to 47. Nat. Genet. 43, 246-252 (2011).
131. Franke, A. et al. Genome-wide meta-analysis increases to 71 the number of confirmed Crohn's disease susceptibility loci. Nat. Genet. 42, 1118-1125 (2010).
132. Hom, G. et al. Association of systemic lupus erythematosus with C8orf13-BLK and ITGAM-ITGAX. N. Engl. J. Med. 358, 900 (2008).
133. Harley, J. B. et al. Genome-wide association scan in women with systemic lupus erythematosus identifies susceptibility variants in ITGAM, PXK, KIAA1542 and other loci. Nat. Genet. 40, 204-210 (2008).

Example II

Screening Assays for Identifying Efficacious Therapeutics for the Treatment of Aids The information herein above can be applied clinically to patients for diagnosing an increased susceptibility for developing one or more AID (including pAIDs) and therapeutic intervention. An embodiment of the invention comprises clinical application of the information described herein to a patient. Diagnostic compositions, including microarrays, and methods can be designed to identify the SNPs described herein in nucleic acids from a patient to assess susceptibility for developing AID. This can occur after a patient arrives in the clinic; the patient has blood drawn, and using the diagnostic methods described herein, a clinician can detect a genetic alteration such as a single nucleotide polymorphism as described in Example I. The information obtained from the patient sample, which can optionally be amplified prior to assessment, may be used to diagnose a patient with an increased or decreased susceptibility for developing AID or used to direct treatment in a patient previously diagnosed with AID. Kits for performing diagnostic methods of the invention are also provided herein. Such kits may comprise a microarray comprising at least one of the SNVs/SNPs provided herein and the necessary reagents for assessing the patient samples as described above.

The identity of AID involved genes and the patient results will indicate which variants are present, and may be used to identify those that have, or possess an altered risk for developing AID. The information provided herein may allow for therapeutic intervention at earlier times in disease progression than previously possible. Also as described herein above, the genes listed in Supplemental Table 1b and provided the tables herein were shown to associate with one or more pAIDs at genome wide significance (GWS) levels, while an additional set (see Table 2b) were shown to associate with one or more pAIDs at genome wide marginal significance (GWM) levels, and these genes thus may provide a novel targets for the development of new therapeutic agents efficacious for the treatment of autoimmune disorders.

Example III

Test and Treat Method for Ameliorating Symptoms Associated with AID

In order to treat an individual having AID (including pAID), for example, to alleviate a sign or symptom of the disease, suitable agents targeting the genes disclosed in the tables herein can be administered in combination in order to provide therapeutic benefit to the patient. Such agents should be administered in an effective dose.

First, a biological sample, or genotyping information would be obtained from a patient. Genetic information gleaned from nucleic acids present in the sample would then be assessed for the presence or absence of the AID SNV/SNP containing nucleic acids associated with onset of one or more AID. The presence of these SNVs indicating the presence of an AID, along with the simultaneous identification of the genes affected, providing the clinician with guidance as to which therapeutic agents are appropriate. The total treatment dose or doses (when two or more targets are to be modulated) can be administered to a subject as a single dose or can be administered using a fractionated treatment protocol, in which multiple/separate doses are administered over a more prolonged period of time, for example, over the period of a day to allow administration of a daily dosage or over a longer period of time to administer a dose over a desired period of time. One skilled in the art would know that the amount of AID agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having AID.

The effective dose of AID therapeutic agent(s) will depend on the mode of administration, and the weight of the individual being treated. The dosages described herein are generally those for an average adult but can be adjusted for the treatment of children. The dose will generally range from about 0.001 mg to about 1000 mg.

In an individual suffering from AID, in particular a more severe form of the disease, administration of AID therapeutic agents can be particularly useful when administered in combination, for example, with a conventional agent for treating such a disease. The skilled artisan would administer AID therapeutic agent(s), alone or in combination and would monitor the effectiveness of such treatment using routine methods such as pulmonary, bowel, thryroid, inflammatory function determination, radiologic, immunologic assays, or, where indicated, histopathologic methods. Other conventional agents for the treatment of AID include steroid or administration of other agents that alleviate the symptoms underlying the disease.

Administration of the pharmaceutical preparation is preferably in an "effective amount" this being sufficient to show benefit to the individual. This amount prevents, alleviates, abates, or otherwise reduces the severity of at least one AID symptom in a patient.

In a preferred embodiment of this invention, a method is provided for the synergistic treatment of AID using the pharmaceutical agents disclosed in the present example in combinatorial approaches. Advantageously, the synergistic method of this invention reduces the development of AID, or reduces symptoms of AID in a mammalian host. Additionally, therapeutic regimens suitable for simultaneous treatment of two or more AID disorders are also provided. As shown in the tables, certain genes appear to modulate the autoimmune phenotypes in more than one pAID. Moreover, it is known that certain patients present with more than one AID in the clinic. The information provided herein guides the clinician in new treatment modalities for the management of AID.

Methods for the safe and effective administration of FDA-approved pharmaceutical agents are known to those skilled in the art. In addition, their administration is described in the standard literature. For example, the administration of many anti-inflammatory agents is described in the "Physicians' Desk Reference" (PDR), e.g., 1996 edition (Medical Economics Company, Montvale, N.J. 07645-1742, USA); the disclosure of which is incorporated herein by reference thereto.

The present invention also encompasses a pharmaceutical composition useful in the treatment of AID, comprising the administration of a therapeutically effective amount of the combinations of this invention, with or without pharmaceutically acceptable carriers or diluents. The synergistic pharmaceutical compositions of this invention comprise two or more of the agents listed in the table below and a pharmaceutically acceptable carrier. The compositions of the present invention may further comprise one or more pharmaceutically acceptable additional ingredient(s) such as alum, stabilizers, antimicrobial agents, buffers, coloring agents, flavoring agents, adjuvants, and the like. The anti-AID compositions of the present invention may be administered orally or parenterally including the intravenous, intramuscular, intraperitoneal, subcutaneous, rectal and topical routes of administration.

Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain AIDs can be treated effectively with a plurality of the compounds listed above. Such triple and quadruple combinations can provide greater efficacy. When used in such triple and quadruple combinations the dosages can be determined according to known protocols.

The combinations of the instant invention may also be co-administered with other therapeutic agents selected for their particular usefulness against the condition that is being treated. Combinations of the instant invention may alternatively be used sequentially with known pharmaceutically acceptable agent(s) when a multiple combination formulation is inappropriate.

Also, in general, the compounds listed above do not have to be administered in the same pharmaceutical composition, and may, because of different physical and chemical characteristics, have to be administered by different routes. For example, first compound may be administered orally to generate and maintain good blood levels thereof, while a second compound may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

As described previously in Example I, genome wide association studies (GWAS) have identified hundreds of susceptibility genes associated with autoimmune diseases with some shared across clinically-distinct disease groups. To investigate the genetic architecture of pediatric autoimmune diseases (pAIDs), we performed a heterogeneity-sensitive GWAS (hsGWAS) across 10 pAIDs in a nested case-control study including over 5,200 cases and 11,000 controls (Table 10). We identified 86 independent pAID association loci ($P<5\times10^{-8}$) (See Tables herein below), including genes with established immunoregulatory functions (e.g., CD40LG; $P<3.08\times10^{-11}$ and NFATC3; $P<1.18\times10^{-8}$). Of those, 97% were supported by functional (n=30), regulatory (n=55), conservational (n=30) or literature-reported (n=40) data, and demonstrated disease-specific gene expression patterns across specific immune cell lineages. Integration of multiple in silico analytical approaches identified highly shared autoimmune signals (e.g., IL2-IL21 $P<6.24\times10^{-12}$) and converging roles for JAK-STAT, innate, and TH1-TH2/TH17 mediated T-cell signaling among attractive pharmacological targets involving pAID biology. Targets with known drugs available are shown in Tables 11 and 12. These drugs can be combined to synergistically treat pAID or to simultaneously reduce symptoms or progression of multiple pAIDs (2-5 separate pAIDs) as shown in Tables 11 and 12 below. The numbers in the last column of Table 11 correspond to the subtype of pAID listed in Table 10.

TABLE 10

Cohort characteristics of the ten pediatric autoimmune disease patient cohorts

| Abbrev. | Subtype[a] | pAID | Count | F:M Ratio | Genomic Inflation $(\lambda)^d$ |
|---|---|---|---|---|---|
| THY | 1 | Thyroiditis | 99 | 0.758 | 1.004 |
| SPA | 2 | Spondyloarthropathy | 111 | 0.550 | 1.012 |
| PSOR | 3 | Psoriasis | 113 | 0.584 | 1.001 |
| CEL | 4 | Celiac Disease | 183 | 0.632 | 1.025 |
| SLE | 5 | Systemic Lupus Erythematosus | 256 | 0.877 | 1.022 |
| CVID | 6 | Common Variable Immundeficiency | 309 | 0.542 | 1.038 |
| UC | 7 | Ulcerative Colitis | 895 | .0542 | 1.038 |
| T1D | 8 | Type 1 Diabetes | 1139 | 0.486 | 1.037 |
| JIA | 9 | Juvenile Idiopathic Arthritis | 1165 | 0.687 | 1.009 |
| CD | 10 | Crohn's Disease | 2039 | 0.422 | 1.089 |
| CTRL | 0 | Non-AID Ascertained Controls | 11179 | 0.479 | — |
| Classical GWAS Method | | All AI disease cases merged | 5589 | 0.464 | $1.026^e$ |
| hsGWAS Method | | All AI disease cases non-overlapping | 5589 | 0.464 | $1.061^f$ |

[a] pAID abbreviations correspond to and are cross-referenced in Table 1B, 1C and 2A
b) Case counts are those from the respective pAID cohorts after all QC and filtering
c) Controls were ascertained based on EMR records showing no diagnosis for ICD9 codes across all immune-mediated (autoimmune, immunodeficiency, and inflammatory) diseases
[d] Genomic inflation ($\lambda$) was calculated based on single disease case-(shared) control association analysis summary statistics
[e] Mean $\lambda$ across the ten respective classic GWAS studies
[f] Adjusted for a 1000-case-100-control cohort size, excluding MHC; see supplemental methods

TABLE 11

(Numbers listed in last column correspond to pAID listed in Table 10 above.)

| Gene | Entrez Gene Name | Chr | Start | Stop | Pvalue | Best-5NP | SNP-pvalue | Cellular Location | Protein Type | Drug | pAIDs |
|---|---|---|---|---|---|---|---|---|---|---|---|
| PLA2G4A | Phospholipase A2, group IVA (cytosolic, calcium-dependent) | 1 | 185064654 | 185224736 | <1 × 10−6 | rs932476 | 2.3844E-07 | Cytoplasm | enzyme | Quinacrine A003 AK106 ASB14780 AVX001 AVX002 AVX003 AVX235 Bactoderm C Bactoderm GM Bactoderm N Bestasol Bet-Vet-N Betnogard C Betval-C BL3030 CB24 Clobetasol SAVA cPLA2 Inhibitors MERCKLE Fenspiride FARMAPROJECTS Fenspogal Inzitan IPP201007 IS741 Lifuzon LY315920 LY333013 Momesone PO-LING MRX4 MRX5 MRX6 OPX1 PLA695 PLA725 PLA902 Pulneo SKMS10 Tirfens Topidin Troxerutin SYNTEZA VRCTC310 ZPL5212372 | 3\|4\|7\|10 |
| MST1R | Macrophage stimulating 1 receptor (c-met-related tyrosine kinase) | 3 | 49899439 | 49916310 | <1 × 10−6 | rs2246832 | 3.5048E-09 | Plasma Membrane | kinase | Crizotinib AL2846 Anti-RON antibody ABZYME Anti-RON proteolytic antibody ABZYME Anti-RONXAnti-CD3 EMERGENT IMC41A10 IMCRON8 Kinase Inhibitors MIRATI MGCD265 RON Receptor Monoclonal Antibody AVEO | 3\|4\|7\|10 |
| IL13 | Interleukin 13 | 5 | 132021763 | 132024700 | <1 × 10−6 | Rs2227284 | 2.4747E-08 | Extracellular Space | ctyokine | CAT-354 GSK679586 IL-4/IL-13 Inhibiting Peptide SYNAIRGEN IMA026 MEDI7836 MILR1444A QAX576 QBX258 R256 | 2\|3\|10 |
| IL12B | Interleukin 12B (natural killer cell stimulatory factor 2, cytotoxic lymphocyte maturation factor 2, p40) | 5 | 158674368 | 158690059 | <1 × 10−6 | rs4921484 | 6.9104E-12 | Extracellular Space | ctyokine | Ustekinumab; Ad-IL12 Immunogene Therapy MOMOTARO | 1\|3\|4\|7\|10 |
| GABBR1 | Gamma-aminobutyric acid (GABA) B receptor, 1 | 6 | 29677983 | 29708941 | <1 × 10−6 | rs2071653 | 2.87275E-08 | Plasma Membrane | G-protein coupled receptor | baclofen, vigabatrin ADX71943 ADX71441 AMRS001 Aero-Itan Ansielix Digest Apo-Chlorax AwaLibrin Baby-tal Belladona alkaloids with Phenobarbital WEST WARD Belladonna alkaloids W/Phenobarbital Bralix Braxidin Chlordiazepoxide hydrochloride with Clidinium bromide-ACTAVIS Chlordiazepoxide hydrochloride with Clidinium bromide QUALITEST Chlorspas Cibis Cliad Clidinium-C Clidinium-C HAKIM Clidinium-C ZAHRAVI Clidox M Clidox MORACEAE Clixid-D Cloxide Coliwin Tablets CVXL0060 Cylospas Debridat B Distedon Donnatal Epirax Euciton | 4\|6\|8\|10 |

TABLE 11-continued (Numbers listed in last column correspond to pAID listed in Table 10 above.)

| Gene | Entrez Gene Name | Chr | Start | Stop | Pvalue | Best-5NP | SNP-pvalue | Cellular Location | Protein Type | Drug | pAIDs |
|---|---|---|---|---|---|---|---|---|---|---|---|
| | | | | | | | | | | Stress Eudon Eumotil-T Faradil Faradil Novo Laberax Lebraxim Libkol Liblan Librax Librax COMBIPHAR Libtrax Malzorir Mebeverine hydrochloride with Alprazolam STERLING No-Ref Normaxin Normaxin RT Normib Pasminox Somatico Pipdole Piplar Poxidium Profisin Ranicom-AS Renagas Sinpasmon Spasrax Spaz-CD Tensium Gastric Ulic Vertipam Zibra PF0713 | |
| TNF | Tumor necrosis factor | 6 | 31651328 | 31654091 | <1 × 10-6 | rs2269475 | 6.9605E-11 | Extracellular Space | cytokine | etanercept, infliximab, certolizumab, golimumab, pomalidomide, thalidomide; Remicade Humera F45D9 Apocept Enbrel GWP42003 Revlimid TACIfc5 Atrosab Genz29155 KAHR101 PUR0110 Onercept Cinzia Rensima CEP37247 DLX105 ABP501 ACE772 BM02 CHS0214 Etanercept Infnitam ISIS104838 Tinefcon TuNEX Nanercpt AG014 ATB429 BTI9 CB0112 HMPL004 Humicade LexaGard SAR252067 TAK114 URL12746S ATN103 Infliximab MDR06155 Simponi Shinbaro CC1088 KIN219 AVX470 Prolia ABP710 ABT122 Adalimumab ALKS6931 Altebrel AMAB Anbainuo APG103 APX001 OX40 Ligand Monoclonal Ab Pegsunercept PF06410293 PF06438179 CHRONTECH ORCHID SAREPTA PROTELICA ANTYRA EDEXGEN Xtend-TNF ENSEMBLE TNFPEG20 TriptoSar Xgeva ONL101 ONL1204 OPK20018 Recombinant Human Nerve Growth Factor DOMPE Dom0101 GSK1995057 GSK2862277 RG4930 | 2\|3\|5\|8\|9 |
| HLA-DRB1 | Major histocompatibility complex, class II, DR beta 1 | 6 | 32654524 | 32665540 | <1 × 10-6 | rs9271366 | 2.37686E-42 | Plasma Membrane | Transmembrane receptor | Apolizumab; Anti-HLA-DR (DENDREON) CAP31 CD79BxDR Dantes DN1924 HLA-DQ2 Blockers ALVINE IMMU114 Remitogen | 6\|8 |
| PSMB9 | Proteasome (prosome, macropain) subunit, beta type, 9 | 6 | 32929915 | 32935606 | <1 × 10-6 | rs241407 | 3.21942E-27 | Cytoplasm | peptidase | Carfilzomib | 1\|8 |
| COL11A2 | Collagen, type XI, alpha 2 | 6 | 33238446 | 33268223 | <1 × 10-6 | rs1977090 | 6.68314E-13 | Extracellular Space | other | collagenase clostridium histolyticum ABT518; Abbott | 8 |
| IL2RA | Interleukin 2 receptor, alpha | 10 | 6093511 | 6144278 | <1 × 10-6 | rs12722563 | 3.5412E-11 | Plasma Membrane | Transmembrane receptor | LMB-2, daclizumab, basilliximab, aldesleukin, denileukin diftitox; ADCT301 | 3\|6\|7\|8\|9 |

TABLE 11-continued (Numbers listed in last column correspond to pAID listed in Table 10 above.)

| Gene | Entrez Gene Name | Chr | Start | Stop | Pvalue | Best-5NP | SNP-pvalue | Cellular Location | Protein Type | Drug | pAIDs |
|---|---|---|---|---|---|---|---|---|---|---|---|
| TH | Tyrosine hydroxylase | 11 | 2141734 | 2149611 | <1 × 10-6 | rs3842727 | 1.4786E-38 | Cytoplasm | enzyme | 5,6,7,8-tetrahydrobiopterin Denser OXB102 Parkinson Gene Therapy SHIRE Prosavin | 8 |
| CDK2 | Cyclin-dependent kinase 2 | 12 | 54646822 | 54652835 | <1 × 10-6 | rs772921 | 3.3821E-13 | Nucleus | kinase | BMS-387032, flavopiridol; AG24322 Pfizer | 3\|8 |
| ERBB3 | v-erb-b2 avian erythroblastic leukemia viral oncogene homolog 3 | 12 | 54760158 | 54783395 | <1 × 10-6 | rs705704 | 1.5348E-12 | Plasma Membrane | kinase | Sapitinib; AV203 | 3\|8 |
| PSMB10 | Proteasome (prosome, macropain) subunit, beta type, 10 | 16 | 66525907 | 66528254 | 1 × 10-6 | rs3785098 | 1.6024E-08 | Cytoplasm | peptidase | Carfilzomib ARRY520 Bitezo Bortecad Bortemib Bortenat NATCO Bortenat RADIANCE Bortezomib ACCURE Bortezomib ACTAVIS Bortezomib ADMAC Bortezomib HETERO Bortezomib Micelle NANOCARRIER Bortezomib NAPROD Bortezomib NERVIANO Bortezomib SALIUS Bortezomib SAVA Bortezomib SYNCHRONY Bortezomib TEVA Bortezomib UNITED BIOTECH Bortiad Bortrac Borviz BT062 CEP18770 CEP28331 DSF-C Fellutamide C and D MERCK FV162 FV214 HIV 26S Proteasome Inhibitor VIROLOGIK IAV Proteasome Inhibitor VIROLOGIK Kyprolis Mibor Milanfor MLN273 MLN519 MLN9708 Myezom Mylosome NEOSH101 NOXA12 NPI0052 Oncodox Peg with Bortezomib CIPLA ONX0912 ONX0914 Ortez PR924 Proteasome inhibitor JEIL Proteasome Inhibitors MABVAX Proteasome Inhibitors QUIMATRYX Rolcade Tazenta Tetra-acridines PIERRE FABRE Velcade VL01 VLX1570 VPE001 VPEA002 VPEA004 VR23 Zolinza | 5\|6\|8 |
| SLC12A4 | Solute carrier family 12 (potassium/chloride transporter), member 4 | 16 | 66535730 | 66560026 | <1 × 10-6 | rs3785098 | 1.6024E-08 | Plasma Membrane | transporter | Butetanide; CL301 CLP290 CLP635 Reformulated Bumetanide | 5\|6\|8 |

TABLE 12

Certain Molecules in Development Associated with Particular Genes

| Gene | Therapeutic Molecules on U.S. Market or in Development |
|---|---|
| CD40LG | Anti-CD40LG antibodies (e.g. BMS986004; dapirolizumab (CDP7657); toralizumab (IDEC131)); CD40 antibodies (e.g. BI655064); CD40LG inhibitors (e.g. PEPSCAN); MEDI4920; TDI846 |
| LRRK2 | LRRK2 inhibitors (e.g. ARN1104; H1337) |
| IL-21 | Anti-IL21 antibodies (e.g. NN8828); KD025; ATR107; BNZ2; BNZ3 |
| ADCY7 | ACP003; Adehl; Corgenic; NKH477; RT100; Type 5 Adenylyl Cyclase Inhibitors |
| SMAD3 | GED0301 |
| NOD2 | Mifamurtide (Mepact ™); MIS416; SB9200 |
| IL2RA | Recombinant IL2 (e.g. Aldesleukin; ligen-2; Inleusin ™; Interking ™); inolimomab (BLNP007 or BT563); anti-IL2RA antibody (HuMax-TAC); MDNA12; dinutuximab; LMB-2; basilliximab; denileukin diftitox; ADCT301 |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for detecting a single nucleotide variation (SNV) in rs2807264 on Xq26.3 in CD40LG in a celiac disease (CEL), ulcerative colitis (UC), or Crohn's disease (CD) human patient comprising:
   a) obtaining a biological sample from the human patient; and
   b) detecting a single nucleotide variation (SNV) in rs2807264 nucleic acid on Xq26.3 by contacting the sample with a probe specific for said SNV and detecting binding between said probe and said SNV nucleic acid.

2. The method of claim 1, wherein the method further comprises detecting a single nucleotide variation (SNV) in at least one of IL23R, LPHN2, PTPN22, TNFSF18, CRB1, IL10, TSSC1, IL18R1, ATG16L1, GPR35, DAG1, CYTL1, IL21, TNM3, PTGER4, ANKRD55, ERAP2, IL5, IL12B, 8q24.23, JAK2, LURAP1L, TNFSF15, FNBP1, CARD5, IL2RA, ANKRD30A, ZNF365, ZMIZ1, NKX2-3, INS, LRRK2, SUOX, EFNB2, SMAD3, SBK1, ATXN2L, ADCY7, NOD2, IKZF3, TYK2, FUT2, TNFRSF6B, PSMG1, and RBMX.

3. The method of claim 1, wherein the patient is a pediatric patient.

4. The method of claim 1, wherein the method comprises treating UC, or CEL or CD by administering an anti-CD40LG antibody, CD40 antibody, or CD40LG inhibitor to the patient.

5. The method of claim 1, wherein the method further comprises detecting a single nucleotide variation (SNV) in one or more of LPHN2, TNM3, and ADCY7.

6. The method claim 4, wherein the method comprises treating ulcerative colitis (UC) and further comprises detecting a single nucleotide variation (SNV) in one or more of IL23R, LPHN2, DAG1, PTGER4, SBK1, TNFSF15, CD40LG, IL21, CARD9, and PSMG1.

7. The method of claim 6, wherein the method further comprises detecting a single nucleotide variation (SNV) in one or more of IL10, TSSC1, IL18R1, GPR35, CYTL1, IL12B, JAK2, NKX2, SMAD3, ATXN2L, IKZF3, and TNFRSF6B.

8. The method of claim 4, wherein the method comprises treating Crohn's Disease (CD) and further comprises detecting a single nucleotide variation (SNV) in one or more of IL23R, PTPN22, DAG1, ATG16L1, PTGER4, ANKRD55, LRRK2, SBK1, ADCY7, IL2RA, TNFSF15, ZMIZ1, IL21, CARD9, and PSMG1.

9. The method of claim 8, wherein the method further comprises detecting a single nucleotide variation (SNV) in one or more of CRB1, IL10, TSSC1, IL18R1, CYTL1, ERAP2, IL5, IL12B, 8q24.23, JAK2, FNBP1, ZNF365, NKX2, SMAD3, ATXN2L, NOD2, IKZF3, TYK2, FUT2, TNFRSF6B, and RBMX.

10. The method of claim 1, wherein the method comprises detecting a single nucleotide variation (SNV) in one or more of PTPN22, TNM3, SBK1, IL2RA, and IL21.

11. The method of claim 10, wherein the method further comprises detecting a single nucleotide variation (SNV) in one or more of IL18R1, CYTL1, FNBP1, IKZF3, TYK2, and TNFRSF6B is present.

12. The method of claim 4, wherein the method comprises treating Celiac Disease (CEL) and further comprises detecting a single nucleotide variation (SNV) in one or more of TNM3, DAG1, SBK1, IL2RA, ZMIZ1, or IL21.

13. The method of claim 12, wherein the method further comprises detecting a single nucleotide variation (SNV) in one or more of IL18R1, CYTL1, ERAP2, IL5, IL12B, 8q24.23, IKZF3, or RBMX.

* * * * *

UNITED STATES PATENT AND TRADEMARK OFFICE
CERTIFICATE OF CORRECTION

PATENT NO. : 10,385,398 B2
APPLICATION NO. : 15/242091
DATED : August 20, 2019
INVENTOR(S) : Hakonarson et al.

Page 1 of 1

It is certified that error appears in the above-identified patent and that said Letters Patent is hereby corrected as shown below:

In the Specification

Column 1, Lines 14-18, delete the following paragraph:
"This invention was made with funds from the National Institutes of Health, Grant Nos. DP3DK085708, RC1AR058606, U01HG006830, CA127334, and R01-HG006849. Accordingly, the United States Government has rights in this invention."

And insert the following paragraph in its place:
--This invention was made with government support under grant numbers DK085708, AR058606, and HG006830 awarded by the National Institutes of Health. The government has certain rights in this invention.--

Signed and Sealed this
Eleventh Day of February, 2020

Andrei Iancu
*Director of the United States Patent and Trademark Office*